US012733602B2

(12) United States Patent
Lippman et al.

(10) Patent No.: US 12,733,602 B2
(45) Date of Patent: Sep. 15, 2026

(54) MUTATIONS IN MADS-BOX GENES AND USES THEREOF

(71) Applicant: Cold Spring Harbor Laboratory, Cold Spring Harbor, NY (US)

(72) Inventors: Zachary Lippman, North Bellmore, NY (US); Sebastian Soyk, Cold Spring Harbor, NY (US); Zachary Hartford Lemmon, Huntington Station, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 31 days.

(21) Appl. No.: 16/613,660

(22) PCT Filed: May 17, 2018

(86) PCT No.: PCT/US2018/033126

§ 371 (c)(1),
(2) Date: Nov. 14, 2019

(87) PCT Pub. No.: WO2018/213538

PCT Pub. Date: Nov. 22, 2018

(65) Prior Publication Data

US 2020/0299706 A1 Sep. 24, 2020
US 2022/0002740 A2 Jan. 6, 2022

Related U.S. Application Data

(60) Provisional application No. 62/507,369, filed on May 17, 2017.

(51) Int. Cl.
*A01H 5/08* (2018.01)
*C12N 15/00* (2006.01)
*A01H 6/82* (2018.01)

(52) U.S. Cl.
CPC ............... *A01H 5/08* (2013.01); *C12N 15/00* (2013.01); *A01H 6/825* (2018.05)

(58) Field of Classification Search
None
See application file for complete search history.

(56) References Cited

U.S. PATENT DOCUMENTS

| | | | | |
|---|---|---|---|---|
| 9,732,352 | B2 | 8/2017 | Lippman et al. | |
| 2015/0284732 | A1 | 10/2015 | Lippman et al. | |
| 2016/0017347 | A1* | 1/2016 | Allen ................. | C12N 15/8218 800/275 |
| 2018/0105819 | A1* | 4/2018 | Brower-Toland ........................... | C12N 15/8261 |
| 2020/0199604 | A1 | 6/2020 | Lippman et al. | |

FOREIGN PATENT DOCUMENTS

WO WO 2014/081730 A1 5/2014

OTHER PUBLICATIONS

Thouet et al., 2012, PLoS ONE 7(2):e31096. doi:10.1371/journal.pone.0031096.*

Bolger et al., GenEmbl Database, Accession No. HG975516, Mar. 7, 2015.*

U.S. Appl. No. 14/443,357, filed May 15, 2015, Lippman et al.

U.S. Appl. No. 16/092,862, filed Oct. 11, 2018, Lippman et al.

PCT/US2018/033126, Oct. 17, 2018, International Search Report and Written Opinion.

PCT/US2018/033126, Nov. 28, 2019, International Preliminary Report on Patentability.

International Search Report and Written Opinion for Application No. PCT/US2018/033126 mailed Oct. 17, 2018.

International Preliminary Report on Patentability for Application No. PCT/US2018/033126 mailed Nov. 28, 2019.

Ampomah-Dwamena et al., Down-regulation of TM29, a tomato SEPALLATA homolog, causes parthenocarpic fruit development and floral reversion. Plant Physiol. Oct. 2002;130(2):605-17.

Anders et al., HTSeq—a Python framework to work with high-throughput sequencing data. Bioinformatics. Jan. 15, 2015;31(2):166-9.

Ashikari et al., Cytokinin oxidase regulates rice grain production. Science. Jul. 29, 2005;309(5735):741-5.

Belhaj et al., Plant genome editing made easy: targeted mutagenesis in model and crop plants using the CRISPR/Cas system. Plant Methods. Oct. 11, 2013;9(1):39.

Bemer et al., The tomato FRUITFULL homologs TDR4/FUL1 and MBP7/FUL2 regulate ethylene-independent aspects of fruit ripening. Plant Cell. Nov. 2012;24(11):4437-51.

Blanca et al., Genomic variation in tomato, from wild ancestors to contemporary breeding accessions. BMC Genomics. Apr. 1, 2015;16:257.

Boden et al., Ppd-1 is a key regulator of inflorescence architecture and paired spikelet development in wheat. Nat Plants. Jan. 26, 2015;1:14016.

Bolger et al., The genome of the stress-tolerant wild tomato species *Solanum pennellii*. Nat Genet. Sep. 2014;46(9):1034-8.

Bolger et al., Trimmomatic: a flexible trimmer for Illumina sequence data. Bioinformatics. Aug. 1, 2014;30(15):2114-20.

Bomblies et al., Hybrid necrosis: autoimmunity as a potential gene-flow barrier in plant species. Nat Rev Genet. May 2007;8(5):382-93.

Brooks et al., Efficient gene editing in tomato in the first generation using the clustered regularly interspaced short palindromic repeats/CRISPR-associated9 system. Plant Physiol. Nov. 2014;166(3):1292-7.

Buckler et al., The genetic architecture of maize flowering time. Science. Aug. 7, 2009;325(5941):714-8.

(Continued)

*Primary Examiner* — Phuong T Bui

(74) *Attorney, Agent, or Firm* — Wolf, Greenfield & Sacks, P.C.

(57) ABSTRACT

Aspects of the disclosure relate to plants, such as Solanaceae plants containing one or more branching events of a mutant Solyc04g005320 gene (or a homolog thereof), a mutant Solycl2g038510 gene (or a homolog thereof), and a mutant Solyc03gl 14840 gene (or a homolog thereof), as well as methods of producing such plants. In some aspects, such plants have one or more improved traits, such as modified inflorescence architecture, modified flower number, modified fruit number, higher yield, higher quality products, and higher fruit productivity.

16 Claims, 33 Drawing Sheets

Specification includes a Sequence Listing.

(56) References Cited

OTHER PUBLICATIONS

Budiman et al., Localization of jointless-2 gene in the centromeric region of tomato chromosome 12 based on high resolution genetic and physical mapping. Theor Appl Genet. Jan. 2004;108(2):190-6.
Butler. Inherited characters in the tomato. 11. Jointless pedicels. J. Hered. 1936;27:25-26.
Chae et al., Species-wide genetic incompatibility analysis identifies immune genes as hot spots of deleterious epistasis. Cell. Dec. 4, 2014;159(6):1341-51.
Chakrabarti et al., A cytochrome P450 regulates a domestication trait in cultivated tomato. Proc Natl Acad Sci U S A. Oct. 15, 2013;110(42):17125-30.
Chou et al., Diminishing returns epistasis among beneficial mutations decelerates adaptation. Science. Jun. 3, 2011;332(6034):1190-2.
Ditta et al., The SEP4 gene of *Arabidopsis thaliana* functions in floral organ and meristem identity. Curr Biol. Nov. 9, 2004;14(21):1935-40.
Doebley et al., The evolution of apical dominance in maize. Nature. Apr. 3, 1997;386(6624):485-8.
Doebley et al., The molecular genetics of crop domestication. Cell. Dec. 29, 2006;127(7):1309-21.
Doust et al., Beyond the single gene: How epistasis and gene-by-environment effects influence crop domestication. Proc Natl Acad Sci U S A. Apr. 29, 2014;111(17):6178-83.
Eshed et al., Less-than-additive epistatic interactions of quantitative trait loci in tomato. Genetics. Aug. 1996;143(4):1807-17.
Famoso et al., Genetic architecture of aluminum tolerance in rice (*Oryza sativa*) determined through genome-wide association analysis and QTL mapping. PLoS Genet. Aug. 2011;7(8):e1002221.
Futschik. Mfuzz: Soft clustering of time series gene expression data. R package version 2.30.0. 2015. 4 pages.
Gao et al., The additive effects of GS3 and qGL3 on rice grain length regulation revealed by genetic and transcriptome comparisons. BMC Plant Biol. Jun. 24, 2015;15:156.
Graaff et al., The WUS homeobox-containing (WOX) protein family. Genome Biol. 2009;10(12):248. doi: 10.1186/GB-2009-10-12-248.
Gupta et al., Modification of plant regeneration medium decreases the time for recovery of Solanum lycopersicum cul ti var M82 stable transgenic lines. Plant Cell Tissue Organ Cult. 2016;127:417-423.
Hartmann et al., Molecular cloning of SVP: a negative regulator of the floral transition in *Arabidopsis*. Plant J. Feb. 2000;21(4):351-60.
Heck et al., Negative epistasis between natural variants of the *Saccharomyces cerevisiae* MLH1 and PMS1 genes results in a defect in mismatch repair. Proc Natl Acad Sci U S A. Feb. 28, 2006;103(9):3256-61.
Hu et al., Overexpression of SIREV alters the development of the flower pedicel abscission zone and fruit formation in tomato. Plant Sci. Dec. 2014;229:86-95. doi: 10.1016/j.plantsci.2014.08.010. Epub Sep. 2, 2014.
Huang et al., Natural variation at the DEP1 locus enhances grain yield in rice. Nat Genet. Apr. 2009;41(4):494-7.
Jiao et al., Regulation of OsSPL14 by OsmiR156 defines ideal plant architecture in rice. Nat Genet. Jun. 2010;42(6):541-4.
Khan et al., Negative epistasis between beneficial mutations in an evolving bacterial population. Science. Jun. 3, 2011;332(6034):1193-6.
Kim et al., TopHat2:accurate alignment of transcriptomes in the presence of insertions, deletions and gene fusions. Genome Biol. Apr. 25, 2013;14(4):R36.
Klee et al., Genetics and control of tomato fruit ripening and quality attributes. Annu Rev Genet. 2011;45:41-59.
Kobayashi et al., Inflorescence meristem identity in rice is specified by overlapping functions of three AP1/FUL-like MADS box genes and PAP2, a SEPALLATA MADS box gene. Plant Cell. May 2012;24(5):1848-59.
Komatsuda et al., Six-rowed barley originated from a mutation in a homeodomain-leucine zipper I-class homeobox gene. Proc Natl Acad Sci U S A. Jan. 23, 2007;104(4):1424-9.
Kvitek et al., Reciprocal sign epistasis between frequently experimentally evolved adaptive mutations causes a rugged fitness landscape. PLoS Genet. Apr. 2011;7(4):e1002056.
Kyozuka et al., Control of grass inflorescence form by the fine-tuning of meristem phase change. Curr Opin Plant Biol. Feb. 2014;17:110-5.
Lei et al., CRISPR-P: a web tool for synthetic single-guide RNA design of CRISPR-system in plants. Mol Plant. Sep. 2014;7(9):1494-1496.
Lemmon et al., The evolution of inflorescence diversity in the nightshades and heterochrony during meristem maturation. Genome Res. Dec. 2016;26(12):1676-1686.
Leseberg et al., Interaction study of MADS-domain proteins in tomato. J Exp Bot. 2008;59(8):2253-65.
Li, A statistical framework for SNP calling, mutation discovery, association mapping and population genetical parameter estimation from sequencing data. Bioinformatics. Nov. 1, 2011;27(21):2987-93.
Li, Aligning sequence reads, clone sequences and assembly contigs with BWAMEM. arXiv Prepr. arXiv 0, 3. 2013:1-3.
Li et al., Fast and accurate short read alignment with Burrows-Wheeler transform. Bioinformatics. Jul. 15, 2009;25(14):1754-60.
Li et al., The Sequence Alignment/Map format and SAMtools. Bioinformatics. Aug. 15, 2009;25(16):2078-9.
Lin et al., Genomic analyses provide insights into the history of tomato breeding. Nat Genet. Nov. 2014;46(11):1220-6.
Lippman et al., The making of a compound inflorescence in tomato and related nightshades. PLoS Biol. Nov. 18, 2008;6(11):e288.
Liu et al., A conserved genetic pathway determines inflorescence architecture in *Arabidopsis* and rice. Dev Cell. Mar. 25, 2013;24(6):612-22.
Liu et al., The SEPALLATA MADS-box protein SLMBP21 forms protein complexes with JOINTLESS and MACROCALYX as a transcription activator for development of the tomato flower abscission zone. Plant J. Jan. 2014;77(2):284-96.
Macarthur et al., Cytogenetic Notes on Tomato Species and Hybrids. Genetics. Mar. 1947;32(2):165-77.
Mackay, Epistasis and quantitative traits: using model organisms to study gene-gene interactions. Nat Rev Genet. Jan. 2014;15(1):22-33.
Mao et al., JOINTLESS is a MADS-box gene controlling tomato flower abscission zone development. Nature. Aug. 24, 2000;406(6798):910-3.
Matsubara et al., Hybrid breakdown caused by epistasis-based recessive incompatibility in a cross of rice (*Oryza sativa* L.). J Hered. Jan.-Feb. 2015;106(1):113-22.
Meyer et al., Evolution of crop species: genetics of domestication and diversification. Nat Rev Genet. Dec. 2013;14(12):840-52.
Nakano et al., MACROCALYX and JOINTLESS interact in the transcriptional regulation of tomato fruit abscission zone development. Plant Physiol. Jan. 2012;158(1):439-50.
Park et al., Rate of meristem maturation determines inflorescence architecture in tomato. Proc Natl Acad Sci U S A. Jan. 10, 2012;109(2):639-44.
Park et al., Meristem maturation and inflorescence architecture—lessons from the Solanaceae. Curr Opin Plant Biol. Feb. 2014;17:70-7.
Park et al., Optimization of crop productivity in tomato using induced mutations in the florigen pathway. Nat Genet. Dec. 2014;46(12):1337-42.
Peet et al., Greenhouse tomato production. N Tomatoes, E. 20 Heuvelink, Ed. Wallingford, U.K. CABI Publ. 2005:257-304.
Pelaz et al., B and C floral organ identity functions require SEPALLATA MADS-box genes. Nature. May 11, 2000;405(6783):200-3. PubMed PMID: 10821278.
Peralta et al., Morphological Characterization and Relationships of Wild Tomatoes (*Solanum* L. sect. *lycopersicon*). Mono Syst Bot. 2005;104:227-257.
Pnueli et al., The TM5 MADS Box Gene Mediates Organ Differentiation in the Three Inner Whorls of Tomato Flowers. Plant Cell. Feb. 1994;6(2):175-186.

(56) References Cited

OTHER PUBLICATIONS

Prusinkiewicz et al., Evolution and development of inflorescence architectures. Science. Jun. 8, 2007;316(5830):1452-6.
Purugganan et al., The nature of selection during plant domestication. Nature. Feb. 12, 2009;457(7231):843-8.
Ramsay et al., INTERMEDIUM-C, a modifier of lateral spikelet fertility in barley, is an ortholog of the maize domestication gene TEOSINTE BRANCHED 1. Nat Genet. Feb. 2011;43(2):169-72.
Reynard, New Source of the j2 Gene Governing Jointless Pedicel in Tomato. Science. Dec. 29, 1961; 134(3496):2102.
Rick, Genetic and Systematic Studies on Accessions of Lycospersicon from the Galapagos Islands. Am J Bot. 1956a;43:687-696.
Rick, A new jointless gene from the *Galapagos* L. *pimpinellifolium*. TGC Rep. 1956b;45:23.
Robinson, Pleiotropic effects of the j-2 gene. The. TGC Rep. 1980;30:32.
Robinson et al., edgeR: a Bioconductor package for differential expression analysis of digital gene expression data. Bioinformatics. Jan. 1, 2010;26(1):139-40.
Shalit et al., The flowering hormone florigen functions as a general systemic regulator of growth and termination. Proc Natl Acad Sci U S A. May 19, 2009;106(20):8392-7.
Shang et al., Epistasis together with partial dominance, over-dominance and QTL by environment interactions contribute to yield heterosis in upland cotton. Theor Appl Genet. Jul. 2016;129(7):1429-1446.
Singh et al., The oil palm SHELL gene controls oil yield and encodes a homologue of SEEDSTICK. Nature. Aug. 15, 2013;500(7462):340-4.
Soyk et al., Bypassing Negative Epistasis on Yield in Tomato Imposed by a Domestication Gene. Cell. Jun. 1, 2017;169(6):1142-1155.e12. doi: 10.1016/j.cell.2017.04.032. Epub May 18, 2017.
Soyk et al., Variation in the flowering gene Self Pruning 5G promotes day-neutrality in tomato and early yield. Nat Genet 2016;1-37.
Stephenson, Flower and fruit abortion: proximate causes and ultimate functions. Ann Rev Ecol Syst 1981;12:253-279.
Stubbe, Mutanten der Kulturtomate Lycopersicon esculentum Miller VI. Die Kult. 1972;16:185-230.
Swinnen et al., Lessons from Domestication: Targeting Cis-Regulatory Elements for Crop Improvement. Trends Plant Sci. Jun. 2016;21(6):506-515.
Tamura et al., MEGA6: Molecular Evolutionary Genetics Analysis version 6.0. Mol Biol Evol. Dec. 2013;30(12):2725-9.
Theissen et al., MADS-domain transcription factors and the floral quartet model of flower development: linking plant development and evolution. Development. Sep. 15, 2016;143(18):3259-71.
Tieman et al., A chemical genetic roadmap to improved tomato flavor. Science. Jan. 27, 2017;355(6323):391-394.
Tomato Gene Consortium, The tomato genome sequence provides insights into fleshy fruit evolution. Nature. May 30, 2012;485(7400):635-41.
Tzfira et al., Genome modifications in plant cells by custom-made restriction enzymes. Plant Biotechnol J. May 2012;10(4):373-89. doi: 10.1111/j.1467-7652.2011.00672.x. Epub Jan. 3, 2012.
Vrebalov et al., A MADS-box gene necessary for fruit ripening at the tomato ripening-inhibitor (rin) locus. Science. Apr. 12, 2002;296(5566):343-6.
Wang et al., Members of the tomato FRUITFULL MADS-box family regulate style abscission and fruit ripening. J Exp Bot. Jul. 2014;65(12):3005-14.
Werner et al., Fast track assembly of multigene constructs using Golden Gate cloning and the MoClo system. Bioeng Bugs. Jan. 1, 2012;3(1):38-43.
Williams et al., Negative epistasis between the malaria-protective effects of alpha+-thalassemia and the sickle cell trait. Nat Genet. Nov. 2005;37(11):1253-7.
Xu et al., A cascade of arabinosyltransferases controls shoot meristem size in tomato. Nat Genet. Jul. 2015;47(7):784-92.
Yang et al., In-depth sequence analysis of the tomato chromosome 12 centromeric region: identification of a large CAA block and characterization of pericentromere retrotranposons. Chromosoma. Jul. 2005;114(2):103-17.
Zahara et al., Hand-harvesting jointless vs. jointed-stem tomatoes. Calif Agric. 1988;42:14-14.
Zamir, Improving plant breeding with exotic genetic libraries. Nat Rev Genet. Dec. 2001;2(12):983-9.
Zhang et al., Genetic and correlation analysis of silique-traits in *Brassica napus* L. by quantitative trait locus mapping. Theor. Appl. Genet. 2011;122:21-31.
Zhang et al., Fine mapping of fw3.2 controlling fruit weight in tomato. Theor Appl Genet. Jul. 2012;125(2):273-84.
Zhao et al., MADS-box genes of maize: frequent targets of selection during domestication. Genet Res (Camb). Feb. 2011;93(1):65-75.
Extended European Search Report mailed Feb. 5, 2021, for Application No. EP18801850.1.
Japanese Office Action mailed May 27, 2022, for Application No. JP 2019-564092.
Soyk et al., Duplication of a domestication locus neutralized a cryptic variant that caused a breeding barrier in tomato. Nat Plants. May 2019;5(5):471-479. doi: 10.1038/s41477-019-0422-z. Epub May 6, 2019. Erratum in: Nat Plants. Aug. 2019;5(8):903.
Philouze et al. Tomato. Sep. 26, 2015. Accessed:May 23, 2022, from: <https://web.archive.org/web/20150926235813/http://dbarchive.biosciencedbc.jp/archive/diam_safety_literature/LATEST/document/081/081-f009.html> 15 pages.

* cited by examiner

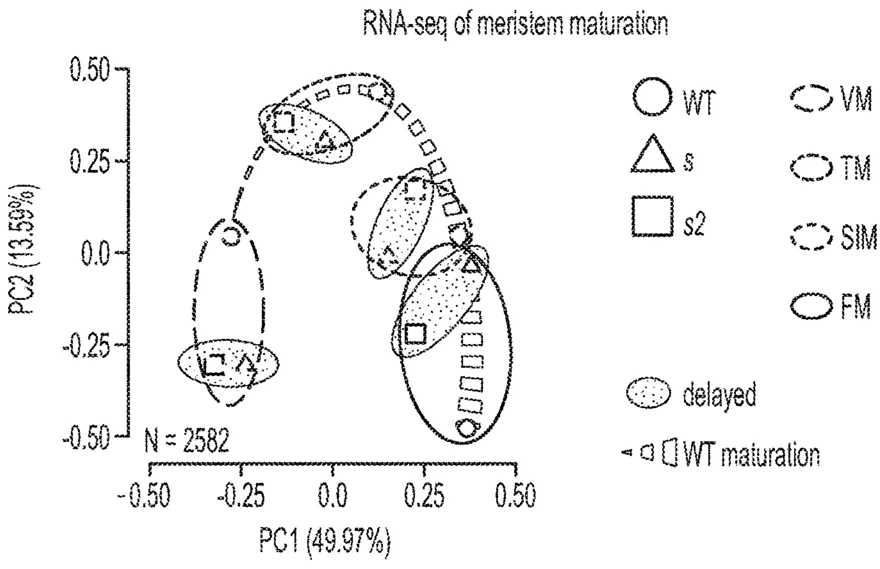
FIG. 1I
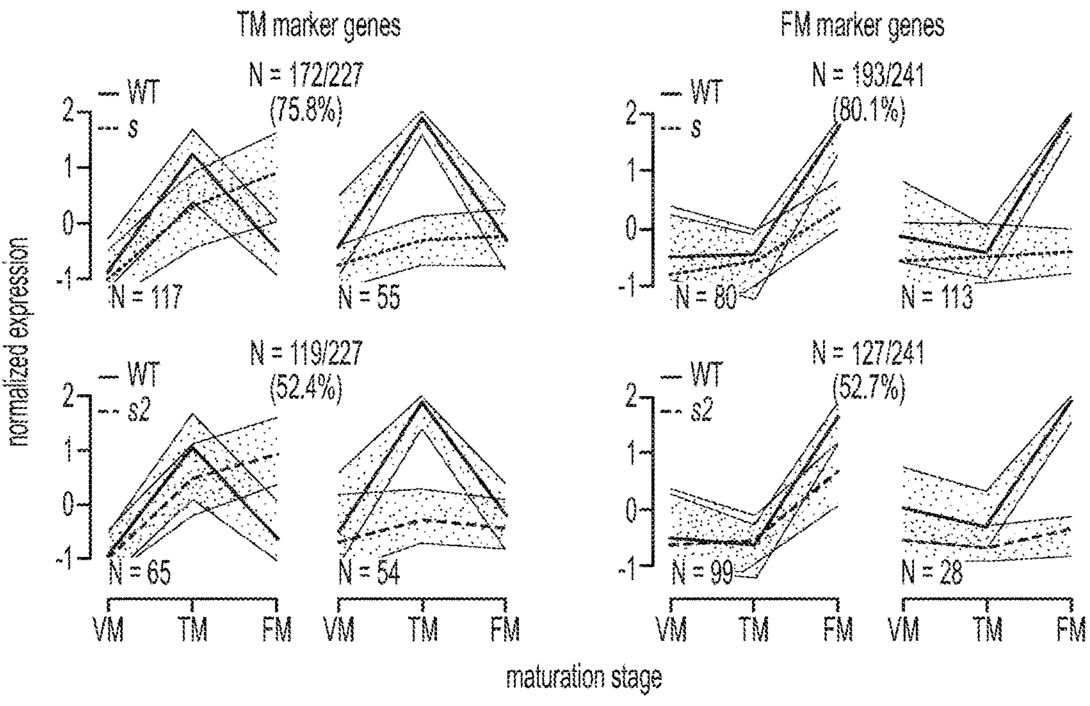
FIG. 1J
FIG. 1K

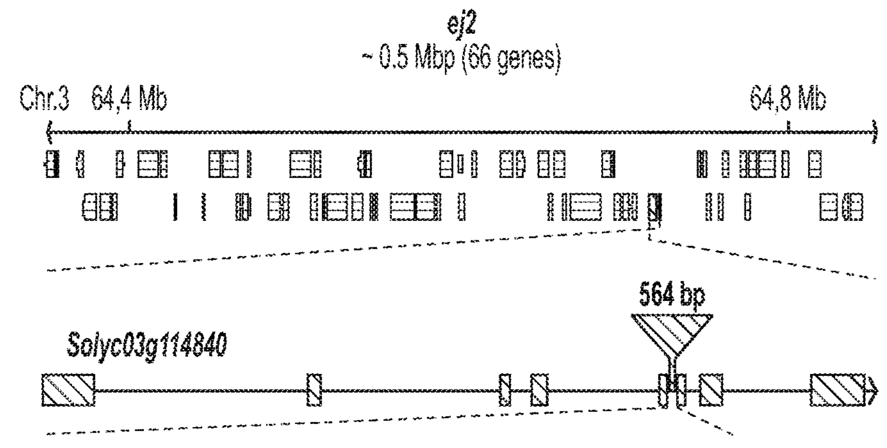
FIG. 2H
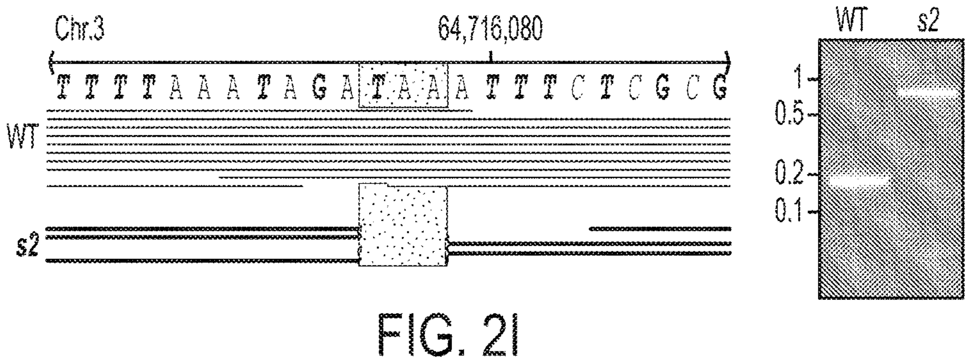
FIG. 2I
FIG. 2J

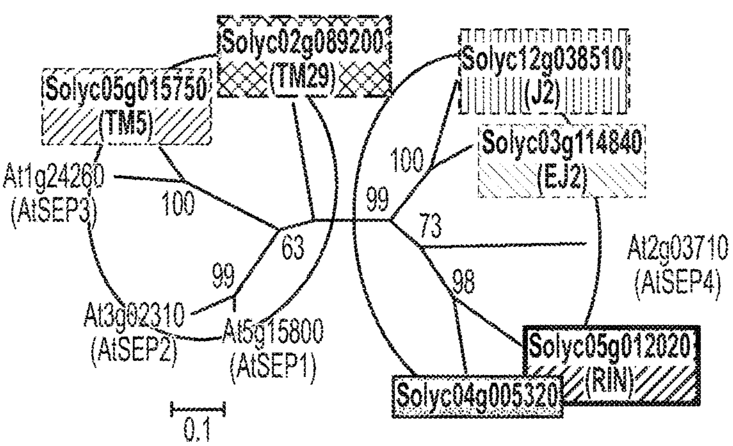
FIG. 5A
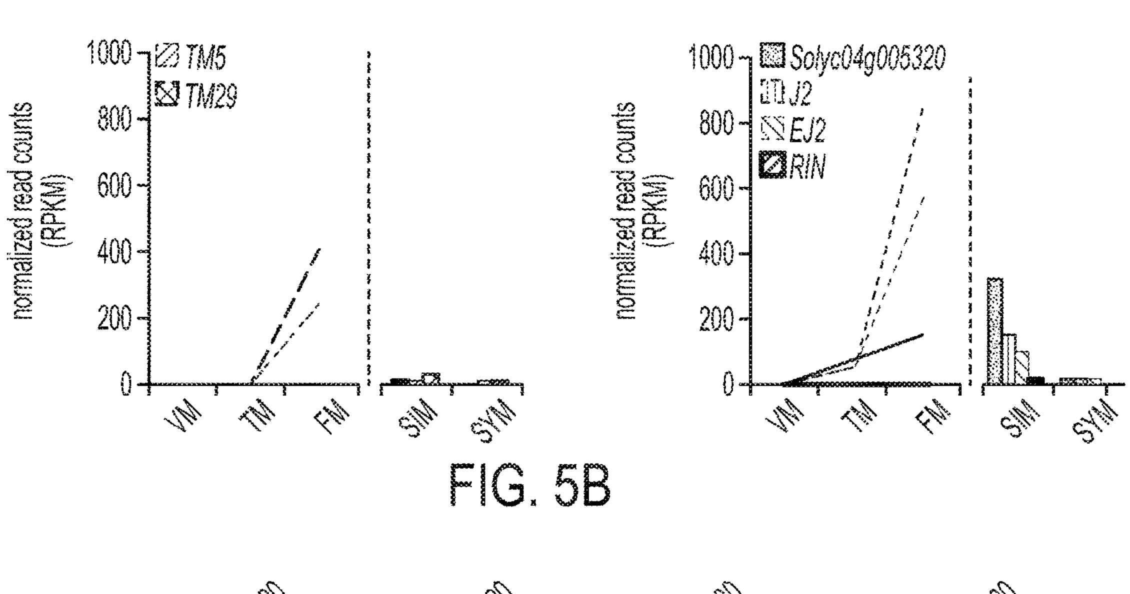
FIG. 5B
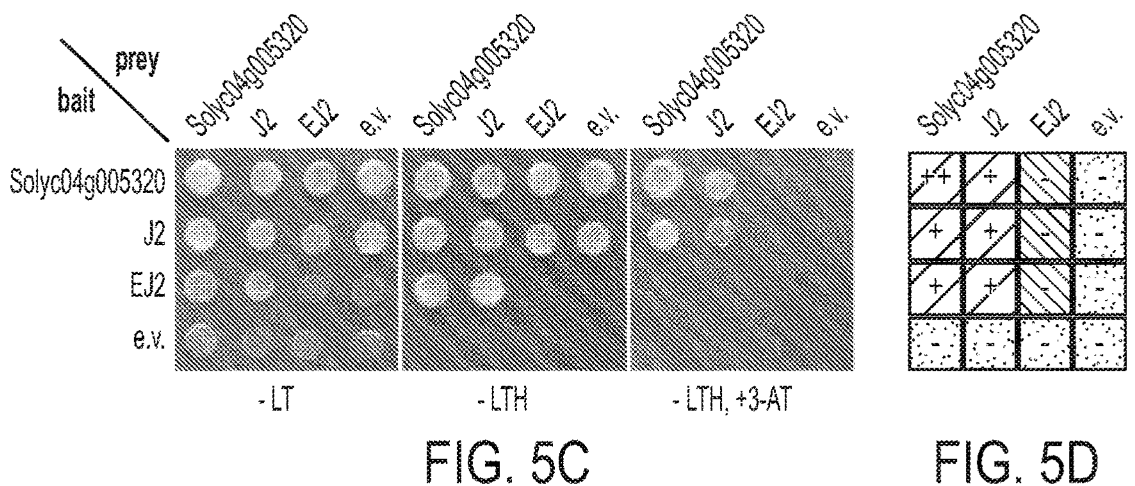
FIG. 5C
FIG. 5D

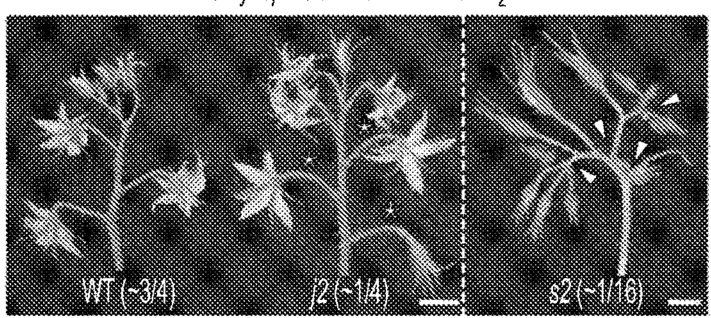
FIG. 9A
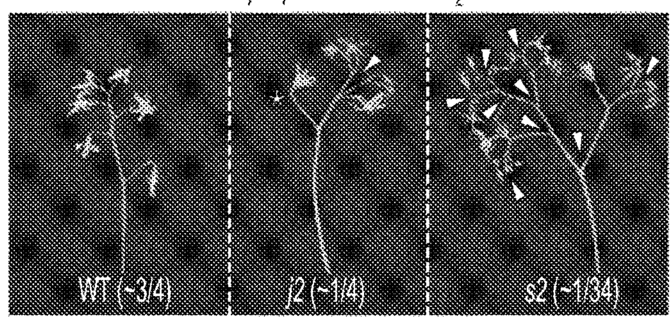
FIG. 9B
| Population | total | s2 | ratio |
|---|---|---|---|
| *S. lyc* x *s2* $F_2$ | 464 | 30 | ~1/16 |
| *S. pim* x *s2* $F_2$ | 576 | 17 | ~1/34 |
FIG. 9C

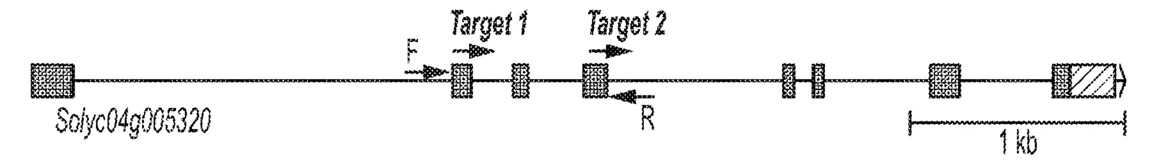

CRISPR/Cas9 in S. lycopersicum cv. M82

```
WT TTTTTCTAGTATGTCTGATACACTGGAGAGATACCATAGATGCAGCTAT(626)ATTTGGAACAGCTTGAGCGTCAACTGGATTCATCTTTGAGGCT
a1 TTTTTCTAGTATGTCT-------------GATACCATAGATGCAGCTAT(626)ATTTGGAACAGCTTGAGC---AACTGGATTCATCTTTGAGGCT
a2 TTTTTCTAGTATGTC-----CACTGGAGAGATACCATAGATGCAGCTAT(626)ATTTGGAA-------------AACTGGATTCATCTTTGAGGCT
```

CRISPR/Cas9 in S. pimpinellifolium

```
WT TTTTTCTAGTATGTCTGATACACTGGAGAGATACCATAGATGCAGCTAT(626)ATTTGGAACAGCTTGAGCGTCAACTGGATTCATCTTTGAGGCT
Solyc04005320^CR #4
a1 TTTTTCT--------------ACTGGAGAGATACCATAGATGCAGCTAT(626)ATT---------------------------CATCTTTGAGGCT
a2 TTTTTCTAG-------------------------------------TAT(626)ATTTGGAACAGCTTGAGCGTC-ACTGGATTCATCTTTGAGGCT
Solyc04005320^CR #8
a3 TTTTTCTAGTATGTCTGATACACTGGAGAGATACCATAGATGCAGCTAT(626)ATTTGGAACAGCTTGAGC---AACTGGATTCATCTTTGAGGCT
Solyc04005320^CR #9
a4 TTTTTCTAGTATGTCTGATACACTGGAGAGATACCATAGATGCAGCTAT(626)ATTTGGAACAGCTTGAG-----------------------GCT
a5 TTTTTCTAGTATGTCTGATACACTGGAGAGATACCATAGATGCAGCTAT(626)ATTTGGAACAGCTTGAG----AACTGGATTCATCTTTGAGGCT
a6 TTTTTCTAGTATGTCTGATACACTGGAGAGATACCATAGATGCAGCTAT(626)ATTTGGAACAGCTTGAGCGT-ACCTGGATTCATCTTTGAGGCT
```

FIG. 10D

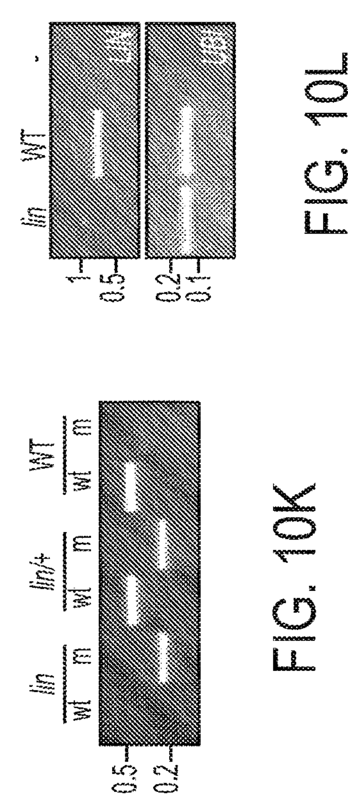
FIG. 10L
FIG. 10K
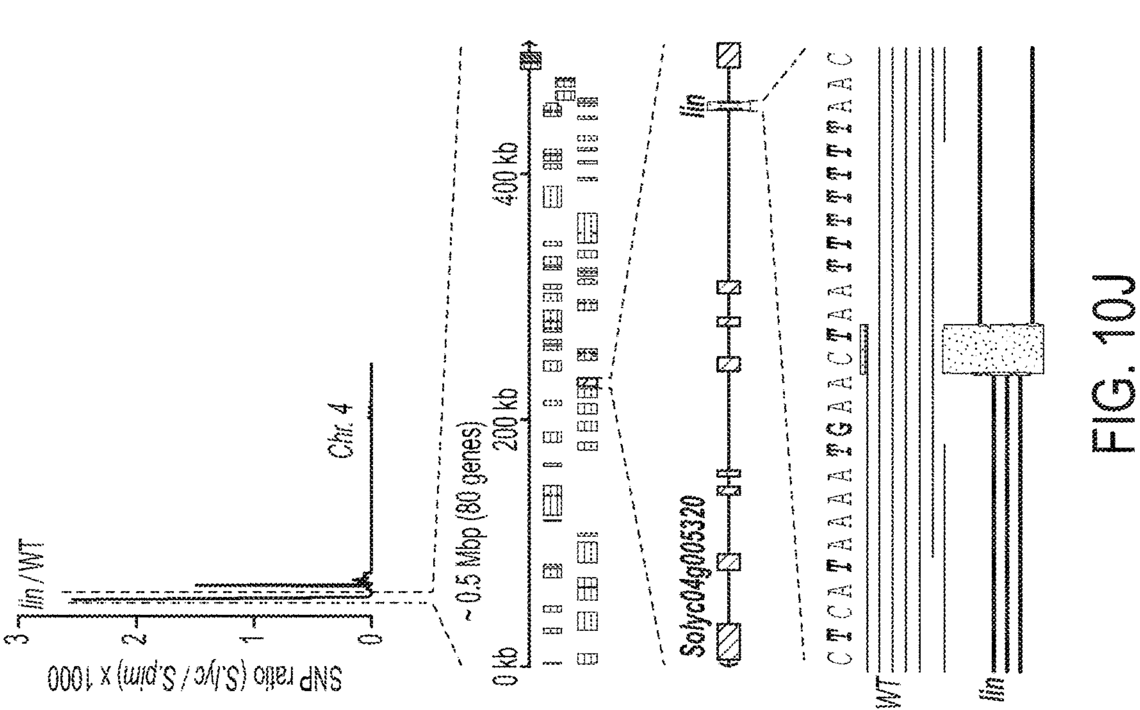
FIG. 10J

CRISPR/Cas9 in *S. lycopersicum* cv. Sweet 100

| | |
|---|---|
| *LIN* | TTTTCTTCTAGTATGTCTGATACACTGGAGAGA (647) GATTTGGAACAGCTTGAGCGTCAACTGGATTCAT |
| *lin*$^{CR}$ a1 | TTTTCTTCTAGTATGTCTGATAACACTGGAGAGA (647) GATTTGGAACAGCTTGAGCTATCA (65) AAAGG |
| *lin*$^{CR}$ a2 | TTTTCTTCTAGTATGTCTGA--CACTGGAGAGA (647) GATTTGGAACAGCTTGAGCGT-AACTGGATTCAT |

SEQUENCE LISTING

```
<160> NUMBER OF SEQ ID NOS: 127

<210> SEQ ID NO 1
<211> LENGTH: 4843
<212> TYPE: DNA
<213> ORGANISM: Unknown
<220> FEATURE:
<223> OTHER INFORMATION: Solanaceae

<400> SEQUENCE: 1

atgggaagag gtaaggtaga attgaagaga atagaaaata agataaacag gcaagttact     60

tttgctaaga gaagaaatgg attactcaaa aaagcttatg agctttctat tttgtgtgaa    120

gctgaagttg ctcttatcat tttctctaat agaggcaaac tctatgaatt ttgcagtacc    180

tctaggtaat atttttatgt ttatgtcgtt ccgtttaagc tttacattta cgtttttata    240

cgcaaaactt taaattagtt ctaaatgtat taaaaaattg aaattttgag atttaatttc    300

aaaatctatg gttaaacgaa tgtttatatg cattatgatt ttgttatctt cttttttttt    360

aaaaaaagaa ataaaatata ttgatgttat agatctgagt gagaatagag tttttggtac    420

atttattaag ggtgaataat caaatgtttc atttgattag atctaggttt tcttgaacat    480

taaaattgtt aaaaaaatta gttcatttta tgaggtaaat tttgttatga tttgatgttc    540

cacctccatt ttttcttatt tttattataa ataaataagt tttaaaatat ccttactttt    600

atatgttctt ttaagtacag acacatgaat caaaaagaag ttttataata tgaattgaat    660

taaagctggt tgaatttcta tcttcagttt ttgaaaacaa ctaaaaactt tgaaaaggaa    720

tttgatttta ttatttatgg caacaaataa cacctaacta cttatcgagt cggaattgac    780

gatatgaatc ctttaacttt tcatttaagc tcaatttata tagaaaattc tgtattgtgg    840

attgaagtaa tttctggagt tgatcaattc tatttaaaaa attatttaat taataatcat    900

tatcccaaaa aattatattg aaattaaaaa ataatattaa ttttttttaaa taacaaactt    960

attaattgag tgaccatcta aatcgtcttt ttcttaaagt tagggtcttg cctttcatct   1020

aattttgata gtaatgttct tgaaccgaca aattttgtca tttactctta tctgttataa   1080

tttatgtgat tcgagtttta cgaatcaatt tttgtttata atttcaatca tgtataagaa   1140

gtattttaag ttataataat taacaatttt aagaaagcat aatcaagatc aaataactta   1200
```

```
gtagaaataa tattggttta tgtaacctct atgcattgac aatatagtgt ttttttata   1260
ctatcaagtc atttattgga taattataat taaagaatat taactaatga gtaaatcaat   1320
agtttaatat taatgagtta tcatagtagc gtatacttat tactcgatat ttgtaatcta   1380
aacattttca atatgcttaa acttgatttt tttatttgga tcaagtatac aatttttttg   1440
ttaataataa atgacattga aacttataac taattttatt taaacaattt tctttctttc   1500
tttcctcaag gagagcatag ttctaattat tatcaatatc attattatta ttatctctat   1560
gtttatttta ttattactgt tgtttctttt acttggattg tctgtactat tttacttca    1620
tggactttaa ttttttgtct atcgtatttt tatcatagtt tttactcttg tattggctaa   1680
acctagtttt gaaattgttt ttcataagct gaaagagtct atcaaaaaca acttctcacg   1740
agatagaaat aaagtttacg tatattccat tcttctcaaa ccccacttat gagattatac   1800
tgaaatgtta ctattattat tatactttgt aacatgctaa aaaaactagt aataattaca   1860
cttcttgcca aagagtaaat aaagtatgat cctttaataa gttgaaaatc cctctaaatc   1920
aaattatcac ttttgtgcaa cttgtcttct tttttttctt ctagtatgtc tgatacactg   1980
gagagatacc atagatgcag ctatggtgac cttgaaactg gccagtcttc aaaggattca   2040
caggttactt catcttcctc agaattacaa tttactaata aatttaactt atatactctg   2100
acacagtatc gatgcaattt aaacctttta taacagatta tctgttttta ttttaatttc   2160
ttcgtaaata attaataagt cgatattgat aactaacgcc aagcacccta tcttcatcta   2220
actaattagt gttattatgc aatagaataa ctaccaagag tatatgaagc tgaaagcaag   2280
agttgaagtg ctacaacagt cacaaaggtg atacattatt tgttttaaaa acacttttac   2340
ttgtctcatt ttgattggct catctgaaca cctgaaccgg tctagaagta ttttgaacat   2400
gcataattgg acatgttcaa tcatgcgttt gtttgatcag gttcaggatg tttagatgag   2460
acctcgtaaa ataaattaag gggaggcttt ttaatatgat atttgtgtct caaatatatc   2520
acttttctac cctaattctt aataacattg tatttactta attattctta atctttaagg   2580
catatacttg gagaggactt aggacaatta aacacaaaag atttggaaca gcttgagcgt   2640
caactggatt catctttgag gctaataaga tcaagaaggg tatgttctat gcaccttcaa   2700
tttatttgtc aaattttagg ctttcagatc atgtcttaat cttaatgtcc gatgacagtt   2760
tcagtggcgg aattagaaat ttatgcaaga caattcaagc aatattatat attatagaat   2820
gtcagacttg aaatttgaac ttgagacatt gaacctcttt acaaatacac taatatctaa   2880
cctcgtatca acggggttca acaatttata tatatataaa aaacacttaa ttttgcccta   2940
tttggtgtaa tatataattt tatcaaaggt atgttgggaa aatgataaaa attacttatg   3000
aataatatcc aaatggaata atataataac aattacttac tattacttga tagtgccaca   3060
aaactactaa accttaaaat aagttctttt attttacata attcattata atctttggca   3120
tgaatttact caagcattgc ttcagaatga tcaaagcctc cttaatattt ttgggtacag   3180
acataaagtc tagacatgca atcaaagata tagatgcacg agatgactaa tcaaaggaaa   3240
caataggaac gatcaaaaaa attgaaattg aaaatatatt ttttttaaac taaaggtaag   3300
tcaagattac caagtaagtg tattattgta acttttgtat tatttatcct aagtaaacat   3360
gtatcaaaaa catacacaaa tttactttct cttttattac taacatcaac ttacatgcta   3420
attataaata attaaagggt aaatagttgg ttgcatgatt tggtaaaaga agttgttaac   3480
ctactctttg ataacatata tgttttcaga cacaaaacat gcttgatcaa ctttctgatc   3540
ttcaacaaaa ggtatgtatt gtataatata atcccttaag ttgacaatta aatagattgt   3600
```

```
tcaattgtta atttgacatt gtatgtgttc ttttttcttt ttttctacag gaacaatctc   3660

ttcttgaaat caacagatcc ttgaaaacaa aggtacaaag cacacatttt ggaccttttta  3720

tgagtttttt agggcgtgtt tgatttattt attttttctg aatttttttca tgtttggttg  3780

atctaaattc tgggaaaata cttttttcta tgaaagtaag tttttaaaa atgacttagc   3840

cagtggaagt agggaaaaca agttgtgacg acattccacg ttgattgttt tctctcgatc   3900

ttcctacaca ccttaagttc gccaccacct ctcgcagtat ttgtttagat tatataaaaa   3960

tgtatcaaga atgacacttt ttatttgtgt acataataaa agaaaataag taagaaaccg   4020

aacattttcc catggaaaat attatttttc ataccaaaca cacccttagt ctttgtttta   4080

gggtatatga ctaatttgtt ctccatttcg gatatttaga ttcgtatggg tttttctttg   4140

atgtctaact tatcgtactt tttacgcgat tttatgaaat tcttataata gttggaagaa   4200

aactctgtag cacattggca tatcactgga gagcaaaatg tacaattcag acaacaacct   4260

gctcagtcag aggggttctt tcagccttta caatgcaata ctaatatagt gccaaacagg   4320

taacatataa ttttatgttt tctttttttc ctttaaatag catatttttt gcaacatttt   4380

aaattgaacc gttgaattga gtcgttgaga ggtgaattca gaatctgaag taacagatac   4440

attcaaatta atttctttgt gtatttatcg aagtgagtca agtcgtaagt ctagaggtga   4500

atttagaatc taaagtaata gatacagtcg aatcaatctc tttgtgtatt tattgaagtg   4560

agtcgttttg taaagtttga gacgaattca aaacctaaag taatactaaa tacatacatt   4620

caaaataatt tctaaagcga gttatgttgg aagtcgagag acgaaagtat attatatatg   4680

gatcaattca aattaatttc ttaatgtatt tgatgagcgt tgttgtaggg gcgaattcag   4740

aatctgaagt tcatgtaagt acaggtacaa tgtggctcca ttggatagta tagaaccatc   4800

aacacagaat gctactggaa ttttaccagg atggatgctt tga                    4843
```

<210> SEQ ID NO 2
<211> LENGTH: 717
<212> TYPE: DNA
<213> ORGANISM: Unknown
<220> FEATURE:
<223> OTHER INFORMATION: Solanaceae

<400> SEQUENCE: 2

```
atgggaagag gtaaggtaga attgaagaga atagaaaata agataaacag gcaagttact     60

tttgctaaga gaagaaatgg attactcaaa aaagcttatg agctttctat tttgtgtgaa    120

gctgaagttg ctcttatcat ttctctaat agaggcaaac tctatgaatt ttgcagtacc     180

tctagtatgt ctgatacact ggagagatac catagatgca gctatggtga ccttgaaact    240

ggccagtctt caaaggattc acagaataac taccaagagt atatgaagct gaaagcaaga    300

gttgaagtgc tacaacagtc acaaaggcat atacttggag aggacttagg acaattaaac    360

acaaaagatt tggaacagct tgagcgtcaa ctggattcat ctttgaggct aataagatca    420

agaaggacac aaaacatgct tgatcaactt tctgatcttc aacaaaagga acaatctctt    480

cttgaaatca acagatcctt gaaaacaaag ttggaagaaa actctgtagc acattggcat    540

atcactggag agcaaaatgt acaattcaga caacaacctg ctcagtcaga ggggttcttt    600

cagcctttac aatgcaatac taatatagtg ccaaacaggt acaatgtggc tccattggat    660

agtatagaac catcaacaca gaatgctact ggaattttac caggatggat gctttga       717
```

<210> SEQ ID NO 3

```
<211> LENGTH: 5233
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(6)
<223> OTHER INFORMATION: n is a, c, g, or t

<400> SEQUENCE: 3

nnnnnnatca ataaaaatac ggaagctcac aatttgttag agtaaccaat caaatcatcg     60
tctaaagtct attacacata aagtcatcac atcaaggaca tttgttctca atttccaagt    120
ctaaaatttt tgaaaatacc aaataagtaa aaacgatggt ccatatccga aatttaagga    180
catcatgaca tgaatgagag aatctagcac gagctagaaa taatagctta ccctgaattc    240
tgatatgctg gaggctggct agagctgagg gcgagtcgaa gtcgatggta cacttgctgc    300
actccacaaa agaacaacac aaaaaataca agtaaggatc agtacaagga acacgtattg    360
agtaggtatc atcagccacc caaaatagaa accaatatat attgaataat aatataaaat    420
caactacaat acttggcatg tgacaaacaa caaacaacat aaaccagtga caacaacacc    480
atagtaggta cacaatatca agcacaccta tgaggagtca tgcctccaca ccatactcat    540
ttagaaaatg ggttcattca gattgagtat attaagttaa tttaagattc ctttacttta    600
atgttatcgt gttgaaatgt gatactccga tcccatatac cgtgtcagaa caagaaattc    660
cgattgcata atatcgtgtt agaatgtgac actccgatcc aactataccg tgtcagaacg    720
tgacactccg atccaattat ctcattaatt tatttcatca agcgttcttt attcaacgcg    780
tcatttcgat aaagagggtt caagcttata attcaacagt ctcaaaattt ttggtcaacc    840
acaatcgcaa ccaagatata caaccacaca atcaagtaca taatcaactt cttcatttta    900
tgaggtaaat tttgttatga tttgatgttc cacctccatt ttttcttatt tttattataa    960
ataaataagt tttaaaatat ccttactttt atatgttctt ttaagtacag acacatgaat   1020
caaaaagaag ttttataata tgaattgaat taaagctggt tgaatttcta tcttcagttt   1080
ttgaaaacaa ctaaaaactt tgaaaaggaa tttgatttta ttatttatgg caacaaataa   1140
cacctaacta cttatcgagt cggaattgac gatatgaatc ctttaacttt tcatttaagc   1200
tcaatttata tagaaaattc tgtattgtgg attgaagtaa tttctggagt tgatcaattc   1260
tatttaaaaa attatttaat taataatcat tatcccaaaa aattatattg aaattaaaaa   1320
ataaatattaa ttttttttaaa taacaaactt attaattgag tgaccatcta aatcgtcttt   1380
ttcttaaagt tagggtcttg cctttcatct aattttgata gtaatgttct tgaaccgaca   1440
aattttgtca tttactctta tctgttataa tttatgtgat tcgagtttta cgaatcaatt   1500
tttgtttata atttcaatca tgtataagaa gtattttaag ttataataat taacaatttt   1560
aagaaagcat aatcaagatc aaataactta gtagaaataa tattggttta tgtaacctct   1620
atgcattgac aatatagtgt ttttttata ctatcaagtc atttattgga taattataat   1680
taaagaatat taactaatga gtaaatcaat agtttaatat taatgagtta tcatagtagc   1740
gtatacttat tactcgatat ttgtaatcta aacattttca atatgcttaa acttgatttt   1800
tttatttgga tcaagtatac aatttttttg ttaataataa atgacattga aacttataac   1860
taattttatt taaacaattt tctttctttc tttcctcaag gagagcatag ttctaattat   1920
tatcaatatc attattatta ttatctctat gtttatttta ttattactgt tgtttctttt   1980
acttggattg tctgtactat ttttacttca tggactttaa tttttgtct atcgtatttt    2040
```

```
tatcatagtt tttactcttg tattggctaa acctagtttt gaaattgttt ttcataagct   2100
gaaagagtct atcaaaaaca acttctcacg agatagaaat aaagtttacg tatattccat   2160
tcttctcaaa ccccacttat gagattatac tgaaatgtta ctattattat tatactttgt   2220
aacatgctaa aaaaactagt aataattaca cttcttgcca aagagtaaat aaagtatgat   2280
cctttaataa gttgaaaatc cctctaaatc aaattatcac ttttgtgcaa cttgtcttct   2340
ttttttcttt ctagtatgtc tgatacactg gagagatacc atagatgcag ctatggtgac   2400
cttgaaactg gccagtcttc aaaggattca caggttactt catcttcctc agaattacaa   2460
tttactaata aatttaactt atatactctg acacagtatc gatgcaattt aaacctttta   2520
taacagatta tctgttttta ttttaatttc ttcgtaaata attaataagt cgatattgat   2580
aactaacgcc aagcacccta tcttcatcta actaattagt gttattatgc aatagaataa   2640
ctaccaagag tatatgaagc tgaaagcaag agttgaagtg ctacaacagt cacaaaggtg   2700
atacattatt tgttttaaaa acacttttac ttgtctcatt ttgattggct catctgaaca   2760
cctgaaccgg tctagaagta ttttgaacat gcataattgg acatgttcaa tcatgcgttt   2820
gtttgatcag gttcaggatg tttagatgag acctcgtaaa ataaattaag gggaggcttt   2880
ttaatatgat atttgtgtct caaatatatc acttttctac cctaattctt aataacattg   2940
tatttactta attattctta atctttaagg catatacttg gagaggactt aggacaatta   3000
aacacaaaag atttggaaca gcttgagcgt caactggatt catctttgag gctaataaga   3060
tcaagaaggg tatgttctat gcaccttcaa tttatttgtc aaattttagg ctttcagatc   3120
atgtcttaat cttaatgtcc gatgacagtt tcagtggcgg aattagaaat ttatgcaaga   3180
caattcaagc aatattatat attatagaat gtcagacttg aaatttgaac ttgagacatt   3240
gaacctcttt acaaatacac taatatctaa cctcgtatca acggggttca acaatttata   3300
tatatataaa aaacacttaa ttttgcccta tttggtgtaa tatataattt tatcaaaggt   3360
atgttgggaa aatgataaaa attacttatg aataatatcc aaatggaata atataataac   3420
aattacttac tattacttga tagtgccaca aaactactaa accttaaaat aagttctttt   3480
attttacata attcattata atctttggca tgaatttact caagcattgc ttcagaatga   3540
tcaaagcctc cttaatattt ttgggtacag acataaagtc tagacatgca atcaaagata   3600
tagatgcacg agatgactaa tcaaaggaaa caataggaac gatcaaaaaa attgaaattg   3660
aaaatatatt ttttttaaac taaaggtaag tcaagattac caagtaagtg tattattgta   3720
acttttgtat tatttatcct aagtaaacat gtatcaaaaa catacacaaa tttactttct   3780
cttttattac taacatcaac ttacatgcta attataaata attaaagggt aaatagttgg   3840
ttgcatgatt tggtaaaaga agttgttaac ctactctttg ataacatata tgttttcaga   3900
cacaaaacat gcttgatcaa ctttctgatc ttcaacaaaa ggtatgtatt gtataatata   3960
atcccttaag ttgacaatta aatagattgt tcaattgtta atttgacatt gtatgtgttc   4020
ttttttcttt ttttctacag gaacaatctc ttcttgaaat caacagatcc ttgaaaacaa   4080
aggtacaaag cacacatttt ggacctttta tgagtttttt agggcgtgtt tgatttattt   4140
atttttctg aatttttttca tgtttggttg atctaaattc tgggaaaata ctttttttcta   4200
tgaaagtaag tttttttaaaa atgacttagc cagtggaagt agggaaaaca agttgtgacg   4260
acattccacg ttgattgttt tctctcgatc ttcctacaca ccttaagttc gccaccacct   4320
ctcgcagtat ttgtttagat tatataaaaa tgtatcaaga atgacacttt ttatttgtgt   4380
```

```
acataataaa agaaaataag taagaaaccg aacattttcc catggaaaat attatttttc   4440
ataccaaaca caccccttagt ctttgtttta gggtatatga ctaatttgtt ctccatttcg   4500
gatatttaga ttcgtatggg tttttctttg atgtctaact tatcgtactt tttacgcgat   4560
tttatgaaat tcttataata gttggaagaa aactctgtag cacattggca tatcactgga   4620
gagcaaaatg tacaattcag acaacaacct gctcagtcag aggggttctt tcagccttta   4680
caatgcaata ctaatatagt gccaaacagg taacatataa ttttatgttt tcttttttc   4740
ctttaaatag catatttttt gcaacatttt aaattgaacc gttgaattga gtcgttgaga   4800
ggtgaattca gaatctgaag taacagatac attcaaatta atttctttgt gtatttatcg   4860
aagtgagtca agtcgtaagt ctagaggtga atttagaatc taaagtaata gatacagtcg   4920
aatcaatctc tttgtgtatt tattgaagtg agtcgttttg taaagtttga gacgaattca   4980
aaacctaaag taatactaaa tacatacatt caaaataatt tctaaagcga gttatgttgg   5040
aagtcgagag acgaaagtat attatatatg gatcaattca aattaatttc ttaatgtatt   5100
tgatgagcgt tgttgtaggg gcgaattcag aatctgaagt tcatgtaagt acaggtacaa   5160
tgtggctcca ttggatagta tagaaccatc aacacagaat gctactggaa ttttaccagg   5220
atggatgctt tga                                                      5233
```

<210> SEQ ID NO 4
<211> LENGTH: 4822
<212> TYPE: DNA
<213> ORGANISM: Artificial Sequence
<220> FEATURE:
<223> OTHER INFORMATION: Synthetic polynucleotide

<400> SEQUENCE: 4

```
atgggaagag gtaaggtaga attgaagaga atagaaaata agataaacag gcaagttact     60
tttgctaaga gaagaaatgg attactcaaa aaagcttatg agctttctat tttgtgtgaa    120
gctgaagttg ctcttatcat ttctctaat agaggcaaac tctatgaatt ttgcagtacc    180
tctaggtaat atttttatgt ttatgtcgtt ccgtttaagc tttacattta cgtttttata    240
cgcaaaactt taaattagtt ctaaatgtat taaaaaattg aaattttgag atttaatttc    300
aaaatctatg gttaaacgaa tgtttatatg cattatgatt ttgttatctt cttttttttt    360
aaaaaaagaa ataaaatata ttgatgttat agatctgagt gagaatagag tttttggtac    420
atttattaag ggtgaataat caaatgtttc atttgattag atctaggttt tcttgaacat    480
taaaattgtt aaaaaaatta gttcatttta tgaggtaaat tttgttatga tttgatgttc    540
cacctccatt ttttcttatt tttattataa ataaataagt tttaaaatat ccttactttt    600
atatgttctt ttaagtacag acacatgaat caaaaagaag ttttataata tgaattgaat    660
taaagctggt tgaatttcta tcttcagttt ttgaaaacaa ctaaaaactt tgaaaaggaa    720
tttgatttta ttatttatgg caacaaataa cacctaacta cttatcgagt cggaattgac    780
gatatgaatc ctttaacttt tcatttaagc tcaatttata tagaaaattc tgtattgtgg    840
attgaagtaa tttctggagt tgatcaattc tatttaaaaa attatttaat taataatcat    900
tatcccaaaa aattatattg aaattaaaaa ataatattaa ttttttttaaa taacaaactt   960
attaattgag tgaccatcta aatcgtcttt ttcttaaagt tagggtcttg cctttcatct   1020
aattttgata gtaatgttct tgaaccgaca aattttgtca tttactctta tctgttataa   1080
tttatgtgat tcgagtttta cgaatcaatt tttgtttata atttcaatca tgtataagaa   1140
gtattttaag ttataataat taacaatttt aagaaagcat aatcaagatc aaataactta   1200
```

```
gtagaaataa tattggttta tgtaacctct atgcattgac aatatagtgt tttttttata   1260
ctatcaagtc atttattgga taattataat taaagaatat taactaatga gtaaatcaat   1320
agtttaatat taatgagtta tcatagtagc gtatacttat tactcgatat ttgtaatcta   1380
aacattttca atatgcttaa acttgatttt tttatttgga tcaagtatac aatttttttg   1440
ttaataataa atgacattga aacttataac taattttatt taaacaattt tctttctttc   1500
tttcctcaag gagagcatag ttctaattat tatcaatatc attattatta ttatctctat   1560
gtttatttta ttattactgt tgtttctttt acttggattg tctgtactat ttttacttca   1620
tggactttaa ttttttgtct atcgtatttt tatcatagtt tttactcttg tattggctaa   1680
acctagtttt gaaattgttt ttcataagct gaaagagtct atcaaaaaca acttctcacg   1740
agatagaaat aaagtttacg tatattccat tcttctcaaa ccccacttat gagattatac   1800
tgaaatgtta ctattattat tatactttgt aacatgctaa aaaaactagt aataattaca   1860
cttcttgcca aagagtaaat aaagtatgat cctttaataa gttgaaaatc cctctaaatc   1920
aaattatcac ttttgtgcaa cttgtcttct ttttttttctt ctagtatgtc ccatagatgc   1980
agctatggtg accttgaaac tggccagtct tcaaaggatt cacaggttac ttcatcttcc   2040
tcagaattac aatttactaa taaatttaac ttatatactc tgacacagta tcgatgcaat   2100
ttaaaccttt tataacagat tatctgtttt tattttaatt tcttcgtaaa taattaataa   2160
gtcgatattg ataactaacg ccaagcaccc tatcttcatc taactaatta gtgttattat   2220
gcaatagaat aactaccaag agtatatgaa gctgaaagca agagttgaag tgctacaaca   2280
gtcacaaagg tgatacatta tttgttttaa aaacactttt acttgtctca ttttgattgg   2340
ctcatctgaa cacctgaacc ggtctagaag tattttgaac atgcataatt ggacatgttc   2400
aatcatgcgt ttgtttgatc aggttcagga tgtttagatg agacctcgta aaataaatta   2460
aggggaggct ttttaatatg atatttgtgt ctcaaatata tcacttttct accctaattc   2520
ttaataacat tgtatttact taattattct taatctttaa ggcatatact tggagaggac   2580
ttaggacaat taaacacaaa agatttggaa cagcttgagc aactggattc atctttgagg   2640
ctaataagat caagaagggt atgttctatg caccttcaat ttatttgtca aattttaggc   2700
tttcagatca tgtcttaatc ttaatgtccg atgacagttt cagtggcgga attagaaatt   2760
tatgcaagac aattcaagca atattatata ttatagaatg tcagacttga aatttgaact   2820
tgagacattg aacctcttta caaatacact aatatctaac ctcgtatcaa cggggttcaa   2880
caatttatat atatataaaa aacacttaat tttgccctat ttggtgtaat atataatttt   2940
atcaaaggta tgttgggaaa atgataaaaa ttacttatga ataatatcca aatggaataa   3000
tataataaca attacttact attacttgat agtgccacaa aactactaaa ccttaaaata   3060
agttctttta ttttacataa ttcattataa tctttggcat gaatttactc aagcattgct   3120
tcagaatgat caaagcctcc ttaatatttt tgggtacaga cataaagtct agacatgcaa   3180
tcaaagatat agatgcacga gatgactaat caaaggaaac aataggaacg atcaaaaaaa   3240
ttgaaattga aaatatattt tttttaaact aaaggtaagt caagattacc aagtaagtgt   3300
attattgtaa cttttgtatt atttatccta agtaaacatg tatcaaaaac atacacaaat   3360
ttactttctc ttttattact aacatcaact tacatgctaa ttataaataa ttaaagggta   3420
aatagttggt tgcatgattt ggtaaaagaa gttgttaacc tactctttga taacatatat   3480
gttttcagac acaaaacatg cttgatcaac tttctgatct tcaacaaaag gtatgtattg   3540
```

```
tataatataa tcccttaagt tgacaattaa atagattgtt caattgttaa tttgacattg   3600

tatgtgttct tttttctttt tttctacagg aacaatctct tcttgaaatc aacagatcct   3660

tgaaaacaaa ggtacaaagc acacattttg gaccttttat gagtttttta gggcgtgttt   3720

gatttattta ttttttctga attttttcat gtttggttga tctaaattct gggaaaatac   3780

ttttttctat gaaagtaagt tttttaaaaa tgacttagcc agtggaagta gggaaaacaa   3840

gttgtgacga cattccacgt tgattgtttt ctctcgatct tcctacacac cttaagttcg   3900

ccaccacctc tcgcagtatt tgtttagatt atataaaaat gtatcaagaa tgacactttt   3960

tatttgtgta cataataaaa gaaaataagt aagaaaccga acattttccc atggaaaata   4020

ttatttttca taccaaacac acccttagtc tttgttttag ggtatatgac taatttgttc   4080

tccatttcgg atatttagat tcgtatgggt ttttctttga tgtctaactt atcgtacttt   4140

ttacgcgatt ttatgaaatt cttataatag ttggaagaaa actctgtagc acattggcat   4200

atcactggag agcaaaatgt acaattcaga caacaacctg ctcagtcaga ggggttcttt   4260

cagcctttac aatgcaatac taatatagtg ccaaacaggt aacatataat tttatgtttt   4320

cttttttttcc tttaaatagc atattttttg caacatttta aattgaaccg ttgaattgag   4380

tcgttgagag gtgaattcag aatctgaagt aacagataca ttcaaattaa tttctttgtg   4440

tatttatcga agtgagtcaa gtcgtaagtc tagaggtgaa tttagaatct aaagtaatag   4500

atacagtcga atcaatctct ttgtgtattt attgaagtga gtcgttttgt aaagtttgag   4560

acgaattcaa aacctaaagt aatactaaat acatacattc aaaataattt ctaaagcgag   4620

ttatgttgga agtcgagaga cgaaagtata ttatatatgg atcaattcaa attaatttct   4680

taatgtattt gatgagcgtt gttgtagggg cgaattcaga atctgaagtt catgtaagta   4740

caggtacaat gtggctccat tggatagtat agaaccatca acacagaatg ctactggaat   4800

tttaccagga tggatgcttt ga                                             4822
```

<210> SEQ ID NO 5
<211> LENGTH: 4830
<212> TYPE: DNA
<213> ORGANISM: Artificial Sequence
<220> FEATURE:
<223> OTHER INFORMATION: Synthetic polynucleotide

<400> SEQUENCE: 5

```
atgggaagag gtaaggtaga attgaagaga atagaaaata agataaacag gcaagttact     60

tttgctaaga gaagaaatgg attactcaaa aaagcttatg agctttctat tttgtgtgaa    120

gctgaagttg ctcttatcat ttctctaat  agaggcaaac tctatgaatt ttgcagtacc    180

tctaggtaat atttttatgt ttatgtcgtt ccgtttaagc tttacattta cgtttttata    240

cgcaaaactt taaattagtt ctaaatgtat taaaaaattg aaattttgag atttaatttc    300

aaaatctatg gttaaacgaa tgtttatatg cattatgatt ttgttatctt cttttttttt    360

aaaaaaagaa ataaaatata ttgatgttat agatctgagt gagaatagag tttttggtac    420

atttattaag ggtgaataat caaatgtttc atttgattag atctaggttt tcttgaacat    480

taaaattgtt aaaaaaatta gttcatttta tgaggtaaat tttgttatga tttgatgttc    540

cacctccatt ttttcttatt tttattataa ataaataagt tttaaaatat ccttactttt    600

atatgttctt ttaagtacag acacatgaat caaaaagaag ttttataata tgaattgaat    660

taaagctggt tgaatttcta tcttcagttt ttgaaaacaa ctaaaaactt tgaaaaggaa    720

tttgatttta ttatttatgg caacaaataa cacctaacta cttatcgagt cggaattgac    780
```

```
gatatgaatc ctttaacttt tcatttaagc tcaatttata tagaaaattc tgtattgtgg    840
attgaagtaa tttctggagt tgatcaattc tatttaaaaa attatttaat taataatcat    900
tatcccaaaa aattatattg aaattaaaaa ataatattaa ttttttttaaa taacaaactt    960
attaattgag tgaccatcta aatcgtcttt ttcttaaagt tagggtcttg cctttcatct   1020
aattttgata gtaatgttct tgaaccgaca aattttgtca tttactctta tctgttataa   1080
tttatgtgat tcgagtttta cgaatcaatt tttgtttata atttcaatca tgtataagaa   1140
gtattttaag ttataataat taacaatttt aagaaagcat aatcaagatc aaataactta   1200
gtagaaataa tattggttta tgtaacctct atgcattgac aatatagtgt tttttttata   1260
ctatcaagtc atttattgga taattataat taaagaatat taactaatga gtaaatcaat   1320
agtttaatat taatgagtta tcatagtagc gtatacttat tactcgatat ttgtaatcta   1380
aacattttca atatgcttaa acttgatttt tttatttgga tcaagtatac aatttttttg   1440
ttaataataa atgacattga aacttataac taattttatt taaacaattt tctttctttc   1500
tttcctcaag gagagcatag ttctaattat tatcaatatc attattatta ttatctctat   1560
gtttatttta ttattactgt tgtttctttt acttggattg tctgtactat ttttacttca   1620
tggactttaa ttttttgtct atcgtatttt tatcatagtt tttactcttg tattggctaa   1680
acctagtttt gaaattgttt ttcataagct gaaagagtct atcaaaaaca acttctcacg   1740
agatagaaat aaagtttacg tatattccat tcttctcaaa ccccacttat gagattatac   1800
tgaaatgtta ctattattat tatactttgt aacatgctaa aaaaactagt aataattaca   1860
cttcttgcca aagagtaaat aaagtatgat cctttaataa gttgaaaatc cctctaaatc   1920
aaattatcac ttttgtgcaa cttgtcttct ttttttttctt ctagtatgtc tgatacactg   1980
gagagatacc atagatgcag ctatggtgac cttgaaactg gccagtcttc aaaggattca   2040
caggttactt catcttcctc agaattacaa tttactaata aatttaactt atatactctg   2100
acacagtatc gatgcaattt aaacctttta taacagatta tctgttttta ttttaatttc   2160
ttcgtaaata attaataagt cgatattgat aactaacgcc aagcacccta tcttcatcta   2220
actaattagt gttattatgc aatagaataa ctaccaagag tatatgaagc tgaaagcaag   2280
agttgaagtg ctacaacagt cacaaaggtg atacattatt tgttttaaaa acacttttac   2340
ttgtctcatt ttgattggct catctgaaca cctgaaccgg tctagaagta ttttgaacat   2400
gcataattgg acatgttcaa tcatgcgttt gtttgatcag gttcaggatg tttagatgag   2460
acctcgtaaa ataaattaag gggaggcttt ttaatatgat atttgtgtct caaatatatc   2520
acttttctac cctaattctt aataacattg tatttactta attattctta atctttaagg   2580
catatacttg gagaggactt aggacaatta aacacaaaag atttggaaaa ctggattcat   2640
ctttgaggct aataagatca agaagggtat gttctatgca ccttcaattt atttgtcaaa   2700
ttttaggctt tcagatcatg tcttaatctt aatgtccgat gacagtttca gtggcggaat   2760
tagaaattta tgcaagacaa ttcaagcaat attatatatt atagaatgtc agacttgaaa   2820
tttgaacttg agacattgaa cctctttaca aatacactaa tatctaacct cgtatcaacg   2880
gggttcaaca atttatatat atataaaaaa cacttaattt tgccctattt ggtgtaatat   2940
ataattttat caaaggtatg ttgggaaaat gataaaaatt acttatgaat aatatccaaa   3000
tggaataata taataacaat tacttactat tacttgatag tgccacaaaa ctactaaacc   3060
ttaaaataag ttcttttatt ttacataatt cattataatc tttggcatga atttactcaa   3120
```

```
gcattgcttc agaatgatca aagcctcctt aatatttttg ggtacagaca taaagtctag   3180
acatgcaatc aaagatatag atgcacgaga tgactaatca aaggaaacaa taggaacgat   3240
caaaaaaatt gaaattgaaa atatattttt tttaaactaa aggtaagtca agattaccaa   3300
gtaagtgtat tattgtaact tttgtattat ttatcctaag taaacatgta tcaaaaacat   3360
acacaaattt actttctctt ttattactaa catcaactta catgctaatt ataaataatt   3420
aaagggtaaa tagttggttg catgatttgg taaaagaagt tgttaaccta ctctttgata   3480
acatatatgt tttcagacac aaaacatgct tgatcaactt tctgatcttc aacaaaaggt   3540
atgtattgta taatataatc ccttaagttg acaattaaat agattgttca attgttaatt   3600
tgacattgta tgtgttcttt tttctttttt tctacaggaa caatctcttc ttgaaatcaa   3660
cagatccttg aaaacaaagg tacaaagcac acattttgga ccttttatga gttttttagg   3720
gcgtgtttga tttatttatt ttttctgaat tttttcatgt ttggttgatc taaattctgg   3780
gaaaatactt ttttctatga aagtaagttt tttaaaaatg acttagccag tggaagtagg   3840
gaaaacaagt tgtgacgaca ttccacgttg attgttttct ctcgatcttc ctacacacct   3900
taagttcgcc accacctctc gcagtatttg tttagattat ataaaaatgt atcaagaatg   3960
acacttttta tttgtgtaca taataaaaga aaataagtaa gaaaccgaac attttcccat   4020
ggaaaatatt atttttcata ccaaacacac ccttagtctt tgttttaggg tatatgacta   4080
atttgttctc catttcggat atttagattc gtatgggttt ttctttgatg tctaacttat   4140
cgtacttttt acgcgatttt atgaaattct tataatagtt ggaagaaaac tctgtagcac   4200
attggcatat cactggagag caaaatgtac aattcagaca acaacctgct cagtcagagg   4260
ggttctttca gcctttacaa tgcaatacta atatagtgcc aaacaggtaa catataattt   4320
tatgttttct tttttccttt taaatagcat attttttgca acattttaaa ttgaaccgtt   4380
gaattgagtc gttgagaggt gaattcagaa tctgaagtaa cagatacatt caaattaatt   4440
tctttgtgta tttatcgaag tgagtcaagt cgtaagtcta gaggtgaatt tagaatctaa   4500
agtaatagat acagtcgaat caatctcttt gtgtatttat tgaagtgagt cgttttgtaa   4560
agtttgagac gaattcaaaa cctaaagtaa tactaaatac atacattcaa aataatttct   4620
aaagcgagtt atgttggaag tcgagagacg aaagtatatt atatatggat caattcaaat   4680
taatttctta atgtatttga tgagcgttgt tgtagggggcg aattcagaat ctgaagttca   4740
tgtaagtaca ggtacaatgt ggctccattg gatagtatag aaccatcaac acagaatgct   4800
actggaattt taccaggatg gatgctttga                                    4830
```

<210> SEQ ID NO 6
<211> LENGTH: 11812
<212> TYPE: DNA
<213> ORGANISM: Unknown
<220> FEATURE:
<223> OTHER INFORMATION: Solanaceae

<400> SEQUENCE: 6

```
atgggaagag gaagagtaga actaaagaga atagagaaca aaataaacag gcaagttact     60
tttgctaaga gaagaaatgg acttcttaag aaagcttatg agttatctat actttgtgat    120
gctgaagttg ctctcatcat cttctctagc cgcggaaaac tctatgagtt ttcaagtgct    180
tccaggtata tatatatata catatgtttt tcttcttttt gtgtgtgcgt atgtgtttac    240
ttactttcat taattaactc aaccatatat atacatctct cacctcaatt atatatatgt    300
ttgagatctg aatgtctacg gactccattt aggtacatat ctttgtttag atcataaatc    360
```

```
atctatcttc attcctaaga tctactaata tatatgtata agaagatcca tccatctatt    420
aggtttttca acaacatata cagtgaaatc ttatatgtgg gcccacgtat agccatatga    480
gaaaatagtg tgcacgtaaa cattatcatt acttaattat aggaatatac atccattagg    540
tttatcaaca acaataaaat cctctaaatg gagtctagtc ataggtctag ccgtttgaaa    600
atgtaaaata tatgccgatc ttatcactat gtcataataa tagatatgtt gttattgaaa    660
gattctcaat cttttttttt cttcaaggta gagattctta agtggattca tgtttttttt    720
atcaaaaaag aaaaaaacaa aagtgtccat ttgttcatct aatgggtttt ccatgttacc    780
aattcactac actgttgaga tttgattatc agatgtgtca agtttcgttt ggttccctag    840
aagggagaaa aggctgctta tgcaggcagg gtattaaaga tgatattaat atctgcagta    900
atcagtaaca gaatatataa acttaataat aaacttgaag gtacttaatt atccagcaga    960
taatcttctg tctcaccgta cacttttgtt atatcataag cataagaatt gttttatcaa   1020
atattaccaa acaaaactta gttttgtttg gtaatatttt ataaaatatg ttaccgaaag   1080
ttacttccta taacatattt tataaagaaa aaaattaaaa actccatata cctaagaaat   1140
gtaacccccc ctccataaca acaatttaac aaaaataaaa acctactttt tttgaatttg   1200
gtaaattagt tttctatcct ttttagtaac ttcctttctt attttctttt tatattggta   1260
aagtttaata ttacacatta ttttaacatg ttataatttt ttgtgatgct taattatttg   1320
atacatgtaa taaaccatat attagagcta taaatcaatg acaatgcatg tagatacaac   1380
tcatttatga tatattttgt ttatatatat aaccaattag ataatttgtc tgcgctttgt   1440
gcagtcataa ataataattg cattgaactt gcaaatattt tttttaata tccatacatt    1500
aaaaaaaaag aaagaggaaa attggttcct aaaatattag caatattcaa acatttattt   1560
gattattaat cattatcaca taacttaaga acgtctaatg aatgaattat tcacgaaata   1620
ataaatcatt ggttctaaaa aggaatttcg taataaaata aaaatttaag ttaccatatt   1680
caaaaaaaga aattgtgctt gaacatgaaa ataattataa tttttgaact tgtataatga   1740
atttcttcaa ttcataagtg ggaaatttca tatttatgta ataatagata atatgtaagc   1800
tctaatatag tactttaggt tatagaattt aatataaaat atcaaaacat gaattcttga   1860
aattgagtag agtaattatt ttctgcacaa tgaatcggag acaataactt tgaagaaata   1920
taaacaatag agttcaaaag atgtagtcaa aaacaacaat taatatcata agaataaatt   1980
aatgagtgta aaaatgcata ccacgatatg taaaaacaga atggaatata ataaaaaaaa   2040
tcgagttcac tgaatacaca atgttccttt aagaaaatta ttctcctcca ataccaacga   2100
gattacatcc tctaaggatg gaaatgattt cattccccaa cttatccata taaaaatagt   2160
ggtgttagta tgtaactcaa taggagtaaa atacacaaat atttaatttt gcgaaagtag   2220
aagaagaaga tcatattttt tttttaaaat gagaggatat atcactattt ttaaacaaca   2280
aagggtagtg ttaacaaatt tttattgtgt cttgtctaaa aggttacagc tatttgaaaa   2340
agttacaaca cttcgaaaag tgaacaacat ttcataaaag tcgtaacttt tcataaagtc   2400
gtaactcttc ataaatgtcg caactcttca taaaaattac aactattgat aaaagtcacc   2460
actcttgata aagatcacca ctcttcattg aagttgcaac ttttcataaa aatcacatct   2520
tttaataaaa aagaaagact agtttttgga ataaattaat ttaaaagaaa atttttgttt   2580
gtggtggggc gccaagtagg caggcgtagg gttcttttta tataaatata tatgatatat   2640
gattcaatat ttgatatata tatatataga gagagagatg acaatataag acaattgcaa   2700
```

-continued

```
aaaataaaat aaaaaactaa tcgagtaagt aggcaaaaaa ttatttataa aatatatgta   2760
gaatttcttt atcagatatg actgcccaaa tcttatattc aaactaaaat gcaagatcaa   2820
tggtgctata tatagggttt tacacaaaaa tcaagatcta gtcttgcaaa tttaaataaa   2880
aaacagtggt ttacgatgag ataatgtagc ttttgtaaac aataaaacta gaaaaataaa   2940
tgcaaaggca ttttaaagga tataataatg aagatcaaag gcagagaagg gaagaggcag   3000
caatataatg aaggtaacat catggttcca ttctaatata tatgctattt ttctttagta   3060
aatttcaaaa ataatgatac attttcatat ttgataaata tttaatgata ctatcaacat   3120
tttatctata ttgagttcca tttatttgac caaaacctca caaagatgtg ctcttcgatc   3180
tattcaaaat ttattcaatt taaggatagc tttaaaacat gacaaagttt tctcatatat   3240
ttcttaaatt ttatatccag tctaaatacg tatataaact aaaatgaaga gaataatatg   3300
aagctttatt tgatgacatt gttgaaataa ccaaaagcta taagtgatac aatagtaaat   3360
ttaccattgg tcaattcaga attatttaaa agctaaaaaa gtcatataag ttggggttgc   3420
tcaatgtata gtttttggct tgttttaagc attttaaaac tttttttaag cgctttttaa   3480
cattgctaaa cactcaaaaa atgataaata gtatttaaat ttgatatgat tagcttaaaa   3540
gtgaactcat ataccttcaa agtaaaaatc cccaattcga gctttcaaac cacttgattt   3600
tgtggatgaa attatactga agttgaatat atcactattt ataggggtta gtgaactaat   3660
acctttgatt atttggtaga aatatgtatc ttagatcacc ctaatgagct cccactttta   3720
aaataggaaa aacctcatat gaagttcatc actgttcatt atatatcact tttattcaaa   3780
aacgtttaca aatgttcatt gtgactaaat acccttgagt gtcgagtttt cacaccaata   3840
aggcctaatt aataggtaaa caaaactatg tcaatcttca aaacgcaaat ctaattatat   3900
ttttaacaag attagaggta tatatacata ttctcttatg ttaactctta ttcattattg   3960
aacaaactaa gtaagtgtac ccaaggtctc aaacaacagt tggtacattc tttgtatgtc   4020
ttcctttgtc tcttaatagt cgtctcctcc tgtcgatgat tcctccaaat acattaatca   4080
aaggaaaatc tttcgccctc aacttgcaaa cttgtctatc taaaattgtt aacaaagttt   4140
cttcattaga gaaactatga tttcttgaat gtagcaattt gatgtgccat gactatcatc   4200
ttgatcaaca tgcttcttaa ccatcaaaag atcctaaact agatgcatgt catgttagga   4260
gacatattaa gcttgtatat aactacacca acatgcttta ggatctcata agatccaaaa   4320
tttcttattt gggagatttt caatccaaca accatcataa tgagcaacgt gatgttataa   4380
catctctctc acactgccag aacagtctta taccttgtcg gagtgaagga catccttaac   4440
taagtagatt cactaagcta tacttaaaaa gcaataagga atcatctaaa atgtgtgact   4500
cttaacccat attggcatac atggtttatg ggggttatta attgtctgaa cactccccca   4560
tataaatcag tgatcaatat taatcccaat aatatacact attatgattt gagactacac   4620
cctggaagtg gccggctctc aagaaccatt gctgatctcc aagccaaacc ctcattctgg   4680
ttgactacaa gctgaaggca aactcaagta tacaaagctt aaaacataat aaaaataata   4740
tactcaactc gccacaaaat aggcatttaa gtctttaaaa catttttaaa aataaatgaa   4800
acaaacttct caaactgtaa tgtatatcta tgaagcctct aaatgaaaaa aatgaaggca   4860
gatgagacat acggcatcct aacaactgat ataactaaga gtacaagtgg agcccttcgg   4920
atgtaaggag gctcatcaaa gctaatgtga actccatgtg gtatcaatga agcacctatt   4980
gatgaccgtg aatacatgta tctgcatcat gaaacgatgc aggccaaagg gcttagtacg   5040
tgaaatgtac gagcatgtaa agggaattca aatacataaa cataggcttg aactttgata   5100
```

```
taaaggaaac atacttacct atttttaact caagaataaa aaacatagtt caactcaatg   5160
aaaagacact caagtcagtg aaataggccg caactcaata ataagatatt cgactatggg   5220
taatcaactc tgggtactct attcaatata aagtaagaat acaaatgcat tatatggaaa   5280
gactttaaaa cggtagaaaa caactcaatg tattgaaaat tcaatagtaa attagtttgt   5340
atgtaaggaa caatataaac tttgtttgta tatgaaaata caaaataaac tttgtgtata   5400
taaaagtaca aaatatctct gtgaaagttt ctctaaccaa caaccatcac tatgagcttt   5460
ctgataatac cacgtttcgc ccatgatgtc agaactgtcc tatgattttc cagttcataa   5520
gacctactca ctaagtggat ccacaagtct atgctaaaaa atatttaagg aatcgtctaa   5580
aaagtatgac tcattctacc cacgttggct acatgattta tgggggtcgt aagttatcta   5640
aactctcctc catatcgatg cgtaatgcta ctcacaaata tactagctca catgtttaaa   5700
aatataactc gttttgtttg agatcattac tcaaaatcct tctcttaaaa gagatgatac   5760
tcaaactgct caaaactctt ttggaaatct caaattcgtc tcatcttaaa tgtaaaaata   5820
tttactcttg ggaatacata gttatcatat atcattttaa agaaaatgaa ctcaactctg   5880
ttctttctca actcaagtgc tcagtcttaa accaaattaa aaaaaagact tctcaaaata   5940
aagtttatgt cgaattatgg acgtgaacaa ttcaattcaa agttttcgat aaccataact   6000
aaaactaaat actcgagact caacatctta gaactcaaga acttaaatgg taatacttct   6060
ttcaagaatg ctcgactcag aaggttaatg cagaataatg tgcatgaatt actcaactaa   6120
aggactcact gatactactc aatctcaaga ttgctcgact cgtagggtta atgcagaatt   6180
atgtgcatga actactcaac tcaaagacct tcataggtaa catgtagtag ccccatgatt   6240
tggaatataa tcccaaaatg attaggaact caatactcag gacttagaac ttgaagataa   6300
tactacttct ctcaaagata cccaactgac ggagttcatg cagaatttat gggcatgaac   6360
tactcgactc aagagtctaa aacacaatat gacactcatg tatataactc ttctcattct   6420
aatacttgtt ttctcaaaac tcggtttaac taaatagttg atctcaaagg attcacaatt   6480
gaactcaaag actttctttg actccactct taattctctc ttaaatttgt atttgaatta   6540
tgaatttaag agttatgatt catgatatgg ggaatctcaa taacaatata gaaatttgat   6600
aattaggaat agtactttta aaagaaaaca tgaattcaac ttaaaatcaa cttatctaaa   6660
aaatattcaa atatagggaa agtatcctag actactgtgc tactgatctg aaagtagatg   6720
taggatgtga ggatgaacta gtccaacact atgatagcct tacatacctg gaataacgag   6780
gttcttggaa aatcttcact tgaagaagaa cttgattaga agccttgaaa cctagcttga   6840
aggtaaacaa tcaagaaaac ctttcttaag attcttgaat tagtttatga aaatctctat   6900
gaccaagcat tttgattttc actagtgatt cataattgta tggaggaatt tgaattgaaa   6960
aagatgaaat gcttggagaa aagctatctt tgaagaagct tgaaaaagat tggaaagtcc   7020
tgtactttga ttttccctta ggattttgtc ttagggtttg agatagaaaa gaatgatgga   7080
ctaaaagatg aaaatctaat tgtttggatc ctttttcagc caagaaatcc gtttagggtt   7140
ttcttggaga caaacaaaat aaaaaagacc atttttaata tttttccgtc ggctaattcg   7200
taataacatt gtatcatgtt attgaaagag tcataacttt ttactcaaaa attggattga   7260
tgcgaaatta gtggtgttgg aaagtagatt caagtacctc taattggata ggttattccc   7320
tacataagtc tttatattct aaaagatatg gttgtttgca cttgacctaa gtagaatttt   7380
acatgaaaac ttaatagaga aggaaacttc aagaactcat caagaaattt caattgctca   7440
```

```
atatttatgg ataaatttgt agaagaaact catgattgac atgcgggtga ataaacccaa   7500
cactatggaa gcttacatac ctcaaagaac taggttcttg gcgaaatctt gaatttcttc   7560
aacgaacgct tgaaactttg aactttttct cttcttgaac tctcaactaa aaccctaggc   7620
gtatattagg attataaaag ttaacatgat aggattagac ctttaaaaac tttctaaaat   7680
gaattaaatc tgatttagca tgaaaaagac caaaataccc cttactattt tcggataact   7740
tttcttaatt ggactgcctg acttcaaaaa ggtatatctc actcatccga cctcaaaatt   7800
tagcaaattc agtggcgtta gaaagctaat ttaaacacct ttcattttcc atctcatggc   7860
acacataact cattctttaa agagagctat gatcgttcaa attaactcaa atcttagaag   7920
aatttaggaa tgtcttgaac gagctacatc tagtgacctt aacactttgg aaaattttaa   7980
atttcttagt aaaaacttac tcactatgaa ggatggttca agtcttagct caaaattttc   8040
ctaagttgct atatatactc atgctcatat gtttaaaacc aaaacccttc ctcgatttga   8100
attaattacc aaaaagattc tcttaaaaag ataatgctca aaactccccc taaactcatt   8160
tggaaatcta ggtttccctt gttttaaata taaaaacatt tactcttgga aatatttagt   8220
tctcagatat tcacttgaaa aaaattaaac tcgactctca tcatcttcat actcaagtgc   8280
tcaagtccta aaacaattta taactaattg tataagactt ctcaaaatag ggttcattcc   8340
gaattatgga cgtgaacgac tcaattcaag gatttcaata accatatata taactcaata   8400
ataggaactc aacaactcca gaactcaatg atactactca tctcaagaat gctcgactca   8460
cagggtcttt gcgaaattat tgggcatgaa caactcaact caaagacctt catttatacc   8520
atatggtagt cccataatag gaatataatc ccaaaaaaat taggaactca atactcaaaa   8580
acttagaact cgaagatatt actcatctca aagatattca atttatggaa ttcatgctga   8640
attatgagca tgaacgactt gactcaagga tctcaataat aatgtagact catgaataca   8700
ctcttctcat tctcatactc acatactcga gtattaaaat aaattataag taattgcaga   8760
agactccttg aacagactca aaaggactcc ttcgaatttt actcttaatg ctacctgaat   8820
tttgtattat aaatttaagg atcatgatta tgatataaag aatttctcag catatatgaa   8880
atgaacgaat ttgagcattg aacgtctaac ctcatttttt aattattgtg atatgtagag   8940
tggtgcaaaa tcacagatac ctctcttgat gcatttctat agttacgttg atgtgagatt   9000
atatatagtt cagcagcagc atgttgggaa aattactaat aactcttctt ttatatcaaa   9060
ttgttgaagc atgatgacaa cacttgaaaa gtatcaacaa tgcagttacg catctttgga   9120
cccgatgtta ccggttagtg atactcaggt attgtttatc tactttatca tgtcgtaagt   9180
atattatttg taaagatata tatcaagata gttcgattgc gtacacttac attttgatta   9240
tgtttggtga atactattct aataccttttt tttttcctaa agcctaacaa ataaagataa   9300
ttaagatggg aacgtaattc aagtacaaca tggttccata cgtgacatat ttacacatat   9360
agtggaacca aaagagcaat ttttcctaat atcattttct aaatatcacg tgtgcccgtg   9420
attctttttt atggacatga attttttttt taatatgagt ggaagtaagg ttcgatcttt   9480
ctatctgctt tgatatcata ttgaatcgtg tgattgtctc tttaaaaaat taagcaagag   9540
catattttat taattaattg tctttctcga cgtttttctc tttcaacaga tgaactacaa   9600
tgagtatgtg aggctaaaag ctagagttga gctccttcaa cgttctcaaa ggtaagatat   9660
tagtgatgta attaaatgat tttagttaga tttacataag tttttaataa gtgaaaatta   9720
atagacatat tcttggagag gatttgggca cactaaactc gaaagaactt gagcagcttg   9780
agcaccaatt ggatgcatct ttgaagaaag ttagatcaaa aaaggtatat ccaaatacta   9840
```

```
taacttaaat atattgtaac gatttaatta atagcatgtg tcacgttcat ctattcttta   9900
gtcacaatat ataggggcat gtccttaaca acgtgccatg cctcgatagt catttttgtc   9960
tttttgtgcg tatgaattta actttgacac aaatttttgt agtaataata actcatgctt  10020
tagcatctta ggaagcagtc atatgaaaaa cagaagcata tatatatatt acatgagtta  10080
atttaattta atataaaatt taataaaatt gtgtctcgct ataaataatt ttattaaaaa  10140
attatataaa tatattattt ttttaactgg ccgcaaagtt atataaattg atagagaaag  10200
aggttttggt gtaaggttca ttttccaaca attagtttta taatttgtaa gtgcacactt  10260
tatcagactc aatctatgct ggatcagctg gcagaccttc aagaaaaggt acactgcctt  10320
aacattacaa aattaattta tttcatcaaa agcatatcat aaaattctga caaataaata  10380
tattaggagc aaatgctgga agaagcaaat aaacaactaa aaaacaaggt acatatctat  10440
atatgtgtgt taattaatta agttgatttt gtatttttgt ttaatgaata attgtttgtg  10500
atcatcagct ggaagaaagt gcagctagaa ttccacttgg attgtcatgg ggaaataatg  10560
gaggacaaac aatggaatac aatcgactcc ctccacaaac tactgcacaa cctttctttc  10620
aacctctccg tttgaattct tcatcgcctc aattcgggta agtatcttat tttatatgac  10680
ttagtttgac ttgacataaa gtttaataaa gaaagaaaga cttttaaaac ttatagtgta  10740
aaataagtga atagatatat atgtggttgt actaacacta caacaaaaat aattttcagc  10800
ggcattaaat attgacatta ataatgagtg ctaaagactt tatcggtatt agttaagtgt  10860
cattaggatc aatgtcgtta aaggcttcac ggacatatac aaagagtgac aattgccgct  10920
aatgattatt tttgttgtag tgaaaatgag tattttaaag ttaaattgtt acataatata  10980
gaaatatgtc agaaacagga caaatatacc accgaactat catatatgtt atggagatat  11040
tctcagtcat acttctgcga cattggtact catgtcgtcc aaaaactaga acatatatat  11100
accctttata tattaacgaa gatacaagtg tcataatctt atgcaccgat tcgatattta  11160
ttaaatatcg aatcgacgga taaaattatg tcacgtgtcc ctattaagtc ttctattaga  11220
gtaaaaagca tatattctct agtttttgaa cgaaaaaagg tattaatgtc tcaaaagtat  11280
aacgaaaagc atttgcatac aatttatgat aatttggggc atattaattt atcattcccc  11340
cttttttggg cactgattaa aaagaaaaag aaagttataa aaattgggat agagggaata  11400
attgtttcat agggaaaact tagaagcttc tcagtatgtc agtgagaatg tgtttcctaa  11460
ttagtgaact atggtttggt gaaaaataaa gagaaaaaaa tcagtacaaa ttttccactg  11520
attagcaatg agaaaaatat ttgtttctag tagtatgagg agaggatagt ccgcataaat  11580
aatccttaaa tttgtggata aataaactat tttcaataga ttatcgtctc aaaataaaat  11640
aaaatgattg caagaaaaga ataataggta tgctggtaat atgtataata cactcaaatt  11700
tatttgctgt ccatgcagat acaatccaaa tatgggtgca aatgatcatg aggttaatgc  11760
agcaacaact gctcataata ttaatggatt tattccaggg tggatgctct aa          11812
```

```
<210> SEQ ID NO 7
<211> LENGTH: 753
<212> TYPE: DNA
<213> ORGANISM: Unknown
<220> FEATURE:
<223> OTHER INFORMATION: Solanaceae

<400> SEQUENCE: 7

atgggaagag gaagagtaga actaaagaga atagagaaca aaataaacag gcaagttact     60
```

```
tttgctaaga gaagaaatgg acttcttaag aaagcttatg agttatctat actttgtgat    120

gctgaagttg ctctcatcat cttctctagc cgcggaaaac tctatgagtt ttcaagtgct    180

tccagcatga tgacaacact tgaaaagtat caacaatgca gttacgcatc tttggacccg    240

atgttaccgg ttagtgatac tcagatgaac tacaatgagt atgtgaggct aaaagctaga    300

gttgagctcc ttcaacgttc tcaaagacat attcttggag aggatttggg cacactaaac    360

tcgaaagaac ttgagcagct tgagcaccaa ttggatgcat ctttgaagaa agttagatca    420

aaaaagactc aatctatgct ggatcagctg gcagaccttc aagaaaagga gcaaatgctg    480

gaagaagcaa ataaacaact aaaaaacaag ctggaagaaa gtgcagctag aattccactt    540

ggattgtcat ggggaaataa tggaggacaa acaatggaat acaatcgact ccctccacaa    600

actactgcac aacctttctt tcaacctctc cgtttgaatt cttcatcgcc tcaattcgga    660

tacaatccaa atatgggtgc aaatgatcat gaggttaatg cagcaacaac tgctcataat    720

attaatggat ttattccagg gtggatgctc taa                                  753
```

<210> SEQ ID NO 8
<211> LENGTH: 12504
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (607)..(619)
<223> OTHER INFORMATION: n is a, c, g, or t

<400> SEQUENCE: 8

```
atgggaagag gaagagtaga actaaagaga atagagaaca aaataaacag gcaagttact     60

tttgctaaga gaagaaatgg acttcttaag aaagcttatg agttatctat actttgtgat    120

gctgaagttg ctctcatcat cttctctagc cgcggaaaac tctatgagtt ttcaagtgct    180

tccaggtata tatatatata catatgctgt tgaatgcctt gaatcggacc cgctacaaac    240

agaaaggacg gggtctcgc tgcccggtca gcgagtcggg gggtccaggg gggcgacgcg    300

cccccctggcc tgggggtccg ggggggcgga gacgcccccg ggccgacggt atacaatgtt    360

gttgtattgg gcccttaatt ttctgttgat tctgtatgtt gggcccaagc ctgttagggc    420

gtagcttagc actatatata gacgctatgg gaaaccctat tctgtaattc tgtttttgcc    480

tctccataat aaaactgctc cctctcttcc cgtggacgta gccaatttgt tggtgaacca    540

cgtaaatctg ttgtcttatt tttcgcgttt atattttctc gtattatctc aaattccgca    600

caacaannnn nnnnnnnnnc cccgggccga cggtatacaa tgttgttgta ttgggccctt    660

aattttctgt tgattctgta tgttgggccc aagcctgtta gggcgtagct tagcactata    720

tatagacgct atgggaaacc ctattctgta attctgtttt tgcctctcca taataaaact    780

gctccctctc ttcccgtgga cgtagccaat ttgttggtga accacgtaaa tctgttgtct    840

tatttttcgc gtttatattt tctcgtatta tctcaaattc cgcacaacaa tatatatgtt    900

tttcttcttt ttgtgtgtgc gtatgtgttt acttactttc attaattaac tcaaccatat    960

atatacatct ctcacctcaa ttatatatat gtttgagatc tgaatgtcta cggactccat   1020

ttaggtacat atctttgttt agatcataaa tcatctatct tcattcctaa gatctactaa   1080

tatatatgta taagaagatc catccatcta ttaggttttt caacaacata tacagtgaaa   1140

tcttatatgt gggcccacgt atagccatat gagaaaatag tgtgcacgta aacattatca   1200

ttacttaatt ataggaatat acatccatta ggtttatcaa caacaataaa atcctctaaa   1260
```

```
tggagtctag tcataggtct agccgtttga aaatgtaaaa tatatgccga tcttatcact   1320
atgtcataat aatagatatg ttgttattga aagattctca atcttttttt ttcttcaagg   1380
tagagattct taagtggatt catgtttttt ttatcaaaaa agaaaaaaac aaaagtgtcc   1440
atttgttcat ctaatgggtt ttccatgtta ccaattcact acactgttga gatttgatta   1500
tcagatgtgt caagtttcgt ttggttccct agaagggaga aaaggctgct tatgcaggca   1560
gggtattaaa gatgatatta atatctgcag taatcagtaa cagaatatat aaacttaata   1620
ataaacttga aggtacttaa ttatccagca gataatcttc tgtctcaccg tacacttttg   1680
ttatatcata agcataagaa ttgtttttatc aaatattacc aaacaaaact tagttttgtt   1740
tggtaatatt ttataaaata tgttaccgaa agttacttcc tataacatat tttataaaga   1800
aaaaaattaa aaactccata tacctaagaa atgtaacccc ccctccataa caacaattta   1860
acaaaaataa aaacctactt tttttgaatt tggtaaatta gttttctatc ctttttagta   1920
acttcctttc ttattttctt tttatattgg taaagtttaa tattacacat tattttaaca   1980
tgttataatt ttttgtgatg cttaattatt tgatacatgt aataaaccat atattagagc   2040
tataaatcaa tgacaatgca tgtagataca actcatttat gatatatttt gtttatatat   2100
ataaccaatt agataatttg tctgcgcttt gtgcagtcat aaataataat tgcattgaac   2160
ttgcaaatat tttttttaa tatccataca ttaaaaaaaa agaaagagga aaattggttc   2220
ctaaaatatt agcaatattc aaacatttat ttgattatta atcattatca cataacttaa   2280
gaacgtctaa tgaatgaatt attcacgaaa taataaatca ttggttctaa aaaggaattt   2340
cgtaataaaa taaaaattta agttaccata ttcaaaaaaa gaaattgtgc ttgaacatga   2400
aaataattat aatttttgaa cttgtataat gaatttcttc aattcataag tgggaaattt   2460
catatttatg taataataga taatatgtaa gctctaatat agtactttag gttatagaat   2520
ttaatataaa atatcaaaac atgaattctt gaaattgagt agagtaatta ttttctgcac   2580
aatgaatcgg agacaataac tttgaagaaa tataaacaat agagttcaaa agatgtagtc   2640
aaaaacaaca attaatatca taagaataaa ttaatgagtg taaaaatgca taccacgata   2700
tgtaaaaaca gaatggaata taataaaaaa aatcgagttc actgaataca caatgttcct   2760
ttaagaaaat tattctcctc caataccaac gagattacat cctctaagga tggaaatgat   2820
ttcattcccc aacttatcca tataaaaata gtggtgttag tatgtaactc aataggagta   2880
aaatacacaa atatttaatt ttgcgaaagt agaagaagaa gatcatattt tttttttaaa   2940
atgagaggat atatcactat ttttaaacaa caaagggtag tgttaacaaa tttttattgt   3000
gtcttgtcta aaaggttaca gctatttgaa aaagttacaa cacttcgaaa agtgaacaac   3060
atttcataaa agtcgtaact tttcataaag tcgtaactct tcataaatgt cgcaactctt   3120
cataaaaatt acaactattg ataaaagtca ccactcttga taaagatcac cactcttcat   3180
tgaagttgca acttttcata aaaatcacat cttttaataa aaaagaaaga ctagtttttg   3240
gaataaatta atttaaaaga aaatttttgt ttgtggtggg gcgccaagta ggcaggcgta   3300
gggttctttt tatataaata tatatgatat atgattcaat atttgatata tatatatata   3360
gagagagaga tgacaatata agacaattgc aaaaaataaa ataaaaaact aatcgagtaa   3420
gtaggcaaaa aattatttat aaaatatatg tagaatttct ttatcagata tgactgccca   3480
aatcttatat tcaaactaaa atgcaagatc aatggtgcta tatatagggt tttacacaaa   3540
aatcaagatc tagtcttgca aatttaaata aaaaacagtg gtttacgatg agataatgta   3600
```

-continued

```
gcttttgtaa acaataaaac tagaaaaata aatgcaaagg cattttaaag gatataataa   3660
tgaagatcaa aggcagagaa gggaagaggc agcaatataa tgaaggtaac atcatggttc   3720
cattctaata tatatgctat ttttctttag taaatttcaa aataatgat acattttcat    3780
atttgataaa tatttaatga tactatcaac attttatcta tattgagttc catttatttg   3840
accaaaacct cacaaagatg tgctcttcga tctattcaaa atttattcaa tttaaggata   3900
gctttaaaac atgacaaagt tttctcatat atttcttaaa ttttatatcc agtctaaata   3960
cgtatataaa ctaaaatgaa gagaataata tgaagcttta tttgatgaca ttgttgaaat   4020
aaccaaaagc tataagtgat acaatagtaa atttaccatt ggtcaattca gaattattta   4080
aaagctaaaa aagtcatata agttggggtt gctcaatgta tagtttttgg cttgttttaa   4140
gcattttaaa actttttta agcgcttttt aacattgcta aacactcaaa aaatgataaa    4200
tagtatttaa atttgatatg attagcttaa aagtgaactc atataccttc aaagtaaaaa   4260
tccccaattc gagctttcaa accacttgat tttgtggatg aaattatact gaagttgaat   4320
atatcactat ttataggggt tagtgaacta atacctttga ttatttggta gaaatatgta   4380
tcttagatca ccctaatgag ctcccacttt taaaatagga aaaacctcat atgaagttca   4440
tcactgttca ttatatatca cttttattca aaaacgttta caaatgttca ttgtgactaa   4500
ataccttga gtgtcgagtt ttcacaccaa taaggcctaa ttaataggta aacaaaacta    4560
tgtcaatctt caaaacgcaa atctaattat atttttaaca agattagagg tatatataca   4620
tattctctta tgttaactct tattcattat tgaacaaact aagtaagtgt acccaaggtc   4680
tcaaacaaca gttggtacat tctttgtatg tcttcctttg tctcttaata gtcgtctcct   4740
cctgtcgatg attcctccaa atacattaat caaaggaaaa tctttcgccc tcaacttgca   4800
aacttgtcta tctaaaattg ttaacaaagt ttcttcatta gagaaactat gatttcttga   4860
atgtagcaat ttgatgtgcc atgactatca tcttgatcaa catgcttctt aaccatcaaa   4920
agatcctaaa ctagatgcat gtcatgttag gagacatatt aagcttgtat ataactacac   4980
caacatgctt taggatctca taagatccaa aatttcttat ttgggagatt ttcaatccaa   5040
caaccatcat aatgagcaac gtgatgttat aacatctctc tcacactgcc agaacagtct   5100
tataccttgt cggagtgaag gacatcctta actaagtaga ttcactaagc tatacttaaa   5160
aagcaataag gaatcatcta aaatgtgtga ctcttaaccc atattggcat acatggttta   5220
tgggggttat taattgtctg aacactcccc catataaatc agtgatcaat attaatccca   5280
ataatataca ctattatgat ttgagactac accctggaag tggccggctc tcaagaacca   5340
ttgctgatct ccaagccaaa ccctcattct ggttgactac aagctgaagg caaactcaag   5400
tatacaaagc ttaaaacata ataaaaataa tatactcaac tcgccacaaa ataggcattt   5460
aagtctttaa aacattttta aaaataaatg aaacaaactt ctcaaactgt aatgtatatc   5520
tatgaagcct ctaaatgaaa aaaatgaagg cagatgagac atacggcatc ctaacaactg   5580
atataactaa gagtacaagt ggagcccttc ggatgtaagg aggctcatca aagctaatgt   5640
gaactccatg tggtatcaat gaagcaccta ttgatgaccg tgaatacatg tatctgcatc   5700
atgaaacgat gcaggccaaa gggcttagta cgtgaaatgt acgagcatgt aaagggaatt   5760
caaatacata aacataggct tgaactttga tataaaggaa acatacttac ctatttttaa   5820
ctcaagaata aaaaacatag ttcaactcaa tgaaaagaca ctcaagtcag tgaaataggc   5880
cgcaactcaa taataagata ttcgactatg ggtaatcaac tctgggtact ctattcaata   5940
taaagtaaga atacaaatgc attatatgga aagactttaa aacggtagaa aacaactcaa   6000
```

```
tgtattgaaa attcaatagt aaattagttt gtatgtaagg aacaatataa actttgtttg   6060
tatatgaaaa tacaaaataa actttgtgta tataaaagta caaaatatct ctgtgaaagt   6120
ttctctaacc aacaaccatc actatgagct ttctgataat accacgtttc gcccatgatg   6180
tcagaactgt cctatgattt tccagttcat aagacctact cactaagtgg atccacaagt   6240
ctatgctaaa aaatatttaa ggaatcgtct aaaaagtatg actcattcta cccacgttgg   6300
ctacatgatt tatgggggtc gtaagttatc taaactctcc tccatatcga tgcgtaatgc   6360
tactcacaaa tatactagct cacatgttta aaaatataac tcgttttgtt tgagatcatt   6420
actcaaaatc cttctcttaa aagagatgat actcaaactg ctcaaaactc ttttggaaat   6480
ctcaaattcg tctcatctta aatgtaaaaa tatttactct tgggaataca tagttatcat   6540
atatcatttt aaagaaaatg aactcaactc tgttctttct caactcaagt gctcagtctt   6600
aaaccaaatt aaaaaaaaga cttctcaaaa taaagtttat gtcgaattat ggacgtgaac   6660
aattcaattc aaagttttcg ataaccataa ctaaaactaa atactcgaga ctcaacatct   6720
tagaactcaa gaacttaaat ggtaatactt ctttcaagaa tgctcgactc agaaggttaa   6780
tgcagaataa tgtgcatgaa ttactcaact aaaggactca ctgatactac tcaatctcaa   6840
gattgctcga ctcgtagggt taatgcagaa ttatgtgcat gaactactca actcaaagac   6900
cttcataggt aacatgtagt agccccatga tttggaatat aatcccaaaa tgattaggaa   6960
ctcaatactc aggacttaga acttgaagat aatactactt ctctcaaaga tacccaactg   7020
acggagttca tgcagaattt atgggcatga actactcgac tcaagagtct aaaacacaat   7080
atgacactca tgtatataac tcttctcatt ctaatacttg ttttctcaaa actcggttta   7140
actaaatagt tgatctcaaa ggattcacaa ttgaactcaa agactttctt tgactccact   7200
cttaattctc tcttaaattt gtatttgaat tatgaattta agagttatga ttcatgatat   7260
ggggaatctc aataacaata tagaaatttg ataattagga atagtacttt taaaagaaaa   7320
catgaattca acttaaaatc aacttatcta aaaaatattc aaatataggg aaagtatcct   7380
agactactgt gctactgatc tgaaagtaga tgtaggatgt gaggatgaac tagtccaaca   7440
ctatgatagc cttacatacc tggaataacg aggttcttgg aaaatcttca cttgaagaag   7500
aacttgatta gaagccttga aacctagctt gaaggtaaac aatcaagaaa acctttctta   7560
agattcttga attagtttat gaaaatctct atgaccaagc attttgattt tcactagtga   7620
ttcataattg tatggaggaa tttgaattga aaaagatgaa atgcttggag aaaagctatc   7680
tttgaagaag cttgaaaaag attggaaagt cctgtacttt gattttccct taggattttg   7740
tcttagggtt tgagatagaa aagaatgatg gactaaaaga tgaaaatcta attgtttgga   7800
tcctttttca gccaagaaat ccgtttaggg ttttcttgga gacaaacaaa ataaaaaaga   7860
ccatttttaa tatttttccg tcggctaatt cgtaataaca ttgtatcatg ttattgaaag   7920
agtcataact ttttactcaa aaattggatt gatgcgaaat tagtggtgtt ggaaagtaga   7980
ttcaagtacc tctaattgga taggttattc cctacataag tctttatatt ctaaaagata   8040
tggttgtttg cacttgacct aagtagaatt ttacatgaaa acttaataga gaaggaaact   8100
tcaagaactc atcaagaaat ttcaattgct caatatttat ggataaattt gtagaagaaa   8160
ctcatgattg acatgcgggt gaataaaccc aacactatgg aagcttacat acctcaaaga   8220
actaggttct tggcgaaatc ttgaatttct tcaacgaacg cttgaaactt tgaacttttt   8280
ctcttcttga actctcaact aaaaccctag gcgtatatta ggattataaa agttaacatg   8340
```

-continued

```
ataggattag acctttaaaa actttctaaa atgaattaaa tctgatttag catgaaaaag   8400
accaaaatac cccttactat tttcggataa cttttcttaa ttggactgcc tgacttcaaa   8460
aaggtatatc tcactcatcc gacctcaaaa tttagcaaat tcagtggcgt tagaaagcta   8520
atttaaacac ctttcatttt ccatctcatg gcacacataa ctcattcttt aaagagagct   8580
atgatcgttc aaattaactc aaatcttaga agaatttagg aatgtcttga acgagctaca   8640
tctagtgacc ttaacacttt ggaaaatttt aaatttctta gtaaaaactt actcactatg   8700
aaggatggtt caagtcttag ctcaaaattt tcctaagttg ctatatatac tcatgctcat   8760
atgtttaaaa ccaaaaccct tcctcgattt gaattaatta ccaaaaagat tctcttaaaa   8820
agataatgct caaaactccc cctaaactca tttggaaatc taggtttccc ttgttttaaa   8880
tataaaaaca tttactcttg gaaatattta gttctcagat attcacttga aaaaaattaa   8940
actcgactct catcatcttc atactcaagt gctcaagtcc taaaacaatt tataactaat   9000
tgtataagac ttctcaaaat agggttcatt ccgaattatg gacgtgaacg actcaattca   9060
aggatttcaa taaccatata tataactcaa taataggaac tcaacaactc cagaactcaa   9120
tgatactact catctcaaga atgctcgact cacagggtct ttgcgaaatt attgggcatg   9180
aacaactcaa ctcaaagacc ttcatttata ccatatggta gtcccataat aggaatataa   9240
tcccaaaaaa attaggaact caatactcaa aaacttagaa ctcgaagata ttactcatct   9300
caaagatatt caatttatgg aattcatgct gaattatgag catgaacgac ttgactcaag   9360
gatctcaata ataatgtaga ctcatgaata cactcttctc attctcatac tcacatactc   9420
gagtattaaa ataaattata agtaattgca gaagactcct tgaacagact caaaaggact   9480
ccttcgaatt ttactcttaa tgctacctga attttgtatt ataaatttaa ggatcatgat   9540
tatgatataa agaatttctc agcatatatg aaatgaacga atttgagcat tgaacgtcta   9600
acctcatttt ttaattattg tgatatgtag agtggtgcaa aatcacagat acctctcttg   9660
atgcatttct atagttacgt tgatgtgaga ttatatatag ttcagcagca gcatgttggg   9720
aaaattacta ataactcttc ttttatatca aattgttgaa gcatgatgac aacacttgaa   9780
aagtatcaac aatgcagtta cgcatctttg gacccgatgt taccggttag tgatactcag   9840
gtattgttta tctactttat catgtcgtaa gtatattatt tgtaaagata tatatcaaga   9900
tagttcgatt gcgtacactt acattttgat tatgtttggt gaatactatt ctaatacctt   9960
tttttttcct aaagcctaac aaataaagat aattaagatg ggaacgtaat tcaagtacaa  10020
catggttcca tacgtgacat atttacacat atagtggaac caaaagagca atttttccta  10080
atatcatttt ctaaatatca cgtgtgcccg tgattctttt ttatggacat gaattttttt  10140
tttaatatga gtggaagtaa ggttcgatct ttctatctgc tttgatatca tattgaatcg  10200
tgtgattgtc tctttaaaaa attaagcaag agcatatttt attaattaat tgtctttctc  10260
gacgtttttc tctttcaaca gatgaactac aatgagtatg tgaggctaaa agctagagtt  10320
gagctccttc aacgttctca aaggtaagat attagtgatg taattaaatg attttagtta  10380
gatttacata agtttttaat aagtgaaaat taatagacat attcttggag aggatttggg  10440
cacactaaac tcgaaagaac ttgagcagct tgagcaccaa ttggatgcat ctttgaagaa  10500
agttagatca aaaaaggtat atccaaatac tataacttaa atatattgta acgatttaat  10560
taatagcatg tgtcacgttc atctattctt tagtcacaat atataggggc atgtccttaa  10620
caacgtgcca tgcctcgata gtcatttttg tctttttgtg cgtatgaatt taactttgac  10680
acaaattttt gtagtaataa taactcatgc tttagcatct taggaagcag tcatatgaaa  10740
```

```
aacagaagca tatatatata ttacatgagt taatttaatt taatataaaa tttaataaaa  10800
ttgtgtctcg ctataaataa ttttattaaa aaattatata aatatattat ttttttaact  10860
ggccgcaaag ttatataaat tgatagagaa agaggttttg gtgtaaggtt cattttccaa  10920
caattagttt tataatttgt aagtgcacac tttatcagac tcaatctatg ctggatcagc  10980
tggcagacct tcaagaaaag gtacactgcc ttaacattac aaaattaatt tatttcatca  11040
aaagcatatc ataaaattct gacaaataaa tatattagga gcaaatgctg gaagaagcaa  11100
ataaacaact aaaaaacaag gtacatatct atatatgtgt gttaattaat taagttgatt  11160
ttgtattttt gtttaatgaa taattgtttg tgatcatcag ctggaagaaa gtgcagctag  11220
aattccactt ggattgtcat ggggaaataa tggaggacaa acaatggaat acaatcgact  11280
ccctccacaa actactgcac aacctttctt tcaacctctc cgtttgaatt cttcatcgcc  11340
tcaattcggg taagtatctt attttatatg acttagtttg acttgacata aagtttaata  11400
aagaaagaaa gacttttaaa acttatagtg taaaataagt gaatagatat atatgtggtt  11460
gtactaacac tacaacaaaa ataattttca gcggcattaa atattgacat taataatgag  11520
tgctaaagac tttatcggta ttagttaagt gtcattagga tcaatgtcgt taaaggcttc  11580
acggacatat acaaagagtg acaattgccg ctaatgatta tttttgttgt agtgaaaatg  11640
agtattttaa agttaaattg ttacataata tagaaatatg tcagaaacag gacaaatata  11700
ccaccgaact atcatatatg ttatggagat attctcagtc atacttctgc gacattggta  11760
ctcatgtcgt ccaaaaacta gaacatatat ataccottta tatattaacg aagatacaag  11820
tgtcataatc ttatgcaccg attcgatatt tattaaatat cgaatcgacg gataaaatta  11880
tgtcacgtgt ccctattaag tcttctatta gagtaaaaag catatattct ctagtttttg  11940
aacgaaaaaa ggtattaatg tctcaaaagt ataacgaaaa gcatttgcat acaatttatg  12000
ataatttggg gcatattaat ttatcattcc cccttttttt ggcactgatt aaaaagaaaa  12060
agaaagttat aaaaaattggg atagagggaa taattgtttc atagggaaaa cttagaagct  12120
tctcagtatg tcagtgagaa tgtgtttcct aattagtgaa ctatggtttg gtgaaaaata  12180
aagagaaaaa aatcagtaca aattttccac tgattagcaa tgagaaaaat atttgtttct  12240
agtagtatga ggagaggata gtccgcataa ataatcctta aatttgtgga taaataaact  12300
attttcaata gattatcgtc tcaaaataaa ataaaatgat tgcaagaaaa gaataatagg  12360
tatgctggta atatgtataa tacactcaaa tttatttgct gtccatgcag atacaatcca  12420
aatatgggtg caaatgatca tgaggttaat gcagcaacaa ctgctcataa tattaatgga  12480
tttattccag ggtggatgct ctaa                                          12504
```

<210> SEQ ID NO 9
<211> LENGTH: 11812
<212> TYPE: DNA
<213> ORGANISM: Artificial Sequence
<220> FEATURE:
<223> OTHER INFORMATION: Synthetic polynucleotide

<400> SEQUENCE: 9

```
atgggaagag gaagagtaga actaaagaga atagagaaca aaataaacag gcaagttact     60
tttgctaaga gaagaaatgg acttcttaag aaagcttatg agttatctat actttgtgat    120
gctgaagttg ctctcatcat cttctctagc cgcggaaaac tctatgagtt ttcaagtgct    180
tccaggtata tatatatata catatgtttt tcttcttttt gtgtgtgcgt atgtgtttac    240
```

```
ttactttcat taattaactc aaccatatat atacatctct cacctcaatt atatatatgt    300
ttgagatctg aatgtctacg gactccattt aggtacatat ctttgtttag atcataaatc    360
atctatcttc attcctaaga tctactaata tatatgtata agaagatcca tccatctatt    420
aggtttttca acaacatata cagtgaaatc ttatatgtgg gcccacgtat agccatatga    480
gaaaatagtg tgcacgtaaa cattatcatt acttaattat aggaatatac atccattagg    540
tttatcaaca acaataaaat cctctaaatg gagtctagtc ataggtctag ccgtttgaaa    600
atgtaaaata tatgccgatc ttatcactat gtcataataa tagatatgtt gttattgaaa    660
gattctcaat cttttttttt cttcaaggta gagattctta agtggattca tgtttttttt    720
atcaaaaaag aaaaaaacaa aagtgtccat ttgttcatct aatgggtttt ccatgttacc    780
aattcactac actgttgaga tttgattatc agatgtgtca agtttcgttt ggttccctag    840
aagggagaaa aggctgctta tgcaggcagg gtattaaaga tgatattaat atctgcagta    900
atcagtaaca gaatatataa acttaataat aaacttgaag gtacttaatt atccagcaga    960
taatcttctg tctcaccgta cacttttgtt atatcataag cataagaatt gttttatcaa   1020
atattaccaa acaaaactta gttttgtttg gtaatatttt ataaaatatg ttaccgaaag   1080
ttacttccta taacatattt tataaagaaa aaaattaaaa actccatata cctaagaaat   1140
gtaacccccc ctccataaca acaatttaac aaaaataaaa acctactttt tttgaatttg   1200
gtaaattagt tttctatcct ttttagtaac ttcctttctt attttctttt tatattggta   1260
aagtttaata ttacacatta ttttaacatg ttataatttt ttgtgatgct taattatttg   1320
atacatgtaa taaaccatat attagagcta taaatcaatg acaatgcatg tagatacaac   1380
tcatttatga tatattttgt ttatatatat aaccaattag ataatttgtc tgcgctttgt   1440
gcagtcataa ataataattg cattgaactt gcaaatattt ttttttaata tccatacatt   1500
aaaaaaaaag aaagaggaaa attggttcct aaaatattag caatattcaa acatttattt   1560
gattattaat cattatcaca taacttaaga acgtctaatg aatgaattat tcacgaaata   1620
ataaatcatt ggttctaaaa aggaatttcg taataaaata aaaatttaag ttaccatatt   1680
caaaaaaaga aattgtgctt gaacatgaaa ataattataa tttttgaact tgtataatga   1740
atttcttcaa ttcataagtg ggaaatttca tatttatgta ataatagata atatgtaagc   1800
tctaatatag tactttaggt tatagaattt aatataaaat atcaaaacat gaattcttga   1860
aattgagtag agtaattatt ttctgcacaa tgaatcggag acaataactt tgaagaaata   1920
taaacaatag agttcaaaag atgtagtcaa aaacaacaat taatatcata agaataaatt   1980
aatgagtgta aaaatgcata ccacgatatg taaaaacaga atggaatata ataaaaaaaa   2040
tcgagttcac tgaatacaca atgttccttt aagaaaatta ttctcctcca ataccaacga   2100
gattacatcc tctaaggatg gaaatgattt cattccccaa cttatccata taaaaatagt   2160
ggtgttagta tgtaactcaa taggagtaaa atacacaaat atttaatttt gcgaaagtag   2220
aagaagaaga tcatattttt tttttaaaat gagaggatat atcactattt ttaaacaaca   2280
aagggtagtg ttaacaaatt tttattgtgt cttgtctaaa aggttacagc tatttgaaaa   2340
agttacaaca cttcgaaaag tgaacaacat ttcataaaag tcgtaacttt tcataaagtc   2400
gtaactcttc ataaatgtcg caactcttca taaaaattac aactattgat aaaagtcacc   2460
actcttgata aagatcacca ctcttcattg aagttgcaac ttttcataaa aatcacatct   2520
tttaataaaa aagaaagact agtttttgga ataaattaat ttaaaagaaa atttttgttt   2580
gtggtggggc gccaagtagg caggcgtagg gttcttttta tataaatata tatgatatat   2640
```

```
gattcaatat ttgatatata tatatataga gagagagatg acaatataag acaattgcaa   2700
aaaataaaat aaaaaactaa tcgagtaagt aggcaaaaaa ttatttataa aatatatgta   2760
gaatttcttt atcagatatg actgcccaaa tcttatattc aaactaaaat gcaagatcaa   2820
tggtgctata tatagggttt tacacaaaaa tcaagatcta gtcttgcaaa tttaaataaa   2880
aaacagtggt ttacgatgag ataatgtagc ttttgtaaac aataaaacta gaaaaataaa   2940
tgcaaaggca ttttaaagga tataataatg aagatcaaag gcagagaagg gaagaggcag   3000
caatataatg aaggtaacat catggttcca ttctaatata tatgctattt ttctttagta   3060
aatttcaaaa ataatgatac attttcatat ttgataaata tttaatgata ctatcaacat   3120
tttatctata ttgagttcca tttatttgac caaaacctca caaagatgtg ctcttcgatc   3180
tattcaaaat ttattcaatt taaggatagc tttaaaacat gacaaagttt tctcatatat   3240
ttcttaaatt ttatatccag tctaaatacg tatataaact aaaatgaaga gaataatatg   3300
aagctttatt tgatgacatt gttgaaataa ccaaaagcta taagtgatac aatagtaaat   3360
ttaccattgg tcaattcaga attatttaaa agctaaaaaa gtcatataag ttggggttgc   3420
tcaatgtata gtttttggct tgttttaagc attttaaaac tttttttaag cgctttttaa   3480
cattgctaaa cactcaaaaa atgataaata gtatttaaat ttgatatgat tagcttaaaa   3540
gtgaactcat ataccttcaa agtaaaaatc cccaattcga gctttcaaac cacttgattt   3600
tgtggatgaa attatactga agttgaatat atcactattt ataggggtta gtgaactaat   3660
acctttgatt atttggtaga aatatgtatc ttagatcacc ctaatgagct cccactttta   3720
aaataggaaa aacctcatat gaagttcatc actgttcatt atatatcact tttattcaaa   3780
aacgtttaca aatgttcatt gtgactaaat acccttgagt gtcgagtttt cacaccaata   3840
aggcctaatt aataggtaaa caaaactatg tcaatcttca aaacgcaaat ctaattatat   3900
ttttaacaag attagaggta tatatacata ttctcttatg ttaactctta ttcattattg   3960
aacaaactaa gtaagtgtac ccaaggtctc aaacaacagt tggtacattc tttgtatgtc   4020
ttcctttgtc tcttaatagt cgtctcctcc tgtcgatgat tcctccaaat acattaatca   4080
aaggaaaatc tttcgccctc aacttgcaaa cttgtctatc taaaattgtt aacaaagttt   4140
cttcattaga gaaactatga tttcttgaat gtagcaattt gatgtgccat gactatcatc   4200
ttgatcaaca tgcttcttaa ccatcaaaag atcctaaact agatgcatgt catgttagga   4260
gacatattaa gcttgtatat aactacacca acatgcttta ggatctcata agatccaaaa   4320
tttcttattt gggagatttt caatccaaca accatcataa tgagcaacgt gatgttataa   4380
catctctctc acactgccag aacagtctta taccttgtcg gagtgaagga catccttaac   4440
taagtagatt cactaagcta tacttaaaaa gcaataagga atcatctaaa atgtgtgact   4500
cttaacccat attggcatac atggtttatg ggggttatta attgtctgaa cactccccca   4560
tataaatcag tgatcaatat taatcccaat aatatacact attatgattt gagactacac   4620
cctggaagtg gccggctctc aagaaccatt gctgatctcc aagccaaacc ctcattctgg   4680
ttgactacaa gctgaaggca aactcaagta tacaaagctt aaaacataat aaaaataata   4740
tactcaactc gccacaaaat aggcatttaa gtctttaaaa catttttaaa aataaatgaa   4800
acaaacttct caaactgtaa tgtatatcta tgaagcctct aaatgaaaaa aatgaaggca   4860
gatgagacat acggcatcct aacaactgat ataactaaga gtacaagtgg agcccttcgg   4920
atgtaaggag gctcatcaaa gctaatgtga actccatgtg gtatcaatga agcacctatt   4980
```

```
gatgaccgtg aatacatgta tctgcatcat gaaacgatgc aggccaaagg gcttagtacg   5040
tgaaatgtac gagcatgtaa agggaattca aatacataaa cataggcttg aactttgata   5100
taaaggaaac atacttacct atttttaact caagaataaa aaacatagtt caactcaatg   5160
aaaagacact caagtcagtg aaataggccg caactcaata ataagatatt cgactatggg   5220
taatcaactc tgggtactct attcaatata aagtaagaat acaaatgcat tatatggaaa   5280
gactttaaaa cggtagaaaa caactcaatg tattgaaaat tcaatagtaa attagtttgt   5340
atgtaaggaa caatataaac tttgtttgta tatgaaaata caaaataaac tttgtgtata   5400
taaaagtaca aaatatctct gtgaaagttt ctctaaccaa caaccatcac tatgagcttt   5460
ctgataatac cacgtttcgc ccatgatgtc agaactgtcc tatgattttc cagttcataa   5520
gacctactca ctaagtggat ccacaagtct atgctaaaaa atatttaagg aatcgtctaa   5580
aaagtatgac tcattctacc cacgttggct acatgattta tgggggtcgt aagttatcta   5640
aactctcctc catatcgatg cgtaatgcta ctcacaaata tactagctca catgtttaaa   5700
aatataactc gttttgtttg agatcattac tcaaaatcct tctcttaaaa gagatgatac   5760
tcaaactgct caaaactctt ttggaaatct caaattcgtc tcatcttaaa tgtaaaaata   5820
tttactcttg ggaatacata gttatcatat atcattttaa agaaaatgaa ctcaactctg   5880
ttctttctca actcaagtgc tcagtcttaa accaaattaa aaaaaagact tctcaaaata   5940
aagtttatgt cgaattatgg acgtgaacaa ttcaattcaa agttttcgat aaccataact   6000
aaaactaaat actcgagact caacatctta gaactcaaga acttaaatgg taatacttct   6060
ttcaagaatg ctcgactcag aaggttaatg cagaataatg tgcatgaatt actcaactaa   6120
aggactcact gatactactc aatctcaaga ttgctcgact cgtagggtta atgcagaatt   6180
atgtgcatga actactcaac tcaaagacct tcataggtaa catgtagtag ccccatgatt   6240
tggaatataa tcccaaaatg attaggaact caatactcag gacttagaac ttgaagataa   6300
tactacttct ctcaaagata cccaactgac ggagttcatg cagaatttat gggcatgaac   6360
tactcgactc aagagtctaa aacacaatat gacactcatg tatataactc ttctcattct   6420
aatacttgtt ttctcaaaac tcggtttaac taaatagttg atctcaaagg attcacaatt   6480
gaactcaaag actttctttg actccactct taattctctc ttaaatttgt atttgaatta   6540
tgaatttaag agttatgatt catgatatgg ggaatctcaa taacaatata gaaatttgat   6600
aattaggaat agtactttta aaagaaaaca tgaattcaac ttaaaatcaa cttatctaaa   6660
aaatattcaa atatagggaa agtatcctag actactgtgc tactgatctg aaagtagatg   6720
taggatgtga ggatgaacta gtccaacact atgatagcct tacatacctg gaataacgag   6780
gttcttggaa aatcttcact tgaagaagaa cttgattaga agccttgaaa cctagcttga   6840
aggtaaacaa tcaagaaaac ctttcttaag attcttgaat tagtttatga aaatctctat   6900
gaccaagcat tttgattttc actagtgatt cataattgta tggaggaatt tgaattgaaa   6960
aagatgaaat gcttggagaa aagctatctt tgaagaagct tgaaaaagat tggaaagtcc   7020
tgtactttga ttttccctta ggattttgtc ttagggtttg agatagaaaa gaatgatgga   7080
ctaaaagatg aaaatctaat tgtttggatc ctttttcagc caagaaatcc gtttagggtt   7140
ttcttggaga caaacaaaat aaaaaagacc atttttaata tttttccgtc ggctaattcg   7200
taataacatt gtatcatgtt attgaaagag tcataacttt ttactcaaaa attggattga   7260
tgcgaaatta gtggtgttgg aaagtagatt caagtacctc taattggata ggttattccc   7320
tacataagtc tttatattct aaaagatatg gttgtttgca cttgacctaa gtagaatttt   7380
```

```
acatgaaaac ttaatagaga aggaaacttc aagaactcat caagaaattt caattgctca   7440
atatttatgg ataaatttgt agaagaaact catgattgac atgcgggtga ataaacccaa   7500
cactatggaa gcttacatac ctcaaagaac taggttcttg gcgaaatctt gaatttcttc   7560
aacgaacgct tgaaactttg aactttttct cttcttgaac tctcaactaa aaccctaggc   7620
gtatattagg attataaaag ttaacatgat aggattagac ctttaaaaac tttctaaaat   7680
gaattaaatc tgatttagca tgaaaaagac caaaataccc cttactattt tcggataact   7740
tttcttaatt ggactgcctg acttcaaaaa ggtatatctc actcatccga cctcaaaatt   7800
tagcaaattc agtggcgtta gaaagctaat ttaaacacct ttcattttcc atctcatggc   7860
acacataact cattctttaa agagagctat gatcgttcaa attaactcaa atcttagaag   7920
aatttaggaa tgtcttgaac gagctacatc tagtgacctt aacactttgg aaaattttaa   7980
atttcttagt aaaaacttac tcactatgaa ggatggttca agtcttagct caaaattttc   8040
ctaagttgct atatatactc atgctcatat gtttaaaacc aaaacccttc ctcgatttga   8100
attaattacc aaaaagattc tcttaaaaag ataatgctca aaactccccc taaactcatt   8160
tggaaatcta ggtttccctt gttttaaata taaaaacatt tactcttgga aatatttagt   8220
tctcagatat tcacttgaaa aaaattaaac tcgactctca tcatcttcat actcaagtgc   8280
tcaagtccta aaacaattta taactaattg tataagactt ctcaaaatag ggttcattcc   8340
gaattatgga cgtgaacgac tcaattcaag gatttcaata accatatata taactcaata   8400
ataggaactc aacaactcca gaactcaatg atactactca tctcaagaat gctcgactca   8460
cagggtcttt gcgaaattat tggcatgaa caactcaact caaagacctt catttatacc   8520
atatggtagt cccataatag gaatataatc ccaaaaaaat taggaactca atactcaaaa   8580
acttagaact cgaagatatt actcatctca aagatattca atttatggaa ttcatgctga   8640
attatgagca tgaacgactt gactcaagga tctcaataat aatgtagact catgaataca   8700
ctcttctcat tctcatactc acatactcga gtattaaaat aaattataag taattgcaga   8760
agactccttg aacagactca aaaggactcc ttcgaatttt actcttaatg ctacctgaat   8820
tttgtattat aaatttaagg atcatgatta tgatataaag aatttctcag catatatgaa   8880
atgaacgaat ttgagcattg aacgtctaac ctcatttttt aattattgtg atatgtagag   8940
tggtgcaaaa tcacagatac ctctcttgat gcatttctat agttacgttg atgtgagatt   9000
atatatagtt cagcagcagc atgttgggaa aattactaat aactcttctt ttatatcaaa   9060
ttgttgaagc atgatgacaa cacttgaaaa gtatcaacaa tgcagttacg catctttgga   9120
cccgatgtaa ccggttagtg atactcaggt attgtttatc tactttatca tgtcgtaagt   9180
atattatttg taaagatata tatcaagata gttcgattgc gtacacttac attttgatta   9240
tgtttggtga atactattct aataccttttt tttttcctaa agcctaacaa ataaagataa   9300
ttaagatggg aacgtaattc aagtacaaca tggttccata cgtgacatat ttacacatat   9360
agtggaacca aaagagcaat ttttcctaat atcattttct aaatatcacg tgtgcccgtg   9420
attcttttttt atggacatga attttttttt taatatgagt ggaagtaagg ttcgatcttt   9480
ctatctgctt tgatatcata ttgaatcgtg tgattgtctc tttaaaaaat taagcaagag   9540
catattttat taattaattg tctttctcga cgtttttctc tttcaacaga tgaactacaa   9600
tgagtatgtg aggctaaaag ctagagttga gctccttcaa cgttctcaaa ggtaagatat   9660
tagtgatgta attaaatgat tttagttaga tttacataag tttttaataa gtgaaaatta   9720
```

```
atagacatat tcttggagag gatttgggca cactaaactc gaaagaactt gagcagcttg   9780
agcaccaatt ggatgcatct ttgaagaaag ttagatcaaa aaaggtatat ccaaatacta   9840
taacttaaat atattgtaac gatttaatta atagcatgtg tcacgttcat ctattcttta   9900
gtcacaatat ataggggcat gtccttaaca acgtgccatg cctcgatagt catttttgtc   9960
tttttgtgcg tatgaattta actttgacac aaatttttgt agtaataata actcatgctt  10020
tagcatctta ggaagcagtc atatgaaaaa cagaagcata tatatatatt acatgagtta  10080
atttaattta atataaaatt taataaaatt gtgtctcgct ataaataatt ttattaaaaa  10140
attatataaa tatattattt ttttaactgg ccgcaaagtt atataaattg atagagaaag  10200
aggttttggt gtaaggttca ttttccaaca attagtttta taatttgtaa gtgcacactt  10260
tatcagactc aatctatgct ggatcagctg gcagaccttc aagaaaaggt acactgcctt  10320
aacattacaa aattaattta tttcatcaaa agcatatcat aaaattctga caaataaata  10380
tattaggagc aaatgctgga agaagcaaat aaacaactaa aaaacaaggt acatatctat  10440
atatgtgtgt taattaatta agttgatttt gtatttttgt ttaatgaata attgtttgtg  10500
atcatcagct ggaagaaagt gcagctagaa ttccacttgg attgtcatgg ggaaataatg  10560
gaggacaaac aatggaatac aatcgactcc ctccacaaac tactgcacaa cctttctttc  10620
aacctctccg tttgaattct tcatcgcctc aattcgggta agtatcttat tttatatgac  10680
ttagtttgac ttgacataaa gtttaataaa gaaagaaaga cttttaaaac ttatagtgta  10740
aaataagtga atagatatat atgtggttgt actaacacta caacaaaaat aattttcagc  10800
ggcattaaat attgacatta ataatgagtg ctaaagactt tatcggtatt agttaagtgt  10860
cattaggatc aatgtcgtta aaggcttcac ggacatatac aaagagtgac aattgccgct  10920
aatgattatt tttgttgtag tgaaaatgag tattttaaag ttaaattgtt acataatata  10980
gaaatatgtc agaaacagga caaatatacc accgaactat catatatgtt atggagatat  11040
tctcagtcat acttctgcga cattggtact catgtcgtcc aaaaactaga acatatatat  11100
accctttata tattaacgaa gatacaagtg tcataatctt atgcaccgat tcgatattta  11160
ttaaatatcg aatcgacgga taaaattatg tcacgtgtcc ctattaagtc ttctattaga  11220
gtaaaaagca tatattctct agtttttgaa cgaaaaaagg tattaatgtc tcaaaagtat  11280
aacgaaaagc atttgcatac aatttatgat aatttggggc atattaattt atcattcccc  11340
cttttttggg cactgattaa aaagaaaaag aaagttataa aaattgggat agagggaata  11400
attgtttcat agggaaaact tagaagcttc tcagtatgtc agtgagaatg tgtttcctaa  11460
ttagtgaact atggtttggt gaaaaataaa gagaaaaaaa tcagtacaaa ttttccactg  11520
attagcaatg agaaaaatat ttgtttctag tagtatgagg agaggatagt ccgcataaat  11580
aatccttaaa tttgtggata aataaactat tttcaataga ttatcgtctc aaaataaaat  11640
aaaatgattg caagaaaaga ataataggta tgctggtaat atgtataata cactcaaatt  11700
tatttgctgt ccatgcagat acaatccaaa tatgggtgca aatgatcatg aggttaatgc  11760
agcaacaact gctcataata ttaatggatt tattccaggg tggatgctct aa          11812
```

<210> SEQ ID NO 10
<211> LENGTH: 11810
<212> TYPE: DNA
<213> ORGANISM: Artificial Sequence
<220> FEATURE:
<223> OTHER INFORMATION: Synthetic polynucleotide

<400> SEQUENCE: 10

```
atgggaagag gaagagtaga actaaagaga atagagaaca aaataaacag gcaagttact     60
tttgctaaga gaagaaatgg acttcttaag aaagcttatg agttatctat actttgtgat    120
gctgaagttg ctctcatcat cttctctagc cgcggaaaac tctatgagtt ttcaagtgct    180
tccaggtata tatatatata catatgtttt tcttcttttt gtgtgtgcgt atgtgtttac    240
ttactttcat taattaactc aaccatatat atacatctct cacctcaatt atatatatgt    300
ttgagatctg aatgtctacg gactccattt aggtacatat ctttgtttag atcataaatc    360
atctatcttc attcctaaga tctactaata tatatgtata agaagatcca tccatctatt    420
aggtttttca acaacatata cagtgaaatc ttatatgtgg gcccacgtat agccatatga    480
gaaaatagtg tgcacgtaaa cattatcatt acttaattat aggaatatac atccattagg    540
tttatcaaca acaataaaat cctctaaatg gagtctagtc ataggtctag ccgtttgaaa    600
atgtaaaata tatgccgatc ttatcactat gtcataataa tagatatgtt gttattgaaa    660
gattctcaat cttttttttt cttcaaggta gagattctta agtggattca tgtttttttt    720
atcaaaaaag aaaaaaacaa aagtgtccat ttgttcatct aatgggtttt ccatgttacc    780
aattcactac actgttgaga tttgattatc agatgtgtca agtttcgttt ggttccctag    840
aagggagaaa aggctgctta tgcaggcagg gtattaaaga tgatattaat atctgcagta    900
atcagtaaca gaatatataa acttaataat aaacttgaag gtacttaatt atccagcaga    960
taatcttctg tctcaccgta cacttttgtt atatcataag cataagaatt gttttatcaa   1020
atattaccaa acaaaactta gttttgtttg gtaatatttt ataaaatatg ttaccgaaag   1080
ttacttccta taacatattt tataaagaaa aaaattaaaa actccatata cctaagaaat   1140
gtaacccccc ctccataaca acaatttaac aaaaataaaa acctactttt tttgaatttg   1200
gtaaattagt tttctatcct ttttagtaac ttcctttctt attttctttt tatattggta   1260
aagtttaata ttacacatta ttttaacatg ttataatttt ttgtgatgct taattatttg   1320
atacatgtaa taaaccatat attagagcta taaatcaatg acaatgcatg tagatacaac   1380
tcatttatga tatattttgt ttatatatat aaccaattag ataatttgtc tgcgctttgt   1440
gcagtcataa ataataattg cattgaactt gcaaatattt ttttttaata tccatacatt   1500
aaaaaaaaag aaagaggaaa attggttcct aaaatattag caatattcaa acatttattt   1560
gattattaat cattatcaca taacttaaga acgtctaatg aatgaattat tcacgaaata   1620
ataaatcatt ggttctaaaa aggaatttcg taataaaata aaaatttaag ttaccatatt   1680
caaaaaaaga aattgtgctt gaacatgaaa ataattataa tttttgaact tgtataatga   1740
atttcttcaa ttcataagtg ggaaatttca tatttatgta ataatagata atatgtaagc   1800
tctaatatag tactttaggt tatagaattt aatataaaat atcaaaacat gaattcttga   1860
aattgagtag agtaattatt ttctgcacaa tgaatcggag acaataactt tgaagaaata   1920
taaacaatag agttcaaaag atgtagtcaa aaacaacaat taatatcata agaataaatt   1980
aatgagtgta aaaatgcata ccacgatatg taaaaacaga atggaatata ataaaaaaaa   2040
tcgagttcac tgaatacaca atgttccttt aagaaaatta ttctcctcca ataccaacga   2100
gattacatcc tctaaggatg gaaatgattt cattccccaa cttatccata taaaaatagt   2160
ggtgttagta tgtaactcaa taggagtaaa atacacaaat atttaatttt gcgaaagtag   2220
aagaagaaga tcatattttt tttttaaaat gagaggatat atcactattt ttaaacaaca   2280
aagggtagtg ttaacaaatt tttattgtgt cttgtctaaa aggttacagc tatttgaaaa   2340
```

-continued

```
agttacaaca cttcgaaaag tgaacaacat ttcataaaag tcgtaacttt tcataaagtc   2400
gtaactcttc ataaatgtcg caactcttca taaaaattac aactattgat aaaagtcacc   2460
actcttgata aagatcacca ctcttcattg aagttgcaac ttttcataaa aatcacatct   2520
tttaataaaa aagaaagact agtttttgga ataaattaat ttaaaagaaa atttttgttt   2580
gtggtggggc gccaagtagg caggcgtagg gttcttttta tataaatata tatgatatat   2640
gattcaatat ttgatatata tatatataga gagagagatg acaatataag acaattgcaa   2700
aaaataaaat aaaaaactaa tcgagtaagt aggcaaaaaa ttatttataa aatatatgta   2760
gaatttcttt atcagatatg actgcccaaa tcttatattc aaactaaaat gcaagatcaa   2820
tggtgctata tatagggttt tacacaaaaa tcaagatcta gtcttgcaaa tttaaataaa   2880
aaacagtggt ttacgatgag ataatgtagc ttttgtaaac aataaaacta gaaaaataaa   2940
tgcaaaggca ttttaaagga tataataatg aagatcaaag gcagagaagg gaagaggcag   3000
caatataatg aaggtaacat catggttcca ttctaatata tatgctattt ttctttagta   3060
aatttcaaaa ataatgatac attttcatat ttgataaata tttaatgata ctatcaacat   3120
tttatctata ttgagttcca tttatttgac caaaacctca caaagatgtg ctcttcgatc   3180
tattcaaaat ttattcaatt taaggatagc tttaaaacat gacaaagttt tctcatatat   3240
ttcttaaatt ttatatccag tctaaatacg tatataaact aaaatgaaga gaataatatg   3300
aagctttatt tgatgacatt gttgaaataa ccaaaagcta taagtgatac aatagtaaat   3360
ttaccattgg tcaattcaga attatttaaa agctaaaaaa gtcatataag ttggggttgc   3420
tcaatgtata gtttttggct tgttttaagc attttaaaac ttttttaag cgctttttaa   3480
cattgctaaa cactcaaaaa atgataaata gtatttaaat ttgatatgat tagcttaaaa   3540
gtgaactcat ataccttcaa agtaaaaatc cccaattcga gctttcaaac cacttgattt   3600
tgtggatgaa attatactga agttgaatat atcactattt ataggggtta gtgaactaat   3660
acctttgatt atttggtaga aatatgtatc ttagatcacc ctaatgagct cccactttta   3720
aaataggaaa aacctcatat gaagttcatc actgttcatt atatatcact tttattcaaa   3780
aacgtttaca aatgttcatt gtgactaaat acccttgagt gtcgagtttt cacaccaata   3840
aggcctaatt aataggtaaa caaaactatg tcaatcttca aaacgcaaat ctaattatat   3900
ttttaacaag attagaggta tatatacata ttctcttatg ttaactctta ttcattattg   3960
aacaaactaa gtaagtgtac ccaaggtctc aaacaacagt tggtacattc tttgtatgtc   4020
ttcctttgtc tcttaatagt cgtctcctcc tgtcgatgat tcctccaaat acattaatca   4080
aaggaaaatc tttcgccctc aacttgcaaa cttgtctatc taaaattgtt aacaaagttt   4140
cttcattaga gaaactatga tttcttgaat gtagcaattt gatgtgccat gactatcatc   4200
ttgatcaaca tgcttcttaa ccatcaaaag atcctaaact agatgcatgt catgttagga   4260
gacatattaa gcttgtatat aactacacca acatgcttta ggatctcata agatccaaaa   4320
tttcttattt gggagatttt caatccaaca accatcataa tgagcaacgt gatgttataa   4380
catctctctc acactgccag aacagtctta taccttgtcg gagtgaagga catccttaac   4440
taagtagatt cactaagcta tacttaaaaa gcaataagga atcatctaaa atgtgtgact   4500
cttaacccat attggcatac atggtttatg gggttatta attgtctgaa cactcccccca   4560
tataaatcag tgatcaatat taatcccaat aatatacact attatgattt gagactacac   4620
cctggaagtg gccggctctc aagaaccatt gctgatctcc aagccaaacc ctcattctgg   4680
ttgactacaa gctgaaggca aactcaagta tacaaagctt aaaacataat aaaaataata   4740
```

```
tactcaactc gccacaaaat aggcatttaa gtctttaaaa catttttaaa aataaatgaa   4800
acaaacttct caaactgtaa tgtatatcta tgaagcctct aaatgaaaaa aatgaaggca   4860
gatgagacat acggcatcct aacaactgat ataactaaga gtacaagtgg agcccttcgg   4920
atgtaaggag gctcatcaaa gctaatgtga actccatgtg gtatcaatga agcacctatt   4980
gatgaccgtg aatacatgta tctgcatcat gaaacgatgc aggccaaagg gcttagtacg   5040
tgaaatgtac gagcatgtaa agggaattca aatacataaa cataggcttg aactttgata   5100
taaaggaaac atacttacct atttttaact caagaataaa aaacatagtt caactcaatg   5160
aaaagacact caagtcagtg aaataggccg caactcaata ataagatatt cgactatggg   5220
taatcaactc tgggtactct attcaatata aagtaagaat acaaatgcat tatatggaaa   5280
gactttaaaa cggtagaaaa caactcaatg tattgaaaat tcaatagtaa attagtttgt   5340
atgtaaggaa caatataaac tttgtttgta tatgaaaata caaaataaac tttgtgtata   5400
taaaagtaca aaatatctct gtgaaagttt ctctaaccaa caaccatcac tatgagcttt   5460
ctgataatac cacgtttcgc ccatgatgtc agaactgtcc tatgattttc cagttcataa   5520
gacctactca ctaagtggat ccacaagtct atgctaaaaa atatttaagg aatcgtctaa   5580
aaagtatgac tcattctacc cacgttggct acatgattta tgggggtcgt aagttatcta   5640
aactctcctc catatcgatg cgtaatgcta ctcacaaata tactagctca catgtttaaa   5700
aatataactc gttttgtttg agatcattac tcaaaatcct tctcttaaaa gagatgatac   5760
tcaaactgct caaaactctt ttggaaatct caaattcgtc tcatcttaaa tgtaaaaata   5820
tttactcttg ggaatacata gttatcatat atcattttaa agaaaatgaa ctcaactctg   5880
ttctttctca actcaagtgc tcagtcttaa accaaattaa aaaaaagact tctcaaaata   5940
aagtttatgt cgaattatgg acgtgaacaa ttcaattcaa agttttcgat aaccataact   6000
aaaactaaat actcgagact caacatctta gaactcaaga acttaaatgg taatacttct   6060
ttcaagaatg ctcgactcag aaggttaatg cagaataatg tgcatgaatt actcaactaa   6120
aggactcact gatactactc aatctcaaga ttgctcgact cgtagggtta atgcagaatt   6180
atgtgcatga actactcaac tcaaagacct tcataggtaa catgtagtag ccccatgatt   6240
tggaatataa tcccaaaatg attaggaact caatactcag gacttagaac ttgaagataa   6300
tactacttct ctcaaagata cccaactgac ggagttcatg cagaatttat gggcatgaac   6360
tactcgactc aagagtctaa aacacaatat gacactcatg tatataactc ttctcattct   6420
aatacttgtt ttctcaaaac tcggtttaac taaatagttg atctcaaagg attcacaatt   6480
gaactcaaag actttctttg actccactct taattctctc ttaaatttgt atttgaatta   6540
tgaatttaag agttatgatt catgatatgg ggaatctcaa taacaatata gaaatttgat   6600
aattaggaat agtactttta aaagaaaaca tgaattcaac ttaaaatcaa cttatctaaa   6660
aaatattcaa atatagggaa agtatcctag actactgtgc tactgatctg aaagtagatg   6720
taggatgtga ggatgaacta gtccaacact atgatagcct tacatacctg gaataacgag   6780
gttcttggaa aatcttcact tgaagaagaa cttgattaga agccttgaaa cctagcttga   6840
aggtaaacaa tcaagaaaac ctttcttaag attcttgaat tagtttatga aaatctctat   6900
gaccaagcat tttgattttc actagtgatt cataattgta tggaggaatt tgaattgaaa   6960
aagatgaaat gcttggagaa aagctatctt tgaagaagct tgaaaaagat tggaaagtcc   7020
tgtactttga ttttccctta ggattttgtc ttagggtttg agatagaaaa gaatgatgga   7080
```

```
ctaaaagatg aaaatctaat tgtttggatc ctttttcagc caagaaatcc gtttagggtt   7140
ttcttggaga caaacaaaat aaaaaagacc atttttaata tttttccgtc ggctaattcg   7200
taataacatt gtatcatgtt attgaaagag tcataacttt ttactcaaaa attggattga   7260
tgcgaaatta gtggtgttgg aaagtagatt caagtacctc taattggata ggttattccc   7320
tacataagtc tttatattct aaaagatatg gttgtttgca cttgacctaa gtagaatttt   7380
acatgaaaac ttaatagaga aggaaacttc aagaactcat caagaaattt caattgctca   7440
atatttatgg ataaatttgt agaagaaact catgattgac atgcgggtga ataaacccaa   7500
cactatggaa gcttacatac ctcaaagaac taggttcttg gcgaaatctt gaatttcttc   7560
aacgaacgct tgaaactttg aactttttct cttcttgaac tctcaactaa aaccctaggc   7620
gtatattagg attataaaag ttaacatgat aggattagac ctttaaaaac tttctaaaat   7680
gaattaaatc tgatttagca tgaaaaagac caaaataccc cttactattt tcggataact   7740
tttcttaatt ggactgcctg acttcaaaaa ggtatatctc actcatccga cctcaaaatt   7800
tagcaaattc agtggcgtta gaaagctaat ttaaacacct ttcattttcc atctcatggc   7860
acacataact cattctttaa agagagctat gatcgttcaa attaactcaa atcttagaag   7920
aatttaggaa tgtcttgaac gagctacatc tagtgacctt aacactttgg aaaattttaa   7980
atttcttagt aaaaacttac tcactatgaa ggatggttca agtcttagct caaaattttc   8040
ctaagttgct atatatactc atgctcatat gtttaaaacc aaaacccttc ctcgatttga   8100
attaattacc aaaaagattc tcttaaaaag ataatgctca aaactccccc taaactcatt   8160
tggaaatcta ggtttccctt gttttaaata taaaaacatt tactcttgga aatatttagt   8220
tctcagatat tcacttgaaa aaaattaaac tcgactctca tcatcttcat actcaagtgc   8280
tcaagtccta aaacaattta taactaattg tataagactt ctcaaaatag ggttcattcc   8340
gaattatgga cgtgaacgac tcaattcaag gatttcaata accatatata taactcaata   8400
ataggaactc aacaactcca gaactcaatg atactactca tctcaagaat gctcgactca   8460
cagggtcttt gcgaaattat tggcatgaa caactcaact caaagacctt catttatacc    8520
atatggtagt cccataatag gaatataatc ccaaaaaaat taggaactca atactcaaaa   8580
acttagaact cgaagatatt actcatctca aagatattca atttatggaa ttcatgctga   8640
attatgagca tgaacgactt gactcaagga tctcaataat aatgtagact catgaataca   8700
ctcttctcat tctcatactc acatactcga gtattaaaat aaattataag taattgcaga   8760
agactccttg aacagactca aaaggactcc ttcgaatttt actcttaatg ctacctgaat   8820
tttgtattat aaatttaagg atcatgatta tgatataaag aatttctcag catatatgaa   8880
atgaacgaat ttgagcattg aacgtctaac ctcatttttt aattattgtg atatgtagag   8940
tggtgcaaaa tcacagatac ctctcttgat gcatttctat agttacgttg atgtgagatt   9000
atatatagtt cagcagcagc atgttgggaa aattactaat aactcttctt ttatatcaaa   9060
ttgttgaagc atgatgacaa cacttgaaaa gtatcaacaa tgcagttacg catctttgga   9120
cccgatgtta ccggttagtg atactcaggt attgtttatc tactttatca tgtcgtaagt   9180
atattatttg taaagatata tatcaagata gttcgattgc gtacacttac attttgatta   9240
tgtttggtga atactattct aataccttttt tttttcctaa agcctaacaa ataaagataa  9300
ttaagatggg aacgtaattc aagtacaaca tggttccata cgtgacatat ttacacatat   9360
agtggaacca aaagagcaat ttttcctaat atcattttct aaatatcacg tgtgcccgtg   9420
attctttttt atggacatga attttttttt taatatgagt ggaagtaagg ttcgatcttt   9480
```

```
ctatctgctt tgatatcata ttgaatcgtg tgattgtctc tttaaaaaat taagcaagag   9540
catattttat taattaattg tctttctcga cgtttttctc tttcaacaga tgaactacaa   9600
tgagtatgtg aggctaaaag ctagagttga gctccttcaa cgttcttcaa aggtaagata   9660
ttagtgatgt aattaaatga ttttagttag atttacataa gtttttaata agtgaaaatt   9720
aatagacata ttcttggaga tttgggcaca ctaaactcga aagaacttga gcagcttgag   9780
caccaattgg atgcatcttt gaagaaagtt agatcaaaaa aggtatatcc aaatactata   9840
acttaaatat attgtaacga tttaattaat agcatgtgtc acgttcatct attctttagt   9900
cacaatatat aggggcatgt ccttaacaac gtgccatgcc tcgatagtca tttttgtctt   9960
tttgtgcgta tgaatttaac tttgacacaa atttttgtag taataataac tcatgcttta  10020
gcatcttagg aagcagtcat atgaaaaaca gaagcatata tatatattac atgagttaat  10080
ttaatttaat ataaaattta ataaaattgt gtctcgctat aaataatttt attaaaaaat  10140
tatataaata tattattttt ttaactggcc gcaaagttat ataaattgat agagaaagag  10200
gttttggtgt aaggttcatt ttccaacaat tagttttata atttgtaagt gcacacttta  10260
tcagactcaa tctatgctgg atcagctggc agaccttcaa gaaaaggtac actgccttaa  10320
cattacaaaa ttaatttatt tcatcaaaag catatcataa aattctgaca aataaatata  10380
ttaggagcaa atgctggaag aagcaaataa acaactaaaa aacaaggtac atatctatat  10440
atgtgtgtta attaattaag ttgattttgt atttttgttt aatgaataat tgtttgtgat  10500
catcagctgg aagaaagtgc agctagaatt ccacttggat tgtcatgggg aaataatgga  10560
ggacaaacaa tggaatacaa tcgactccct ccacaaacta ctgcacaacc tttctttcaa  10620
cctctccgtt tgaattcttc atcgcctcaa ttcgggtaag tatcttattt tatatgactt  10680
agtttgactt gacataaagt ttaataaaga aagaaagact tttaaaactt atagtgtaaa  10740
ataagtgaat agatatatat gtggttgtac taacactaca acaaaaaataa ttttcagcgg  10800
cattaaatat tgacattaat aatgagtgct aaagacttta tcggtattag ttaagtgtca  10860
ttaggatcaa tgtcgttaaa ggcttcacgg acatatacaa agagtgacaa ttgccgctaa  10920
tgattatttt tgttgtagtg aaaatgagta ttttaaagtt aaattgttac ataatataga  10980
aatatgtcag aaacaggaca aatataccac cgaactatca tatatgttat ggagatattc  11040
tcagtcatac ttctgcgaca ttggtactca tgtcgtccaa aaactagaac atatatatac  11100
cctttatata ttaacgaaga tacaagtgtc ataatcttat gcaccgattc gatatttatt  11160
aaatatcgaa tcgacggata aaattatgtc acgtgtccct attaagtctt ctattagagt  11220
aaaaagcata tattctctag tttttgaacg aaaaaaggta ttaatgtctc aaaagtataa  11280
cgaaaagcat ttgcatacaa tttatgataa tttggggcat attaatttat cattccccct  11340
ttttttggca ctgattaaaa agaaaaagaa agttataaaa attgggatag agggaataat  11400
tgtttcatag ggaaaactta gaagcttctc agtatgtcag tgagaatgtg tttcctaatt  11460
agtgaactat ggtttggtga aaaataaaga gaaaaaaatc agtacaaatt ttccactgat  11520
tagcaatgag aaaaatattt gtttctagta gtatgaggag aggatagtcc gcataaataa  11580
tccttaaatt tgtggataaa taaactattt tcaatagatt atcgtctcaa aataaaataa  11640
aatgattgca agaaaagaat aataggtatg ctggtaatat gtataataca ctcaaattta  11700
tttgctgtcc atgcagatac aatccaaata tgggtgcaaa tgatcatgag gttaatgcag  11760
caacaactgc tcataatatt aatggattta ttccagggtg gatgctctaa             11810
```

<210> SEQ ID NO 11
<211> LENGTH: 11906
<212> TYPE: DNA
<213> ORGANISM: Artificial Sequence
<220> FEATURE:
<223> OTHER INFORMATION: Synthetic polynucleotide

<400> SEQUENCE: 11
atgggaagag gaagagtaga actaaagaga atagagaaca aaataaacag gcaagttact 60
tttgctaaga gaagaaatgg acttcttaag aaagcttatg agttatctat actttgtgat 120
gctgaagttg ctctcatcat cttctctagc cgcggaaaac tctatgagtt ttcaagtgct 180
tccaggtata tatatatata catatgtttt tcttcttttt gtgtgtgcgt atgtgtttac 240
ttactttcat taattaactc aaccatatat atacatctct cacctcaatt atatatatgt 300
ttgagatctg aatgtctacg gactccattt aggtacatat ctttgtttag atcataaatc 360
atctatcttc attcctaaga tctactaata tatatgtata agaagatcca tccatctatt 420
aggtttttca acaacatata cagtgaaatc ttatatgtgg gcccacgtat agccatatga 480
gaaaatagtg tgcacgtaaa cattatcatt acttaattat aggaatatac atccattagg 540
tttatcaaca acaataaaat cctctaaatg gagtctagtc ataggtctag ccgtttgaaa 600
atgtaaaata tatgccgatc ttatcactat gtcataataa tagatatgtt gttattgaaa 660
gattctcaat cttttttttt cttcaaggta gagattctta agtggattca tgtttttttt 720
atcaaaaaag aaaaaaacaa aagtgtccat ttgttcatct aatgggtttt ccatgttacc 780
aattcactac actgttgaga tttgattatc agatgtgtca agtttcgttt ggttccctag 840
aagggagaaa aggctgctta tgcaggcagg gtattaaaga tgatattaat atctgcagta 900
atcagtaaca gaatatataa acttaataat aaacttgaag gtacttaatt atccagcaga 960
taatcttctg tctcaccgta cacttttgtt atatcataag cataagaatt gttttatcaa 1020
atattaccaa acaaaactta gttttgtttg gtaatatttt ataaaatatg ttaccgaaag 1080
ttacttccta taacatattt tataaagaaa aaaattaaaa actccatata cctaagaaat 1140
gtaacccccc ctccataaca acaatttaac aaaaataaaa acctactttt tttgaatttg 1200
gtaaattagt tttctatcct ttttagtaac ttcctttctt atttcttttt tatattggta 1260
aagtttaata ttacacatta ttttaacatg ttataatttt ttgtgatgct taattatttg 1320
atacatgtaa taaaccatat attagagcta taaatcaatg acaatgcatg tagatacaac 1380
tcatttatga tatattttgt ttatatatat aaccaattag ataatttgtc tgcgctttgt 1440
gcagtcataa ataataattg cattgaactt gcaaatattt ttttttaata tccatacatt 1500
aaaaaaaaag aaagaggaaa attggttcct aaaatattag caatattcaa acatttattt 1560
gattattaat cattatcaca taacttaaga acgtctaatg aatgaattat tcacgaaata 1620
ataaatcatt ggttctaaaa aggaatttcg taataaaata aaaatttaag ttaccatatt 1680
caaaaaaaga aattgtgctt gaacatgaaa ataattataa tttttgaact tgtataatga 1740
atttcttcaa ttcataagtg ggaaatttca tatttatgta ataatagata atatgtaagc 1800
tctaatatag tactttaggt tatagaattt aatataaaat atcaaaacat gaattcttga 1860
aattgagtag agtaattatt ttctgcacaa tgaatcggag acaataactt tgaagaaata 1920
taaacaatag agttcaaaag atgtagtcaa aaacaacaat taatatcata agaataaatt 1980
aatgagtgta aaaatgcata ccacgatatg taaaaacaga atggaatata ataaaaaaaa 2040
tcgagttcac tgaatacaca atgttccttt aagaaaatta ttctcctcca ataccaacga 2100

```
gattacatcc tctaaggatg gaaatgattt cattccccaa cttatccata taaaaatagt   2160

ggtgttagta tgtaactcaa taggagtaaa atacacaaat atttaatttt gcgaaagtag   2220

aagaagaaga tcatattttt tttttaaaat gagaggatat atcactattt ttaaacaaca   2280

aagggtagtg ttaacaaatt tttattgtgt cttgtctaaa aggttacagc tatttgaaaa   2340

agttacaaca cttcgaaaag tgaacaacat ttcataaaag tcgtaacttt tcataaagtc   2400

gtaactcttc ataaatgtcg caactcttca taaaaattac aactattgat aaaagtcacc   2460

actcttgata aagatcacca ctcttcattg aagttgcaac ttttcataaa aatcacatct   2520

tttaataaaa aagaaagact agtttttgga ataaattaat ttaaaagaaa atttttgttt   2580

gtggtggggc gccaagtagg caggcgtagg gttcttttta tataaatata tatgatatat   2640

gattcaatat ttgatatata tatatataga gagagagatg acaatataag acaattgcaa   2700

aaaataaaat aaaaaactaa tcgagtaagt aggcaaaaaa ttatttataa aatatatgta   2760

gaatttcttt atcagatatg actgcccaaa tcttatattc aaactaaaat gcaagatcaa   2820

tggtgctata tatagggttt tacacaaaaa tcaagatcta gtcttgcaaa tttaaataaa   2880

aaacagtggt ttacgatgag ataatgtagc ttttgtaaac aataaaacta gaaaaataaa   2940

tgcaaaggca ttttaaagga tataataatg aagatcaaag gcagagaagg gaagaggcag   3000

caatataatg aaggtaacat catggttcca ttctaatata tatgctattt ttctttagta   3060

aatttcaaaa ataatgatac attttcatat ttgataaata tttaatgata ctatcaacat   3120

tttatctata ttgagttcca tttatttgac caaaacctca caaagatgtg ctcttcgatc   3180

tattcaaaat ttattcaatt taaggatagc tttaaaacat gacaaagttt tctcatatat   3240

ttcttaaatt ttatatccag tctaaatacg tatataaact aaaatgaaga gaataatatg   3300

aagctttatt tgatgacatt gttgaaataa ccaaaagcta taagtgatac aatagtaaat   3360

ttaccattgg tcaattcaga attatttaaa agctaaaaaa gtcatataag ttggggttgc   3420

tcaatgtata gtttttggct tgttttaagc attttaaaac tttttttaag cgctttttaa   3480

cattgctaaa cactcaaaaa atgataaata gtatttaaat ttgatatgat tagcttaaaa   3540

gtgaactcat ataccttcaa agtaaaaatc cccaattcga gctttcaaac cacttgattt   3600

tgtggatgaa attatactga agttgaatat atcactattt atagggggtta gtgaactaat   3660

acctttgatt atttggtaga aatatgtatc ttagatcacc ctaatgagct cccactttta   3720

aaataggaaa aacctcatat gaagttcatc actgttcatt atatatcact tttattcaaa   3780

aacgtttaca aatgttcatt gtgactaaat acccttgagt gtcgagtttt cacaccaata   3840

aggcctaatt aataggtaaa caaaactatg tcaatcttca aaacgcaaat ctaattatat   3900

ttttaacaag attagaggta tatatacata ttctcttatg ttaactctta ttcattattg   3960

aacaaactaa gtaagtgtac ccaaggtctc aaacaacagt tggtacattc tttgtatgtc   4020

ttcctttgtc tcttaatagt cgtctcctcc tgtcgatgat tcctccaaat acattaatca   4080

aaggaaaatc tttcgccctc aacttgcaaa cttgtctatc taaaattgtt aacaaagttt   4140

cttcattaga gaaactatga tttcttgaat gtagcaattt gatgtgccat gactatcatc   4200

ttgatcaaca tgcttcttaa ccatcaaaag atcctaaact agatgcatgt catgttagga   4260

gacatattaa gcttgtatat aactacacca acatgcttta ggatctcata agatccaaaa   4320

tttcttattt gggagatttt caatccaaca accatcataa tgagcaacgt gatgttataa   4380

catctctctc acactgccag aacagtctta taccttgtcg gagtgaagga catccttaac   4440
```

-continued

```
taagtagatt cactaagcta tacttaaaaa gcaataagga atcatctaaa atgtgtgact   4500
cttaacccat attggcatac atggtttatg ggggttatta attgtctgaa cactccccca   4560
tataaatcag tgatcaatat taatcccaat aatatacact attatgattt gagactacac   4620
cctggaagtg gccggctctc aagaaccatt gctgatctcc aagccaaacc ctcattctgg   4680
ttgactacaa gctgaaggca aactcaagta tacaaagctt aaaacataat aaaaataata   4740
tactcaactc gccacaaaat aggcatttaa gtctttaaaa catttttaaa aataaatgaa   4800
acaaacttct caaactgtaa tgtatatcta tgaagcctct aaatgaaaaa aatgaaggca   4860
gatgagacat acggcatcct aacaactgat ataactaaga gtacaagtgg agcccttcgg   4920
atgtaaggag gctcatcaaa gctaatgtga actccatgtg gtatcaatga agcacctatt   4980
gatgaccgtg aatacatgta tctgcatcat gaaacgatgc aggccaaagg gcttagtacg   5040
tgaaatgtac gagcatgtaa agggaattca aatacataaa cataggcttg aactttgata   5100
taaaggaaac atacttacct atttttaact caagaataaa aaacatagtt caactcaatg   5160
aaaagacact caagtcagtg aaataggccg caactcaata ataagatatt cgactatggg   5220
taatcaactc tgggtactct attcaatata aagtaagaat acaaatgcat tatatggaaa   5280
gactttaaaa cggtagaaaa caactcaatg tattgaaaat tcaatagtaa attagtttgt   5340
atgtaaggaa caatataaac tttgtttgta tatgaaaata caaaataaac tttgtgtata   5400
taaaagtaca aaatatctct gtgaaagttt ctctaaccaa caaccatcac tatgagcttt   5460
ctgataatac cacgtttcgc ccatgatgtc agaactgtcc tatgattttc cagttcataa   5520
gacctactca ctaagtggat ccacaagtct atgctaaaaa atatttaagg aatcgtctaa   5580
aaagtatgac tcattctacc cacgttggct acatgattta tgggggtcgt aagttatcta   5640
aactctcctc catatcgatg cgtaatgcta ctcacaaata tactagctca catgtttaaa   5700
aatataactc gttttgtttg agatcattac tcaaaatcct tctcttaaaa gagatgatac   5760
tcaaactgct caaaactctt ttggaaatct caaattcgtc tcatcttaaa tgtaaaaata   5820
tttactcttg ggaatacata gttatcatat atcattttaa agaaaatgaa ctcaactctg   5880
ttctttctca actcaagtgc tcagtcttaa accaaattaa aaaaaagact tctcaaaata   5940
aagtttatgt cgaattatgg acgtgaacaa ttcaattcaa agttttcgat aaccataact   6000
aaaactaaat actcgagact caacatctta gaactcaaga acttaaatgg taatacttct   6060
ttcaagaatg ctcgactcag aaggttaatg cagaataatg tgcatgaatt actcaactaa   6120
aggactcact gatactactc aatctcaaga ttgctcgact cgtagggtta atgcagaatt   6180
atgtgcatga actactcaac tcaaagacct tcataggtaa catgtagtag ccccatgatt   6240
tggaatataa tcccaaaatg attaggaact caatactcag gacttagaac ttgaagataa   6300
tactacttct ctcaaagata cccaactgac ggagttcatg cagaatttat gggcatgaac   6360
tactcgactc aagagtctaa aacacaatat gacactcatg tatataactc ttctcattct   6420
aatacttgtt ttctcaaaac tcggtttaac taaatagttg atctcaaagg attcacaatt   6480
gaactcaaag actttctttg actccactct taattctctc ttaaatttgt atttgaatta   6540
tgaatttaag agttatgatt catgatatgg ggaatctcaa taacaatata gaaatttgat   6600
aattaggaat agtactttta aaagaaaaca tgaattcaac ttaaaatcaa cttatctaaa   6660
aaatattcaa atatagggaa agtatcctag actactgtgc tactgatctg aaagtagatg   6720
taggatgtga ggatgaacta gtccaacact atgatagcct tacatacctg gaataacgag   6780
gttcttggaa aatcttcact tgaagaagaa cttgattaga agccttgaaa cctagcttga   6840
```

```
aggtaaacaa tcaagaaaac ctttcttaag attcttgaat tagtttatga aaatctctat   6900
gaccaagcat tttgattttc actagtgatt cataattgta tggaggaatt tgaattgaaa   6960
aagatgaaat gcttggagaa aagctatctt tgaagaagct tgaaaaagat tggaaagtcc   7020
tgtactttga ttttccctta ggattttgtc ttagggtttg agatagaaaa gaatgatgga   7080
ctaaaagatg aaaatctaat tgtttggatc ctttttcagc caagaaatcc gtttagggtt   7140
ttcttggaga caaacaaaat aaaaaagacc atttttaata tttttccgtc ggctaattcg   7200
taataacatt gtatcatgtt attgaaagag tcataacttt ttactcaaaa attggattga   7260
tgcgaaatta gtggtgttgg aaagtagatt caagtacctc taattggata ggttattccc   7320
tacataagtc tttatattct aaaagatatg gttgtttgca cttgacctaa gtagaatttt   7380
acatgaaaac ttaatagaga aggaaacttc aagaactcat caagaaattt caattgctca   7440
atatttatgg ataaatttgt agaagaaact catgattgac atgcgggtga ataaacccaa   7500
cactatggaa gcttacatac ctcaaagaac taggttcttg gcgaaatctt gaatttcttc   7560
aacgaacgct tgaaactttg aactttttct cttcttgaac tctcaactaa aaccctaggc   7620
gtatattagg attataaaag ttaacatgat aggattagac ctttaaaaac tttctaaaat   7680
gaattaaatc tgatttagca tgaaaaagac caaaataccc cttactattt tcggataact   7740
tttcttaatt ggactgcctg acttcaaaaa ggtatatctc actcatccga cctcaaaatt   7800
tagcaaattc agtggcgtta gaaagctaat ttaaacacct ttcattttcc atctcatggc   7860
acacataact cattctttaa agagagctat gatcgttcaa attaactcaa atcttagaag   7920
aatttaggaa tgtcttgaac gagctacatc tagtgacctt aacactttgg aaaattttaa   7980
atttcttagt aaaaacttac tcactatgaa ggatggttca agtcttagct caaaattttc   8040
ctaagttgct atatatactc atgctcatat gtttaaaacc aaaacccttc ctcgatttga   8100
attaattacc aaaaagattc tcttaaaaag ataatgctca aaactccccc taaactcatt   8160
tggaaatcta ggtttccctt gttttaaata taaaaacatt tactcttgga aatatttagt   8220
tctcagatat tcacttgaaa aaaattaaac tcgactctca tcatcttcat actcaagtgc   8280
tcaagtccta aaacaattta taactaattg tataagactt ctcaaaatag ggttcattcc   8340
gaattatgga cgtgaacgac tcaattcaag gatttcaata accatatata taactcaata   8400
ataggaactc aacaactcca gaactcaatg atactactca tctcaagaat gctcgactca   8460
cagggtcttt gcgaaattat tgggcatgaa caactcaact caaagacctt catttatacc   8520
atatggtagt cccataatag gaatataatc ccaaaaaaat taggaactca atactcaaaa   8580
acttagaact cgaagatatt actcatctca aagatattca atttatggaa ttcatgctga   8640
attatgagca tgaacgactt gactcaagga tctcaataat aatgtagact catgaataca   8700
ctcttctcat tctcatactc acatactcga gtattaaaat aaattataag taattgcaga   8760
agactccttg aacagactca aaaggactcc ttcgaatttt actcttaatg ctacctgaat   8820
tttgtattat aaatttaagg atcatgatta tgatataaag aatttctcag catatatgaa   8880
atgaacgaat ttgagcattg aacgtctaac ctcatttttt aattattgtg atatgtagag   8940
tggtgcaaaa tcacagatac ctctcttgat gcatttctat agttacgttg atgtgagatt   9000
atatatagtt cagcagcagc atgttgggaa aattactaat aactcttctt ttatatcaaa   9060
ttgttgaagc atgatgacaa cacttgaaaa gtatcaacaa tgcagttacg catctttgga   9120
cccgatgtta ccggttagtg atactcaggt attgtttatc tactttatca tgtcgtaagt   9180
```

```
atattatttg taaagatata tatcaagata gttcgattgc gtacacttac attttgatta   9240
tgtttggtga atactattct aatacctttt tttttcctaa agcctaacaa ataaagataa   9300
ttaagatggg aacgtaattc aagtacaaca tggttccata cgtgacatat ttacacatat   9360
agtggaacca aaagagcaat ttttcctaat atcattttct aaatatcacg tgtgcccgtg   9420
attctttttt atggacatga attttttttt taatatgagt ggaagtaagg ttcgatcttt   9480
ctatctgctt tgatatcata ttgaatcgtg tgattgtctc tttaaaaaat taagcaagag   9540
catattttat taattaattg tctttctcga cgtttttctc tttcaacaga tgaactacaa   9600
tgagtatgtg aggctaaaag ctagagttga gctccttcaa cgttcatgca aaaaatgatt   9660
ataaaaaaag tactgcataa aaaaattagt taattttta gggaatcact atgtaggcca   9720
tagctagggg tgttggtggt tcaaaggtaa gatattagtg atgtaattaa atgattttag   9780
ttagatttac ataagttttt aataagtgaa aattaataga catattcttg gagagatttg   9840
ggcacactaa actcgaaaga acttgagcag cttgagcacc aattggatgc atctttgaag   9900
aaagttagat caaaaaaggt atatccaaat actataactt aaatatattg taacgattta   9960
attaatagca tgtgtcacgt tcatctattc tttagtcaca atatataggg gcatgtcctt  10020
aacaacgtgc catgcctcga tagtcatttt tgtctttttg tgcgtatgaa tttaactttg  10080
acacaaattt ttgtagtaat aataactcat gctttagcat cttaggaagc agtcatatga  10140
aaaacagaag catatatata tattacatga gttaatttaa tttaatataa aatttaataa  10200
aattgtgtct cgctataaat aattttatta aaaaattata taaatatatt atttttttaa  10260
ctggccgcaa agttatataa attgatagag aaagaggttt tggtgtaagg ttcattttcc  10320
aacaattagt tttataattt gtaagtgcac actttatcag actcaatcta tgctggatca  10380
gctggcagac cttcaagaaa aggtacactg ccttaacatt acaaaattaa tttatttcat  10440
caaaagcata tcataaaatt ctgacaaata aatatattag gagcaaatgc tggaagaagc  10500
aaataaacaa ctaaaaaaca aggtacatat ctatatatgt gtgttaatta attaagttga  10560
ttttgtattt ttgtttaatg aataattgtt tgtgatcatc agctggaaga aagtgcagct  10620
agaattccac ttggattgtc atggggaaat aatggaggac aaacaatgga atacaatcga  10680
ctccctccac aaactactgc acaacctttc tttcaacctc tccgtttgaa ttcttcatcg  10740
cctcaattcg ggtaagtatc ttattttata tgacttagtt tgacttgaca taaagtttaa  10800
taaagaaaga aagactttta aaacttatag tgtaaaataa gtgaatagat atatatgtgg  10860
ttgtactaac actacaacaa aaataatttt cagcggcatt aaatattgac attaataatg  10920
agtgctaaag actttatcgg tattagttaa gtgtcattag gatcaatgtc gttaaaggct  10980
tcacggacat atacaaagag tgacaattgc cgctaatgat tatttttgtt gtagtgaaaa  11040
tgagtatttt aaagttaaat tgttacataa tatagaaata tgtcagaaac aggacaaata  11100
taccaccgaa ctatcatata tgttatggag atattctcag tcatacttct gcgacattgg  11160
tactcatgtc gtccaaaaac tagaacatat atataccctt tatatattaa cgaagataca  11220
agtgtcataa tcttatgcac cgattcgata tttattaaat atcgaatcga cggataaaat  11280
tatgtcacgt gtccctatta agtcttctat tagagtaaaa agcatatatt ctctagtttt  11340
tgaacgaaaa aaggtattaa tgtctcaaaa gtataacgaa aagcatttgc atacaattta  11400
tgataatttg gggcatatta atttatcatt ccccctttt ttggcactga ttaaaaagaa  11460
aaagaaagtt ataaaaattg ggatagaggg aataattgtt tcatagggaa aacttagaag  11520
cttctcagta tgtcagtgag aatgtgtttc ctaattagtg aactatggtt tggtgaaaaa  11580
```

```
taaagagaaa aaaatcagta caaattttcc actgattagc aatgagaaaa atatttgttt  11640

ctagtagtat gaggagagga tagtccgcat aaataatcct taaatttgtg gataaataaa  11700

ctattttcaa tagattatcg tctcaaaata aaataaaatg attgcaagaa aagaataata  11760

ggtatgctgg taatatgtat aatacactca aatttatttg ctgtccatgc agatacaatc  11820

caaatatggg tgcaaatgat catgaggtta atgcagcaac aactgctcat aatattaatg  11880

gatttattcc agggtggatg ctctaa                                        11906
```

```
<210> SEQ ID NO 12
<211> LENGTH: 5813
<212> TYPE: DNA
<213> ORGANISM: Unknown
<220> FEATURE:
<223> OTHER INFORMATION: Solanaceae

<400> SEQUENCE: 12
```

```
atgggaagag gaagagttga gcttaagaga atagaaaata aaataaatag gcaagtcact     60

tttgctaaga gaagaaatgg acttcttaaa aaagcttatg aactttctgt tctttgtgat    120

gctgaagttg cccttataat cttctctaat aggggtaaac tctatgaatt ttgcagcact    180

tcaaggtatt ttttatttta ttatattaac atcaaagatt ttattttttt aaaaaaaacc    240

ttaagtcctt cattaccaaa acccttaatt gatttacaaa gtactttcat taaatttagt    300

aattcttttt ttttttatct ctgacttcaa ttataatgca agatctatgt tgtctttata    360

tatattgaat tatatatgta ctgtattttt actatataca tataagatcc tttttctttt    420

tttttctgtc tctttatata aatatatttt aaatagttga ttttgaaaga tctactaatg    480

tatatttatt tttggaactt ttgtgtatat ggaatttttt tctttttttat gtttttttt    540

tgttctaatt gttttaaaag cgtttaagat cagaatgttc ttgattattc ttttaggaaa    600

aagatttccc atacattgag ttattttttg atctgtagat tgaatttttt taatgagttc    660

cgatagattt tcgttcaatt tttcaatgaa actattgagg gttgatgatt agataattac    720

tcgattgaaa gtttttattt caaaaaaatt ataattcttc ttaattttat atttatgaga    780

tagagttagt ttagtgatta tatgaaaaat cgtatcagat tattgggaat cgaaacttaa    840

aaattctgaa aatattatta taaattttac atgttacaat atttttactg ttaagatttg    900

atttgcagac taggtgtcat gtttgacagt tgataaaaaa tctgttattt ttgttcttta    960

attcccaaga cggataaaca aaggctgctt atgttggttt ccaataagca gccataattt   1020

taaatatttt tgttaagatt aattaataac aattatttcc accagataat tttcaaaatt   1080

tgtgaccccg agttcatata aattgttaat tttactgcta gaaattacat cgataataat   1140

ttatttagtg taatcttata aatacgaggg cagtagtgta tagactgttt tttattaatc   1200

ctgactcaaa gtgaggtaag ttaagtatat tttgattaaa aggactacat ttcatttatg   1260

tatgtttaat taatattatt ttgtaagtca ataaatctaa acaacatgag tttatctaga   1320

cccttaatta tgcaccttca ttatcaattt tttcaatact ctcctcagaa catatgcttc   1380

tctataattt tgtgcacgag ttaatcaatt cttccttttc aataattaaa tatgtgattt   1440

atgtttagca cttatttttc ggttagttaa ttgataatag gaaaaagcct cttttttttt   1500

gtgtgtgtgg taattaggat ctttattgaa tttaaaatga cctactatag aacttgggag   1560

tttttcttca taataatgca ctgcaacgtg ttaaaaaaaa agaatcaaat gaaattaata   1620

gatgtttact ggattgccat ggtaaagtga taagtattaa tttcgcttta actaagagat   1680
```

-continued

```
cattatattc aagtcccctt gatacaaact tgcctttgta aataagtgtt ttatttttca   1740
atgtgaaact ttcgctgtta atttaaattt aattatactt ctatataaat accaaacaat   1800
aatgtaataa aacaaaaaat aaaagagtag atgtttcata ttgttaatgc agcatggtga   1860
aaacaattga aaagtaccaa cgttgcagct atgctacttt ggaagccaac caatcagtta   1920
ctgatactca ggtactgctt tatattttaa tttatttggc tttttttaa aaaaataatt   1980
agttttgatt aatatgcatc atttattta tttttggcaa ctctttattt atcagtaata   2040
agtaataact ttttaactag tatatttaaa aatcacaaaa tttaagaata ttttaataga   2100
ttcgacatat tttagtttaa aaataacaaa ttaaattatg tttttaattt tttaaatatt   2160
cttactataa ttatcatgta ctctttgatc tgttcatctt ttccatgata atattatttg   2220
gtcagttagt gacataagag tttgaaattt agaaaaaagg aatatttgga gaaaactgaa   2280
atggatattt agaaatgaaa gttatttaat ataaatataa gtatgggctg ctgagttggg   2340
aatccacgct ggagatctca agtttgaagc gtctcacaaa caatagtaat gtctttttgg   2400
tcgagtttgt cggattggac ttgtccgtgg cctgtgggtt acttttccta tatggtttgc   2460
aagctatcgg gaattttatc ctggcgcacc caaatttgag ttatttttga gtttttatat   2520
gaaatagctt tgtgaattca tcgaactccc gaaaacattg aactttactc caagttgaat   2580
tgcagtaaaa taatagtagc gattctttaa tttatcctaa cagtttttcg aaataataat   2640
cccaaaaaag tttaaaataa ccataccata aacttactgg gtaagatatt atctgtctaa   2700
taatatatag tagtttcttt tgttttatta gtttatctaa tccatatttc atttcttgat   2760
aagttattct taataggaaa ataaacttat ttcgaaaaac tgtttttaaa atttcttga   2820
gttgagtctt ggatgaaaaa tagttaattt tgcattaatt aattttgttc taacaaaaac   2880
taattaaatt tttttgaagc gcatattcac tcaaaaaaata aataaaaacc atcatgcata   2940
caggaaatgt tcttttttta atttattttt tcattggagc cctgactaat tttatatcgg   3000
ttcatacttt cataaattac aaaaagttca aaatttaaac taaccatata agtgaataaa   3060
ataaatcaac aaaatattca ccacataata ctttttaaat agaattttc ataccaaaga   3120
ccttacttta attaattagg gtgagagaat cctataagtc aatgcaaaac aattctatct   3180
atcggattat aatcgttgat tcataaaatt ttaaaatcga cgattttcat ttaaatgacc   3240
ctttttttc tttcattttt tattgttatt catctattta acttgtgagc atctttcata   3300
ttgatatttc agacccttaa attaattgtt ttcttacaga ataactacca cgaatatctg   3360
aggctaaaag ctagagttga gctcctccaa cgatctcaga ggtaatttct gttcactatc   3420
tttatctcaa atgaattctc atgtttttat ttttcgagat tcagattaaa tataatttga   3480
tgtattatta atttaaatac gttatttaat atggtcctta tgtccaacca ttgatttaat   3540
ttgatatttt tttaatgaaa attacacaga aactttcttg gtgaagattt gggcacgtta   3600
agctcgaagg accttgagca gcttgagaat caattagagt cttccttaaa gcaaatcagg   3660
tcaaggaagg taaattattt aatctaatta tacagaaaaa tcatctaaaa gttaccttaa   3720
ttgctagccc aataagtttg ctatctgttg atcctcacat tattttactc acagaaattc   3780
acaatacctt tatttttgtt tgagtttgaa gtatacaatt tctttaaaat gtaaaatttg   3840
aaatctcaac aataagatat gttattgatc cttgcaatta tgggtagatt gcgaattaaa   3900
ctatcttgtc tttgcttaca acagtcattt tgtttataaa ctaattatac ataaatccta   3960
actgatagat agtttataaa gatgaataat gaacataggt catatattaa aaaaacaaaa   4020
aacaaaaaaa aactaaacaa gatgagcgag tcaaaaatag tcttaacaaa agaatatata   4080
```

tatatgtata tatcatattt gatttgtcta tttttaattt tgaaaaaact aagttaatcg 4140
atatataata tgaaggcata atgcataaat atgtccttta acttggtttt aaatcacatt 4200
tatacctctt cgactttggg tgtatacaaa caaacactta aacttatata atgttgaaca 4260
aatagatata tatgtcctac atgtcatttt tcgtcctaaa tggtgtccta agtgtattgt 4320
gtcacgcagg actcatgtgt ctatttgttc aaatttatac aagtttaagt gcttacttat 4380
gtataaacaa agttgaatga cataaatgtg aaataaaatc aaattaaagg gcatatttat 4440
gcattatacc taatacgaaa atccatatta ttcactaaaa aatgagtcgg attatatgat 4500
tactttttta ttcattttgc caatcgtatc ctacgacatt gtttttaatt tgcagacaca 4560
attcatgctg gatcagcttg cagatcttca acaaaaggta attataaaat tctacaaatt 4620
tccaataatt aataaatgga ataattatgc gcgagaaatt tatctattta aaatttacga 4680
tgaattttaa ttttacagga gcaaatgctt gcagaatcta atagattact ccgtagaaag 4740
gtaaactaac ttgatagccg tgcgtaatga ataacttatt ttattttcaa aattataaat 4800
ctaaatactt aggtaactcg ataacataag aagtatttat actgatgata ttggtgttgt 4860
gttttttttt attagttaga agaaagtgta gctggatttc cacttcgatt gtgttgggaa 4920
gatggaggtg atcatcaact tatgcatcaa caaaatcgtc tccctaacac agagggtttc 4980
tttcagcctc ttggattgca ttcttcttct ccacattttg ggtaattact tttattatta 5040
ttaaaaataa tttcaatttt ttttactttt atttcgatta ataaatcaat gtgcaccaag 5100
gtacggtcta acataaacaa aaatgtgggg aatgctctta aagccctaac aaaagttatt 5160
tggtacgtgt actaatgtaa tcgtactata tatcttactt gattagtgga tggacagtac 5220
tgggcacaca caattgacat aagttattat aaggaaaaaa aaaggccaat aatcaatata 5280
gtccaacatt acattattta ttataacagg tcactctaga ttaaatgtta atgaataaca 5340
aaaagtctca tattgatgat taatgtgatg ggtgggcttc ttataaggct ttgacaatcc 5400
tactctcttt gagctagttt tgggggtgtg acctaattca acagaacgta gttaagattg 5460
tgaagtaaag ttgatcattg ttataacagg tttaaatact tctagtaaaa atagttccta 5520
gataatccat cgcaaaatag ctcctatata gttagttgga ttttcatata atctatagct 5580
tatacatagc taaatgggaa tagatgagag tttctgttgt ttagatatga tatttgatcg 5640
gtttctaaat cgttactatc atgtagtgaa taattttcat gttattacta ttacatttga 5700
ttgtttctgt ggttattttt ttttctaggt acaatcctgt taatacagat gaggtgaatg 5760
cagcggcaac tgcacacaat atgaatggat ttattcatgg atggatgctt taa 5813

<210> SEQ ID NO 13
<211> LENGTH: 741
<212> TYPE: DNA
<213> ORGANISM: Unknown
<220> FEATURE:
<223> OTHER INFORMATION: Solanaceae

<400> SEQUENCE: 13
atgggaagag gaagagttga gcttaagaga atagaaaata aaataaatag gcaagtcact 60
tttgctaaga gaagaaatgg acttcttaaa aaagcttatg aactttctgt tctttgtgat 120
gctgaagttg cccttataat cttctctaat aggggtaaac tctatgaatt ttgcagcact 180
tcaagcatgg tgaaaacaat tgaaaagtac caacgttgca gctatgctac tttggaagcc 240
aaccaatcag ttactgatac tcagaataac taccacgaat atctgaggct aaaagctaga 300
gttgagctcc tccaacgatc tcagagaaac tttcttggtg aagatttggg cacgttaagc 360
tcgaaggacc ttgagcagct tgagaatcaa ttagagtctt ccttaaagca aatcaggtca 420
aggaagacac aattcatgct ggatcagctt gcagatcttc aacaaaagga gcaaatgctt 480
gcagaatcta atagattact ccgtagaaag ttagaagaaa gtgtagctgg atttccactt 540
cgattgtgtt gggaagatgg aggtgatcat caacttatgc atcaacaaaa tcgtctccct 600
aacacagagg gtttctttca gcctcttgga ttgcattctt cttctccaca ttttgggtac 660
aatcctgtta atacagatga ggtgaatgca gcggcaactg cacacaatat gaatggattt 720
attcatggat ggatgcttta a 741

<210> SEQ ID NO 14
<211> LENGTH: 6374
<212> TYPE: DNA
<213> ORGANISM: Artificial Sequence
<220> FEATURE:
<223> OTHER INFORMATION: Synthetic polynucleotide

<400> SEQUENCE: 14
atgggaagag gaagagttga gcttaagaga atagaaaata aaataaatag gcaagtcact 60
tttgctaaga gaagaaatgg acttcttaaa aaagcttatg aactttctgt tctttgtgat 120
gctgaagttg cccttataat cttctctaat aggggtaaac tctatgaatt ttgcagcact 180
tcaaggtatt ttttatttta ttatattaac atcaaagatt ttattttttt aaaaaaaacc 240
ttaagtcctt cattaccaaa acccttaatt gatttacaaa gtactttcat taaatttagt 300
aattcttttt tttttatct ctgacttcaa ttataatgca agatctatgt tgtctttata 360
tatattgaat tatatatgta ctgtattttt actatataca tataagatcc tttttcttt 420 tttttctgtc tctttatata aatatatttt aaatagttga ttttgaaaga tctactaatg 480
tatatttatt tttggaactt ttgtgtatat ggaatttttt tctttttat gttttttttt 540 tgttctaatt gttttaaaag cgtttaagat cagaatgttc ttgattattc ttttaggaaa 600
aagatttccc atacattgag ttattttttg atctgtagat tgaatttttt taatgagttc 660
cgatagattt tcgttcaatt tttcaatgaa actattgagg gttgatgatt agataattac 720
tcgattgaaa gtttttattt caaaaaaatt ataattcttc ttaattttat atttatgaga 780
tagagttagt ttagtgatta tatgaaaaat cgtatcagat tattgggaat cgaaacttaa 840
aaattctgaa aatattatta taaattttac atgttacaat atttttactg ttaagatttg 900
atttgcagac taggtgtcat gtttgacagt tgataaaaaa tctgttattt ttgttcttta 960
attcccaaga cggataaaca aaggctgctt atgttggttt ccaataagca gccataattt 1020
taaatatttt tgttaagatt aattaataac aattatttcc accagataat tttcaaaatt 1080
tgtgaccccg agttcatata aattgttaat tttactgcta gaaattacat cgataataat 1140
ttatttagtg taatcttata aatacgaggg cagtagtgta tagactgttt tttattaatc 1200
ctgactcaaa gtgaggtaag ttaagtatat tttgattaaa aggactacat ttcatttatg 1260
tatgtttaat taatattatt ttgtaagtca ataaatctaa acaacatgag tttatctaga 1320
cccttaatta tgcaccttca ttatcaattt tttcaatact ctcctcagaa catatgcttc 1380
tctataattt tgtgcacgag ttaatcaatt cttccttttc aataattaaa tatgtgattt 1440
atgtttagca cttatttttc ggttagttaa ttgataatag gaaaaagcct cttttttttt 1500
gtgtgtgtgg taattaggat ctttattgaa tttaaaatga cctactatag aacttgggag 1560
tttttcttca taataatgca ctgcaacgtg ttaaaaaaaa agaatcaaat gaaattaata 1620

```
gatgtttact ggattgccat ggtaaagtga taagtattaa tttcgcttta actaagagat   1680
cattatattc aagtcccctt gatacaaact tgcctttgta aataagtgtt ttatttttca   1740
atgtgaaact ttcgctgtta atttaaattt aattatactt ctatataaat accaaacaat   1800
aatgtaataa aacaaaaaat aaaagagtag atgtttcata ttgttaatgc agcatggtga   1860
aaacaattga aaagtaccaa cgttgcagct atgctacttt ggaagccaac caatcagtta   1920
ctgatactca ggtactgctt tatattttaa tttatttggc ttttttttaa aaaaataatt   1980
agttttgatt aatatgcatc attttattta tttttggcaa ctctttattt atcagtaata   2040
agtaataact ttttaactag tatatttaaa aatcacaaaa tttaagaata ttttaataga   2100
ttcgacatat tttagtttaa aaataacaaa ttaaattatg tttttaattt tttaaatatt   2160
cttactataa ttatcatgta ctctttgatc tgttcatctt ttccatgata atattatttg   2220
gtcagttagt gacataagag tttgaaattt agaaaaaagg aatatttgga gaaaactgaa   2280
atggatattt agaaatgaaa gttatttaat ataaatataa gtatgggctg ctgagttggg   2340
aatccacgct ggagatctca agtttgaagc gtctcacaaa caatagtaat gtctttttgg   2400
tcgagtttgt cggattggac ttgtccgtgg cctgtgggtt acttttccta tatggtttgc   2460
aagctatcgg gaattttatc ctggcgcacc caaatttgag ttatttttga gtttttatat   2520
gaaatagctt tgtgaattca tcgaactccc gaaaacattg aactttactc caagttgaat   2580
tgcagtaaaa taatagtagc gattctttaa tttatcctaa cagtttttcg aaataataat   2640
cccaaaaaag tttaaaataa ccataccata aacttactgg gtaagatatt atctgtctaa   2700
taatatatag tagtttcttt tgttttatta gtttatctaa tccatatttc atttcttgat   2760
aagttattct taataggaaa ataaacttat ttcgaaaaac tgtttttaaa attttcttga   2820
gttgagtctt ggatgaaaaa tagttaattt tgcattaatt aattttgttc taacaaaaac   2880
taattaaatt tttttgaagc gcatattcac tcaaaaaata aataaaaacc atcatgcata   2940
caggaaatgt tctttttta atttatttt tcattggagc cctgactaat tttatatcgg   3000
ttcatacttt cataaattac aaaaagttca aaatttaaac taaccatata agtgaataaa   3060
ataaatcaac aaaatattca ccacataata ctttttaaat agaatttttc ataccaaaga   3120
ccttacttta attaattagg gtgagagaat cctataagtc aatgcaaaac aattctatct   3180
atcggattat aatcgttgat tcataaaatt ttaaaatcga cgattttcat ttaaatgacc   3240
cttttttttc tttcattttt tattgttatt catctattta acttgtgagc atctttcata   3300
ttgatatttc agacccttaa attaattgtt ttcttacaga ataactacca cgaatatctg   3360
aggctaaaag ctagagttga gctcctccaa cgatctcaga ggtaatttct gttcactatc   3420
tttatctcaa atgaattctc atgtttttat ttttcgagat tcagattaaa tataatttga   3480
tgtattatta atttaaatac gttatttaat atggtcctta tgtccaacca ttgatttaat   3540
ttgatatttt tttaatgaaa attacacaga aactttcttg gtgaagattt gggcacgtta   3600
agctcgaagg accttgagca gcttgagaat caattagagt cttccttaaa gcaaatcagg   3660
tcaaggaagg taaattattt aatctaatta tacagaaaaa tcatctaaaa gttaccttaa   3720
ttgctagccc aataagtttg ctatctgttg atcctcacat tattttactc acagaaattc   3780
acaatacctt tatttttgtt tgagtttgaa gtatacaatt tctttaaaat gtaaaatttg   3840
aaatctcaac aataagatat gttattgatc cttgcaatta tgggtagatt gcgaattaaa   3900
ctatcttgtc tttgcttaca acagtcattt tgtttataaa ctaattatac ataaatccta   3960
```

-continued

```
actgatagat agtttataaa gatgaataat gaacataggt catatattaa aaaaacaaaa   4020
aacaaaaaaa aactaaacaa gatgagcgag tcaaaaatag tcttaacaaa agaatatata   4080
tatatgtata tatcatattt gatttgtcta tttttaattt tgaaaaaact aagttaatcg   4140
atatataata tgaaggcata atgcataaat atgtccttta acttggtttt aaatcacatt   4200
tatacctctt cgactttggg tgtatacaaa caaacactta aacttatata atgttgaaca   4260
aatagatata tatgtcctac atgtcatttt tcgtcctaaa tggtgtccta agtgtattgt   4320
gtcacgcagg actcatgtgt ctatttgttc aaatttatac aagtttaagt gcttacttat   4380
gtataaacaa agttgaatga cataaatgtg aaataaaatc aaattaaagg gcatatttat   4440
gcattatacc taatacgaaa atccatatta ttcactaaaa aatgagtcgg attatatgat   4500
tactttttta ttcattttgc caatcgtatc ctacgacatt gtttttaatt tgcagacaca   4560
attcatgctg gatcagcttg cagatcttca acaaaaggta attataaaat tctacaaatt   4620
tccaataatt aataaatgga ataattatgc gcgagaaatg gatgggcttg tctataatgg   4680
tagacaaatg aaagactttc tcaagatttt gcgggcggtc cggggggggac caccacggct   4740
cctctcttct cgagaatccg ccggagtcag atcagtaggg gagttcacac cgggacttgt   4800
gcaggccccc gtcaattcct ttgagtttcg gtcttgcgac cgtactcccc aggcggagtg   4860
tttcacggcc aactcgaagg ggctgaagtt cgacgcagag caaagcattc ttttctaccc   4920
tatgtaggcg gaatcctctt ttcgactctg actctcccac tccagtcgtg aaaaaacaac   4980
aaactagtca aaggacagcc tgccttattc ttctcccgtt cgggacccct attttctcgg   5040
agatagcctg gtctgagcta gaacagcaga ttcgtgagca agagcgtatt tcacagctga   5100
ttcaacaaca gccatttttt ctgggacccg caattccgta gaaagacatc acgattcctt   5160
gtggacgggg aatcggcaga aagagatggg tcggatactg gaatctgccc aaaagtcctg   5220
acttctattt aaaatttacg atgaatttta attttacagg agcaaatgct tgcagaatct   5280
aatagattac tccgtagaaa ggtaaactaa cttgatagcc gtgcgtaatg aataacttat   5340
tttattttca aaattataaa tctaaatact taggtaactc gataacataa gaagtattta   5400
tactgatgat attggtgttg tgtttttttt tattagttag aagaaagtgt agctggattt   5460
ccacttcgat tgtgttggga agatggaggt gatcatcaac ttatgcatca acaaaatcgt   5520
ctccctaaca cagagggttt ctttcagcct cttggattgc attcttcttc tccacatttt   5580
gggtaattac ttttattatt attaaaaata atttcaattt tttttacttt tatttcgatt   5640
aataaatcaa tgtgcaccaa ggtacggtct aacataaaca aaaatgtggg gaatgctctt   5700
aaagccctaa caaaagttat ttggtacgtg tactaatgta atcgtactat atatcttact   5760
tgattagtgg atggacagta ctgggcacac acaattgaca taagttatta taaggaaaaa   5820
aaaaggccaa taatcaatat agtccaacat tacattattt attataacag gtcactctag   5880
attaaatgtt aatgaataac aaaaagtctc atattgatga ttaatgtgat gggtgggctt   5940
cttataaggc tttgacaatc ctactctctt tgagctagtt ttgggggtgt gacctaattc   6000
aacagaacgt agttaagatt gtgaagtaaa gttgatcatt gttataacag gtttaaatac   6060
ttctagtaaa aatagttcct agataatcca tcgcaaaata gctcctatat agttagttgg   6120
attttcatat aatctatagc ttatacatag ctaaatggga atagatgaga gtttctgttg   6180
tttagatatg atatttgatc ggtttctaaa tcgttactat catgtagtga ataattttca   6240
tgttattact attacatttg attgtttctg tggttatttt tttttctagg tacaatcctg   6300
ttaatacaga tgaggtgaat gcagcggcaa ctgcacacaa tatgaatgga tttattcatg   6360
```

gatggatgct ttaa 6374

<210> SEQ ID NO 15
<211> LENGTH: 5788
<212> TYPE: DNA
<213> ORGANISM: Artificial Sequence
<220> FEATURE:
<223> OTHER INFORMATION: Synthetic polynucleotide

<400> SEQUENCE: 15
atgggaagag gaagagttga gcttaagaga atagaaaata aaataaatag gcaagtcact 60
tttgctaaga gaagaaatgg acttcttaaa aaagcttatg aactttctgt tctttgtgat 120
gctgaagttg cccttataat cttctctaat aggggtaaac tctatgaatt ttgcagcact 180
tcaaggtatt ttttatttta ttatattaac atcaaagatt ttattttttt aaaaaaaacc 240
ttaagtcctt cattaccaaa acccttaatt gatttacaaa gtactttcat taaatttagt 300
aattcttttt ttttttatct ctgacttcaa ttataatgca agatctatgt tgtctttata 360
tatattgaat tatatatgta ctgtattttt actatataca tataagatcc tttttctttt 420
tttttctgtc tctttatata aatatatttt aaatagttga ttttgaaaga tctactaatg 480
tatatttatt tttggaactt ttgtgtatat ggaatttttt tctttttat gtttttttttt 540 tgttctaatt gttttaaaag cgtttaagat cagaatgttc ttgattattc ttttaggaaa 600
aagatttccc atacattgag ttattttttg atctgtagat tgaatttttt taatgagttc 660
cgatagattt tcgttcaatt tttcaatgaa actattgagg gttgatgatt agataattac 720
tcgattgaaa gtttttattt caaaaaaatt ataattcttc ttaattttat atttatgaga 780
tagagttagt ttagtgatta tatgaaaaat cgtatcagat tattgggaat cgaaacttaa 840
aaattctgaa aatattatta taaattttac atgttacaat atttttactg ttaagatttg 900
atttgcagac taggtgtcat gtttgacagt tgataaaaaa tctgttattt ttgttcttta 960
attcccaaga cggataaaca aaggctgctt atgttggttt ccaataagca gccataattt 1020
taaatatttt tgttaagatt aattaataac aattatttcc accagataat tttcaaaatt 1080
tgtgaccccg agttcatata aattgttaat tttactgcta gaaattacat cgataataat 1140
ttatttagtg taatcttata aatacgaggg cagtagtgta tagactgttt tttattaatc 1200
ctgactcaaa gtgaggtaag ttaagtatat tttgattaaa aggactacat ttcatttatg 1260
tatgtttaat taatattatt ttgtaagtca ataaatctaa acaacatgag tttatctaga 1320
cccttaatta tgcaccttca ttatcaattt tttcaatact ctcctcagaa catatgcttc 1380
tctataattt tgtgcacgag ttaatcaatt cttccttttc aataattaaa tatgtgattt 1440
atgtttagca cttatttttc ggttagttaa ttgataatag gaaaaagcct cttttttttt 1500
gtgtgtgtgg taattaggat ctttattgaa tttaaaatga cctactatag aacttgggag 1560
tttttcttca taataatgca ctgcaacgtg ttaaaaaaaa agaatcaaat gaaattaata 1620
gatgtttact ggattgccat ggtaaagtga taagtattaa tttcgcttta actaagagat 1680
cattatattc aagtcccctt gatacaaact tgcctttgta aataagtgtt ttatttttca 1740
atgtgaaact ttcgctgtta atttaaattt aattatactt ctatataaat accaaacaat 1800
aatgtaataa aacaaaaaat aaaagagtag atgtttcata ttgttaatgc agcatggtga 1860
aaacaattga aaagtaccaa cgttgcagct atgctacttt ggaagccaac caatcagtta 1920
ctgatactca ggtactgctt tatattttaa tttatttggc tttttttttaa aaaaataatt 1980

```
agttttgatt aatatgcatc attttattta tttttggcaa ctctttattt atcagtaata   2040
agtaataact ttttaactag tatatttaaa aatcacaaaa tttaagaata ttttaataga   2100
ttcgacatat tttagtttaa aaataacaaa ttaaattatg tttttaattt tttaaatatt   2160
cttactataa ttatcatgta ctctttgatc tgttcatctt ttccatgata atattatttg   2220
gtcagttagt gacataagag tttgaaattt agaaaaaagg aatatttgga gaaaactgaa   2280
atggatattt agaaatgaaa gttatttaat ataaatataa gtatgggctg ctgagttggg   2340
aatccacgct ggagatctca agtttgaagc gtctcacaaa caatagtaat gtctttttgg   2400
tcgagtttgt cggattggac ttgtccgtgg cctgtgggtt acttttccta tatggtttgc   2460
aagctatcgg gaattttatc ctggcgcacc caaatttgag ttatttttga gtttttatat   2520
gaaatagctt tgtgaattca tcgaactccc gaaaacattg aactttactc caagttgaat   2580
tgcagtaaaa taatagtagc gattctttaa tttatcctaa cagtttttcg aaataataat   2640
cccaaaaaag tttaaaataa ccataccata aacttactgg gtaagatatt atctgtctaa   2700
taatatatag tagtttcttt tgttttatta gtttatctaa tccatatttc atttcttgat   2760
aagttattct taataggaaa ataaacttat ttcgaaaaac tgtttttaaa attttcttga   2820
gttgagtctt ggatgaaaaa tagttaattt tgcattaatt aattttgttc taacaaaaac   2880
taattaaatt tttttgaagc gcatattcac tcaaaaaata aataaaaacc atcatgcata   2940
caggaaatgt tcttttttta atttattttt tcattggagc cctgactaat tttatatcgg   3000
ttcatacttt cataaattac aaaaagttca aaatttaaac taaccatata agtgaataaa   3060
ataaatcaac aaaatattca ccacataata ctttttaaat agaatttttc ataccaaaga   3120
ccttacttta attaattagg gtgagagaat cctataagtc aatgcaaaac aattctatct   3180
atcggattat aatcgttgat tcataaaatt ttaaaatcga cgattttcat ttaaatgacc   3240
cttttttttc tttcattttt tattgttatt catctattta acttgtgagc atctttcata   3300
ttgatatttc agacccttaa attaattgtt ttcttacaga ataactacca cgaatatctg   3360
aggctaaaag ctagagttga gctcctccaa cgatctcaga ggtaatttct gttcactatc   3420
tttatctcaa atgaattctc atgtttttat ttttcgagat tcagattaaa tataatttga   3480
tgtattatta atttaaatac gttatttaat atggtcctta tgtccaacca ttgatttaat   3540
ttgatatttt tttaatgaaa attacacaga aactttcttg gtgaagattt gggcaccttg   3600
agcagcttga gaatcaatta gagtcttcct taaagtcaag gaaggtaaat tatttaatct   3660
aattatacag aaaaatcatc taaaagttac cttaattgct agcccaataa gtttgctatc   3720
tgttgatcct cacattattt tactcacaga aattcacaat acctttattt ttgtttgagt   3780
ttgaagtata caatttcttt aaaatgtaaa atttgaaatc tcaacaataa gatatgttat   3840
tgatccttgc aattatgggt agattgcgaa ttaaactatc ttgtctttgc ttacaacagt   3900
cattttgttt ataaactaat tatacataaa tcctaactga tagatagttt ataaagatga   3960
ataatgaaca taggtcatat attaaaaaaa caaaaaacaa aaaaaaacta aacaagatga   4020
gcgagtcaaa aatagtctta acaaaagaat atatatatat gtatatatca tatttgattt   4080
gtctattttt aattttgaaa aaactaagtt aatcgatata taatatgaag gcataatgca   4140
taaatatgtc ctttaacttg gttttaaatc acatttatac ctcttcgact ttgggtgtat   4200
acaaacaaac acttaaactt atataatgtt gaacaaatag atatatatgt cctacatgtc   4260
atttttcgtc ctaaatggtg tcctaagtgt attgtgtcac gcaggactca tgtgtctatt   4320
tgttcaaatt tatacaagtt taagtgctta cttatgtata aacaaagttg aatgacataa   4380
```

```
atgtgaaata aaatcaaatt aaagggcata tttatgcatt atacctaata cgaaaatcca   4440

tattattcac taaaaaatga gtcggattat atgattactt ttttattcat tttgccaatc   4500

gtatcctacg acattgtttt taatttgcag acacaattca tgctggatca gcttgcagat   4560

cttcaacaaa aggtaattat aaaattctac aaatttccaa taattaataa atggaataat   4620

tatgcgcgag aaatttatct atttaaaatt tacgatgaat tttaatttta caggagcaaa   4680

tgcttgcaga atctaataga ttactccgta gaaaggtaaa ctaacttgat agccgtgcgt   4740

aatgaataac ttattttatt ttcaaaatta taaatctaaa tacttaggta actcgataac   4800

ataagaagta tttatactga tgatattggt gttgtgtttt tttttattag ttagaagaaa   4860

gtgtagctgg atttccactt cgattgtgtt gggaagatgg aggtgatcat caacttatgc   4920

atcaacaaaa tcgtctccct aacacagagg gtttctttca gcctcttgga ttgcattctt   4980

cttctccaca ttttgggtaa ttacttttat tattattaaa aataatttca attttttta    5040

cttttatttc gattaataaa tcaatgtgca ccaaggtacg gtctaacata aacaaaaatg   5100

tggggaatgc tcttaaagcc ctaacaaaag ttatttggta cgtgtactaa tgtaatcgta   5160

ctatatatct tacttgatta gtggatggac agtactgggc acacacaatt gacataagtt   5220

attataagga aaaaaaaagg ccaataatca atatagtcca acattacatt atttattata   5280

acaggtcact ctagattaaa tgttaatgaa taacaaaaag tctcatattg atgattaatg   5340

tgatgggtgg gcttcttata aggctttgac aatcctactc tctttgagct agttttgggg   5400

gtgtgaccta attcaacaga acgtagttaa gattgtgaag taaagttgat cattgttata   5460

acaggtttaa atacttctag taaaaatagt tcctagataa tccatcgcaa aatagctcct   5520

atatagttag ttggattttc atataatcta tagcttatac atagctaaat gggaatagat   5580

gagagtttct gttgtttaga tatgatattt gatcggtttc taaatcgtta ctatcatgta   5640

gtgaataatt ttcatgttat tactattaca tttgattgtt tctgtggtta tttttttttc   5700

taggtacaat cctgttaata cagatgaggt gaatgcagcg gcaactgcac acaatatgaa   5760

tggatttatt catggatgga tgctttaa                                      5788
```

<210> SEQ ID NO 16
<211> LENGTH: 5814
<212> TYPE: DNA
<213> ORGANISM: Artificial Sequence
<220> FEATURE:
<223> OTHER INFORMATION: Synthetic polynucleotide

<400> SEQUENCE: 16

```
atgggaagag gaagagttga gcttaagaga atagaaaata aaataaatag gcaagtcact     60

tttgctaaga gaagaaatgg acttcttaaa aaagcttatg aactttctgt tctttgtgat    120

gctgaagttg cccttataat cttctctaat aggggtaaac tctatgaatt ttgcagcact    180

tcaaggtatt ttttatttta ttatattaac atcaaagatt ttattttttt aaaaaaaacc    240

ttaagtcctt cattaccaaa acccttaatt gatttacaaa gtactttcat taaatttagt    300

aattcttttt ttttttatct ctgacttcaa ttataatgca agatctatgt tgtctttata    360

tatattgaat tatatatgta ctgtattttt actatataca tataagatcc ttttttcttt    420

tttttctgtc tctttatata aatatatttt aaatagttga ttttgaaaga tctactaatg    480

tatatttatt tttggaactt ttgtgtatat ggaatttttt tctttttat gttttttttt     540

tgttctaatt gttttaaaag cgtttaagat cagaatgttc ttgattattc ttttaggaaa    600
```

-continued

```
aagatttccc atacattgag ttattttttg atctgtagat tgaatttttt taatgagttc    660
cgatagattt tcgttcaatt tttcaatgaa actattgagg gttgatgatt agataattac    720
tcgattgaaa gtttttattt caaaaaaatt ataattcttc ttaattttat atttatgaga    780
tagagttagt ttagtgatta tatgaaaaat cgtatcagat tattgggaat cgaaacttaa    840
aaattctgaa aatattatta taaattttac atgttacaat atttttactg ttaagatttg    900
atttgcagac taggtgtcat gtttgacagt tgataaaaaa tctgttattt ttgttcttta    960
attcccaaga cggataaaca aaggctgctt atgttggttt ccaataagca gccataattt   1020
taaatatttt tgttaagatt aattaataac aattatttcc accagataat tttcaaaatt   1080
tgtgaccccg agttcatata aattgttaat tttactgcta gaaattacat cgataataat   1140
ttatttagtg taatcttata aatacgaggg cagtagtgta tagactgttt tttattaatc   1200
ctgactcaaa gtgaggtaag ttaagtatat tttgattaaa aggactacat ttcatttatg   1260
tatgtttaat taatattatt ttgtaagtca ataaatctaa acaacatgag tttatctaga   1320
cccttaatta tgcaccttca ttatcaattt tttcaatact ctcctcagaa catatgcttc   1380
tctataattt tgtgcacgag ttaatcaatt cttccttttc aataattaaa tatgtgattt   1440
atgtttagca cttatttttc ggttagttaa ttgataatag gaaaaagcct cttttttttt   1500
gtgtgtgtgg taattaggat ctttattgaa tttaaaatga cctactatag aacttgggag   1560
tttttcttca taataatgca ctgcaacgtg ttaaaaaaaa agaatcaaat gaaattaata   1620
gatgtttact ggattgccat ggtaaagtga taagtattaa tttcgcttta actaagagat   1680
cattatattc aagtcccctt gatacaaact tgcctttgta aataagtgtt ttatttttca   1740
atgtgaaact ttcgctgtta atttaaattt aattatactt ctatataaat accaaacaat   1800
aatgtaataa aacaaaaaat aaaagagtag atgtttcata ttgttaatgc agcatggtga   1860
aaacaattga aaagtaccaa cgttgcagct atgctacttt ggaagccaac caatcagtta   1920
ctgatactca ggtactgctt tatattttaa tttatttggc ttttttttaa aaaaataatt   1980
agttttgatt aatatgcatc attttattta tttttggcaa ctctttattt atcagtaata   2040
agtaataact ttttaactag tatatttaaa aatcacaaaa tttaagaata ttttaataga   2100
ttcgacatat tttagtttaa aaataacaaa ttaaattatg tttttaattt tttaaatatt   2160
cttactataa ttatcatgta ctctttgatc tgttcatctt ttccatgata atattatttg   2220
gtcagttagt gacataagag tttgaaattt agaaaaaagg aatatttgga gaaaactgaa   2280
atggatattt agaaatgaaa gttatttaat ataaatataa gtatgggctg ctgagttggg   2340
aatccacgct ggagatctca agtttgaagc gtctcacaaa caatagtaat gtctttttgg   2400
tcgagtttgt cggattggac ttgtccgtgg cctgtgggtt acttttccta tatggtttgc   2460
aagctatcgg gaattttatc ctggcgcacc caaatttgag ttatttttga gtttttatat   2520
gaaatagctt tgtgaattca tcgaactccc gaaaacattg aactttactc caagttgaat   2580
tgcagtaaaa taatagtagc gattctttaa tttatcctaa cagtttttcg aaataataat   2640
cccaaaaaag tttaaaataa ccataccata aacttactgg gtaagatatt atctgtctaa   2700
taatatatag tagtttcttt tgttttatta gtttatctaa tccatatttc atttcttgat   2760
aagttattct taataggaaa ataaacttat ttcgaaaaac tgtttttaaa attttcttga   2820
gttgagtctt ggatgaaaaa tagttaattt tgcattaatt aattttgttc taacaaaaac   2880
taattaaatt tttttgaagc gcatattcac tcaaaaaata aataaaaacc atcatgcata   2940
caggaaatgt tcttttttta atttattttt tcattggagc cctgactaat tttatatcgg   3000
```

```
ttcatacttt cataaattac aaaaagttca aaatttaaac taaccatata agtgaataaa   3060
ataaatcaac aaaatattca ccacataata ctttttaaat agaatttttc ataccaaaga   3120
ccttacttta attaattagg gtgagagaat cctataagtc aatgcaaaac aattctatct   3180
atcggattat aatcgttgat tcataaaatt ttaaaatcga cgattttcat ttaaatgacc   3240
cttttttttc tttcattttt tattgttatt catctattta acttgtgagc atctttcata   3300
ttgatatttc agacccttaa attaattgtt ttcttacaga ataactacca cgaatatctg   3360
aggctaaaag ctagagttga gctcctccaa cgatctcaga ggtaatttct gttcactatc   3420
tttatctcaa atgaattctc atgtttttat ttttcgagat tcagattaaa tataatttga   3480
tgtattatta atttaaatac gttatttaat atggtcctta tgtccaacca ttgatttaat   3540
ttgatatttt tttaatgaaa attacacaga aactttcttg gtgaagattt gggcacgtta   3600
agcttcgaag gaccttgagc agcttgagaa tcaattagag tcttccttaa agcaaatcag   3660
gtcaaggaag gtaaattatt taatctaatt atacagaaaa atcatctaaa agttacctta   3720
attgctagcc caataagttt gctatctgtt gatcctcaca ttattttact cacagaaatt   3780
cacaatacct ttatttttgt ttgagtttga agtatacaat ttctttaaaa tgtaaaattt   3840
gaaatctcaa caataagata tgttattgat ccttgcaatt atgggtagat tgcgaattaa   3900
actatcttgt ctttgcttac aacagtcatt ttgtttataa actaattata cataaatcct   3960
aactgataga tagtttataa agatgaataa tgaacatagg tcatatatta aaaaaacaaa   4020
aaacaaaaaa aaactaaaca agatgagcga gtcaaaaata gtcttaacaa aagaatatat   4080
atatatgtat atatcatatt tgatttgtct atttttaatt ttgaaaaaac taagttaatc   4140
gatatataat atgaaggcat aatgcataaa tatgtccttt aacttggttt taaatcacat   4200
ttatacctct tcgactttgg gtgtatacaa acaaacactt aaacttatat aatgttgaac   4260
aaatagatat atatgtccta catgtcattt ttcgtcctaa atggtgtcct aagtgtattg   4320
tgtcacgcag gactcatgtg tctatttgtt caaatttata caagtttaag tgcttactta   4380
tgtataaaca aagttgaatg acataaatgt gaaataaaat caaattaaag ggcatattta   4440
tgcattatac ctaatacgaa aatccatatt attcactaaa aaatgagtcg gattatatga   4500
ttactttttt attcattttg ccaatcgtat cctacgacat tgtttttaat ttgcagacac   4560
aattcatgct ggatcagctt gcagatcttc aacaaaaggt aattataaaa ttctacaaat   4620
ttccaataat taataaatgg aataattatg cgcgagaaat ttatctattt aaaatttacg   4680
atgaatttta attttacagg agcaaatgct tgcagaatct aatagattac tccgtagaaa   4740
ggtaaactaa cttgatagcc gtgcgtaatg aataacttat tttattttca aaattataaa   4800
tctaaatact taggtaactc gataacataa gaagtattta tactgatgat attggtgttg   4860
tgtttttttt tattagttag aagaaagtgt agctggattt ccacttcgat tgtgttggga   4920
agatggaggt gatcatcaac ttatgcatca acaaaatcgt ctccctaaca cagagggttt   4980
ctttcagcct cttggattgc attcttcttc tccacatttt gggtaattac ttttattatt   5040
attaaaaata atttcaattt tttttacttt tatttcgatt aataaatcaa tgtgcaccaa   5100
ggtacggtct aacataaaca aaaatgtggg gaatgctctt aaagccctaa caaaagttat   5160
ttggtacgtg tactaatgta atcgtactat atatcttact tgattagtgg atggacagta   5220
ctgggcacac acaattgaca taagttatta taaggaaaaa aaaaggccaa taatcaatat   5280
agtccaacat tacattattt attataacag gtcactctag attaaatgtt aatgaataac   5340
```

aaaaagtctc atattgatga ttaatgtgat gggtgggctt cttataaggc tttgacaatc 5400
ctactctctt tgagctagtt ttgggggtgt gacctaattc aacagaacgt agttaagatt 5460
gtgaagtaaa gttgatcatt gttataacag gtttaaatac ttctagtaaa aatagttcct 5520
agataatcca tcgcaaaata gctcctatat agttagttgg attttcatat aatctatagc 5580
ttatacatag ctaaatggga atagatgaga gtttctgttg tttagatatg atatttgatc 5640
ggtttctaaa tcgttactat catgtagtga ataattttca tgttattact attacatttg 5700
attgtttctg tggttatttt tttttctagg tacaatcctg ttaatacaga tgaggtgaat 5760
gcagcggcaa ctgcacacaa tatgaatgga tttattcatg gatggatgct ttaa 5814

<210> SEQ ID NO 17
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 17
caccgaattc atgggaagag gtaaggtaga a 31

<210> SEQ ID NO 18
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 18
ttcggatcct caaagcatcc atcctggtaa 30

<210> SEQ ID NO 19
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 19
caccgaattc atgggaagag gaagagtaga ac 32

<210> SEQ ID NO 20
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 20
ttcggatcct tagagcatcc accctggaat 30

<210> SEQ ID NO 21
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 21
caccgaattc atgggaagag gaagagttga g 31

<210> SEQ ID NO 22
<211> LENGTH: 35

<212> TYPE: DNA
<213> ORGANISM: Artificial Sequence
<220> FEATURE:
<223> OTHER INFORMATION: Synthetic polynucleotide

<400> SEQUENCE: 22
ttcggatcct taaagcatcc atccatgaat aaatc 35

<210> SEQ ID NO 23
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 23
caccgaattc atgggtagag ggaaagtaga a 31

<210> SEQ ID NO 24
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 24
ttcggatcct caaagcatcc atccaggtac a 31

<210> SEQ ID NO 25
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 25
gcaaaacttt aaattagttc taaatg 26

<210> SEQ ID NO 26
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 26
ctttttgatt catgtgtctg tac 23

<210> SEQ ID NO 27
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 27
aatatcgtgt tagaatgtga cac 23

<210> SEQ ID NO 28
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 28 cttttgatt catgtgtctg tac 23

<210> SEQ ID NO 29
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 29
ttacttttgc taagagaaga aatgg 25

<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 30
ccgtcctttc tgtttgtagc 20

<210> SEQ ID NO 31
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 31
ttacttttgc taagagaaga aatgg 25

<210> SEQ ID NO 32
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 32
gaatccactt aagaatctct acc 23

<210> SEQ ID NO 33
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 33
tattgtgata tgtagagtgg tgc 23

<210> SEQ ID NO 34
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 34
aatacctgag tatcactaac cgtt 24

<210> SEQ ID NO 35
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 35
cacaattcat gctggatcag c 21

<210> SEQ ID NO 36
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 36
cggagtaatc tattagattc tgc 23

<210> SEQ ID NO 37
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 37
cctttaataa gttgaaaatc cctc 24

<210> SEQ ID NO 38
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 38
ttgaaggtgc atagaacata cc 22

<210> SEQ ID NO 39
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 39
cctttaataa gttgaaaatc cctc 24

<210> SEQ ID NO 40
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 40
ttgaaggtgc atagaacata cc 22

<210> SEQ ID NO 41
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 41
atattgaatc gtgtgattgt ctc 23

<210> SEQ ID NO 42
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 42
taactttctt caaagatgca tcc 23

<210> SEQ ID NO 43
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 43
atattgaatc gtgtgattgt ctc 23

<210> SEQ ID NO 44
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 44
taactttctt caaagatgca tcc 23

<210> SEQ ID NO 45
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 45
aatatggtcc ttatgtccaa cc 22

<210> SEQ ID NO 46
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 46
tagcaaactt attgggctag c 21

<210> SEQ ID NO 47
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 47
aatatggtcc ttatgtccaa cc 22

<210> SEQ ID NO 48
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 48
tagcaaactt attgggctag c 21

<210> SEQ ID NO 49
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 49
ctgacgtaag ggatgacgca c 21

<210> SEQ ID NO 50
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 50
catctcatta ctaaagatct cc 22

<210> SEQ ID NO 51
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 51
atgggaagag gtaaggtaga a 21

<210> SEQ ID NO 52
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 52
tcaaagcatc catcctggta aa 22

<210> SEQ ID NO 53
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 53
atgggaagag gaagagtaga ac 22

<210> SEQ ID NO 54
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 54
ttagagcatc caccctggaa t 21

<210> SEQ ID NO 55

<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 55
atgggaagag gaagagttga g 21

<210> SEQ ID NO 56
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 56
ttaaagcatc catccatgaa taaatc 26

<210> SEQ ID NO 57
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 57
cgtggtggtg ctaagaagag 20

<210> SEQ ID NO 58
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 58
acgaagcctc tgaacctttc 20

<210> SEQ ID NO 59
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 59
tgtggtctca atttctagt atgtctgata cacgttttag agctagaaat agcaag 56

<210> SEQ ID NO 60
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 60
tgtggtctca agcgtaatgc caactttgta c 31

<210> SEQ ID NO 61
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 61
tgtggtctca attggaacag cttgagcgtc aacgttttag agctagaaat agcaag 56

<210> SEQ ID NO 62
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 62
tgtggtctca agcgtaatgc caactttgta c 31

<210> SEQ ID NO 63
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 63
tgtggtctca attagctcct tcaacgttct caagttttag agctagaaat agcaag 56

<210> SEQ ID NO 64
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 64
tgtggtctca agcgtaatgc caactttgta c 31

<210> SEQ ID NO 65
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 65
tgtggtctca attacatatt cttggagagg attgttttag agctagaaat agcaag 56

<210> SEQ ID NO 66
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 66
tgtggtctca agcgtaatgc caactttgta c 31

<210> SEQ ID NO 67
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 67
tgtggtctca atttttgggc acgttaagct cgagttttag agctagaaat agcaag 56

<210> SEQ ID NO 68
<211> LENGTH: 31
<212> TYPE: DNA

<213> ORGANISM: Artificial Sequence
<220> FEATURE:
<223> OTHER INFORMATION: Synthetic polynucleotide

<400> SEQUENCE: 68
tgtggtctca agcgtaatgc caactttgta c 31

<210> SEQ ID NO 69
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 69
tgtggtctca attccttaaa gcaaatcagg tcagttttag agctagaaat agcaag 56

<210> SEQ ID NO 70
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 70
tgtggtctca agcgtaatgc caactttgta c 31

<210> SEQ ID NO 71
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 71
tgtggtctca attgcttttg ctaagagaag aaagttttag agctagaaat agcaag 56

<210> SEQ ID NO 72
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 72
tgtggtctca agcgtaatgc caactttgta c 31

<210> SEQ ID NO 73
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 73
tgtggtctca attgcagtct tcaaaggatt cacgttttag agctagaaat agcaag 56

<210> SEQ ID NO 74
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 74
tgtggtctca agcgtaatgc caactttgta c 31

<210> SEQ ID NO 75
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 75
gtaaaacgac ggccag 16

<210> SEQ ID NO 76
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 76
caggaaacag ctatgac 17

<210> SEQ ID NO 77
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 77
tcctgtcaaa cactgatag 19

<210> SEQ ID NO 78
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 78
taatgtactg gggtggatgc ag 22

<210> SEQ ID NO 79
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 79
ataagcccat cagggagcag 20

<210> SEQ ID NO 80
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 80
cggataaacc ttttcacgcc 20

<210> SEQ ID NO 81
<211> LENGTH: 20
<212> TYPE: DNA
<213> ORGANISM: Artificial Sequence
<220> FEATURE:

<223> OTHER INFORMATION: Synthetic polynucleotide

<400> SEQUENCE: 81
ttctagtatg tctgatacac 20

<210> SEQ ID NO 82
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 82
ggaacagctt gagcgtcaac 20

<210> SEQ ID NO 83
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 83
agctccttca acgttctcaa 20

<210> SEQ ID NO 84
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 84
acatattctt ggagaggatt 20

<210> SEQ ID NO 85
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 85
tttgggcacg ttaagctcga 20

<210> SEQ ID NO 86
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 86
ccttaaagca aatcaggtca 20

<210> SEQ ID NO 87
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 87
gcttttgcta agagaagaaa 20

<210> SEQ ID NO 88
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 88
gcagtcttca aaggattcac 20

<210> SEQ ID NO 89
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 89
tatatataca tatgtttttc ttct 24

<210> SEQ ID NO 90
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 90
agttgagctc cttcaacgtt ctcaaaggta agatagacat attcttggag aggatttggg 60
caca 64

<210> SEQ ID NO 91
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 91
agttgagctc cttcaacgtt cttcaaaggt aagatagaca tattcttgga gagtttgggc 60
aca 63

<210> SEQ ID NO 92
<211> LENGTH: 67
<212> TYPE: DNA
<213> ORGANISM: Artificial Sequence
<220> FEATURE:
<223> OTHER INFORMATION: Synthetic polynucleotide

<400> SEQUENCE: 92
agttgagctc cttcaacgtt catgttcaaa ggtaagatag acatattctt ggagagattt 60
gggcaca 67

<210> SEQ ID NO 93
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 93
ttttaaatag ataaatttct cgcg 24

<210> SEQ ID NO 94

```
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 94

gaagatttgg gcacgttaag ctcgaaggac cttcttcctt aaagcaaatc aggtcaagga     60

aggt                                                                  64


<210> SEQ ID NO 95
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 95

gaagatttgg gcaccttctt ccttaaagtc aaggaaggt                            39


<210> SEQ ID NO 96
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 96

gaagatttgg gcacgtcgaa ggaccttctt ccttaaagca aatcaggtca aggaaggt       58


<210> SEQ ID NO 97
<211> LENGTH: 65
<212> TYPE: DNA
<213> ORGANISM: Artificial Sequence
<220> FEATURE:
<223> OTHER INFORMATION: Synthetic polynucleotide

<400> SEQUENCE: 97

gaagatttgg gcacgttaag cttcgaagga ccttcttcct taaagcaaat caggtcaagg     60

aaggt                                                                 65


<210> SEQ ID NO 98
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 98

agttacgcat ctttggaccc gatgttaccg gttagtgata ctcaggtatt g              51


<210> SEQ ID NO 99
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 99

syasdmvsdt v                                                          11


<210> SEQ ID NO 100
<211> LENGTH: 51
<212> TYPE: DNA
<213> ORGANISM: Artificial Sequence
```

<220> FEATURE:
<223> OTHER INFORMATION: Synthetic polynucleotide

<400> SEQUENCE: 100
agttacgcat ctttggaccc gatgtaaccg gttagtgata ctcaggtatt g 51

<210> SEQ ID NO 101
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 101 syasdm 6

<210> SEQ ID NO 102
<211> LENGTH: 92
<212> TYPE: DNA
<213> ORGANISM: Artificial Sequence
<220> FEATURE:
<223> OTHER INFORMATION: Synthetic polynucleotide

<400> SEQUENCE: 102
tttttctagt atgtctgata cactggagag ataccataga tgcagctata tttggaacag 60
cttgagcgtc aactggattc atctttgagg ct 92

<210> SEQ ID NO 103
<211> LENGTH: 76
<212> TYPE: DNA
<213> ORGANISM: Artificial Sequence
<220> FEATURE:
<223> OTHER INFORMATION: Synthetic polynucleotide

<400> SEQUENCE: 103
tttttctagt atgtctgata ccatagatgc agctatattt ggaacagctt gagcaactgg 60
attcatcttt gaggct 76

<210> SEQ ID NO 104
<211> LENGTH: 74
<212> TYPE: DNA
<213> ORGANISM: Artificial Sequence
<220> FEATURE:
<223> OTHER INFORMATION: Synthetic polynucleotide

<400> SEQUENCE: 104
tttttctagt atctccactg gagagatacc atagatgcag ctatatttgg aaaactggat 60
tcatctttga ggct 74

<210> SEQ ID NO 105
<211> LENGTH: 92
<212> TYPE: DNA
<213> ORGANISM: Artificial Sequence
<220> FEATURE:
<223> OTHER INFORMATION: Synthetic polynucleotide

<400> SEQUENCE: 105
tttttctagt atgtctgata cactggagag ataccataga tgcagctata tttggaacag 60
cttgagcgtc aactggattc atctttgagg ct 92

<210> SEQ ID NO 106
<211> LENGTH: 51
<212> TYPE: DNA

<213> ORGANISM: Artificial Sequence
<220> FEATURE:
<223> OTHER INFORMATION: Synthetic polynucleotide

<400> SEQUENCE: 106
tttttctact ggagagatac catagatgca gctatattca tctttgaggc t 51

<210> SEQ ID NO 107
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 107
tttttctagt atatttggaa cagcttgagc gtcactggat tcatctttga ggct 54

<210> SEQ ID NO 108
<211> LENGTH: 89
<212> TYPE: DNA
<213> ORGANISM: Artificial Sequence
<220> FEATURE:
<223> OTHER INFORMATION: Synthetic polynucleotide

<400> SEQUENCE: 108
tttttctagt atgtctgata cactggagag ataccataga tgcagctata tttggaacag 60
cttgagcaac tggattcatc tttgaggct 89

<210> SEQ ID NO 109
<211> LENGTH: 69
<212> TYPE: DNA
<213> ORGANISM: Artificial Sequence
<220> FEATURE:
<223> OTHER INFORMATION: Synthetic polynucleotide

<400> SEQUENCE: 109
tttttctagt atgtctgata cactggagag ataccataga tgcagctata tttggaacag 60
cttgaggct 69

<210> SEQ ID NO 110
<211> LENGTH: 88
<212> TYPE: DNA
<213> ORGANISM: Artificial Sequence
<220> FEATURE:
<223> OTHER INFORMATION: Synthetic polynucleotide

<400> SEQUENCE: 110
tttttctagt atgtctgata cactggagag ataccataga tgcagctata tttggaacag 60
cttgagaact ggattcatct ttgaggct 88

<210> SEQ ID NO 111
<211> LENGTH: 91
<212> TYPE: DNA
<213> ORGANISM: Artificial Sequence
<220> FEATURE:
<223> OTHER INFORMATION: Synthetic polynucleotide

<400> SEQUENCE: 111
tttttctagt atgtctgata cactggagag ataccataga tgcagctata tttggaacag 60
cttgagcgta cctggattca tctttgaggc t 91

<210> SEQ ID NO 112
<211> LENGTH: 27

<212> TYPE: DNA
<213> ORGANISM: Artificial Sequence
<220> FEATURE:
<223> OTHER INFORMATION: Synthetic polynucleotide

<400> SEQUENCE: 112
ctcataaaat gaactaattt ttttaac 27

<210> SEQ ID NO 113
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 113
gaccttgaaa ctggccagtc ttcaaaggat tcacaggtta cttcatgcaa 50

<210> SEQ ID NO 114
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 114
gaccttgaaa ctggccagtc ttcaaaggca caggttactt catgcaa 47

<210> SEQ ID NO 115
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 115
taaacaggca agttactttt gctaagagaa gaaatggact tcttaagaaa gctt 54

<210> SEQ ID NO 116
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 116
taaacaggca agttactttt gctaagagaa ggaaatggac ttcttaagaa agctt 55

<210> SEQ ID NO 117
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 117
taaataggca agtcactttt gctaagagaa gaaatggact tcttaaaaaa gctt 54

<210> SEQ ID NO 118
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 118

```
taaataggca agtcactttt gctaagagaa ggaaatggac ttcttaaaaa agctt          55


<210> SEQ ID NO 119
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 119

gataccatgg ccagtcttca aaggattcac aggttacttc atgcaa                    46


<210> SEQ ID NO 120
<211> LENGTH: 7
<212> TYPE: DNA
<213> ORGANISM: Artificial Sequence
<220> FEATURE:
<223> OTHER INFORMATION: Synthetic polynucleotide

<400> SEQUENCE: 120

gatacaa                                                                7


<210> SEQ ID NO 121
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 121

taaacaggca agttactttt gctaagagaa gaaatggact tcttaagaaa gctt            54


<210> SEQ ID NO 122
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 122

taaacaggca agttactttt gctaagagaa aatggacttc ttaagaaagc tt              52


<210> SEQ ID NO 123
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 123

taaataggca agtcactttt gctaagagaa gaaatggact tcttaaaaaa gctt            54


<210> SEQ ID NO 124
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 124

taaataggca agtcactttt gctaagagaa ggaaatggac ttcttaaaaa agctt          55


<210> SEQ ID NO 125
<211> LENGTH: 67
<212> TYPE: DNA
<213> ORGANISM: Artificial Sequence
```

-continued

```
<220> FEATURE:
<223> OTHER INFORMATION: Synthetic polynucleotide

<400> SEQUENCE: 125

ttttcttcta gtatgtctga tacactggag agagatttgg aacagcttga gcgtcaactg     60

gattcat                                                               67


<210> SEQ ID NO 126
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 126

ttttcttcta gtatgtctga taacactgga gagagatttg gaacagcttg agctatcaaa     60

agg                                                                   63


<210> SEQ ID NO 127
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 127

ttttcttcta gtatgtctga cactggagag agatttggaa cagcttgagc gtaactggat     60

tcat                                                                  64
```

MUTATIONS IN MADS-BOX GENES AND USES THEREOF

CROSS-REFERENCE TO RELATED APPLICATIONS

This application is a national stage filing under 35 U.S.C. § 371 of International Application No. PCT/US2018/033126, filed May 17, 2018, which claims the benefit of the filing date of U.S. Provisional Application No. 62/507,369, filed May 17, 2017. The entire contents of each referenced application is incorporated by reference herein.

GOVERNMENT SUPPORT

This invention was made with government support under IOS-1523423 and IOS-1237880 awarded by the National Science Foundation. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Nov. 14, 2019, is named C130070035US01-SEQ-DQB and is 163,199 bytes in size.

BACKGROUND

The architectures of plant reproductive shoot systems—inflorescences—are major determinants of crop yield, and modified inflorescence complexity was a recurring target during crop domestication and improvement (Doebley et al., 2006; Meyer and Purugganan, 2013). Prominent examples include the cereal crops barley, maize, rice and wheat, for which humans selected variants with greater branching to increase flower and grain production (Ashikari et al., 2005; Boden et al., 2015; Doebley et al., 1997; Huang et al., 2009; Jiao et al., 2010; Komatsuda et al., 2007; Ramsay et al., 2011). Yet, for many crops, particularly fruit-bearing species such as grape and tomato, inflorescence architecture has changed little from wild ancestors, and therefore has been underexploited in breeding (Lippman et al., 2008; Mullins et al., 1992; Peralta and Spooner, 2005).

SUMMARY

Aspects of the present disclosure relate to compositions, such as novel genetic variants of plants, and methods for generating the compositions, which have favorable traits, such as yield-related traits. In some aspects, the combination of mutations in the novel genetic variants increase inflorescence and fruit production. In other aspects, mutations in one or more of the genes of the genetic variants can be used to create a quantitative range of inflorescence types, such as the development of weakly branched genetic variants that results in higher flower and fruit production.

In some aspects, the disclosure provides a genetically-altered Solanaceae plant (e.g., a tomato plant) comprising a mutant Solyc04g005320 gene or a homolog thereof. In some embodiments, the mutant Solyc04g005320 gene or homolog thereof is a null allele or a hypomorphic allele. In some embodiments, the genetically-altered Solanaceae plant (e.g., tomato plant) is heterozygous or homozygous for the mutant Solyc04g005320 gene or homolog thereof.

In some embodiments, the genetically-altered Solanaceae plant (e.g., tomato plant) further comprises a mutant Solyc12g038510 gene or a homolog thereof, a mutant Solyc03g114840 gene or a homolog thereof, or both a mutant Solyc12g038510 gene or a homolog thereof and a mutant Solyc03g114840 gene or a homolog thereof.

In some embodiments, the genetically-altered Solanaceae plant (e.g., tomato plant) further comprises a mutant Solyc12g038510 gene or homolog thereof and the mutant Solyc12g038510 gene or homolog thereof is a null allele or a hypomorphic allele. In some embodiments, the genetically-altered Solanaceae plant is heterozygous or homozygous for the mutant Solyc12g038510 gene or homolog thereof.

In some embodiments, the genetically-altered Solanaceae plant (e.g., tomato plant) further comprises a mutant Solyc03g114840 gene or a homolog thereof and the mutant Solyc03g114840 gene or homolog thereof is a null allele or a hypomorphic allele. In some embodiments, the genetically-altered Solanaceae plant is heterozygous or homozygous for the mutant Solyc03g114840 gene or homolog thereof.

In some embodiments, the genetically-altered Solanaceae plant (e.g., tomato plant) further comprises both a mutant Solyc12g038510 gene or a homolog thereof and a mutant Solyc03g114840 gene or a homolog thereof, each of which are independently a null allele or a hypomorphic allele. In some embodiments, the genetically-altered Solanaceae plant is heterozygous or homozygous for the mutant Solyc12g038510 gene or homolog thereof and is heterozygous or homozygous for the mutant Solyc03g114840 gene or homolog thereof.

In some embodiments, the genetically-altered Solanaceae plant (e.g., tomato plant) comprises the mutant Solyc04g005320 gene or homolog thereof, the mutant Solyc12g038510 gene or homolog thereof, and the mutant Solyc03g114840 gene or homolog thereof, and wherein each is a hypomorphic allele. In some embodiments, the genetically-altered Solanaceae plant (e.g., tomato plant) is heterozygous or homozygous for the mutant Solyc04g005320 gene or homolog thereof, is heterozygous or homozygous for the mutant Solyc03g114840 gene or homolog thereof and is heterozygous or homozygous for the mutant Solyc03g114840 gene or homolog thereof.

In some embodiments, the mutant Solyc04g005320 gene or homolog thereof is a hypermorphic allele. In some embodiments, the genetically-altered Solanaceae plant (e.g., tomato plant) is heterozygous or homozygous for the mutant Solyc04g005320 gene or homolog thereof.

In some embodiments, the genetically-altered Solanaceae plant (e.g., tomato plant) further comprises a mutant Solyc12g038510 gene or a homolog thereof, a mutant Solyc03g114840 gene or a homolog thereof, or both the mutant Solyc12g038510 gene or homolog thereof and the mutant Solyc03g114840 gene or homolog thereof.

In other aspects, the disclosure provides a genetically-altered Solanaceae plant (e.g., a tomato plant), comprising a mutant Solyc12g038510 gene or a homolog thereof and a mutant Solyc03g114840 gene or a homolog thereof, wherein the genetically-altered Solanaceae plant is homozygous for the mutant Solyc12g038510 gene or homolog thereof and heterozygous for the mutant Solyc03g114840 gene or homolog thereof. In some embodiments, the mutant Solyc12g038510 gene or homolog thereof is a null allele or a hypomorphic allele and the mutant Solyc03g114840 gene or homolog thereof is a null allele or a hypomorphic allele.

In some embodiments of any one of the genetically-altered Solanaceae plants (e.g., a tomato plant) provided herein, the mutant Solyc04g005320 gene or homolog thereof, the mutant Solyc12g038510 gene or homolog thereof, and/or the mutant Solyc03g114840 gene or homolog thereof is introduced by technical means. In some embodiments of any one of the genetically-altered Solanaceae plants (e.g., a tomato plant) provided herein, the mutant Solyc04g005320 gene or homolog thereof, the mutant Solyc12g038510 gene or homolog thereof, and/or the mutant Solyc03g114840 gene or homolog thereof is introduced by chemical or physical means. In some embodiments of any one of the genetically-altered Solanaceae plants (e.g., a tomato plant) provided herein, the mutant Solyc04g005320 gene or homolog thereof, the mutant Solyc12g038510 gene or homolog thereof, and/or the mutant Solyc03g114840 gene or homolog thereof is introduced using CRISPR/Cas9, chemical mutagenesis, radiation, *Agrobacterium*-mediated recombination, viral-vector mediated recombination, or transposon mutagenesis. In some embodiments of any one of the genetically-altered Solanaceae plants (e.g., a tomato plant) provided herein, the plants are provided with the provision that plants exclusively obtained by means of an essentially biological process are excluded.

In other aspects, the disclosure provides a crop harvested from a genetically-altered Solanaceae plant (e.g., a tomato plant) of any one of the above embodiments or of any other embodiment described herein.

In yet other aspects, the disclosure provides a seed for producing a genetically-altered Solanaceae plant (e.g., a tomato plant) of any one of the above embodiments or of any other embodiment described herein.

In other aspects, the disclosure provides a method for producing a genetically-altered Solanaceae plant (e.g., a tomato plant), the method comprising introducing a mutation into a Solyc04g005320 gene or a homolog thereof in a Solanaceae plant, thereby producing a genetically-altered Solanaceae plant containing a mutant Solyc04g005320 gene or homolog thereof. In some embodiments, the mutation is introduced using CRISPR/Cas9. In some embodiments, the mutation produces a null allele or a hypomorphic allele of the Solyc04g005320 gene or homolog thereof.

In some embodiments of any one of the methods provided herein, the method further comprises introducing into the Solanaceae plant a mutation into a Solyc12g038510 gene or a homolog thereof, introducing a mutation into a Solyc03g114840 gene or a homolog thereof, or introducing the mutation into the Solyc12g038510 gene or homolog thereof and introducing the mutation into the Solyc03g114840 gene or homolog thereof. In some embodiments, the mutation(s) is/are introduced using CRISPR/Cas9.

In some embodiments of any one of the methods provided herein, the genetically-altered Solanaceae plant (e.g., a tomato plant) containing the mutant Solyc04g005320 gene or homolog thereof is crossed to another genetically-altered Solanaceae plant (e.g., a tomato plant) comprising a mutant Solyc12g038510 gene or homolog thereof, a mutant Solyc03g114840 gene or homolog thereof, or both the mutant Solyc12g038510 gene or homolog thereof and the mutant Solyc03g114840 gene or homolog thereof, thereby producing a genetically-altered Solanaceae plant (e.g., a tomato plant) containing the mutant Solyc04g005320 gene or homolog thereof and the mutant Solyc12g038510 gene or homolog thereof, the mutant Solyc03g114840 gene or homolog thereof, or both the mutant Solyc12g038510 gene or homolog thereof and the mutant Solyc03g114840 gene or homolog thereof.

In other aspects, the disclosure provides a genetically-altered Solanaceae plant (e.g., a tomato plant) produced or obtainable by a method of any one of the above embodiments or of any other embodiment described herein.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIGS. 1A-1K show the s2 inflorescence architecture variant branches due to delayed meristem maturation. FIG. 1A shows a typical wild type (WT) tomato plant with unbranched, multi-flowered inflorescences and jointed pedicels (dotted asterisk in inset). Numbers in FIGS. 1A-1C indicate flowers per inflorescence (mean±SEM, N=number of inflorescences).

Striped arrowheads indicate successive inflorescences. P: two-tailed, two-sample t-test compared to WT. FIG. 1B shows the highly branched inflorescences and jointed pedicels of s mutants. White arrowheads indicate branch points. FIG. 1C shows the s2 mutant with moderately branched inflorescences and jointless pedicels (asterisk). FIG. 1D shows quantification of inflorescence branching events in WT, s, and s2. FIG. 1E shows phenotypic classes in a WT×s2 F2 population. The segregation ratio for the jointless pedicel phenotype and the branched inflorescence phenotype (s2) is given. Asterisks mark jointless pedicels. Scale bars in FIGS. 1A-1C and 1E=1 cm. FIGS. 1F-1H show the transition meristem (TM), sympodial inflorescence meristem (SIM), and floral meristem (FM) from WT (FIG. 1F), s (FIG. 1G), and s2 (FIG. 1H). Scale bars in FIGS. 1F-1H represent 100 μm. L, leaf. F, flower. Schematics depict developing inflorescences. Lines, internodes; circles, FMs/flowers; arrowheads, SIMs. Overproliferating branches are indicated in bolded line. FIG. 1I shows PCA of 2,582 dynamically expressed genes in the vegetative meristem (VM), TM, SIM, and FM of WT, s, and s2, determined by RNA-seq. FIGS. 1J-1K show expression (z-score normalized) of TM (FIG. 1J) and FM (FIG. 1K) marker genes in the vegetative (VM) meristem, TM and FM stage of meristem maturation of WT and mutant (s and s2). Cluster of genes with moderately (left) and strongly (right) delayed expression pattern are shown. Dashed lines indicate median expression with dot-filled-in area representing the $5^{th}$ and $95^{th}$ quantile.

FIG. 2A shows mapping-by-sequencing of s2. Ratio of SNP-ratios (s2/M82) between different pools of segregating phenotypic classes (top: s2/WT; middle: s2/j2; bottom: j2/WT) is shown for chromosome 3 and 12. FIG. 2H shows that the ej2 mapping interval includes the SEP4 homolog Solyc03g114840. FIG. 2I shows the Genomic Illumina-sequence reads showing a breakpoint in Solyc03g114840 and PCR revealing a 564 bp insertion in the 5th intron of Solyc03g114840 in s2 mutants. The sequence corresponds to SEQ ID NO: 93. FIG. 2J shows Sashimi plots for Solyc03g114840 RNA-seq reads in WT and s2 floral meristems indicating partial exon skipping and intron retention in s2 mutants. FIG. 2N shows quantification of relative sepal length (sepal length/petal length±SEM, N=number of flowers) for genotypes in FIG. 2M. P: two-tailed, two-sample t-test compared to WT.

FIG. 3A shows distribution of the $ej2^{w}$ allele in wild tomato species, early domesticates (landraces, *S. lyc.* var. *cerasiforme*), and cultivars (*S. lycopersicum*) (N=number of accessions). FIG. 3B shows relative sepal length (sepal length/petal length) from a subset of accessions in FIG. 3A homozygous EJ2 and $ej2^{w}$. FIG. 3C shows relative sepal length in a subset of confirmed landraces (Blanca et al., 2015). FIG. 3D shows PCR genotyping for the $ej2^{w}$ allele in 10 landraces with the longest and shortest sepals. *S. pimpinellifolium* (*S. pim*) was used as a WT control. FIG. 3E shows inflorescences and flowers (inset) of the accessions with the shortest and longest sepals. See asterisks in FIG. 3D. Numbers indicate relative sepal length. FIG. 3F shows PCR genotyping in 258 cultivars shows enrichment of the $ej2^{w}$ allele in large-fruited types. Data in FIGS. 3B, 3C, and 3E are means (±SEM, n=10 flowers per accession). N=number of accessions. P: two-tailed, two-sample t-test. Scale bars=1 cm.

FIG. 4A shows PCR genotyping of 153 elite breeding lines for $j2^{TE}$ and $ej2^{w}$ reveals the jointless germplasm is dominated by the j2 transposon allele and contains many $j2^{TE}$ $ej2^{w}$ double mutants. Number of accessions is indicated in parenthesis. FIG. 4B shows PCR genotyping of 31 jointless inbreds and hybrids from 4 major seed companies for $ej2^{w}$. Asterisks indicate $j2^{TE}$ $ej2^{w}$ double mutants. FIG. 4C shows representative images of phenotypic classes found in $j2^{TE}$ $ej2^{w}$ double mutants isolated from an *S. pimpinellifolium*×s2 F2 population. N indicates number of plants and percentage of plants in each phenotypic class is indicated in parentheses. FIG. 4D shows mapping-by-sequencing a suppressor of s2 to a 3 Mbp interval on chromosome 2 containing 167 genes. DNA from pools of s2 and suppressed s2 plants was sequenced and the ratio (suppressed s2/s2) of the SNP-ratios (*S. pim*/s2) is presented.

FIGS. 5A-5I show that redundancy among three SEP4 genes regulates inflorescence branching and flower development. FIG. 5A shows the phylogenetic tree of SEP proteins in *Arabidopsis* and tomato. Bootstrap values (%) for 1000 replicates are shown. FIG. 5B shows normalized gene expression (RPKM) for TM5 and TM29 (left) and the SEP4 sub-clade (right) during meristem maturation (VM, vegetative meristem; TM, transition meristem; FM, floral meristem; SIM, sympodial inflorescence meristem; SYM, sympodial shoot meristem). FIG. 5C shows yeast two-hybrid assays showing heteromeric interactions for Solyc04g005320, J2, and EJ2, and homomeric interactions for Solyc04g005320 and J2 (3-AT, 3-amino-1,2,4-triazole; L, leucine; T, tryptophan; H, histidine; e.v., empty vector). FIG. 5D shows the summary of results in FIG. 5C; (−) no interaction; (+) interaction; (++) strong interaction. FIG. 5E shows the longer inflorescence of a $Solyc04g005320^{CR}$ mutant (hereafter referred to as long $inflorescence^{CR}$; $lin^{CR}$) compared to WT. Numbers indicate flowers per inflorescence (mean±SEM, N=10 inflorescences). P: two-tailed, two-sample t-test. Scale bar=1 cm. FIG. 5F shows the longer inflorescence of a $Solyc04g005320^{CR}$ mutant in *S. pimpinellifolium* (*S. pim* $lin^{CR}$) compared to *S. pimpinellifolium* WT. FIG. 5G shows $j2^{CR}$ $ej2^{CR}$ double mutant plant (left) and inflorescence (right) showing SIM overproliferation and few flowers late in development, respectively. FIG. 5H shows $j2^{CR}$ $ej2^{CR}$ $lin^{CR}$ triple mutant. Stereoscope images (insets) of $j2^{CR}$ $ej2^{CR}$ $lin^{CR}$ triple mutants showing massive SIM overproliferation and no floral termination. FIG. 5I shows $j2^{CR}$ $ej2^{CR}$ $lin^{CR}$ triple mutant in *S. pimpinellifolium* as in FIG. 5H showing massive SIM overproliferation and no floral termination. Striped arrowheads indicate successive inflorescences. Scale bars represent 1 cm and 1 mm for photographs and stereoscopic images, respectively.

FIG. 6A shows representative inflorescences from different genotypic combinations of natural and engineered j2 and ej2 mutations in M82. Red arrowheads indicate branching events. FIG. 6B shows the percentage of inflorescences with 1 to 5 or greater branching events for the indicated genotypes. Circled, lower-case letters match genotypes shown in FIG. 6A. Weakly branched genotypes are highlighted with bolded black circles. FIG. 6C shows representative weakly branched inflorescence of a $s^{classic}/+$ heterozygote. FIG. 6D shows the percentage of inflorescences with branching events for $s^{classic}/+$, $s^{multiflora}/-$, and $s^{n5568}/+$ heterozygous genotypes. White arrowheads in FIGS. 6A and 6C mark inflorescence branch points. N indicates number of inflorescences (FIGS. 6B and 6D). Scale bars in FIGS. 6A and 6C indicate 1 cm.

FIGS. 7A-7C show the accessions LA0315 (FIG. 7A), LA3226 (FIG. 7B), and the X-ray-induced mutant fondea (FIG. 7C) (Stubbe, 1972)

develop highly proliferated inflorescences that bear flowers and fruits with jointless pedicels (white asterisks). FIGS. 7D-7F show stereoscope images of primary meristems in LA0315 (FIG. 7D), LA3226 (FIG. 7E), and frondea (FIG. 7F), showing the first inflorescence branching event (white arrowhead) at the base of the first flower (F1). SYM: sympodial shoot meristem; L8: leaf 8. FIGS. 7G-7I show representative inflorescences of $F_1$ progeny from the crosses LA0315×s2 (FIG. 7G), LA3226×s2 (FIG. 7H), and fro×LA0315 (FIG. 7I) showing all four accessions (mutants) are allelic. Scale bars in FIGS. 7A-7C, 7G-7I, and 7D-7F indicate 5 cm and 500 μm, respectively. FIG. 7J shows inflorescences of s (left), s2 (middle), and the s s2 higher-order mutant (right). Greater inflorescence complexity in the s s2 higher-order mutant suggests additivity. FIG. 7K shows a complementation test using an s2-derived jointless mutant plants and the classical j2 mutant. Jointed fruits (dotted asterisk) of WT plants and jointless fruits (white asterisk) of $F_1$ progeny from a cross of s2-derived j2 and j2 are shown. Scale bar=1 cm.

FIG. 8A shows the clustering of 2,582 genes that were dynamically expressed during the early (EVM), middle (MVM), and late (LVM) vegetative meristem, the transition meristem (TM) and floral meristem (FM) stage of meristem maturation in the WT (see STAR Methods). Genes in Cluster 06 and Cluster 08 (solid line boxes) were selected as TM and FM marker genes, respectively. Thick black lines indicate median expression with dotted area representing the $5^{th}$ and $95^{th}$ quantile. N=number of genes. FIGS. 8B and 8C show WT, s (top), and s2 (bottom) z-score normalized expression of TM marker genes in vegetative (VM), transition (TM), and floral (FM) meristem stages. Cluster in dotted line boxes and solid line boxes were selected as moderately and strongly delayed genes, respectively.

FIGS. 9A-9J show that mapping-by-sequencing reveals s2 branching is caused by mutations in two tomato homologs of the SEPALLATA MADS-box genes (J2 and EJ2). FIGS. 9A and 9B show representative images of the phenotypic classes found in the M82×s2 F2 (FIG. 9A) and *S. pimpinellifolium*×s2 F2 populations (FIG. 9B). Asterisks mark jointless pedicels and arrowheads mark inflorescence branching events. Scale bars=1 cm. FIG. 9C shows segregation ratios of the s2 branching phenotype in the two F2 populations. Note that in the M82×s2 F2, the j2 and s2 phenotypes segregated ¼ and 1/16, respectively. FIG. 9D shows mapping-by-sequencing of the loci underlying s2 in an M82×s2 F2 population. Pooled DNA from WT, j2 and s2 plants was sequenced and the ratios of the SNP-ratios (s2/M82) between different phenotypic classes (top: s2/WT; middle: s2/j2; bottom: jointless/WT) are shown. FIG. 9E shows mapping-by-sequencing of the loci underlying s2 in a *S. pimpinellifolium*×s2 $F_2$ population. Pooled DNA from WT, j2, and s2 plants was sequenced and ratios of the SNP-ratios (*S. lyc/S. pim*) are shown as in FIG. 9D. FIG. 9F shows partial sequence alignment of J2 (Solyc12g038510) from M82, the jointless *S. cheesmaniae* (*S. che*) accession LA0166, the classical j2 accession (LA0315) and the s2 accession (LA4371). A *S. cheesmaniae* SNP in the second exon leads to a premature stop-codon (asterisk). Allele designated as $j2^{stop}$. From top to bottom, sequences correspond to SEQ ID NOs: 98, 98, 99, 100, and 101. FIG. 9G shows the CAPS marker PCR genotyping assay for $j2^{stop}$ in accessions from FIG. 9F. Positions of WT and mutant (mut) bands are indicated. FIG. 9H shows gene models showing the position of the Copia/Rider transposable element (TE) insertion in$j2^{TE}$ and the *S. cheesmaniae* SNP in $j2^{stop}$. Predicted RNA transcripts are shown below. The $j2^{stop}$ allele results in a premature stop codon in the second exon. The $j2^{TE}$ allele results in an intronic transcriptional start site and an early stop codon. FIG. 9I shows representative inflorescences of WT, $ej2^{w}$, $ej2^{CR}$, and $ej2^{CR}$×$ej2^{w}$ $F_1$ progeny are shown. Scale bar=1 cm. FIG. 9J shows genotyping of s2, LA0315, LA3226, frondea (fro), and WT plants using diagnostic PCR markers for $j2^{TE}$, $j2^{stop}$, and $ej2^{w}$. Note that both s2 and LA3226 carry the $j2^{TE}$ and $ej2^{w}$ alleles, whereas LA0315 carries $j2^{stop}$ and $ej2^{w}$. The frondea mutant carries $ej2^{w}$, however, failed J2 amplification in frondea using both j2 markers suggest a large structural variant has disrupted the gene (SV). Band sizes are in kilobase pairs (kbp).

FIGS. 10A-10S show that the three SEP4 genes J2, EJ2 and Solyc04g005320/LIN interact to regulate branching and flower development. FIG. 10A shows normalized gene expression (RPKM) for TM5 and TM29 (left) and the SEP4 sub-clade (right) in major tissues. FIG. 10B shows yeast two-hybrid assays showing heteromeric interaction of Solyc04g005320, RIN, J2, and EJ2, and homomeric interaction of Solyc04g005320, RIN and J2 (3-AT, 3-amino-1, 2,4-triazole; L, leucine; T, tryptophan; H, histidine; A, adenine; e.v., empty vector). FIG. 10C shows the summary of results in FIG. 10B; (−) no interaction; (+) interaction; (++) strong interaction. FIG. 10D shows CRISPR/Cas9 targeting of Solyc04g005320. Sequences of Solyc04g005320$^{CR}$ allele 1 (a1) and a2 in *S. lycopersicum* cv. M82 are shown (top). Three independent first-generation ($T_0$) chimeric *S. pimpinellifolium* transgenics were sequenced and 5 reads were obtained per plant (bottom). All sequenced alleles carried mutations, revealing putative biallelic ($T_0$ #4), homozygous ($T_0$ #8), and chimeric ($T_0$ #9) plants. From top to bottom, sequences correspond to SEQ ID NOs: 102-111. FIGS. 10J and 10K show mapping-by-sequencing of the lin mutation in a lin×*S. pim* F2 population to a 0.5 Mbp mapping interval on chromosome 4 containing 80 genes including Solyc04g005320. Reads mapping to chromosome 4 indicate a translocation in Solyc04g005320, which was assayed by PCR (FIG. 10K). The sequence in FIG. 10J corresponds to SEQ ID NO: 112. The WT allele (wt) was amplified with primer-F1 and primer-R2, which bind 5' and 3' to the translocation site, respectively. The lin mutant allele (m) was amplified with primer-F3, which binds the 3' border of the translocated sequence, and primer-R2. FIG. 10L shows semi-quantitative RT-PCR of Solyc04g005320 in WT and lin showing loss of Solyc04g005320 transcript in the lin mutant. UBIQUITIN (UBI) was used as control. FIG. 10P shows CRISPR/Cas9 targeting of LIN in the elite cherry cultivar Sweet 100. Sequences of lin$^{CR}$ allele 1 (a1) and a2 in the first-generation ($T_0$) lin$^{CR}$ plant #1. Five reads were obtained per plant. All sequenced alleles carried mutations, including a complex rearrangement (italicized font). From top to bottom, sequences correspond to SEQ ID NOs: 125-127. FIG. 10Q shows representative images of Sweet 100 and Sweet 100 lin$^{CR}$ $T_0$ #1 mutant inflorescences showing different degrees of branching. FIGS. 10R and 10S show quantification of flowers per inflorescence (FIG. 10R) and inflorescence branching events (FIG. 10S) for Sweet 100 and Sweet 100 lin$^{CR}$ $T_0$ #1. N=number of inflorescences. Bar graphs in FIGS. 10E, 10F, 10H, 10I, 10R, and 10S show means (±SEM). P-values determined by two-tailed, two-sample t-tests. Scale bars represent 1 cm.

SEQUENCES

Below is a brief description of certain sequences described herein.

SEQ ID NO: 1 is a nucleic acid sequence of a wild-type Solyc04g005320 gene.

SEQ ID NO: 2 is a nucleic acid sequence of a wild-type Solyc04g005320 coding sequence.

SEQ ID NO: 3 is a nucleic acid sequence for a mutant Solyc04g005320 gene allele lin$^{trans}$. The border sequences of a translocation site are shown in bold italic letters, with the translocation sequence being represented by the NNNNNN(N*X)NNNNNN sequence.

SEQ ID NO: 4 is a nucleic acid sequence for a mutant Solyc04g005320 gene allele lin$^{CR}$-allele 1.

SEQ ID NO: 5 is a nucleic acid sequence for a mutant Solyc04g005320 gene allele lin$^{CR}$-allele 2.

SEQ ID NO: 6 is a nucleic acid sequence of a wild-type Solyc12g038510 gene.

SEQ ID NO: 7 is a nucleic acid sequence of a wild-type Solyc12g038510 coding sequence.

SEQ ID NO: 8 is a nucleic acid sequence for a mutant Solyc12g038510 gene allele j2$^{TE}$. The border sequences of a transposable element insertion site are shown in bold italic letters, with the transposable element sequence being represented by the NNNNNN(N*X)NNNNNN sequence.

SEQ ID NO: 9 is a nucleic acid sequence of a mutant Solyc12g038510 gene allele j2$^{stop}$.

SEQ ID NO: 10 is a nucleic acid sequence for a mutant Solyc12g038510 gene allele j2$^{CR-}$ allele 1.

SEQ ID NO: 11 is a nucleic acid sequence for a mutant Solyc129038510 gene allele j2$^{CR-}$ allele 2.

SEQ ID NO: 12 is a nucleic acid sequence of a wild-type Solyc03g114840 gene.

SEQ ID NO: 13 is a nucleic acid sequence of a wild-type Solyc03g114840 coding sequence.

SEQ ID NO: 14 is a nucleic acid sequence for a mutant Solyc03g114840 gene allele ej2$^{w}$.

SEQ ID NO: 15 is a nucleic acid sequence for a mutant Solyc03g114840 gene allele ej2$^{CR}$-allele 1.

SEQ ID NO: 16 is a nucleic acid sequence for a mutant Solyc03g114840 gene allele ej2$^{CR}$-allele 3.

DETAILED DESCRIPTION

Figure 1A:
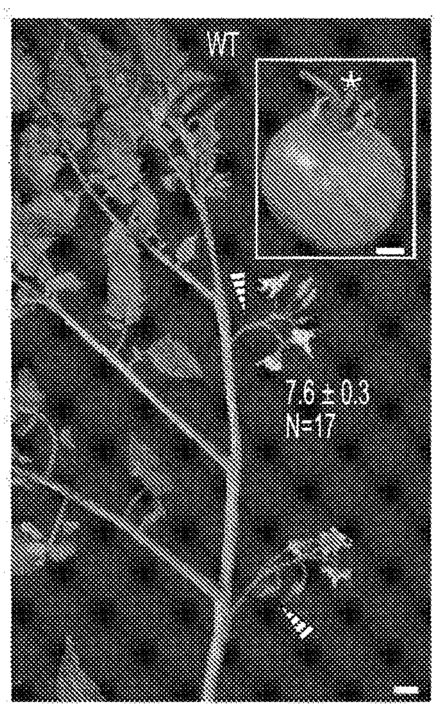

Variation in inflorescence architecture is based on changes in the activity of meristems, small groups of stem cells located at the tips of shoots (Kyozuka et al., 2014; Park et al., 2014a). During the transition to flowering, vegetative meristems gradually mature to a reproductive state and, depending on the species, terminate immediately in a flower or give rise to a variable number of new inflorescence meristems that become additional flowers or flower-bearing branches (Prusinkiewicz et al., 2007). In domesticated tomato (*Solanum lycopersicum*) and its wild progenitor *S. pimpinellifolium*, a new inflorescence meristem emerges at the flank of each previous meristem. Several reiterations of this process give rise to inflorescences with multiple flowers arranged in a zigzag pattern, resulting in the familiar "tomatoes on the vine" architecture (FIG. 1A)(Park et al., 2012).

Improving tomato inflorescence architecture to boost flower production and yield has remained surprisingly challenging, despite a rich resource of wild relatives that develop weakly branched inflorescences with high fertility (Lemmon et al., 2016; Lippman et al., 2008; Park et al., 2012; Zamir, 2001). However, genetic incompatibilities and the challenge of transferring complex polygenic traits without undesired effects from linked genes has precluded exploiting wild species to improve inflorescence architecture (MacArthur and Chiasson, 1947). Another source of potentially valuable inflorescence variation is rare natural and induced highly branched mutants in domesticated germplasm. It was previously shown that branching in one of these variants and branching in a wild species is due to an extended meristem maturation schedule, which allows additional inflorescence meristems to form (Lemmon et al., 2016; Park et al., 2012). This suggested subtle modification of meristem maturation could provide beneficial changes in inflorescence architecture (Park et al., 2014a). Yet, breeders typically select against even moderate branching, primarily due to an imbalance in source-sink relationships that results in high flower abortion and low fruit production, especially in large-fruited varieties (Stephenson, 1981).

In some aspects, the present disclosure relates to the discovery of the identity of mutations in two closely related MADS-box transcription factor genes, one of which arose during domestication and the other within the last century of crop improvement. Each mutant was selected separately based on the phenotype of improved flower morphology and fruit retention traits without knowledge of the locations of the mutations and, therefore, the underlying genes affected by the mutations. However, combining these two mutants revealed some redundancy in controlling meristem maturation, which caused undesirable branching. Breeders overcame this negative epistasis by selecting suppressors of branching, but in so doing limited the potential to improve flower production through weak branching.

As described herein, the identification of the mutations in MADS-box transcription factor genes and the dissection of the interaction between the MADS-box genes by Applicants revealed a dosage relationship among natural and gene-edited mutations in multiple regulators of meristem maturation. Combining two or more of the mutations in the MADS-box genes in homozygous and heterozygous combinations allowed for the creation of a quantitative range of inflorescence types, and the development of weakly branched hybrids with desirable traits, such as higher flower and fruit production. In particular, data described herein in tomato plants demonstrates the utility of mutant MADS-box genes, such as mutant SEP4 homologs, and the interaction between such mutant genes to alter inflorescence phenotypes. In particular, mutants of the MADS-box gene Solyc12g038510, mutants of the MADS-box gene Solyc03g114840, and mutants of the MADS-box gene Solyc04g005320, each of which are homologs of *Arabidopsis* SEPALLA TA4 (SEP4), were shown to be capable of altering inflorescence phenotypes in tomato plants. Specifically, it was found that mixing and matching these mutations in various homozygous and heterozygous combinations resulted in a quantitative range of inflorescence phenotypes and the development of weakly branched hybrids with higher flower and fruit production.

Accordingly, in some aspects, the present disclosure relates to plants (e.g., Solanaceae plants) comprising one or more mutant MADS-box genes such as mutant SEPALLATA4 (SEP4) homologs, which may provide a range of inflorescence phenotypes and may result in improved inflorescence architecture and yield.

In some aspects, provided herein are genetically-altered Solanaceae plants, such as genetically-altered Solanaceae (e.g., *Solanum lycopersicum*) plants comprising one or more of a mutant Solyc04g005320 gene (or a homolog thereof), a mutant Solyc12g038510 gene (or a homolog thereof), and a mutant Solyc03g114840 gene (or a homolog thereof), which exhibit characteristics different from a reference plant such as a corresponding plant that has not been genetically altered (also referred to herein as "wild-type") or a corresponding plant comprising a null mutation of one or more of the Solyc04g005320 gene, the Solyc12g038510 gene, and the Solyc03g114840 gene. The characteristics include, but are not limited to, one or more of the following: modified inflorescence architecture, modified flower number, higher yield, higher quality products (e.g., fruits), and modified fruit productivity (e.g., modified such as higher fruit number).

In some embodiments, genetically-altered Solanaceae plants, e.g., tomato plants (such as *Solanum lycopersicum*), comprise one or more of a mutant Solyc04g005320 gene (heterozygous or homozygous), a mutant Solyc12g038510 gene (heterozygous or homozygous), and a mutant Solyc03g114840 gene (heterozygous or homozygous). In some embodiments, the plants comprise a variety of combinations of the different mutant alleles, such as, for example, mutant Solyc04g005320 with mutant Solyc12g038510; mutant Solyc04g005320 with mutant Solyc03g114840; or mutant Solyc04g005320 with mutant Solyc12g038510 and mutant Solyc03g114840. The genetically-altered plants may be heterozygotes or homozygotes and, in some embodiments, may be double heterozygotes, double homozygotes, triple heterozygotes, or triple homozygotes. In some embodiments, such a plant comprises a mutant Solyc04g005320 gene as described herein. In some embodiments, such a plant comprises a mutant Solyc04g005320 gene as described herein and a mutant Solyc12g038510 gene as described herein. In some embodiments, such a plant comprises a mutant Solyc04g005320 gene as described herein and a mutant Solyc03g114840 gene as described herein. In some embodiments, such a plant comprises a mutant Solyc04g005320 as described herein with a mutant Solyc12g038510 as described herein and a mutant Solyc03g114840 as described herein.

Mutant Solyc04g005320 Gene

Aspects of the disclosure relate to mutants of the Solyc04g005320 gene (or a homolog thereof) as well as plants, plant cells, seeds, and nucleic acids comprising such mutant genes. The Solyc04g005320 gene is also referred to herein as Long Inflorescence or LIN. The Solyc04g005320 gene is a homolog of SEP4 in *Arabidopsis*.

In some embodiments, Solanaceae plants (e.g., *Solanum lycopersicum*) comprising a mutant Solyc04g005320 gene (or a homolog thereof), such as a hypomorphic allele or null allele, have long inflorescences, e.g., producing an average of at least 15 flowers (e.g., 9 to 30 flowers) on each inflorescence per plant. In some embodiments, the number of flowers per inflorescence may vary by variety (e.g. for plum varieties 9-15 flowers and for cherry varieties 20-40 flowers). In some embodiments, Solanaceae plants (e.g., *Solanum lycopersicum*) comprising a mutant Solyc04g005320 gene (or a homolog thereof), such as a hypomorphic allele or null allele, have longer inflorescences than a plant comprising a wild-type Solyc04g005320 gene (or a wild-type homolog thereof). In some embodiments, the mutant Solyc04g005320 gene (or homolog thereof) is a hypomorphic allele that, when crossed to a null allele of the Solyc04g005320 gene (or homolog thereof), does not restore a wild-type Solyc04g005320 gene (or a wild-type homolog thereof) phenotype (such as producing an average of 8 flowers (e.g., 6 to 10 flowers) on each inflorescence per plant). In some embodiments, Solanaceae plants (e.g., *Solanum lycopersicum*) comprising a mutant Solyc04g005320 gene (or a homolog thereof), such as a hypermorphic allele, have short inflorescences, e.g., producing an average of less than 5 flowers (e.g., 2 to 6 flowers) on each inflorescence per plant. In some embodiments, plants comprising a mutant Solyc04g005320 gene, such as a hypermorphic allele, have shorter inflorescence than a plant comprising a wild-type Solyc04g005320 gene.

In some embodiments, Solanaceae plants (e.g., *Solanum lycopersicum*) comprising a mutant Solyc04g005320 gene (or a homolog thereof), such as a hypomorphic allele or null allele, have more branches per inflorescence, e.g., producing 2 or more branches per inflorescence. In some embodiments, Solanaceae plants (e.g., *Solanum lycopersicum*) comprising a mutant Solyc04g005320 gene (or a homolog thereof), such as a hypomorphic allele or null allele, have more branches than a plant comprising a wild-type Solyc04g005320 gene (or a wild-type homolog thereof). In some embodiments, the mutant Solyc04g005320 gene (or homolog thereof) is a hypomorphic allele that, when crossed to a null allele of the Solyc04g005320 gene, does not restore a wild-type Solyc04g005320 gene (or a wild-type homolog thereof) phenotype (such as producing an average of 1 branch per inflorescence).

In some embodiments, the mutant Solyc04g005320 gene (or homolog thereof) contains a mutation in a regulatory region, a coding region or both (e.g., a missense, nonsense, insertion, deletion, duplication, inversion, indel, or translocation mutation in such a region). In some embodiments, the regulatory region is a promoter. In some embodiments, the mutation in the coding region is in an exon. In some embodiments, the mutation is a translocation in the first intron (e.g., $lin^{trans}$, which contains a translocation in the first intron that eliminates transcription). In some embodiments, the mutation is a null mutation in which the coding sequence has been deleted (e.g., $lin^{CR}$ which is a null allele produced by CRISPR/Cas9).

In some embodiments, the mutant Solyc04g005320 gene (or homolog thereof) is a hypomorphic allele or a null allele. In some embodiments, a hypomorphic allele is an allele that results in an mRNA or protein expression level of the gene of interest that is at least 30% lower (e.g., at least 30%, at least 40%, at least 50%, at least 60%, at least 70%, at least 80% or at least 90%) than results from an allele of the gene of interest that does not contain the mutation (e.g., a wild-type allele). As used herein, a "null allele" refers to an allele of a gene of interest in which transcription into RNA does not occur, translation into a functional protein does not occur or neither occurs due to a mutation which may be located within the coding sequence, in a regulatory region of the gene, or in both (e.g., a missense, nonsense, insertion, deletion, duplication, inversion, indel, or translocation). In some embodiments, the null allele is a knock-out allele. As used herein, a "knock out allele" refers to an allele of a gene in which transcription into RNA does not occur, translation into a functional protein does not occur or neither occurs as a result of a deletion of some portion or all of the coding sequence of the gene, e.g., using homologous recombination. One non-limiting approach to creating null mutations is to use CRISPR-Cas9 mutagenesis to target exons that encode functional protein domains or to target a large portion (e.g., at least 80%) of the coding sequence (see, e.g., Shi et al. Nature Biotechnology. (2015) 33(6): 661-667 and Online Methods).

In some embodiments, the mutant Solyc04g005320 gene (or homolog thereof) is a hypermorphic allele. In some embodiments, a hypermorphic allele is an allele that results in an mRNA or protein expression level of the gene of interest that is at least 30% greater (e.g., at least 30%, at least 40%, at least 50%, at least 60%, at least 70%, at least 80%, at least 90%, at least 100%, at least 200% or more) than results from an allele of the gene of interest that does not contain the mutation (e.g., a wild-type allele). mRNA and protein levels can be measured using any method known in the art or described herein, e.g., using qRT-PCR for mRNA levels or an immunoassay for protein levels.

In some embodiments, a Solanaceae plant (e.g., *Solanum lycopersicum*) comprising the mutant Solyc04g005320 gene, or homolog thereof, (e.g., a hypomorphic, knock-out or null allele described herein) is heterozygous for the mutant gene. In some embodiments, a Solanaceae plant (e.g., *Solanum lycopersicum*) comprising the mutant Solyc04g005320 gene, or homolog thereof, (e.g., a hypomorphic, knock-out or null allele described herein) is homozygous for the mutant gene.

In some embodiments, the Solyc04g005320 gene homolog (a) has a sequence that has at least 75%, at least 80%, at least 85%, at least 90%, at least 95%, at least 96%, at least 97%, at least 98%, or at least 99% identity with the sequence of SEQ ID NO: 1 or 2 and (b) is not a *Solanum lycopersicum* gene.

In some embodiments, the mutant $lin^{trans}$ gene comprises, for example, a nucleic acid (e.g., DNA) having the sequence of SEQ ID NO: 3; a portion of SEQ ID NO: 3 that exhibits substantially the same activity (e.g., encoding the same polypeptide or substantially the same polypeptide that has the same activity) as a nucleic acid (e.g., DNA) having the sequence of SEQ ID NO: 3; a nucleic acid (e.g., DNA) having at least 85%, at least 90%, at least 95%, at least 96%, at least 97%, at least 98%, or at least 99% identity with the sequence of SEQ ID NO: 3; an orthologue or homologue of the nucleic acid having the sequence of SEQ ID NO: 3.

In some embodiments, the mutant $lin^{CR}$ gene comprises, for example, a nucleic acid (e.g., DNA) having the sequence of SEQ ID NO: 4 or 5; a portion of SEQ ID NO: 4 or 5 that exhibits substantially the same activity (e.g., encoding the same polypeptide or substantially the same polypeptide that has the same activity) as a nucleic acid (e.g., DNA) having the sequence of SEQ ID NO: 4 or 5; a nucleic acid (e.g., DNA) having at least 85%, at least 90%, at least 95%, at least 96%, at least 97%, at least 98%, or at least 99% identity with the sequence of SEQ ID NO: 4 or 5; an orthologue or homologue of the nucleic acid having the sequence of SEQ ID NO: 4 or 5.

Mutant Solyc12g038510 Gene

Other aspects of the disclosure relate to mutants of the Solyc12g038510 gene (or a homolog thereof) as well as plants, plant cells, seeds, and nucleic acids comprising such mutant genes. The Solyc12g038510 gene is also referred to herein as Jointless-2 or J2. The Solyc12g038510 gene is a homolog of SEP4 in *Arabidopsis*.

In some embodiments, Solanaceae plants (e.g., *Solanum lycopersicum*) comprising a mutant Solyc12g038510 gene (or homolog thereof), such as a hypomorphic allele or null allele, have more branches, e.g., producing 2 or more branches per inflorescence. In some embodiments, Solanaceae plants (e.g., *Solanum lycopersicum*) comprising a mutant Solyc12g038510 gene (or a homolog thereof), such as a hypomorphic allele or null allele, have more branches than a plant comprising a wild-type Solyc12g038510 gene. In some embodiments, the mutant Solyc12g038510 gene (or homolog thereof) is a hypomorphic allele that, when crossed to a null allele of the Solyc12g038510 gene (or homolog thereof), does not restore a wild-type Solyc12g038510 gene (or a wild-type homolog thereof) phenotype (such as producing an average of 1 branch per inflorescence). In some embodiments, Solanaceae plants (e.g., *Solanum lycopersicum*) comprising a mutant Solyc12g038510 gene (or a homolog thereof), such as a hypomorphic allele or null allele, lack the abscission zone on the stems (pedicels) of flowers known as the joint (this absence of the abscission zone is also referred to herein as "jointless pedicels") or produce a visible abscission zone (i.e. joint) but abscission does not occur or requires more force (e.g., hand harvesting) to separate the fruit from the pedicel, providing better fruit retention properties. In some embodiments, Solanaceae plants (e.g., *Solanum lycopersicum*) comprising a mutant Solyc12g038510 gene (or a homolog thereof), such as a hypomorphic allele or null allele, have more jointless pedicels than a plant comprising a wild-type Solyc12g038510 gene (or a wild-type homolog thereof). In some embodiments, the mutant Solyc12g038510 gene (or homolog thereof) is a hypomorphic allele that, when crossed to a null allele of the Solyc12g038510 gene (or homolog thereof), does not restore a wild-type Solyc12g038510 gene (or a wild-type homolog thereof) phenotype (such as having a normal abscission zone on the pedicels).

In some embodiments, the mutant Solyc12g038510 gene (or homolog thereof) contains a mutation in a regulatory region, a coding region or both (e.g., a missense, nonsense, insertion, deletion, duplication, inversion, indel, or translocation mutation in such a region). In some embodiments, the regulatory region is a promoter. In some embodiments, the mutation in the coding region is in an exon. In some embodiments, the mutation is in the first intron (e.g., $j2^{TE}$ which contains a Copia/Rider-type transposable element (TE) in the first intron). In some embodiments, the mutation is a nonsense mutation that results in an early stop codon (e.g., $j2^{stop}$ has an early nonsense mutation). In some embodiments, the mutation is a null mutation in which the coding sequence has been deleted (e.g., $j2^{CR}$ which is a null allele produced by CRISPR/Cas9).

In some embodiments, the mutant Solyc12g038510 gene (or homolog thereof) is a hypomorphic allele or a null allele. In some embodiments, a hypomorphic allele is an allele that results in an mRNA or protein expression level of the gene of interest that is at least 30% lower (e.g., at least 30%, at least 40%, at least 50%, at least 60%, at least 70%, at least 80% or at least 90%) than results from an allele of the gene of interest that does not contain the mutation (e.g., a wild-type allele).

In some embodiments, a Solanaceae plant (e.g., *Solanum lycopersicum*) comprising the mutant Solyc12g038510 gene, or homolog thereof, (e.g., a hypomorphic, knock-out or null allele described herein) is heterozygous for the mutant gene. In some embodiments, a Solanaceae plant (e.g., *Solanum lycopersicum*) comprising the mutant Solyc12g038510 gene, or homolog thereof, (e.g., a hypomorphic, knock-out or null allele described herein) is homozygous for the mutant gene.

In some embodiments, the Solyc12g038510 gene homolog (a) has a sequence that has at least 75%, at least 80%, at least 85%, at least 90%, at least 95%, at least 96%, at least 97%, at least 98%, or at least 99% identity with the sequence of SEQ ID NO: 6 or 7 and (b) is not a *Solanum lycopersicum* gene.

In some embodiments, the mutant $j2^{TE}$ gene comprises, for example, a nucleic acid (e.g., DNA) having the sequence of SEQ ID NO: 8; a portion of SEQ ID NO: 8 that exhibits substantially the same activity (e.g., encoding the same polypeptide or substantially the same polypeptide that has the same activity) as a nucleic acid (e.g., DNA) having the sequence of SEQ ID NO: 8; a nucleic acid (e.g., DNA) having at least 85%, at least 90%, at least 95%, at least 96%, at least 97%, at least 98%, or at least 99% identity with the sequence of SEQ ID NO: 8; an orthologue or homologue of the nucleic acid having the sequence of SEQ ID NO: 8.

In some embodiments, the mutant $j2^{stop}$ gene comprises, for example, a nucleic acid (e.g., DNA) having the sequence of SEQ ID NO: 9; a portion of SEQ ID NO: 9 that exhibits substantially the same activity (e.g., encoding the same polypeptide or substantially the same polypeptide that has the same activity) as a nucleic acid (e.g., DNA) having the sequence of SEQ ID NO: 9; a nucleic acid (e.g., DNA) having at least 85%, at least 90%, at least 95%, at least 96%, at least 97%, at least 98%, or at least 99% identity with the sequence of SEQ ID NO: 9; an orthologue or homologue of the nucleic acid having the sequence of SEQ ID NO: 9.

In some embodiments, the mutant $j2^{CR}$ gene comprises, for example, a nucleic acid (e.g., DNA) having the sequence of SEQ ID NO: 10 or 11; a portion of SEQ ID NO: 10 or 11 that exhibits substantially the same activity (e.g., encoding the same polypeptide or substantially the same polypeptide that has the same activity) as a nucleic acid (e.g., DNA) having the sequence of SEQ ID NO: 10 or 11; a nucleic acid (e.g., DNA) having at least 85%, at least 90%, at least 95%, at least 96%, at least 97%, at least 98%, or at least 99% identity with the sequence of SEQ ID NO: 10 or 11; an orthologue or homologue of the nucleic acid having the sequence of SEQ ID NO: 10 or 11.

Mutant Solyc03g114840 Gene

Other aspects of the disclosure relate to mutants of the Solyc03g114840 gene (or a homolog thereof) as well as plants, plant cells, seeds, and nucleic acids comprising such mutant genes. The Solyc03g114840 gene is also referred to herein as Enhancer-of-Jointless-2 or EJ2. The Solyc03g114840 gene is a homolog of SEP4 in *Arabidopsis*.

In some embodiments, Solanaceae plants (e.g., *Solanum lycopersicum*) comprising a mutant Solyc03g114840 gene (or a homolog thereof), such as a hypomorphic allele or null allele, have more branches, e.g., producing 2 or more branches per inflorescence. In some embodiments, Solanaceae plants (e.g., *Solanum lycopersicum*) comprising a mutant Solyc03g114840 gene (or a homolog thereof), such as a hypomorphic allele or null allele, have more branches than a plant comprising a wild-type Solyc03g114840 gene (or a wild-type homolog thereof). In some embodiments, the mutant Solyc03g114840 gene (or homolog thereof) is a hypomorphic allele that, when crossed to a null allele of the Solyc03g114840 gene (or homolog thereof), does not restore a wild-type Solyc03g114840 gene (or a wild-type homolog thereof) phenotype (such as producing an average of 1 branch per inflorescence). In some embodiments, Solanaceae plants (e.g., *Solanum lycopersicum*) comprising a mutant Solyc03g114840 gene (or a homolog thereof), such as a hypomorphic allele or null allele, have long sepals resulting in larger calyxes, e.g., that are an average sepal to petal ratio (sepal length/petal length) of at least 1.2. In some embodiments, Solanaceae plants (e.g., *Solanum lycopersicum*) comprising a mutant Solyc03g114840 gene (or a homolog thereof), such as a hypomorphic allele or null allele, have longer sepals than a plant comprising a wild-type Solyc03g114840 gene (or a wild-type homolog thereof). In some embodiments, the mutant Solyc03g114840 gene (or homolog thereof) is a hypomorphic allele that, when crossed to a null allele of the Solyc03g114840 gene (or homolog thereof), does not restore a wild-type Solyc03g114840 gene (or wild-type homolog thereof) phenotype (such as having an average sepal to petal ratio (sepal length/petal length) of not more than 0.8).

In some embodiments, the mutant Solyc03g114840 gene (or homolog thereof) contains a mutation in a regulatory region, a coding region or both (e.g., a missense, nonsense, insertion, deletion, duplication, inversion, indel, or translocation mutation in such a region). In some embodiments, the regulatory region is a promoter. In some embodiments, the mutation is a null mutation in which the coding sequence has been deleted (e.g., $ej2^{CR}$ which is a null allele produced by CRISPR/Cas9). In some embodiments, the mutation is an insertion mutation in the 5th intron (e.g., $ej2^{W}$ which is a hypomorphic allele with a 564 bp insertion in the 5th intron).

In some embodiments, the mutant Solyc03g114840 gene (or homolog thereof) is a hypomorphic allele or a null allele. In some embodiments, a hypomorphic allele is an allele that results in an mRNA or protein expression level of the gene of interest that is at least 30% lower (e.g., at least 30%, at least 40%, at least 50%, at least 60%, at least 70%, at least 80% or at least 90%) than results from an allele of the gene of interest that does not contain the mutation (e.g., a wild-type allele).

In some embodiments, a Solanaceae plant (e.g., *Solanum lycopersicum*) comprising the mutant Solyc03g114840 gene, or homolog thereof, (e.g., a hypomorphic, knock-out or null allele described herein) is heterozygous for the mutant gene. In some embodiments, a Solanaceae plant (e.g., *Solanum lycopersicum*) comprising the mutant Solyc03g114840 gene, or homolog thereof, (e.g., a hypomorphic, knock-out or null allele described herein) is homozygous for the mutant gene.

In some embodiments, the Solyc03g114840 gene homolog (a) has a sequence that has at least 75%, at least 80%, at least 85%, at least 90%, at least 95%, at least 96%, at least 97%, at least 98%, or at least 99% identity with the sequence of SEQ ID NO: 12 or 13 and (b) is not a *Solanum lycopersicum* gene.

In some embodiments, the mutant $ej2^{w}$ gene comprises, for example, a nucleic acid (e.g., DNA) having the sequence of SEQ ID NO: 14; a portion of SEQ ID NO: 14 that exhibits substantially the same activity (e.g., encoding the same polypeptide or substantially the same polypeptide that has the same activity) as a nucleic acid (e.g., DNA) having the sequence of SEQ ID NO: 14; a nucleic acid (e.g., DNA) having at least 85%, at least 90%, at least 95%, at least 96%, at least 97%, at least 98%, or at least 99% identity with the sequence of SEQ ID NO: 14; an orthologue or homologue of the nucleic acid having the sequence of SEQ ID NO: 14.

In some embodiments, the mutant ej2$^{CR}$ gene comprises, for example, a nucleic acid (e.g., DNA) having the sequence of SEQ ID NO: 15 or 16; a portion of SEQ ID NO: 15 or 16 that exhibits substantially the same activity (e.g., encoding the same polypeptide or substantially the same polypeptide that has the same activity) as a nucleic acid (e.g., DNA) having the sequence of SEQ ID NO: 15 or 16; a nucleic acid (e.g., DNA) having at least 85%, at least 90%, at least 95%, at least 96%, at least 97%, at least 98%, or at least 99% identity with the sequence of SEQ ID NO: 15 or 16; an orthologue or homologue of the nucleic acid having the sequence of SEQ ID NO: 15 or 16.

Solanaceae plants comprising mutant genes Higher yield, higher quality products (e.g., fruits) and products (e.g., fruits) with different compositions (e.g., brix, also known as enhanced soluble solids or sugar concentration in the fruits), can be manipulated in a wide variety of types of Solanaceae plants that comprise a mutant gene, such as a mutant Solyc04g005320 gene (or homolog thereof), a mutant Solyc12g038510 gene (or homolog thereof), or a mutant Solyc03g114840 gene (or homolog thereof); or two mutant genes, such as both a mutant Solyc04g005320 gene (or homolog thereof) and a mutant Solyc12g038510 gene (or homolog thereof), both a mutant Solyc04g005320 gene (or homolog thereof) and a mutant Solyc03g114840 gene (or homolog thereof), or both a mutant Solyc12g038510 gene (or homolog thereof) and a mutant Solyc03g114840 gene (or homolog thereof); or three mutant genes, such as a mutant Solyc04g005320 gene (or homolog thereof), a mutant Solyc12g038510 gene (or homolog thereof), and a mutant Solyc03g114840 gene (or homolog thereof). In some embodiments, the Solanaceae plant is a genetically-altered Solanaceae plant. In some embodiments, a "genetically-altered" plant includes a plant that has had introduced into it (or introduced into a plant that is used to produce the plant, such as introduced into a parental line) at least one mutation by chemical or physical means (e.g., using CRISPR/Cas9, chemical mutagenesis, radiation, *Agrobacterium*-mediated recombination, viral-vector mediated recombination, or transposon mutagenesis).

The mutant Solyc04g005320 gene (or homolog thereof) can be any of the mutant Solyc04g005320 genes (or homologs thereof) described herein. The mutant Solyc12g038510 gene (or homolog thereof) can be any of the mutant Solyc12g038510 genes (or homologs thereof) described herein. The mutant Solyc03g114840 gene (or homolog thereof) can be any of the mutant Solyc03g114840 genes (or homologs thereof) described herein.

The genetically-altered Solanaceae plant can be, for example, inbred, isogenic or hybrid, as long as the plant comprises a mutant gene, such as a mutant Solyc04g005320 gene (or homolog thereof), a mutant Solyc12g038510 gene (or homolog thereof), or a mutant Solyc03g114840 gene (or homolog thereof); or two mutant genes, such as both a mutant Solyc04g005320 gene (or homolog thereof) and a mutant Solyc12g038510 gene (or homolog thereof), both a mutant Solyc04g005320 gene (or homolog thereof) and a mutant Solyc03g114840 gene (or homolog thereof), or both a mutant Solyc12g038510 gene (or homolog thereof) and a mutant Solyc03g114840 gene (or homolog thereof); or three mutant genes, such as a mutant Solyc04g005320 gene (or homolog thereof), a mutant Solyc12g038510 gene (or homolog thereof), and a mutant Solyc03g114840 gene (or homolog thereof).

Plants in the Solanaceae family include, e.g., tomato, potato, eggplant, *petunia*, tobacco, and pepper. In some embodiments, the Solanaceae plant is a tomato plant. In some embodiments, the Solanaceae plant, e.g. tomato plant, is not a variety.

In some embodiments, the genetically-altered Solanaceae plant comprises one wild-type (WT) copy of the SOLYC04G005320 gene (or homolog thereof) and one mutant copy of the Solyc04g005320 gene (or homolog thereof) as described herein (is heterozygous for the mutant Solyc04g005320 gene or homolog thereof). In some embodiments, the Solanaceae plant comprises two copies of a mutant Solyc04g005320 gene (or homolog thereof) as described herein (is homozygous for the mutant Solyc04g005320 gene or homolog thereof). In some embodiments, the Solanaceae plant comprises a first mutant Solyc04g005320 gene (or homolog thereof) as described herein and a second mutant Solyc04g005320 gene (or homolog thereof) as described herein, wherein the first mutant Solyc04g005320 gene (or homolog thereof) and the second mutant Solyc04g005320 gene (or homolog thereof) are different. In some embodiments, the Solanaceae plant comprises one copy of a mutant Solyc04g005320 gene (or homolog thereof) as described herein and one copy of a mutant Solyc12g038510 gene (or homolog thereof) as described herein (is heterozygous for the mutant Solyc04g005320 gene, or homolog thereof, and heterozygous for the mutant Solyc12g038510 gene, or homolog thereof). In some embodiments, the Solanaceae plant comprises one copy of a mutant Solyc04g005320 gene (or homolog thereof) as described herein and two copies of a mutant Solyc12g038510 gene (or homolog thereof) as described herein (is heterozygous for the mutant Solyc04g005320 gene, or homolog thereof and homozygous for the mutant Solyc12g038510 gene, or homolog thereof). In some embodiments, the Solanaceae plant comprises two copies of a mutant Solyc04g005320 gene (or homolog thereof) as described herein and two copies of a mutant Solyc12g038510 gene (or homolog thereof) as described herein (is homozygous for the mutant Solyc04g005320 gene, or homolog thereof, and homozygous for the mutant Solyc12g038510 gene, or homolog thereof).

In some embodiments, the genetically-altered Solanaceae plant comprises one WT copy of a SOLYC03G114840 gene (or homolog thereof) and one mutant copy of a Solyc03g114840 gene (or homolog thereof) as described herein (is heterozygous for the mutant Solyc03g114840 gene, or homolog thereof). In some embodiments, the Solanaceae plant comprises two copies of a mutant Solyc03g114840 gene (or homolog thereof) as described herein (is homozygous for the mutant Solyc03g114840 gene or homolog thereof). In some embodiments, the Solanaceae plant comprises one copy of a mutant Solyc03g114840 gene (or homolog thereof) as described herein and one copy of a mutant Solyc04g005320 gene (or homolog thereof) as described herein (is heterozygous for the mutant Solyc03g114840 gene, or homolog thereof, and heterozygous for the mutant Solyc04g005320 gene, or homolog thereof). In some embodiments, the Solanaceae plant comprises one copy of a mutant Solyc03g114840 gene (or homolog thereof) as described herein and two copies of a mutant Solyc04g005320 gene (or homolog thereof) as described herein (is heterozygous for the mutant Solyc03g114840 gene, or homolog thereof, and homozygous for the mutant Solyc04g005320 gene, or homolog thereof). In some embodiments, the Solanaceae plant comprises two copies of a mutant Solyc03g114840 gene (or homolog thereof) as described herein and two copies of a mutant Solyc04g005320 gene (or homolog thereof) as described herein (is homozygous for the mutant Solyc03g114840 gene, or homolog thereof, and homozygous for the mutant Solyc04g005320 gene, or homolog thereof).

In some embodiments, the genetically-altered Solanaceae plant comprises one WT copy of a SOLYC03G114840 gene and one mutant copy of a Solyc03g114840 gene as described herein (is heterozygous for the mutant Solyc03g114840 gene) and comprises one WT copy of the SOLYC12G038510 gene and one mutant copy of the Solyc12g038510 gene as described herein (is heterozygous for the mutant Solyc12g038510 gene). In some embodiments, the Solanaceae plant comprises two copies of a mutant Solyc03g114840 gene as described herein (is homozygous for the mutant Solyc03g114840 gene) and comprises two copies of a mutant Solyc12g038510 gene as described herein (is homozygous for the mutant Solyc12g038510 gene). In some embodiments, the Solanaceae plant comprising a mutant Solyc03g114840 gene (one or two copies) as described herein and a mutant Solyc12g038510 gene (one or two copies) further comprises one copy of a mutant Solyc04g005320 gene as described herein (is heterozygous or homozygous for the mutant Solyc03g114840 gene and the mutant Solyc12g038510 gene and heterozygous for the mutant Solyc04g005320 gene). In some embodiments, the Solanaceae plant further comprises two copies of a mutant Solyc04g005320 gene as described herein (is homozygous for the mutant Solyc04g005320 gene).

Other, non-limiting example genotype combinations which a Solanaceae (e.g., *Solanum lycopersicum*) plant may comprise are displayed in Table 1. The combinations in Table 1 may also be with homologs of the genes.

TABLE 1

Example genotype combinations.

| Combination No. | Solyc12g038510 (J2) Genotype | Solyc03g114840 (EJ2) Genotype | Solyc04g005320 (LIN) Genotype |
|---|---|---|---|
| 1 | $j2^{TE}/j2^{TE}$ | $ej2^{W}/ej2^{W}$ | $lin^{trans}/lin^{trans}$ |
| 2 | $j2^{TE}/j2^{TE}$ | $ej2^{W}/+$ | $lin^{trans}/lin^{trans}$ |
| 3 | $j2^{TE}/j2^{TE}$ | +/+ | $lin^{trans}/lin^{trans}$ |
| 4 | $j2^{TE}/j2^{TE}$ | $ej2^{W}/ej2^{W}$ | $lin^{trans}/+$ |
| 5 | $j2^{TE}/j2^{TE}$ | $ej2^{W}/+$ | $lin^{trans}/+$ |
| 6 | $j2^{TE}/j2^{TE}$ | +/+ | $lin^{trans}/+$ |
| 7 | $j2^{TE}/j2^{TE}$ | $ej2^{W}/ej2^{W}$ | +/+ |
| 8 | $j2^{TE}/j2^{TE}$ | $ej2^{W}/+$ | +/+ |
| 9 | $j2^{TE}/j2^{TE}$ | +/+ | +/+ |
| 10 | $j2^{stop}/j2^{stop}$ | $ej2^{W}/ej2^{W}$ | $lin^{trans}/lin^{trans}$ |
| 11 | $j2^{stop}/j2^{stop}$ | $ej2^{W}/+$ | $lin^{trans}/lin^{trans}$ |
| 12 | $j2^{stop}/j2^{stop}$ | +/+ | $lin^{trans}/lin^{trans}$ |
| 13 | $j2^{stop}/j2^{stop}$ | $ej2^{W}/ej2^{W}$ | $lin^{trans}/+$ |
| 14 | $j2^{stop}/j2^{stop}$ | $ej2^{W}/+$ | $lin^{trans}/+$ |
| 15 | $j2^{stop}/j2^{stop}$ | +/+ | $lin^{trans}/+$ |
| 16 | $j2^{stop}/j2^{stop}$ | $ej2^{W}/ej2^{W}$ | +/+ |
| 17 | $j2^{stop}/j2^{stop}$ | $ej2^{W}/+$ | +/+ |
| 18 | $j2^{stop}/j2^{stop}$ | +/+ | +/+ |
| 19 | $j2^{CR}/j2^{CR}$ | $ej2^{W}/ej2^{W}$ | $lin^{trans}/lin^{trans}$ |
| 20 | $j2^{CR}/j2^{CR}$ | $ej2^{W}/+$ | $lin^{trans}/lin^{trans}$ |
| 21 | $j2^{CR}/j2^{CR}$ | +/+ | $lin^{trans}/lin^{trans}$ |
| 22 | $j2^{CR}/j2^{CR}$ | $ej2^{W}/ej2^{W}$ | $lin^{trans}/+$ |
| 23 | $j2^{CR}/j2^{CR}$ | $ej2^{W}/+$ | $lin^{trans}/+$ |
| 24 | $j2^{CR}/j2^{CR}$ | +/+ | $lin^{trans}/+$ |
| 25 | $j2^{CR}/j2^{CR}$ | $ej2^{W}/ej2^{W}$ | +/+ |
| 26 | $j2^{CR}/j2^{CR}$ | $ej2^{W}/+$ | +/+ |
| 27 | $j2^{CR}/j2^{CR}$ | +/+ | +/+ |
| 28 | $j2^{TE}/+$ | $ej2^{W}/ej2^{W}$ | $lin^{trans}/lin^{trans}$ |
| 29 | $j2^{TE}/+$ | $ej2^{W}/+$ | $lin^{trans}/lin^{trans}$ |
| 30 | $j2^{TE}/+$ | +/+ | $lin^{trans}/lin^{trans}$ |
| 31 | $j2^{TE}/+$ | $ej2^{W}/ej2^{W}$ | $lin^{trans}/+$ |
| 32 | $j2^{TE}/+$ | $ej2^{W}/+$ | $lin^{trans}/+$ |
| 33 | $j2^{TE}/+$ | +/+ | $lin^{trans}/+$ |
| 34 | $j2^{TE}/+$ | $ej2^{W}/ej2^{W}$ | +/+ |
| 35 | $j2^{TE}/+$ | $ej2^{W}/+$ | +/+ |
| 36 | $j2^{TE}/+$ | +/+ | +/+ |
| 37 | $j2^{stop}/+$ | $ej2^{W}/ej2^{W}$ | $lin^{trans}/lin^{trans}$ |
| 38 | $j2^{stop}/+$ | $ej2^{W}/+$ | $lin^{trans}/lin^{trans}$ |
| 39 | $j2^{stop}/+$ | +/+ | $lin^{trans}/lin^{trans}$ |
| 40 | $j2^{stop}/+$ | $ej2^{W}/ej2^{W}$ | $lin^{trans}/+$ |
| 41 | $j2^{stop}/+$ | $ej2^{W}/+$ | $lin^{trans}/+$ |
| 42 | $j2^{stop}/+$ | +/+ | $lin^{trans}/+$ |
| 43 | $j2^{stop}/+$ | $ej2^{W}/ej2^{W}$ | +/+ |
| 44 | $j2^{stop}/+$ | $ej2^{W}/+$ | +/+ |
| 45 | $j2^{stop}/+$ | +/+ | +/+ |
| 46 | $j2^{CR}/+$ | $ej2^{W}/ej2^{W}$ | $lin^{trans}/lin^{trans}$ |
| 47 | $j2^{CR}/+$ | $ej2^{W}/+$ | $lin^{trans}/lin^{trans}$ |
| 48 | $j2^{CR}/+$ | +/+ | $lin^{trans}/lin^{trans}$ |
| 49 | $j2^{CR}/+$ | $ej2^{W}/ej2^{W}$ | $lin^{trans}/+$ |
| 50 | $j2^{CR}/+$ | $ej2^{W}/+$ | $lin^{trans}/+$ |
| 51 | $j2^{CR}/+$ | +/+ | $lin^{trans}/+$ |
| 52 | $j2^{CR}/+$ | $ej2^{W}/ej2^{W}$ | +/+ |
| 53 | $j2^{CR}/+$ | $ej2^{W}/+$ | +/+ |
| 54 | $j2^{CR}/+$ | +/+ | +/+ |
| 55 | +/+ | $ej2^{W}/ej2^{W}$ | $lin^{trans}/lin^{trans}$ |
| 56 | +/+ | $ej2^{W}/+$ | $lin^{trans}/lin^{trans}$ |
| 57 | +/+ | +/+ | $lin^{trans}/lin^{trans}$ |
| 58 | +/+ | $ej2^{W}/ej2^{W}$ | $lin^{trans}/+$ |
| 59 | +/+ | $ej2^{W}/+$ | $lin^{trans}/+$ |
| 60 | +/+ | +/+ | $lin^{trans}/+$ |
| 61 | +/+ | $ej2^{W}/ej2^{W}$ | +/+ |
| 62 | +/+ | $ej2^{W}/+$ | +/+ |
| 63 | +/+ | +/+ | +/+ |
| 64 | $j2^{TE}/j2^{TE}$ | $ej2^{CR}/ej2^{CR}$ | $lin^{trans}/lin^{trans}$ |
| 65 | $j2^{TE}/j2^{TE}$ | $ej2^{CR}/+$ | $lin^{trans}/lin^{trans}$ |
| 66 | $j2^{TE}/j2^{TE}$ | +/+ | $lin^{trans}/lin^{trans}$ |
| 67 | $j2^{TE}/j2^{TE}$ | $ej2^{CR}/ej2^{CR}$ | $lin^{trans}/+$ |
| 68 | $j2^{TE}/j2^{TE}$ | $ej2^{CR}/+$ | $lin^{trans}/+$ |
| 69 | $j2^{TE}/j2^{TE}$ | +/+ | $lin^{trans}/+$ |
| 70 | $j2^{TE}/j2^{TE}$ | $ej2^{CR}/ej2^{CR}$ | +/+ |
| 71 | $j2^{TE}/j2^{TE}$ | $ej2^{CR}/+$ | +/+ |
| 72 | $j2^{TE}/j2^{TE}$ | +/+ | +/+ |
| 73 | $j2^{stop}/j2^{stop}$ | $ej2^{CR}/ej2^{CR}$ | $lin^{trans}/lin^{trans}$ |
| 74 | $j2^{stop}/j2^{stop}$ | $ej2^{CR}/+$ | $lin^{trans}/lin^{trans}$ |
| 75 | $j2^{stop}/j2^{stop}$ | +/+ | $lin^{trans}/lin^{trans}$ |
| 76 | $j2^{stop}/j2^{stop}$ | $ej2^{CR}/ej2^{CR}$ | $lin^{trans}/+$ |
| 77 | $j2^{stop}/j2^{stop}$ | $ej2^{CR}/+$ | $lin^{trans}/+$ |
| 78 | $j2^{stop}/j2^{stop}$ | +/+ | $lin^{trans}/+$ |
| 79 | $j2^{stop}/j2^{stop}$ | $ej2^{CR}/ej2^{CR}$ | +/+ |
| 80 | $j2^{stop}/j2^{stop}$ | $ej2^{CR}/+$ | +/+ |
| 81 | $j2^{stop}/j2^{stop}$ | +/+ | +/+ |
| 82 | $j2^{CR}/j2^{CR}$ | $ej2^{CR}/ej2^{CR}$ | $lin^{trans}/lin^{trans}$ |
| 83 | $j2^{CR}/j2^{CR}$ | $ej2^{CR}/+$ | $lin^{trans}/lin^{trans}$ |
| 84 | $j2^{CR}/j2^{CR}$ | +/+ | $lin^{trans}/lin^{trans}$ |
| 85 | $j2^{CR}/j2^{CR}$ | $ej2^{CR}/ej2^{CR}$ | $lin^{trans}/+$ |
| 86 | $j2^{CR}/j2^{CR}$ | $ej2^{CR}/+$ | $lin^{trans}/+$ |
| 87 | $j2^{CR}/j2^{CR}$ | +/+ | $lin^{trans}/+$ |
| 88 | $j2^{CR}/j2^{CR}$ | $ej2^{CR}/ej2^{CR}$ | +/+ |
| 89 | $j2^{CR}/j2^{CR}$ | $ej2^{CR}/+$ | +/+ |
| 90 | $j2^{CR}/j2^{CR}$ | +/+ | +/+ |
| 91 | $j2^{TE}/+$ | $ej2^{CR}/ej2^{CR}$ | $lin^{trans}/lin^{trans}$ |
| 92 | $j2^{TE}/+$ | $ej2^{CR}/+$ | $lin^{trans}/lin^{trans}$ |
| 93 | $j2^{TE}/+$ | +/+ | $lin^{trans}/lin^{trans}$ |
| 94 | $j2^{TE}/+$ | $ej2^{CR}/ej2^{CR}$ | $lin^{trans}/+$ |
| 95 | $j2^{TE}/+$ | $ej2^{CR}/+$ | $lin^{trans}/+$ |
| 96 | $j2^{TE}/+$ | +/+ | $lin^{trans}/+$ |
| 97 | $j2^{TE}/+$ | $ej2^{CR}/ej2^{CR}$ | +/+ |
| 98 | $j2^{TE}/+$ | $ej2^{CR}/+$ | +/+ |
| 99 | $j2^{TE}/+$ | +/+ | +/+ |
| 100 | $j2^{stop}/+$ | $ej2^{CR}/ej2^{CR}$ | $lin^{trans}/lin^{trans}$ |
| 101 | $j2^{stop}/+$ | $ej2^{CR}/+$ | $lin^{trans}/lin^{trans}$ |

TABLE 1-continued

Example genotype combinations.

| Combination No. | Solyc12g038510 (J2) Genotype | Solyc03g114840 (EJ2) Genotype | Solyc04g005320 (LIN) Genotype |
|---|---|---|---|
| 102 | $j2^{stop}/+$ | +/+ | $lin^{trans}/lin^{trans}$ |
| 103 | $j2^{stop}/+$ | $ej2^{CR}/ej2^{CR}$ | $lin^{trans}/+$ |
| 104 | $j2^{stop}/+$ | $ej2^{CR}/+$ | $lin^{trans}/+$ |
| 105 | $j2^{stop}/+$ | +/+ | $lin^{trans}/+$ |
| 106 | $j2^{stop}/+$ | $ej2^{CR}/ej2^{CR}$ | +/+ |
| 107 | $j2^{stop}/+$ | $ej2^{CR}/+$ | +/+ |
| 108 | $j2^{stop}/+$ | +/+ | +/+ |
| 109 | $j2^{CR}/+$ | $ej2^{CR}/ej2^{CR}$ | $lin^{trans}/lin^{trans}$ |
| 110 | $j2^{CR}/+$ | $ej2^{CR}/+$ | $lin^{trans}/lin^{trans}$ |
| 111 | $j2^{CR}/+$ | +/+ | $lin^{trans}/lin^{trans}$ |
| 112 | $j2^{CR}/+$ | $ej2^{CR}/ej2^{CR}$ | $lin^{trans}/+$ |
| 113 | $j2^{CR}/+$ | $ej2^{CR}/+$ | $lin^{trans}/+$ |
| 114 | $j2^{CR}/+$ | +/+ | $lin^{trans}/+$ |
| 115 | $j2^{CR}/+$ | $ej2^{CR}/ej2^{CR}$ | +/+ |
| 116 | $j2^{CR}/+$ | $ej2^{CR}/+$ | +/+ |
| 117 | $j2^{CR}/+$ | +/+ | +/+ |
| 118 | +/+ | $ej2^{CR}/ej2^{CR}$ | $lin^{trans}/lin^{trans}$ |
| 119 | +/+ | $ej2^{CR}/+$ | $lin^{trans}/lin^{trans}$ |
| 120 | +/+ | +/+ | $lin^{trans}/lin^{trans}$ |
| 121 | +/+ | $ej2^{CR}/ej2^{CR}$ | $lin^{trans}/+$ |
| 122 | +/+ | $ej2^{CR}/+$ | $lin^{trans}/+$ |
| 123 | +/+ | +/+ | $lin^{trans}/+$ |
| 124 | +/+ | $ej2^{CR}/ej2^{CR}$ | +/+ |
| 125 | +/+ | $ej2^{CR}/+$ | +/+ |
| 126 | $j2^{TE}/j2^{TE}$ | $ej2^{W}/ej2^{W}$ | $lin^{CR}/lin^{CR}$ |
| 127 | $j2^{TE}/j2^{TE}$ | $ej2^{W}/+$ | $lin^{CR}/lin^{CR}$ |
| 128 | $j2^{TE}/j2^{TE}$ | +/+ | $lin^{CR}/lin^{CR}$ |
| 129 | $j2^{TE}/j2^{TE}$ | $ej2^{W}/ej2^{W}$ | $lin^{CR}/+$ |
| 130 | $j2^{TE}/j2^{TE}$ | $ej2^{W}/+$ | $lin^{CR}/+$ |
| 131 | $j2^{TE}/j2^{TE}$ | +/+ | $lin^{CR}/+$ |
| 132 | $j2^{TE}/j2^{TE}$ | $ej2^{W}/ej2^{W}$ | +/+ |
| 133 | $j2^{TE}/j2^{TE}$ | $ej2^{W}/+$ | +/+ |
| 134 | $j2^{TE}/j2^{TE}$ | +/+ | +/+ |
| 135 | $j2^{stop}/j2^{stop}$ | $ej2^{W}/ej2^{W}$ | $lin^{CR}/lin^{CR}$ |
| 136 | $j2^{stop}/j2^{stop}$ | $ej2^{W}/+$ | $lin^{CR}/lin^{CR}$ |
| 137 | $j2^{stop}/j2^{stop}$ | +/+ | $lin^{CR}/lin^{CR}$ |
| 138 | $j2^{stop}/j2^{stop}$ | $ej2^{W}/ej2^{W}$ | $lin^{CR}/+$ |
| 139 | $j2^{stop}/j2^{stop}$ | $ej2^{W}/+$ | $lin^{CR}/+$ |
| 140 | $j2^{stop}/j2^{stop}$ | +/+ | $lin^{CR}/+$ |
| 141 | $j2^{stop}/j2^{stop}$ | $ej2^{W}/ej2^{W}$ | +/+ |
| 142 | $j2^{stop}/j2^{stop}$ | $ej2^{W}/+$ | +/+ |
| 143 | $j2^{stop}/j2^{stop}$ | +/+ | +/+ |
| 144 | $j2^{CR}/j2^{CR}$ | $ej2^{W}/ej2^{W}$ | $lin^{CR}/lin^{CR}$ |
| 145 | $j2^{CR}/j2^{CR}$ | $ej2^{W}/+$ | $lin^{CR}/lin^{CR}$ |
| 146 | $j2^{CR}/j2^{CR}$ | +/+ | $lin^{CR}/lin^{CR}$ |
| 147 | $j2^{CR}/j2^{CR}$ | $ej2^{W}/ej2^{W}$ | $lin^{CR}/+$ |
| 148 | $j2^{CR}/j2^{CR}$ | $ej2^{W}/+$ | $lin^{CR}/+$ |
| 149 | $j2^{CR}/j2^{CR}$ | +/+ | $lin^{CR}/+$ |
| 150 | $j2^{CR}/j2^{CR}$ | $ej2^{W}/ej2^{W}$ | +/+ |
| 151 | $j2^{CR}/j2^{CR}$ | $ej2^{W}/+$ | +/+ |
| 152 | $j2^{CR}/j2^{CR}$ | +/+ | +/+ |
| 153 | $j2^{TE}/+$ | $ej2^{W}/ej2^{W}$ | $lin^{CR}/lin^{CR}$ |
| 154 | $j2^{TE}/+$ | $ej2^{W}/+$ | $lin^{CR}/lin^{CR}$ |
| 155 | $j2^{TE}/+$ | +/+ | $lin^{CR}/lin^{CR}$ |
| 156 | $j2^{TE}/+$ | $ej2^{W}/ej2^{W}$ | $lin^{CR}/+$ |
| 157 | $j2^{TE}/+$ | $ej2^{W}/+$ | $lin^{CR}/+$ |
| 158 | $j2^{TE}/+$ | +/+ | $lin^{CR}/+$ |
| 159 | $j2^{TE}/+$ | $ej2^{W}/ej2^{W}$ | +/+ |
| 160 | $j2^{TE}/+$ | $ej2^{W}/+$ | +/+ |
| 161 | $j2^{TE}/+$ | +/+ | +/+ |
| 162 | $j2^{stop}/+$ | $ej2^{W}/ej2^{W}$ | $lin^{CR}/lin^{CR}$ |
| 163 | $j2^{stop}/+$ | $ej2^{W}/+$ | $lin^{CR}/lin^{CR}$ |
| 164 | $j2^{stop}/+$ | +/+ | $lin^{CR}/lin^{CR}$ |
| 165 | $j2^{stop}/+$ | $ej2^{W}/ej2^{W}$ | $lin^{CR}/+$ |
| 166 | $j2^{stop}/+$ | $ej2^{W}/+$ | $lin^{CR}/+$ |
| 167 | $j2^{stop}/+$ | +/+ | $lin^{CR}/+$ |
| 168 | $j2^{stop}/+$ | $ej2^{W}/ej2^{W}$ | +/+ |
| 169 | $j2^{stop}/+$ | $ej2^{W}/+$ | +/+ |
| 170 | $j2^{stop}/+$ | +/+ | +/+ |
| 171 | $j2^{CR}/+$ | $ej2^{W}/ej2^{W}$ | $lin^{CR}/lin^{CR}$ |
| 172 | $j2^{CR}/+$ | $ej2^{W}/+$ | $lin^{CR}/lin^{CR}$ |
| 173 | $j2^{CR}/+$ | +/+ | $lin^{CR}/lin^{CR}$ |
| 174 | $j2^{CR}/+$ | $ej2^{W}/ej2^{W}$ | $lin^{CR}/+$ |
| 175 | $j2^{CR}/+$ | $ej2^{W}/+$ | $lin^{CR}/+$ |
| 176 | $j2^{CR}/+$ | +/+ | $lin^{CR}/+$ |
| 177 | $j2^{CR}/+$ | $ej2^{W}/ej2^{W}$ | +/+ |
| 178 | $j2^{CR}/+$ | $ej2^{W}/+$ | +/+ |
| 179 | $j2^{CR}/+$ | +/+ | +/+ |
| 180 | +/+ | $ej2^{W}/ej2^{W}$ | $lin^{CR}/lin^{CR}$ |
| 181 | +/+ | $ej2^{W}/+$ | $lin^{CR}/lin^{CR}$ |
| 182 | +/+ | +/+ | $lin^{CR}/lin^{CR}$ |
| 183 | +/+ | $ej2^{W}/ej2^{W}$ | $lin^{CR}/+$ |
| 184 | +/+ | $ej2^{W}/+$ | $lin^{CR}/+$ |
| 185 | +/+ | +/+ | $lin^{CR}/+$ |
| 186 | +/+ | $ej2^{W}/ej2^{W}$ | +/+ |
| 187 | +/+ | $ej2^{W}/+$ | +/+ |
| 188 | +/+ | +/+ | +/+ |
| 189 | $j2^{TE}/j2^{TE}$ | $ej2^{CR}/ej2^{CR}$ | $lin^{CR}/lin^{CR}$ |
| 190 | $j2^{TE}/j2^{TE}$ | $ej2^{CR}/+$ | $lin^{CR}/lin^{CR}$ |
| 191 | $j2^{TE}/j2^{TE}$ | +/+ | $lin^{CR}/lin^{CR}$ |
| 192 | $j2^{TE}/j2^{TE}$ | $ej2^{CR}/ej2^{CR}$ | $lin^{CR}/+$ |
| 193 | $j2^{TE}/j2^{TE}$ | $ej2^{CR}/+$ | $lin^{CR}/+$ |
| 194 | $j2^{TE}/j2^{TE}$ | +/+ | $lin^{CR}/+$ |
| 195 | $j2^{TE}/j2^{TE}$ | $ej2^{CR}/ej2^{CR}$ | +/+ |
| 196 | $j2^{TE}/j2^{TE}$ | $ej2^{CR}/+$ | +/+ |
| 197 | $j2^{TE}/j2^{TE}$ | +/+ | +/+ |
| 198 | $j2^{stop}/j2^{stop}$ | $ej2^{CR}/ej2^{CR}$ | $lin^{CR}/lin^{CR}$ |
| 199 | $j2^{stop}/j2^{stop}$ | $ej2^{CR}/+$ | $lin^{CR}/lin^{CR}$ |
| 200 | $j2^{stop}/j2^{stop}$ | +/+ | $lin^{CR}/lin^{CR}$ |
| 201 | $j2^{stop}/j2^{stop}$ | $ej2^{CR}/ej2^{CR}$ | $lin^{CR}/+$ |
| 202 | $j2^{stop}/j2^{stop}$ | $ej2^{CR}/+$ | $lin^{CR}/+$ |
| 203 | $j2^{stop}/j2^{stop}$ | +/+ | $lin^{CR}/+$ |
| 204 | $j2^{stop}/j2^{stop}$ | $ej2^{CR}/ej2^{CR}$ | +/+ |
| 205 | $j2^{stop}/j2^{stop}$ | $ej2^{CR}/+$ | +/+ |
| 206 | $j2^{stop}/j2^{stop}$ | +/+ | +/+ |
| 207 | $j2^{CR}/j2^{CR}$ | $ej2^{CR}/ej2^{CR}$ | $lin^{CR}/lin^{CR}$ |
| 208 | $j2^{CR}/j2^{CR}$ | $ej2^{CR}/+$ | $lin^{CR}/lin^{CR}$ |
| 209 | $j2^{CR}/j2^{CR}$ | +/+ | $lin^{CR}/lin^{CR}$ |
| 210 | $j2^{CR}/j2^{CR}$ | $ej2^{CR}/ej2^{CR}$ | $lin^{CR}/+$ |
| 211 | $j2^{CR}/j2^{CR}$ | $ej2^{CR}/+$ | $lin^{CR}/+$ |
| 212 | $j2^{CR}/j2^{CR}$ | +/+ | $lin^{CR}/+$ |
| 213 | $j2^{CR}/j2^{CR}$ | $ej2^{CR}/ej2^{CR}$ | +/+ |
| 214 | $j2^{CR}/j2^{CR}$ | $ej2^{CR}/+$ | +/+ |
| 215 | $j2^{CR}/j2^{CR}$ | +/+ | +/+ |
| 216 | $j2^{TE}/+$ | $ej2^{CR}/ej2^{CR}$ | $lin^{CR}/lin^{CR}$ |
| 217 | $j2^{TE}/+$ | $ej2^{CR}/+$ | $lin^{CR}/lin^{CR}$ |
| 218 | $j2^{TE}/+$ | +/+ | $lin^{CR}/lin^{CR}$ |
| 219 | $j2^{TE}/+$ | $ej2^{CR}/ej2^{CR}$ | $lin^{CR}/+$ |
| 220 | $j2^{TE}/+$ | $ej2^{CR}/+$ | $lin^{CR}/+$ |
| 221 | $j2^{TE}/+$ | +/+ | $lin^{CR}/+$ |
| 222 | $j2^{TE}/+$ | $ej2^{CR}/ej2^{CR}$ | +/+ |
| 223 | $j2^{TE}/+$ | $ej2^{CR}/+$ | +/+ |
| 224 | $j2^{TE}/+$ | +/+ | +/+ |
| 225 | $j2^{stop}/+$ | $ej2^{CR}/ej2^{CR}$ | $lin^{CR}/lin^{CR}$ |
| 226 | $j2^{stop}/+$ | $ej2^{CR}/+$ | $lin^{CR}/lin^{CR}$ |
| 227 | $j2^{stop}/+$ | +/+ | $lin^{CR}/lin^{CR}$ |
| 228 | $j2^{stop}/+$ | $ej2^{CR}/ej2^{CR}$ | $lin^{CR}/+$ |
| 229 | $j2^{stop}/+$ | $ej2^{CR}/+$ | $lin^{CR}/+$ |
| 230 | $j2^{stop}/+$ | +/+ | $lin^{CR}/+$ |
| 231 | $j2^{stop}/+$ | $ej2^{CR}/ej2^{CR}$ | +/+ |
| 232 | $j2^{stop}/+$ | $ej2^{CR}/+$ | +/+ |
| 233 | $j2^{stop}/+$ | +/+ | +/+ |
| 234 | $j2^{CR}/+$ | $ej2^{CR}/ej2^{CR}$ | $lin^{CR}/lin^{CR}$ |
| 235 | $j2^{CR}/+$ | $ej2^{CR}/+$ | $lin^{CR}/lin^{CR}$ |
| 236 | $j2^{CR}/+$ | +/+ | $lin^{CR}/lin^{CR}$ |
| 237 | $j2^{CR}/+$ | $ej2^{CR}/ej2^{CR}$ | $lin^{CR}/+$ |
| 238 | $j2^{CR}/+$ | $ej2^{CR}/+$ | $lin^{CR}/+$ |
| 239 | $j2^{CR}/+$ | +/+ | $lin^{CR}/+$ |
| 240 | $j2^{CR}/+$ | $ej2^{CR}/ej2^{CR}$ | +/+ |
| 241 | $j2^{CR}/+$ | $ej2^{CR}/+$ | +/+ |
| 242 | $j2^{CR}/+$ | +/+ | +/+ |
| 243 | +/+ | $ej2^{CR}/ej2^{CR}$ | $lin^{CR}/lin^{CR}$ |
| 244 | +/+ | $ej2^{CR}/+$ | $lin^{CR}/lin^{CR}$ |
| 245 | +/+ | +/+ | $lin^{CR}/lin^{CR}$ |
| 246 | +/+ | $ej2^{CR}/ej2^{CR}$ | $lin^{CR}/+$ |
| 247 | +/+ | $ej2^{CR}/+$ | $lin^{CR}/+$ |
| 248 | +/+ | +/+ | $lin^{CR}/+$ |
| 249 | +/+ | $ej2^{CR}/ej2^{CR}$ | +/+ |
| 250 | +/+ | $ej2^{CR}/+$ | +/+ |

Solanaceae plant cells are also contemplated herein. A Solanaceae plant cell may comprise any genotype described herein, e.g., as shown without limitation in Table 1, in the context of the Solanaceae plant (e.g., a Solanaceae plant cell heterozygous for a mutant Solyc03g114840 gene, or a homolog thereof, and a mutant Solyc12g038510 gene, or a homolog thereof, or a Solanaceae plant cell homozygous for a mutant Solyc12g038510 gene, or a homolog thereof, and a mutant Solyc04g005320 gene, or a homolog thereof). In some embodiments, the Solanaceae plant cell is isolated. In some embodiments, the Solanaceae plant cell is a non-replicating plant cell.

In some embodiments, any of the Solanaceae plants described herein may an altered phenotype compared to a WT Solanaceae plant (e.g., a Solanaceae plant comprising two copies or one copy of the corresponding WT gene). In some embodiments, any of the Solanaceae plants described herein have a higher yield than a corresponding WT Solanaceae plant. In some embodiments, any of the Solanaceae plants described herein have one or more of the following characteristics: longer sepals, larger calyxes, a different fruit shape, fewer branches, jointless pedicels, long inflorescences, or larger fruit compared to a corresponding WT Solanaceae plant. In some embodiments, such characteristics are appealing to consumers (e.g., products of the Solanaceae plant look fresher) and are advantageous for growers (e.g., products of the Solanaceae plant stay attached to the plant for a longer period of time).

Food products are also contemplated herein. Such food products comprise a Solanaceae plant part, such as a fruit (e.g., a tomato fruit). Non-limiting examples of food products include sauces (e.g., tomato sauce or ketchup), purees, pastes, juices, canned fruits, and soups. Food products may be produced or producible by using methods known in the art.

Isolated polynucleotides are also described herein, including WT and mutant alleles of the Solyc04g005320 gene, or a homolog thereof, e.g., $lin^{trans}$ and $lin^{CR}$. Isolated polynucleotides including WT and mutant alleles of the Solyc12g038510 gene, or a homolog thereof, are also contemplated, e.g., $j2^{CR}$, $j2^{TE}$ and $j2^{stop}$ Isolated polynucleotides including WT and mutant alleles of the Solyc03g114840 gene, or a homolog thereof, are also contemplated, e.g., $ej2^{CR}$ and $ej2^{w}$.

Isolated polynucleotides can comprise, for example, a nucleic acid (e.g., DNA) having the sequence of SEQ ID NO: 3, 4, 5, 8, 9, 10, 11, 14, 15 or 16; a portion of SEQ ID NO: 3, 4, 5, 8, 9, 10, 11, 14, 15 or 16 that exhibits substantially the same activity as a nucleic acid (e.g., DNA) having the sequence of SEQ ID NO: 3, 4, 5, 8, 9, 10, 11, 14, 15 or 16; a nucleic acid (e.g., DNA) having at least 85%, at least 90%, at least 95%, at least 96%, at least 97%, at least 98%, or at least 99% identity with the sequence of SEQ ID NO: 3, 4, 5, 8, 9, 10, 11, 14, 15 or 16; an orthologue or homologue of the nucleic acid having the sequence of SEQ ID NO: 3, 4, 5, 8, 9, 10, 11, 14, 15 or 16. In some embodiments, the isolated polynucleotide is a cDNA. Such isolated polynucleotides can be used, for example, in methods of producing genetically-altered plants.

Other aspects of the disclosure relate to seeds for producing a Solanaceae plant as described herein, e.g., a mutant Solyc04g005320 gene (or a homolog thereof), a mutant Solyc12g038510 gene (or a homolog thereof), or a mutant Solyc03g114840 gene (or a homolog thereof).

Methods of Producing Plants

In other aspects, the disclosure provides methods for producing a genetically-altered Solanaceae plant. In some embodiments, the method comprises introducing a mutation into a Solyc04g005320 gene (or a homolog thereof), into a Solyc12g038510 gene (or a homolog thereof), or into a Solyc03g114840 gene (or a homolog thereof) in the Solanaceae plant, thereby producing a genetically-altered Solanaceae plant containing a mutant version of the gene. In some embodiments, the method comprises introducing a mutation into a Solyc04g005320 gene (or a homolog thereof), into a Solyc12g038510 gene (or a homolog thereof), or into a Solyc03g114840 gene (or a homolog thereof) in the Solanaceae plant part, maintaining the plant part under conditions and for sufficient time for production of a genetically-altered Solanaceae plant, thereby producing a genetically-altered Solanaceae plant (or a homolog thereof) containing a mutant version of the gene. In some embodiments, mutations are introduced into two or all three of a Solyc04g005320 gene (or a homolog thereof), a Solyc12g038510 gene (or a homolog thereof), and a Solyc03g114840 gene (or a homolog thereof).

In any of the methods described herein, the mutant gene can be introduced into a Solanaceae plant or a plant part or produced in a Solanaceae plant or plant part by any method described herein or known to those of skill in the art, such as *Agrobacterium*-mediated recombination, viral-vector mediated recombination, microinjection, gene gun bombardment/biolistic particle delivery, electroporation, mutagenesis (e.g., by ethyl methanesulfonate or fast neutron irradiation), TILLING (Targeting Induced Local Lesions in Genomes), conventional marker-assisted introgression, and nuclease mediated recombination (e.g., use of custom-made restriction enzymes for targeting mutagenesis by gene replacement, see, e.g., CRISPR-Cas9: Genome engineering using the CRISPR-Cas9 system. Ran F A, Hsu P D, Wright J, Agarwala V, Scott D A, Zhang F. Nat Protoc. 2013 November; 8(11):2281-308; TALEN endonucleases: Nucleic Acids Res. 2011 July; 39(12):e82. Efficient design and assembly of custom TALEN and other TAL effector-based constructs for DNA targeting. Cermak T, Doyle E L, Christian M, Wang L, Zhang Y, Schmidt C, Baller J A, Somia N V, Bogdanove A J, Voytas D F and Plant Biotechnol J. 2012 May; 10(4):373-89. Genome modifications in plant cells by custom-made restriction enzymes. Tzfira T, Weinthal D, Marton I, Zeevi V, Zuker A, Vainstein A.). Genetically-altered Solanaceae plants produced by or producible by a method described herein are also claimed.

In some embodiments, the mutation produces a null allele, a hypomorphic allele, or a hypermorphic allele of a Solyc04g005320 gene (or a homolog thereof), a Solyc12g038510 gene (or a homolog thereof), or a Solyc03g114840 gene (or a homolog thereof) as described herein. In some embodiments, the mutation is a null mutation of a Solyc04g005320 gene (or a homolog thereof), a Solyc12g038510 gene (or a homolog thereof), or a Solyc03g114840 gene (or a homolog thereof) that is introduced using CRISPR/Cas9.

Alternatively, a method of producing a genetically-altered Solanaceae plant comprises a reducing (partially or completely) function of a wild-type Solyc04g005320 gene (or a homolog thereof), a wild-type Solyc12g038510 gene (or a homolog thereof), or a wild-type Solyc03g114840 gene (or a homolog thereof) in the plant or plant part. In some embodiments, reducing the function comprises performing any of the following methods of RNA-interference (e.g., administering to the Solanaceae plant a micro-RNA or a small interfering (si)-RNA or hairpin RNA) or translational blocking (e.g., administering to the Solanaceae plant a morpholino). Methods of RNA-interference and translational blocking are well-known in the art. Methods of producing micro-RNAs, si-RNAs, and morpholinos are well-known in the art and can involve use of the nucleotides sequences provided herein.

In some embodiments, the method comprises crossing a produced genetically-altered Solanaceae plant containing a mutant Solyc04g005320 gene (or a homolog thereof) to another genetically-altered Solanaceae plant comprising a mutant Solyc12g038510 gene (or a homolog thereof), a mutant Solyc03g114840 gene (or a homolog thereof), or both a mutant Solyc12g038510 gene (or a homolog thereof) and a mutant Solyc03g114840 gene (or a homolog thereof). In some embodiments, the method comprises crossing a produced genetically-altered Solanaceae plant containing a mutant Solyc12g038510 gene (or a homolog thereof) to another genetically-altered Solanaceae plant comprising a mutant Solyc04g005320 gene (or a homolog thereof), a mutant Solyc03g114840 gene (or a homolog thereof), or both a mutant Solyc04g005320 gene (or a homolog thereof) and a mutant Solyc03g114840 gene (or a homolog thereof). In some embodiments, the method comprises crossing a produced genetically-altered Solanaceae plant containing a mutant Solyc03g114840 gene (or a homolog thereof) to another genetically-altered Solanaceae plant comprising a mutant Solyc12g038510 gene (or a homolog thereof), a mutant Solyc04g005320gene (or a homolog thereof), or both a mutant Solyc12g038510 gene (or a homolog thereof) and a mutant Solyc04g005320 gene (or a homolog thereof).

Example Nucleic Acid Sequences of the Disclosure

```
Wild-type Solyc04g005320 gene
ATGGGAAGAGGTAAGGTAGAATTGAAGAGAATAGAAAATAAGATAAACAGGCAAGTTACTTTTGCTAAGAGAAGA
AATGGATTACTCAAAAAAGCTTATGAGCTTTCTATTTTGTGTGAAGCTGAAGTTGCTCTTATCATTTTCTCTAAT
AGAGGCAAACTCTATGAATTTTGCAGTACCTCTAGGTAATATTTTTATGTTTATGTCGTTCCGTTTAAGCTTTAC
ATTTACGTTTTTATACGCAAAACTTTAAATTAGTTCTAAATGTATTAAAAAATTGAAATTTTGAGATTTAATTTC
AAAATCTATGGTTAAACGAATGTTTATATGCATTATGATTTTGTTATCTTCTTTTTTTTTAAAAAAAGAAATAAA
ATATATTGATGTTATAGATCTGAGTGAGAATAGAGTTTTTGGTACATTTATTAAGGGTGAATAATCAAATGTTTC
ATTTGATTAGATCTAGGTTTTCTTGAACATTAAAATTGTTAAAAAAATTAGTTCATTTTATGAGGTAAATTTTGT
TATGATTTGATGTTCCACCTCCATTTTTTCTTATTTTTATTATAAATAAATAAGTTTTAAAATATCCTTACTTTT
ATATGTTCTTTTAAGTACAGACACATGAATCAAAAAGAAGTTTTATAATATGAATTGAATTAAAGCTGGTTGAAT
TTCTATCTTCAGTTTTTGAAAACAACTAAAAACTTTGAAAAGGAATTTGATTTTATTATTTATGGCAACAAATAA
CACCTAACTACTTATCGAGTCGGAATTGACGATATGAATCCTTTAACTTTTCATTTAAGCTCAATTTATATAGAA
AATTCTGTATTGTGGATTGAAGTAATTTCTGGAGTTGATCAATTCTATTTAAAAAATTATTTAATTAATAATCAT
TATCCCAAAAAATTATATTGAAATTAAAAAATAATATTAATTTTTTTAAATAACAAACTTATTAATTGAGTGACC
ATCTAAATCGTCTTTTTCTTAAAGTTAGGGTCTTGCCTTTCATCTAATTTTGATAGTAATGTTCTTGAACCGACA
AATTTTGTCATTTACTCTTATCTGTTATAATTTATGTGATTCGAGTTTTACGAATCAATTTTTGTTTATAATTTC
AATCATGTATAAGAAGTATTTTAAGTTATAATAATTAACAATTTTAAGAAAGCATAATCAAGATCAAATAACTTA
GTAGAAATAATATTGGTTTATGTAACCTCTATGCATTGACAATATAGTGTTTTTTTTATACTATCAAGTCATTTA
TTGGATAATTATAATTAAAGAATATTAACTAATGAGTAAATCAATAGTTTAATATTAATGAGTTATCATAGTAGC
GTATACTTATTACTCGATATTTGTAATCTAAACATTTTCAATATGCTTAAACTTGATTTTTTTATTTGGATCAAG
TATACAATTTTTTTGTTAATAATAAATGACATTGAAACTTATAACTAATTTTATTTAAACAATTTTCTTTCTTTC
TTTCCTCAAGGAGAGCATAGTTCTAATTATTATCAATATCATTATTATTATTATCTCTATGTTTATTTTATTATT
ACTGTTGTTTCTTTTACTTGGATTGTCTGTACTATTTTTACTTCATGGACTTTAATTTTTTGTCTATCGTATTTT
TATCATAGTTTTTACTCTTGTATTGGCTAAACCTAGTTTTGAAATTGTTTTTCATAAGCTGAAAGAGTCTATCAA
AAACAACTTCTCACGAGATAGAAATAAAGTTTACGTATATTCCATTCTTCTCAAACCCCACTTATGAGATTATAC
TGAAATGTTACTATTATTATTATACTTTGTAACATGCTAAAAAAACTAGTAATAATTACACTTCTTGCCAAAGAG
TAAATAAAGTATGATCCTTTAATAAGTTGAAAATCCCTCTAAATCAAATTATCACTTTTGTGCAACTTGTCTTCT
TTTTTTTCTTCTAGTATGTCTGATACACTGGAGAGATACCATAGATGCAGCTATGGTGACCTTGAAACTGGCCAG
TCTTCAAAGGATTCACAGGTTACTTCATCTTCCTCAGAATTACAATTTACTAATAAATTTAACTTATATACTCTG
ACACAGTATCGATGCAATTTAAACCTTTTATAACAGATTATCTGTTTTTATTTTAATTTCTTCGTAAATAATTAA
TAAGTCGATATTGATAACTAACGCCAAGCACCCTATCTTCATCTAACTAATTAGTGTTATTATGCAATAGAATAA
CTACCAAGAGTATATGAAGCTGAAAGCAAGAGTTGAAGTGCTACAACAGTCACAAAGGTGATACATTATTTGTTT
TAAAAACACTTTTACTTGTCTCATTTTGATTGGCTCATCTGAACACCTGAACCGGTCTAGAAGTATTTTGAACAT
GCATAATTGGACATGTTCAATCATGCGTTTGTTTGATCAGGTTCAGGATGTTTAGATGAGACCTCGTAAAATAAA
TTAAGGGGAGGCTTTTTAATATGATATTTGTGTCTCAAATATATCACTTTTCTACCCTAATTCTTAATAACATTG
TATTTACTTAATTATTCTTAATCTTTAAGGCATATACTTGGAGAGGACTTAGGACAATTAAACACAAAAGATTTG
GAACAGCTTGAGCGTCAACTGGATTCATCTTTGAGGCTAATAAGATCAAGAAGGGTATGTTCTATGCACCTTCAA
TTTATTTGTCAAATTTTAGGCTTTCAGATCATGTCTTAATCTTAATGTCCGATGACAGTTTCAGTGGCGGAATTA
GAAATTTATGCAAGACAATTCAAGCAATATTATATATTATAGAATGTCAGACTTGAAATTTGAACTTGAGACATT
GAACCTCTTTACAAATACACTAATATCTAACCTCGTATCAACGGGGTTCAACAATTTATATATATATAAAAAACA
CTTAATTTTGCCCTATTTGGTGTAATATATAATTTTATCAAAGGTATGTTGGGAAAATGATAAAAATTACTTATG
AATAATATCCAAATGGAATAATATAATAACAATTACTTACTATTACTTGATAGTGCCACAAAACTACTAAACCTT
AAAATAAGTTCTTTTATTTTACATAATTCATTATAATCTTTGGCATGAATTTACTCAAGCATTGCTTCAGAATGA
TCAAAGCCTCCTTAATATTTTTGGGTACAGACATAAAGTCTAGACATGCAATCAAAGATATAGATGCACGAGATG
ACTAATCAAAGGAAACAATAGGAACGATCAAAAAAATTGAAATTGAAAATATATTTTTTTTAAACTAAAGGTAAG
TCAAGATTACCAAGTAAGTGTATTATTGTAACTTTTGTATTATTTATCCTAAGTAAACATGTATCAAAAACATAC
ACAAATTTACTTTCTCTTTTATTACTAACATCAACTTACATGCTAATTATAAATAATTAAAGGGTAAATAGTTGG
TTGCATGATTTGGTAAAAGAAGTTGTTAACCTACTCTTTGATAACATATATGTTTTCAGACACAAAACATGCTTG
ATCAACTTTCTGATCTTCAACAAAAGGTATGTATTGTATAATATAATCCCTTAAGTTGACAATTAAATAGATTGT
TCAATTGTTAATTTGACATTGTATGTGTTCTTTTTTCTTTTTTTCTACAGGAACAATCTCTTCTTGAAATCAACA
GATCCTTGAAAACAAAGGTACAAAGCACACATTTTGGACCTTTTATGAGTTTTTTAGGGCGTGTTTGATTTATTT
ATTTTTTCTGAATTTTTTCATGTTTGGTTGATCTAAATTCTGGGAAAATACTTTTTTCTATGAAAGTAAGTTTTT
TAAAAATGACTTAGCCAGTGGAAGTAGGGAAAACAAGTTGTGACGACATTCCACGTTGATTGTTTTCTCTCGATC
TTCCTACACACCTTAAGTTCGCCACCACCTCTCGCAGTATTTGTTTAGATTATATAAAAATGTATCAAGAATGAC
ACTTTTTATTTGTGTACATAATAAAAGAAAATAAGTAAGAAACCGAACATTTTCCCATGGAAAATATTATTTTTC
ATACCAAACACACCCTTAGTCTTTGTTTTAGGGTATATGACTAATTTGTTCTCCATTTCGGATATTTAGATTCGT
ATGGGTTTTTCTTTGATGTCTAACTTATCGTACTTTTTACGCGATTTTATGAAATTCTTATAATAGTTGGAAGAA
AACTCTGTAGCACATTGGCATATCACTGGAGAGCAAAATGTACAATTCAGACAACAACCTGCTCAGTCAGAGGGG
TTCTTTCAGCCTTTACAATGCAATACTAATATAGTGCCAAACAGGTAACATATAATTTTATGTTTTCTTTTTTTC
CTTTAAATAGCATATTTTTTGCAACATTTTAAATTGAACCGTTGAATTGAGTCGTTGAGAGGTGAATTCAGAATC
TGAAGTAACAGATACATTCAAATTAATTTCTTTGTGTATTTATCGAAGTGAGTCAAGTCGTAAGTCTAGAGGTGA
ATTTAGAATCTAAAGTAATAGATACAGTCGAATCAATCTCTTTGTGTATTTATTGAAGTGAGTCGTTTTGTAAAG
```

-continued

TTTGAGACGAATTCAAAACCTAAAGTAATACTAAATACATACATTCAAAATAATTTCTAAAGCGAGTTATGTTGG
AAGTCGAGAGACGAAAGTATATTATATATGGATCAATTCAAATTAATTTCTTAATGTATTTGATGAGCGTTGTTG
TAGGGGCGAATTCAGAATCTGAAGTTCATGTAAGTACAGGTACAATGTGGCTCCATTGGATAGTATAGAACCATC
AACACAGAATGCTACTGGAATTTTACCAGGATGGATGCTTTGA (SEQ ID NO: 1)

Wild-type Solyc04g005320 coding sequence
ATGGGAAGAGGTAAGGTAGAATTGAAGAGAATAGAAAATAAGATAAACAGGCAAGTTACTTTTGCTAAGAGAAGA
AATGGATTACTCAAAAAAGCTTATGAGCTTTCTATTTTGTGTGAAGCTGAAGTTGCTCTTATCATTTTCTCTAAT
AGAGGCAAACTCTATGAATTTTGCAGTACCTCTAGTATGTCTGATACACTGGAGAGATACCATAGATGCAGCTAT
GGTGACCTTGAAACTGGCCAGTCTTCAAAGGATTCACAGAATAACTACCAAGAGTATATGAAGCTGAAAGCAAGA
GTTGAAGTGCTACAACAGTCACAAAGGCATATACTTGGAGAGGACTTAGGACAATTAAACACAAAAGATTTGGAA
CAGCTTGAGCGTCAACTGGATTCATCTTTGAGGCTAATAAGATCAAGAAGGACACAAAACATGCTTGATCAACTT
TCTGATCTTCAACAAAAGGAACAATCTCTTCTTGAAATCAACAGATCCTTGAAAACAAAGTTGGAAGAAAACTCT
GTAGCACATTGGCATATCACTGGAGAGCAAAATGTACAATTCAGACAACAACCTGCTCAGTCAGAGGGGTTCTTT
CAGCCTTTACAATGCAATACTAATATAGTGCCAAACAGGTACAATGTGGCTCCATTGGATAGTATAGAACCATCA
ACACAGAATGCTACTGGAATTTTACCAGGATGGATGCTTTGA (SEQ ID NO: 2)

Mutant Solyc04g005320 gene allele lin*trans*
ATGGGAAGAGGTAAGGTAGAATTGAAGAGAATAGAAAATAAGATAAACAGGCAAGTTACTTTTGCTAAGAGAAGA
AATGGATTACTCAAAAAAGCTTATGAGCTTTCTATTTTGTGTGAAGCTGAAGTTGCTCTTATCATTTTCTCTAAT
AGAGGCAAACTCTATGAATTTTGCAGTACCTCTAGGTAATATTTTTATGTTTATGTCGTTCCGTTTAAGCTTTAC
ATTTACGTTTTTATACGCAAAACTTTAAATTAGTTCTAAATGTATTAAAAAATTGAAATTTTGAGATTTAATTTC
AAAATCTATGGTTAAACGAATGTTTATATGCATTATGATTTTGTTATCTTCTTTTTTTTAAAAAAAGAAATAAA
ATATATTGATGTTATAGATCTGAGTGAGAATAGAGTTTTTGGTACATTTATTAAGGGTGAATAATCAAATGTTTC
ATTTGATTAGATCTAGGTTTTCTTGAACATTAAAATTGTTAAAAAAATT*TCCCCAATATCACTCAATACATATCA*
*ATCGGTATTAAGATTTTATCTATCAAATAGAAATAAATCATAACCTAACTCCACCAAAGAATCGAAGTCAAACAG*
*ACTACTTCTCCAATGTTTTTCCCTTTCTCAATGTCTGAACCTTTCCAATCTATCAAGTATATATGCATAATTT*
*GTAAGTCAATGAATTTATAAATACTTAAATTATTCTATGTCTAGCCTAAATCGAGTCCAGATTTTAACATGTAAA*
*ATTGAGGTGAGCTACCTATCATTAATCTATTTGACCTAGCTTTACTCTCAACCTGCACCTGACAACAAGTCCAAT*
*ATCTATTCCCATTTAATACTTCCACTTTAGAATGTAGTATCACTTGATAATTAAGCCAATTCTACCGAACAATTG*
***ACCAAATATCACGCCTCCACCTTGCCTCTTTCAATTTTCCAGTNNNNNN (N*X) NNNNNNATCAATAAAAATACG***
*GAAGCTCACAATTTGTTAGAGTAACCAATCAAATCATCGTCTAAAGTCTATTACACATAAAGTCATCACATCAAG*
*GACATTTGTTCTCAATTTCCAAGTCTTAAAAACGATGGTCCATATCCGAAAAAATTTTTGAAAATACCAAATAAG*
*ATTTAAGGACATCATGACATGAATGAGAGAATCTAGCACGAGCTAGAAATAATAGCTTACCCTGAATTCTGATAT*
*GCTGGAGGCTGGCTAGAGCTGAGGGCGAGTCGAAGTCGATGGTACACTTGCTGCACTCCACAAAAGAACAACACA*
*AAAAATACAAGTAAGGATCAGTACAAGGAACACGTATTGAGTAGGTATCATCAGCCACCCAAAATAGAAACCAAT*
*ATATATTGAATAATAATATAAAATCAACTACAATACTTGGCATGTGACAAACAACAAACAACATAAACCAGTGAC*
*AACAACACCATAGTAGGTACACAATATCAAGCACACCTATGAGGAGTCATGCCTCCACACCATACTCATTTAGAA*
*AATGGGTTCATTCAGATTGAGTATATTAAGTTAATTTAAGATTCCTTTACTTTAATGTTATCGTGTTGAAATGTG*
*ATACTCCGATCCCATATATACCGTGTCAGAACAAGAAATTCCGATTGCATAATATCGTGTTAGAATGTGACACTCCG*
*ATCCAACTATACCGTGTCAGAACGTGACACTCCGATCCAATTATCTCATTAATTTATTTCATCAAGCGTTCTTTA*
*TTCAACGCGTCATTTCGATAAAGAGGGTTCAAGCTTATAATTCAACAGTCTCAAAATTTTTGGTCAACCACAATC*
*GCAACCAAGATATACAACCACACAATCAAGTACATAATCAACTTC*TTCATTTTATGAGGTAAATTTTGTTATGAT
TTGATGTTCCACCTCCATTTTTTCTTATTTTTATTATAAATAAATAAGTTTTAAAATATCCTTACTTTTATATGT
TCTTTTAAGTACAGACACATGAATCAAAAAGAAGTTTTATAATATGAATTGAATTAAAGCTGGTTGAATTTCTAT
CTTCAGTTTTTGAAAACAACTAAAAACTTTGAAAAGGAATTTGATTTTATTATTTATGGCAACAAATAACACCTA
ACTACTTATCGAGTCGGAATTGACGATATGAATCCTTTAACTTTTCATTTAAGCTCAATTTATATAGAAAATTCT
GTATTGTGGATTGAAGTAATTTCTGGAGTTGATCAATTCTATTTAAAAAATTATTTAATTAATAATCATTATCCC
AAAAAATTATATTGAAATTAAAAAATAATATTAATTTTTTTAAATAACAAACTTATTAATTGAGTGACCATCTAA
ATCGTCTTTTTCTTAAAGTTAGGGTCTTGCCTTTCATCTAATTTTGATAGTAATGTTCTTGAACCGACAAATTTT
GTCATTTACTCTTATCTGTTATAATTTATGTGATTCGAGTTTTACGAATCAATTTTTGTTTATAATTTCAATCAT
GTATAAGAAGTATTTTAAGTTATAATAATTAACAATTTTAAGAAAGCATAATCAAGATCAAATAACTTAGTAGAA
ATAATATTGGTTTATGTAACCTCTATGCATTGACAATATAGTGTTTTTTTTATACTATCAAGTCATTTATTGGAT
AATTATAATTAAAGAATATTAACTAATGAGTAAATCAATAGTTTAATATTAATGAGTTATCATAGTAGCGTATAC
TTATTACTCGATATTTGTAATCTAAACATTTTCAATATGCTTAAACTTGATTTTTTTATTTGGATCAAGTATACA
ATTTTTTTGTTAATAATAAATGACATTGAAACTTATAACTAATTTTATTTAAACAATTTTCTTTCTTTCTTTCCT
CAAGGAGAGCATAGTTCTAATTATTATCAATATCATTATTATTATTATCTCTATGTTTATTTTATTATTACTGTT
GTTTCTTTTACTTGGATTGTCTGTACTATTTTTACTTCATGGACTTTAATTTTTTGTCTATCGTATTTTTATCAT
AGTTTTTACTCTTGTATTGGCTAAACCTAGTTTTGAAATTGTTTTTCATAAGCTGAAAGAGTCTATCAAAAACAA
CTTCTCACGAGATAGAAATAAAGTTTACGTATATTCCATTCTTCTCAAACCCCACTTATGAGATTATACTGAAAT
GTTACTATTATTATTATACTTTGTAACATGCTAAAAAAACTAGTAATAATTACACTTCTTGCCAAAGAGTAAATA
AAGTATGATCCTTTAATAAGTTGAAAATCCCTCTAAATCAAATTATCACTTTTGTGCAACTTGTCTTCTTTTTTT
TCTTCTAGTATGTCTGATACACTGGAGAGATACCATAGATGCAGCTATGGTGACCTTGAAACTGGCCAGTCTTCA
AAGGATTCACAGGTTACTTCATCTTCCTCAGAATTACAATTTACTAATAAATTTAACTTATATACTCTGACACAG
TATCGATGCAATTTAAACCTTTTATAACAGATTATCTGTTTTTATTTTAATTTCTTCGTAAATAATTAATAAGTC
GATATTGATAACTAACGCCAAGCACCCTATCTTCATCTAACTAATTAGTGTTATTATGCAATAGAATAACTACCA
AGAGTATATGAAGCTGAAAGCAAGAGTTGAAGTGCTACAACAGTCACAAAGGTGATACATTATTTGTTTTAAAAA
CACTTTTACTTGTCTCATTTTGATTGGCTCATCTGAACACCTGAACCGGTCTAGAAGTATTTTGAACATGCATAA
TTGGACATGTTCAATCATGCGTTTGTTTGATCAGGTTCAGGATGTTTAGATGAGACCTCGTAAAATAAATTAAGG
GGAGGCTTTTTAATATGATATTTGTGTCTCAAATATATCACTTTTCTACCCTAATTCTTAATAACATTGTATTTA
CTTAATTATTCTTAATCTTTAAGGCATATACTTGGAGAGGACTTAGGACAATTAAACACAAAAGATTTGGAACAG
CTTGAGCGTCAACTGGATTCATCTTTGAGGCTAATAAGATCAAGAAGGGTATGTTCTATGCACCTTCAATTTATT
TGTCAAATTTTAGGCTTTCAGATCATGTCTTAATCTTAATGTCCGATGACAGTTTCAGTGGCGGAATTAGAAATT
TATGCAAGACAATTCAAGCAATATTATATATTATAGAATGTCAGACTTGAAATTTGAACTTGAGACATTGAACCT
CTTTACAAATACACTAATATCTAACCTCGTATCAACGGGGTTCAACAATTTATATATATATAAAAAACACTTAAT
TTTGCCCTATTTGGTGTAATATATAATTTTATCAAAGGTATGTTGGGAAAATGATAAAAAATTACTTATGAATAAT
ATCCAAATGGAATAATATAATAACAATTACTTACTATTACTTGATAGTGCCACAAAACTACTAAACCTTAAAATA
AGTTCTTTTATTTTACATAATTCATTATAATCTTTGGCATGAATTTACTCAAGCATTGCTTCAGAATGATCAAAG -continued CCTCCTTAATATTTTTGGGTACAGACATAAAGTCTAGACATGCAATCAAAGATATAGATGCACGAGATGACTAAT
CAAAGGAAACAATAGGAACGATCAAAAAAATTGAAATTGAAAATATATTTTTTTAAACTAAAGGTAAGTCAAGA
TTACCAAGTAAGTGTATTATTGTAACTTTTGTATTATTTATCCTAAGTAAACATGTATCAAAAACATACACAAAT
TTACTTTCTCTTTTATTACTAACATCAACTTACATGCTAATTATAAATAATTAAAGGGTAAATAGTTGGTTGCAT
GATTTGGTAAAAGAAGTTGTTAACCTACTCTTTGATAACATATATGTTTTCAGACACAAAACATGCTTGATCAAC
TTTCTGATCTTCAACAAAAGGTATGTATTGTATAATATAATCCCTTAAGTTGACAATTAAATAGATTGTTCAATT
GTTAATTTGACATTGTATGTGTTCTTTTTTCTTTTTTTCTACAGGAACAATCTCTTCTTGAAATCAACAGATCCT
TGAAAACAAAGGTACAAAGCACACATTTTGGACCTTTTATGAGTTTTTTAGGGCGTGTTTGATTTATTTATTTTTT
TCTGAATTTTTTCATGTTTGGTTGATCTAAATTCTGGGAAAATACTTTTTTCTATGAAAGTAAGTTTTTTAAAAA
TGACTTAGCCAGTGGAAGTAGGGAAAACAAGTTGTGACGACATTCCACGTTGATTGTTTTCTCTCGATCTTCCTA
CACACCTTAAGTTCGCCACCACCTCTCGCAGTATTTGTTTAGATTATATAAAAATGTATCAAGAATGACACTTTT
TATTTGTGTACATAATAAAAGAAAATAAGTAAGAAACCGAACATTTTCCCATGGAAAATATTATTTTTCATACCA
AACACACCCTTAGTCTTTGTTTTAGGGTATATGACTAATTTGTTCTCCATTTCGGATATTTAGATTCGTATGGGT
TTTTCTTTGATGTCTAACTTATCGTACTTTTTACGCGATTTTATGAAATTCTTATAATAGTTGGAAGAAAACTCT
GTAGCACATTGGCATATCACTGGAGAGCAAAATGTACAATTCAGACAACAACCTGCTCAGTCAGAGGGGTTCTTT
CAGCCTTTACAATGCAATACTAATATAGTGCCAAACAGGTAACATATAATTTTATGTTTTCTTTTTTTCCTTTAA
ATAGCATATTTTTTGCAACATTTTAAATTGAACCGTTGAATTGAGTCGTTGAGAGGTGAATTCAGAATCTGAAGT
AACAGATACATTCAAATTAATTTCTTTGTGTATTTATCGAAGTGAGTCGAAGTCGTAAGTCTAGAGGTGAATTTAG
AATCTAAAGTAATAGATACAGTCGAATCAATCTCTTTGTGTATTTATTGAAGTGAGTCGTTTTGTAAAGTTTGAG
ACGAATTCAAAACCTAAAGTAATACTAAATACATACATTCAAAATAATTTCTAAAGCGAGTTATGTTGGAAGTCG
AGAGACGAAAGTATATTATATATGGATCAATTCAAATTAATTTCTTAATGTATTTGATGAGCGTTGTTGTAGGGG
CGAATTCAGAATCTGAAGTTCATGTAAGTACAGGTACAATGTGGCTCCATTGGATAGTATAGAACCATCAACACA
GAATGCTACTGGAATTTTACCAGGATGGATGCTTTGA (SEQ ID NO: 3)

Mutant Solyc04g005320 gene allele lin$^{CR}$
>allele-1
ATGGGAAGAGGTAAGGTAGAATTGAAGAGAATAGAAAATAAGATAAACAGGCAAGTTACTTTTGCTAAGAGAAGA
AATGGATTACTCAAAAAGCTTATGAGCTTTCTATTTTGTGTGAAGCTGAAGTTGCTCTTATCATTTTCTCTAAT
AGAGGCAAACTCTATGAATTTTGCAGTACCTCTAGGTAATATTTTTATGTTTATGTCGTTCCGTTTAAGCTTTAC
ATTTACGTTTTTATACGCAAAACTTTAAATTAGTTCTAAATGTATTAAAAAATTGAAATTTTGAGATTTAATTTC
AAAATCTATGGTTAAACGAATGTTTATATGCATTATGATTTTGTTATCTTCTTTTTTTTTAAAAAAAGAAATAAA
ATATATTGATGTTATAGATCTGAGTGAGAATAGAGTTTTTGGTACATTTATTAAGGGTGAATAATCAAATGTTTC
ATTTGATTAGATCTAGGTTTTCTTGAACATTAAAATTGTTAAAAAAATTAGTTCATTTTATGAGGTAAATTTTGT
TATGATTTGATGTTCCACCTCCATTTTTTCTTATTTTTATTATAAATAAATAAGTTTTAAAATATCCTTACTTTT
ATATGTTCTTTTAAGTACAGACACATGAATCAAAAAGAAGTTTTATAATATGAATTGAATTAAAGCTGGTTGAAT
TTCTATCTTCAGTTTTTGAAAACAACTAAAAACTTTGAAAAGGAATTTGATTTTATTATTTATGGCAACAAATAA
CACCTAACTACTTATCGAGTCGGAATTGACGATATGAATCCTTTAACTTTTCATTTAAGCTCAATTTATATAGAA
AATTCTGTATTGTGGATTGAAGTAATTTCTGGAGTTGATCAATTCTATTTAAAAAATTATTTAATTAATAATCAT
TATCCCAAAAAATTATATTGAAATTAAAAAATAATATTAATTTTTTTAAATAACAAACTTATTAATTGAGTGACC
ATCTAAATCGTCTTTTTCTTAAAGTTAGGGTCTTGCCTTTCATCTAATTTTGATAGTAATGTTCTTGAACCGACA
AATTTTGTCATTTACTCTTATCTGTTATAATTTATGTGATTCGAGTTTTACGAATCAATTTTTGTTTATAATTTC
AATCATGTATAAGAAGTATTTTAAGTTATAATAATTAACAATTTTAAGAAAGCATAATCAAGATCAAATAACTTA
GTAGAAATAATATTGGTTTATGTAACCTCTATGCATTGACAATATAGTGTTTTTTTTATACTATCAAGTCATTTA
TTGGATAATTATAATTAAAGAATATTAACTAATGAGTAAATCAATAGTTTAATATTAATGAGTTATCATAGTAGC
GTATACTTATTACTCGATATTTGTAATCTAAACATTTTCAATATGCTTAAACTTGATTTTTTTATTTGGATCAAG
TATACAATTTTTTTGTTAATAATAAATGACATTGAAACTTATAACTAATTTATTTAAACAATTTTCTTTCTTTC
TTTCCTCAAGGAGAGCATAGTTCTAATTATTATCAATATCATTATTATTATTATCTCTATGTTTATTTTATTATT
ACTGTTGTTTCTTTTACTTGGATTGTCTGTACTATTTTTACTTCATGGACTTTAATTTTTTGTCTATCGTATTTT
TATCATAGTTTTTACTCTTGTATTGGCTAAACCTAGTTTTGAAATTGTTTTTCATAAGCTGAAAGAGTCTATCAA
AAACAACTTCTCACGAGATAGAAATAAAGTTTACGTATATTCCATTCTTCTCAAACCCCACTTATGAGATTATAC
TGAAATGTTACTATTATTATTATTATACTTTGTAACATGCTAAAAAAACTAGTAATAATTACACTTCTTGCCAAAGAG
TAAATAAAGTATGATCCTTTAATAAGTTGAAAATCCCTCTAAATCAAATTATCACTTTTGTGCAACTTGTCTTCT
TTTTTTTCTTCTAGTATGTCCCATAGATGCAGCTATGGTGACCTTGAAACTGGCCAGTCTTCAAAGGATTCACAG
GTTACTTCATCTTCCTCAGAATTACAATTTACTAATAAATTTAACTTATATACTCTGACACAGTATCGATGCAAT
TTAAACCTTTTATAACAGATTATCTGTTTTATTTTAATTTCTTCGTAAATAATTAATAAGTCGATATTGATAAC
TAACGCCAAGCACCCTATCTTCATCTAACTAATTAGTGTTATTATGCAATAGAATAACTACCAAGAGTATATGAA
GCTGAAAGCAAGAGTTGAAGTGCTACAACAGTCACAAAGGTGATACATTATTTGTTTTAAAAACACTTTTACTTG
TCTCATTTTGATTGGCTCATCTGAACACCTGAACCGGTCTAGAAGTATTTTGAACATGCATAATTGGACATGTTC
AATCATGCGTTTGTTTGATCAGGTTCAGGATGTTTAGATGAGACCTCGTAAAATAAATTAAGGGGAGGCTTTTTA
ATATGATATTTGTGTCTCAAATATATCACTTTTCTACCCTAATTCTTAATAACATTGTATTTACTTAATTATTCT
TAATCTTTAAGGCATATACTTGGAGAGGACTTAGGACAATTAAACACAAAAGATTTGGAACAGCTTGAGCAACTG
GATTCATCTTTGAGGCTAATAAGATCAAGAAGGGTATGTTCTATGCACCTTCAATTTATTTGTCAAATTTTAGGC
TTTCAGATCATGTCTTAATCTTAATGTCCGATGACAGTTTCAGTGGCGGAATTAGAAATTTATGCAAGACAATTC
AAGCAATATTATATATTATAGAATGTCAGACTTGAAATTTGAACTTGAGACATTGAACCTCTTTACAAATACACT
AATATCTAACCTCGTATCAACGGGGTTCAACAATTTATATATATATAAAAAACACTTAATTTTGCCCTATTTGGT
GTAATATATAATTTTATCAAAGGTATGTTGGGAAAATGATAAAAATTACTTATGAATAATATCCAAATGGAATAA
TATAATAACAATTACTTACTATTACTTGATAGTGCCACAAAACTACTAAACCTTAAAATAAGTTCTTTTATTTTA
CATAATTCATTATAATCTTTGGCATGAATTTACTCAAGCATTGCTTCAGAATGATCAAAGCCTCCTTAATATTTT
TGGGTACAGACATAAAGTCTAGACATGCAATCAAAGATATAGATGCACGAGATGACTAATCAAAGGAAACAATAG
GAACGATCAAAAAAATTGAAATTGAAAATATATTTTTTTAAACTAAAGGTAAGTCAAGATTACCAAGTAAGTGT
ATTATTGTAACTTTTGTATTATTTATCCTAAGTAAACATGTATCAAAAACATACACAAATTTACTTTCTCTTTTA
TTACTAACATCAACTTACATGCTAATTATAAATAATTAAAGGGTAAATAGTTGGTTGCATGATTTGGTAAAAGAA
GTTGTTAACCTACTCTTTGATAACATATATGTTTTCAGACACAAAACATGCTTGATCAACTTTCTGATCTTCAAC
AAAAGGTATGTATTGTATAATATAATCCCTTAAGTTGACAATTAAATAGATTGTTCAATTGTTAATTTGACATTG
TATGTGTTCTTTTTTCTTTTTTTCTACAGGAACAATCTCTTCTTGAAATCAACAGATCCTTGAAAACAAAGGTAC
AAAGCACACATTTTGGACCTTTTATGAGTTTTTTAGGGCGTGTTTGATTTATTTATTTTTTTCTGAATTTTTTCAT
GTTTGGTTGATCTAAATTCTGGGAAAATACTTTTTTCTATGAAAGTAAGTTTTTTAAAAATGACTTAGCCAGTGG
AAGTAGGGAAAACAAGTTGTGACGACATTCCACGTTGATTGTTTTCTCTCGATCTTCCTACACACCTTAAGTTCG
CCACCACCTCTCGCAGTATTTGTTTAGATTATATAAAAATGTATCAAGAATGACACTTTTTATTTGTGTACATAA -continued

```
TAAAAGAAAATAAGTAAGAAACCGAACATTTTCCCATGGAAAATATTATTTTTCATACCAAACACACCCTTAGTC
TTTGTTTTAGGGTATATGACTAATTTGTTCTCCATTTCGGATATTTAGATTCGTATGGGTTTTTCTTTGATGTCT
AACTTATCGTACTTTTTACGCGATTTTATGAAATTCTTATAATAGTTGGAAGAAAACTCTGTAGCACATTGGCAT
ATCACTGGAGAGCAAAATGTACAATTCAGACAACAACCTGCTCAGTCAGAGGGGTTCTTTCAGCCTTTACAATGC
AATACTAATATAGTGCCAAACAGGTAACATATAATTTTATGTTTTCTTTTTTTCCTTTAAATAGCATATTTTTTG
CAACATTTTAAATTGAACCGTTGAATTGAGTCGTTGAGAGGTGAATTCAGAATCTGAAGTAACAGATACATTCAA
ATTAATTTCTTTGTGTATTTATCGAAGTGAGTCAAGTCGTAAGTCTAGAGGTGAATTTAGAATCTAAAGTAATAG
ATACAGTCGAATCAATCTCTTTGTGTATTTATTGAAGTGAGTCGTTTTGTAAAGTTTGAGACGAATTCAAAACCT
AAAGTAATACTAAATACATACATTCAAAATAATTTCTAAAGCGAGTTATGTTGGAAGTCGAGAGACGAAAGTATA
TTATATATGGATCAATTCAAATTAATTTCTTAATGTATTTGATGAGCGTTGTTGTAGGGGCGAATTCAGAATCTG
AAGTTCATGTAAGTACAGGTACAATGTGGCTCCATTGGATAGTATAGAACCATCAACACAGAATGCTACTGGAAT
TTTACCAGGATGGATGCTTTGA (SEQ ID NO: 4)

>allele-2
ATGGGAAGAGGTAAGGTAGAATTGAAGAGAATAGAAAATAAGATAAACAGGCAAGTTACTTTTGCTAAGAGAAGA
AATGGATTACTCAAAAAAGCTTATGAGCTTTCTATTTTGTGTGAAGCTGAAGTTGCTCTTATCATTTTCTCTAAT
AGAGGCAAACTCTATGAATTTTGCAGTACCTCTAGGTAATATTTTTATGTTATGTCGTTCCGTTTAAGCTTTAC
ATTTACGTTTTTATACGCAAAACTTTAAATTAGTTCTAAATGTATTAAAAAATTGAAATTTTGAGATTTAATTTC
AAAATCTATGGTTAAACGAATGTTTATATGCATTATGATTTTGTTATCTTCTTTTTTTTTAAAAAAAGAAATAAA
ATATATTGATGTTATAGATCTGAGTGAGAATAGAGTTTTTGGTACATTTATTAAGGGTGAATAATCAAATGTTTC
ATTTGATTAGATCTAGGTTTTCTTGAACATTAAAATTGTTAAAAAAATTAGTTCATTTTATGAGGTAAATTTTGT
TATGATTTGATGTTCCACCTCCATTTTTTCTTATTTTTATTATAAATAAATAAGTTTTAAAATATCCTTACTTTT
ATATGTTCTTTTAAGTACAGACACATGAATCAAAAAGAAGTTTTATAATATGAATTGAATTAAAGCTGGTTGAAT
TTCTATCTTCAGTTTTTGAAAACAACTAAAAACTTTGAAAAGGAATTTGATTTTATTATTTATGGCAACAAATAA
CACCTAACTACTTATCGAGTCGGAATTGACGATATGAATCCTTTAACTTTTCATTTAAGCTCAATTTATATAGAA
AATTCTGTATTGTGGATTGAAGTAATTTCTGGAGTTGATCAATTCTATTTAAAAAATTATTTAATTAATAATCAT
TATCCCAAAAAATTATATTGAAATTAAAAAATAATATTAATTTTTTTAAATAACAAACTTATTAATTGAGTGACC
ATCTAAATCGTCTTTTTCTTAAAGTTAGGGTCTTGCCTTTCATCTAATTTTGATAGTAATGTTCTTGAACCGACA
AATTTTGTCATTTACTCTTATCTGTTATAATTTATGTGATTCGAGTTTTACGAATCAATTTTTGTTTATAATTTC
AATCATGTATAAGAAGTATTTTAAGTTATAATAATTAACAATTTTAAGAAAGCATAATCAAGATCAAATAACTTA
GTAGAAATAATATTGGTTTATGTAACCTCTATGCATTGACAATATAGTGTTTTTTTATACTATCAAGTCATTTA
TTGGATAATTATAATTAAAGAATATTAACTAATGAGTAAATCAATAGTTTAATATTAATGAGTTATCATAGTAGC
GTATACTTATTACTCGATATTTGTAATCTAAACATTTTCAATATGCTTAAACTTGATTTTTTTATTTGGATCAAG
TATACAATTTTTTTGTTAATAATAAATGACATTGAAACTTATAACTAATTTTATTTAAACAATTTTCTTTCTTTC
TTTCCTCAAGGAGAGCATAGTTCTAATTATTATCAATATCATTATTATTATTATCTCTATGTTTATTTTATTATT
ACTGTTGTTTCTTTTACTTGGATTGTCTGTACTATTTTTACTTCATGGACTTTAATTTTTTGTCTATCGTATTTT
TATCATAGTTTTTACTCTTGTATTGGCTAAACCTAGTTTTGAAATTGTTTTTCATAAGCTGAAAGAGTCTATCAA
AAACAACTTCTCACGAGATAGAAATAAAGTTTACGTATATTCCATTCTTCTCAAACCCCACTTATGAGATTATAC
TGAAATGTTACTATTATTATTATACTTTGTAACATGCTAAAAAAACTAGTAATAATTACACTTCTTGCCAAAGAG
TAAATAAAGTATGATCCTTTAATAAGTTGAAAATCCCTCTAAATCAAATTATCACTTTTGTGCAACTTGTCTTCT
TTTTTTTCTTCTAGTATGTCTGATACACTGGAGAGATACCATAGATGCAGCTATGGTGACCTTGAAACTGGCCAG
TCTTCAAAGGATTCACAGGTTACTTCATCTTCCTCAGAATTACAATTTACTAATAAATTTAACTTATATACTCTG
ACACAGTATCGATGCAATTTAAACCTTTTATAACAGATTATCTGTTTTTATTTTAATTTCTTCGTAAATAATTAA
TAAGTCGATATTGATAACTAACGCCAAGCACCCTATCTTCATCTAACTAATTAGTGTTATTATGCAATAGAATAA
CTACCAAGAGTATATGAAGCTGAAAGCAAGAGTTGAAGTGCTACAACAGTCACAAAGGTGATACATTATTTGTTT
TAAAAACACTTTTACTTGTCTCATTTTGATTGGCTCATCTGAACACCTGAACCGGTCTAGAAGTATTTTGAACAT
GCATAATTGGACATGTTCAATCATGCGTTTGTTTGATCAGGTTCAGGATGTTTAGATGAGACCTCGTAAAATAAA
TTAAGGGGAGGCTTTTTAATATGATATTTGTGTCTCAAATATATCACTTTTCTACCCTAATTCTTAATAACATTG
TATTTACTTAATTATTCTTAATCTTTAAGGCATATACTTGGAGAGGACTTAGGACAATTAAACACAAAAGATTTG
GAAAACTGGATTCATCTTTGAGGCTAATAAGATCAAGAAGGGTATGTTCTATGCACCTTCAATTTATTTGTCAAA
TTTTAGGCTTTCAGATCATGTCTTAATCTTAATGTCCGATGACAGTTTCAGTGGCGGAATTAGAAATTTATGCAA
GACAATTCAAGCAATATTATATATTATAGAATGTCAGACTTGAAATTTGAACTTGAGACATTGAACCTCTTTACA
AATACACTAATATCTAACCTCGTATCAACGGGGTTCAACAATTTATATATATATAAAAAACACTTAATTTTGCCC
TATTTGGTGTAATATATAATTTTATCAAAGGTATGTTGGGAAAATGATAAAAATTACTTATGAATAATATCCAAA
TGGAATAATATAATAACAATTACTTACTATTACTTGATAGTGCCACAAAACTACTAAACCTTAAAATAAGTTCTT
TTATTTTACATAATTCATTATAATCTTTGGCATGAATTTACTCAAGCATTGCTTCAGAATGATCAAAGCCTCCTT
AATATTTTTGGGTACAGACATAAAGTCTAGACATGCAATCAAAGATATAGATGCACGAGATGACTAATCAAAGGA
AACAATAGGAACGATCAAAAAAATTGAAATTGAAAATATATTTTTTTTAAACTAAAGGTAAGTCAAGATTACCAA
GTAAGTGTATTATTGTAACTTTTGTATTATTTATCCTAAGTAAACATGTATCAAAAACATACACAAATTTACTTT
CTCTTTTATTACTAACATCAACTTACATGCTAATTATAAATAATTAAAGGGTAAATAGTTGGTTGCATGATTTGG
TAAAAGAAGTTGTTAACCTACTCTTTGATAACATATATGTTTTCAGACACAAAACATGCTTGATCAACTTTCTGA
TCTTCAACAAAAGGTATGTATTGTATAATATAATCCCTTAAGTTGACAATTAAATAGATTGTTCAATTGTTAATT
TGACATTGTATGTGTTCTTTTTTCTTTTTTTCTACAGGAACAATCTCTTCTTGAAATCAACAGATCCTTGAAAAC
AAAGGTACAAAGCACACATTTTGGACCTTTTATGAGTTTTTTAGGGCGTGTTTGATTTATTTATTTTTTCTGAAT
TTTTTCATGTTTGGTTGATCTAAATTCTGGGAAAATACTTTTTTCTATGAAAGTAAGTTTTTTAAAAATGACTTA
GCCAGTGGAAGTAGGGAAAACAAGTTGTGACGACATTCCACGTTGATTGTTTTCTCTCGATCTTCCTACACACCT
TAAGTTCGCCACCACCTCTCGCAGTATTTGTTTAGATTATATAAAAATGTATCAAGAATGACACTTTTTATTTGT
GTACATAATAAAAGAAAATAAGTAAGAAACCGAACATTTTCCCATGGAAAATATTATTTTTCATACCAAACACAC
CCTTAGTCTTTGTTTTAGGGTATATGACTAATTTGTTCTCCATTTCGGATATTTAGATTCGTATGGGTTTTTCTT
TGATGTCTAACTTATCGTACTTTTTACGCGATTTTATGAAATTCTTATAATAGTTGGAAGAAAACTCTGTAGCAC
ATTGGCATATCACTGGAGAGCAAAATGTACAATTCAGACAACAACCTGCTCAGTCAGAGGGGTTCTTTCAGCCTT
TACAATGCAATACTAATATAGTGCCAAACAGGTAACATATAATTTTATGTTTTCTTTTTTTCCTTTAAATAGCAT
ATTTTTTGCAACATTTTAAATTGAACCGTTGAATTGAGTCGTTGAGAGGTGAATTCAGAATCTGAAGTAACAGAT
ACATTCAAATTAATTTCTTTGTGTATTTATCGAAGTGAGTCAAGTCGTAAGTCTAGAGGTGAATTTAGAATCTAA
AGTAATAGATACAGTCGAATCAATCTCTTTGTGTATTTATTGAAGTGAGTCGTTTTGTAAAGTTTGAGACGAATT
CAAAACCTAAAGTAATACTAAATACATACATTCAAAATAATTTCTAAAGCGAGTTATGTTGGAAGTCGAGAGACG
AAAGTATATTATATATGGATCAATTCAAATTAATTTCTTAATGTATTTGATGAGCGTTGTTGTAGGGGCGAATTC
AGAATCTGAAGTTCATGTAAGTACAGGTACAATGTGGCTCCATTGGATAGTATAGAACCATCAACACAGAATGCT
ACTGGAATTTTACCAGGATGGATGCTTTGA (SEQ ID NO: 5)
```

-continued

```
Wild-type Solyc12g038510 gene
ATGGGAAGAGGAAGAGTAGAACTAAAGAGAATAGAGAACAAAATAAACAGGCAAGTTACTTTTGCTAAGAGAAGA
AATGGACTTCTTAAGAAAGCTTATGAGTTATCTATACTTTGTGATGCTGAAGTTGCTCTCATCATCTTCTCTAGC
CGCGGAAAACTCTATGAGTTTTCAAGTGCTTCCAGGTATATATATATATACATATGTTTTTCTTCTTTTTGTGTG
TGCGTATGTGTTTACTTACTTTCATTAATTAACTCAACCATATATATACATCTCTCACCTCAATTATATATATGT
TTGAGATCTGAATGTCTACGGACTCCATTTAGGTACATATCTTTGTTTAGATCATAAATCATCTATCTTCATTCC
TAAGATCTACTAATATATATGTATAAGAAGATCCATCCATCTATTAGGTTTTTCAACAACATATACAGTGAAATC
TTATATGTGGGCCCACGTATAGCCATATGAGAAAATAGTGTGCACGTAAACATTATCATTACTTAATTATAGGAA
TATACATCCATTAGGTTTATCAACAACAATAAAATCCTCTAAATGGAGTCTAGTCATAGGTCTAGCCGTTTGAAA
ATGTAAAATATATGCCGATCTTATCACTATGTCATAATAATAGATATGTTGTTATTGAAAGATTCTCAATCTTTT
TTTTTCTTCAAGGTAGAGATTCTTAAGTGGATTCATGTTTTTTTATCAAAAAAGAAAAAAACAAAAGTGTCCAT
TTGTTCATCTAATGGGTTTTCCATGTTACCAATTCACTACACTGTTGAGATTTGATTATCAGATGTGTCAAGTTT
CGTTTGGTTCCCTAGAAGGGAGAAAAGGCTGCTTATGCAGGCAGGGTATTAAAGATGATATTAATATCTGCAGTA
ATCAGTAACAGAATATATAAACTTAATAATAAACTTGAAGGTACTTAATTATCCAGCAGATAATCTTCTGTCTCA
CCGTACACTTTTGTTATATCATAAGCATAAGAATTGTTTTATCAAATATTACCAAACAAAACTTAGTTTTGTTTG
GTAATATTTTATAAAATATGTTACCGAAAGTTACTTCCTATAACATATTTTATAAAGAAAAAAATTAAAAACTCC
ATATACCTAAGAAATGTAACCCCCCCTCCATAACAACAATTTAACAAAAATAAAAACCTACTTTTTTTGAATTTG
GTAAATTAGTTTTCTATCCTTTTTAGTAACTTCCTTTCTTATTTTCTTTTTATATTGGTAAAGTTTAATATTACA
CATTATTTTAACATGTTATAATTTTTTGTGATGCTTAATTATTTGATACATGTAATAAACCATATATTAGAGCTA
TAAATCAATGACAATGCATGTAGATACAACTCATTTATGATATATTTTGTTTATATATATAACCAATTAGATAAT
TTGTCTGCGCTTTGTGCAGTCATAAATAATAATTGCATTGAACTTGCAAATATTTTTTTTTAATATCCATACATT
AAAAAAAAAGAAAGAGGAAAATTGGTTCCTAAAATATTAGCAATATTCAAACATTTATTTGATTATTAATCATTA
TCACATAACTTAAGAACGTCTAATGAATGAATTATTCACGAAATAATAAATCATTGGTTCTAAAAAGGAATTTCG
TAATAAAATAAAAATTTAAGTTACCATATTCAAAAAAAGAAATTGTGCTTGAACATGAAAATAATTATAATTTTT
GAACTTGTATAATGAATTTCTTCAATTCATAAGTGGGAAATTTCATATTTATGTAATAATAGATAATATGTAAGC
TCTAATATAGTACTTTAGGTTATAGAATTTAATATAAAATATCAAAACATGAATTCTTGAAATTGAGTAGAGTAA
TTATTTTCTGCACAATGAATCGGAGACAATAACTTTGAAGAAATATAAACAATAGAGTTCAAAAGATGTAGTCAA
AAACAACAATTAATATCATAAGAATAAATTAATGAGTGTAAAAATGCATACCACGATATGTAAAAACAGAATGGA
ATATAATAAAAAAAATCGAGTTCACTGAATACACAATGTTCCTTTAAGAAAATTATTCTCCTCCAATACCAACGA
GATTACATCCTCTAAGGATGGAAATGATTTCATTCCCCAACTTATCCATATAAAAATAGTGGTGTTAGTATGTAA
CTCAATAGGAGTAAAATACACAAATATTTAATTTTGCGAAAGTAGAAGAAGAAGATCATATTTTTTTTTAAAAT
GAGAGGATATATCACTATTTTTAAACAACAAAGGGTAGTGTTAACAAATTTTTATTGTGTCTTGTCTAAAAGGTT
ACAGCTATTTGAAAAAGTTACAACACTTCGAAAAGTGAACAACATTTCATAAAAGTCGTAACTTTTCATAAAGTC
GTAACTCTTCATAAATGTCGCAACTCTTCATAAAAATTACAACTATTGATAAAAGTCACCACTCTTGATAAAGAT
CACCACTCTTCATTGAAGTTGCAACTTTTCATAAAAATCACATCTTTTAATAAAAAAGAAAGACTAGTTTTTGGA
ATAAATTAATTTAAAAGAAAATTTTTGTTTGTGGTGGGGCGCCAAGTAGGCAGGCGTAGGGTTCTTTTTATATAA
ATATATATGATATATGATTCAATATTTGATATATATATATATAGAGAGAGAGATGACAATATAAGACAATTGCAA
AAAATAAAATAAAAAACTAATCGAGTAAGTAGGCAAAAAATTATTTATAAAATATATGTAGAATTTCTTTATCAG
ATATGACTGCCCAAATCTTATATTCAAACTAAAATGCAAGATCAATGGTGCTATATATAGGGTTTTACACAAAAA
TCAAGATCTAGTCTTGCAAATTTAAATAAAAAACAGTGGTTTACGATGAGATAATGTAGCTTTTGTAAACAATAA
AACTAGAAAAATAAATGCAAAGGCATTTTAAAGGATATAATAATGAAGATCAAAGGCAGAGAAGGGAAGAGGCAG
CAATATAATGAAGGTAACATCATGGTTCCATTCTAATATATATGCTATTTTTCTTTAGTAAATTTCAAAAATAAT
GATACATTTTCATATTTGATAAATATTTAATGATACTATCAACATTTTATCTATATTGAGTTCCATTTATTTGAC
CAAAACCTCACAAAGATGTGCTCTTCGATCTATTCAAAATTTATTCAATTTAAGGATAGCTTTAAAACATGACAA
AGTTTTCTCATATATTTCTTAAATTTTATATCCAGTCTAAATACGTATATAAACTAAAATGAAGAGAATAATATG
AAGCTTTATTTGATGACATTGTTGAAATAACCAAAAGCTATAAGTGATACAATAGTAAATTTACCATTGGTCAAT
TCAGAATTATTTAAAAGCTAAAAAAGTCATATAAGTTGGGGTTGCTCAATGTATAGTTTTTGGCTTGTTTTAAGC
ATTTTAAAACTTTTTTTAAGCGCTTTTTAACATTGCTAAACACTCAAAAAATGATAAATAGTATTTAAATTTGAT
ATGATTAGCTTAAAAGTGAACTCATATACCTTCAAAGTAAAAATCCCCAATTCGAGCTTTCAAACCACTTGATTT
TGTGGATGAAATTATACTGAAGTTGAATATATCACTATTTATAGGGGTTAGTGAACTAATACCTTTGATTATTTG
GTAGAAATATGTATCTTAGATCACCCTAATGAGCTCCCACTTTTAAAATAGGAAAAACCTCATATGAAGTTCATC
ACTGTTCATTATATATCACTTTTATTCAAAAACGTTTACAAATGTTCATTGTGACTAAATACCCTTGAGTGTCGA
GTTTTCACACCAATAAGGCCTAATTAATAGGTAAACAAAACTATGTCAATCTTCAAAACGCAAATCTAATTATAT
TTTTAACAAGATTAGAGGTATATATACATATTCTCTTATGTTAACTCTTATTCATTATTGAACAAACTAAGTAAG
TGTACCCAAGGTCTCAAACAACAGTTGGTACATTCTTTGTATGTCTTCCTTTGTCTCTTAATAGTCGTCTCCTCC
TGTCGATGATTCCTCCAAATACATTAATCAAAGGAAAATCTTTCGCCCTCAACTTGCAAACTTGTCTATCTAAAA
TTGTTAACAAAGTTTCTTCATTAGAGAAACTATGATTTCTTGAATGTAGCAATTTGATGTGCCATGACTATCATC
TTGATCAACATGCTTCTTAACCATCAAAAGATCCTAAACTAGATGCATGTCATGTTAGGAGACATATTAAGCTTG
TATATAACTACACCAACATGCTTTAGGATCTCATAAGATCCAAAATTTCTTATTTGGGAGATTTTCAATCCAACA
ACCATCATAATGAGCAACGTGATGTTATAACATCTCTCTCACACTGCCAGAACAGTCTTATACCTTGTCGGAGTG
AAGGACATCCTTAACTAAGTAGATTCACTAAGCTATACTTAAAAAGCAATAAGGAATCATCTAAAATGTGTGACT
CTTAACCCATATTGGCATACATGGTTTATGGGGGTTATTAATTGTCTGAACACTCCCCCATATAAATCAGTGATC
AATATTAATCCCAATAATATACACTATTATGATTTGAGACTACACCCTGGAAGTGGCCGGCTCTCAAGAACCATT
GCTGATCTCCAAGCCAAACCCTCATTCTGGTTGACTACAAGCTGAAGGCAAACTCAAGTATACAAAGCTTAAAAC
ATAATAAAAATAATATACTCAACTCGCCACAAAATAGGCATTTAAGTCTTTAAAACATTTTTAAAAATAAATGAA
ACAAACTTCTCAAACTGTAATGTATATCTATGAAGCCTCTAAATGAAAAAAATGAAGGCAGATGAGACATACGGC
ATCCTAACAACTGATATAACTAAGAGTACAAGTGGAGCCCTTCGGATGTAAGGAGGCTCATCAAAGCTAATGTGA
ACTCCATGTGGTATCAATGAAGCACCTATTGATGACCGTGAATACATGTATCTGCATCATGAAACGATGCAGGCC
AAAGGGCTTAGTACGTGAAATGTACGAGCATGTAAAGGGAATTCAAATACATAAACATAGGCTTGAACTTTGATA
TAAAGGAAACATACTTACCTATTTTTAACTCAAGAATAAAAAACATAGTTCAACTCAATGAAAAGACACTCAAGT
CAGTGAAATAGGCCGCAACTCAATAATAAGATATTCGACTATGGGTAATCAACTCTGGGTACTCTATTCAATATA
AAGTAAGAATACAAATGCATTATATGGAAAGACTTTAAAACGGTAGAAAACAACTCAATGTATTGAAAATTCAAT
AGTAAATTAGTTTGTATGTAAGGAACAATATAAACTTTGTTTGTATATGAAAATACAAAATAAACTTTGTGTATA
TAAAAGTACAAAATATCTCTGTGAAAGTTTCTCTAACCAACAACCATCACTATGAGCTTTCTGATAATACCACGT
TTCGCCCATGATGTCAGAACTGTCCTATGATTTTCCAGTTCATAAGACCTACTCACTAAGTGGATCCACAAGTCT
ATGCTAAAAAATATTTAAGGAATCGTCTAAAAAGTATGACTCATTCTACCCACGTTGGCTACATGATTTATGGGG
GTCGTAAGTTATCTAAACTCTCCTCCATATCGATGCGTAATGCTACTCACAAATATACTAGCTCACATGTTTAAA
AATATAACTCGTTTTGTTTGAGATCATTACTCAAAATCCTTCTCTTAAAAGAGATGATACTCAAACTGCTCAAAA
```

-continued

```
CTCTTTTGGAAATCTCAAATTCGTCTCATCTTAAATGTAAAAATATTTACTCTTGGGAATACATAGTTATCATAT
ATCATTTTAAAGAAAATGAACTCAACTCTGTTCTTTCTCAACTCAAGTGCTCAGTCTTAAACCAAATTAAAAAA
AGACTTCTCAAAATAAAGTTTATGTCGAATTATGGACGTGAACAATTCAATTCAAAGTTTTCGATAACCATAACT
AAAACTAAATACTCGAGACTCAACATCTTAGAACTCAAGAACTTAAATGGTAATACTTCTTTCAAGAATGCTCGA
CTCAGAAGGTTAATGCAGAATAATGTGCATGAATTACTCAACTAAAGGACTCACTGATACTACTCAATCTCAAGA
TTGCTCGACTCGTAGGGTTAATGCAGAATTATGTGCATGAACTACTCAACTCAAAGACCTTCATAGGTAACATGT
AGTAGCCCCATGATTTGGAATATAATCCCAAAATGATTAGGAACTCAATACTCAGGACTTAGAACTTGAAGATAA
TACTACTTCTCTCAAAGATACCCAACTGACGGAGTTCATGCAGAATTTATGGGCATGAACTACTCGACTCAAGAG
TCTAAAACACAATATGACACTCATGTATATAACTCTTCTCATTCTAATACTTGTTTTCTCAAAACTCGGTTTAAC
TAAATAGTTGATCTCAAAGGATTCACAATTGAACTCAAAGACTTTCTTTGACTCCACTCTTAATTCTCTCTTAAA
TTTGTATTTGAATTATGAATTTAAGAGTTATGATTCATGATATGGGGAATCTCAATAACAATATAGAAATTTGAT
AATTAGGAATAGTACTTTTAAAAGAAAACATGAATTCAACTTAAAATCAACTTATCTAAAAAATATTCAAATATA
GGGAAAGTATCCTAGACTACTGTGCTACTGATCTGAAAGTAGATGTAGGATGTGAGGATGAACTAGTCCAACACT
ATGATAGCCTTACATACCTGGAATAACGAGGTTCTTGGAAAATCTTCACTTGAAGAAGAACTTGATTAGAAGCCT
TGAAACCTAGCTTGAAGGTAAACAATCAAGAAAACCTTTCTTAAGATTCTTGAATTAGTTTATGAAAATCTCTAT
GACCAAGCATTTTGATTTTCACTAGTGATTCATAATTGTATGGAGGAATTTGAATTGAAAAAGATGAAATGCTTG
GAGAAAAGCTATCTTTGAAGAAGCTTGAAAAAGATTGGAAAGTCCTGTACTTTGATTTTCCCTTAGGATTTTGTC
TTAGGGTTTGAGATAGAAAAGAATGATGGACTAAAAGATGAAAATCTAATTGTTTGGATCCTTTTTCAGCCAAGA
AATCCGTTTAGGGTTTTCTTGGAGACAAACAAAATAAAAAAGACCATTTTTAATATTTTTCCGTCGGCTAATTCG
TAATAACATTGTATCATGTTATTGAAAGAGTCATAACTTTTTACTCAAAAATTGGATTGATGCGAAATTAGTGGT
GTTGGAAAGTAGATTCAAGTACCTCTAATTGGATAGGTTATTCCCTACATAAGTCTTTATATTCTAAAAGATATG
GTTGTTTGCACTTGACCTAAGTAGAATTTTACATGAAAACTTAATAGAGAAGGAAACTTCAAGAACTCATCAAGA
AATTTCAATTGCTCAATATTTATGGATAAATTTGTAGAAGAAACTCATGATTGACATGCGGGTGAATAAACCCAA
CACTATGGAAGCTTACATACCTCAAAGAACTAGGTTCTTGGCGAAATCTTGAATTTCTTCAACGAACGCTTGAAA
CTTTGAACTTTTTCTCTTCTTGAACTCTCAACTAAAACCCTAGGCGTATATTAGGATTATAAAAGTTAACATGAT
AGGATTAGACCTTTAAAAACTTTCTAAAATGAATTAAATCTGATTTAGCATGAAAAAGACCAAAATACCCCTTAC
TATTTTCGGATAACTTTTCTTAATTGGACTGCCTGACTTCAAAAAGGTATATCTCACTCATCCGACCTCAAAATT
TAGCAAATTCAGTGGCGTTAGAAAGCTAATTTAAACACCTTTCATTTTCCATCTCATGGCACACATAACTCATTC
TTTAAAGAGAGCTATGATCGTTCAAATTAACTCAAATCTTAGAAGAATTTAGGAATGTCTTGAACGAGCTACATC
TAGTGACCTTAACACTTTGGAAAATTTTAAATTTCTTAGTAAAAACTTACTCACTATGAAGGATGGTTCAAGTCT
TAGCTCAAAATTTTCCTAAGTTGCTATATATACTCATGCTCATATGTTTAAAACCAAAACCCTTCCTCGATTTGA
ATTAATTACCAAAAAGATTCTCTTAAAAAGATAATGCTCAAAACTCCCCCTAAACTCATTTGGAAATCTAGGTTT
CCCTTGTTTTAAATATAAAAACATTTACTCTTGGAAATATTTAGTTCTCAGATATTCACTTGAAAAAAATTAAAC
TCGACTCTCATCATCTTCATACTCAAGTGCTCAAGTCCTAAAACAATTTATAACTAATTGTATAAGACTTCTCAA
AATAGGGTTCATTCCGAATTATGGACGTGAACGACTCAATTCAAGGATTTCAATAACCATATATATAACTCAATA
ATAGGAACTCAACAACTCCAGAACTCAATGATACTACTCATCTCAAGAATGCTCGACTCACAGGGTCTTTGCGAA
ATTATTGGGCATGAACAACTCAACTCAAAGACCTTCATTTATACCATATGGTAGTCCCATAATAGGAATATAATC
CCAAAAAAATTAGGAACTCAATACTCAAAAACTTAGAACTCGAAGATATTACTCATCTCAAAGATATTCAATTTA
TGGAATTCATGCTGAATTATGAGCATGAACGACTTGACTCAAGGATCTCAATAATAATGTAGACTCATGAATACA
CTCTTCTCATTCTCATACTCACATACTCGAGTATTAAAATAAATTATAAGTAATTGCAGAAGACTCCTTGAACAG
ACTCAAAAGGACTCCTTCGAATTTTACTCTTAATGCTACCTGAATTTTGTATTATAAATTTAAGGATCATGATTA
TGATATAAAGAATTTCTCAGCATATATGAAATGAACGAATTTGAGCATTGAACGTCTAACCTCATTTTTTAATTA
TTGTGATATGTAGAGTGGTGCAAAATCACAGATACCTCTCTTGATGCATTTCTATAGTTACGTTGATGTGAGATT
ATATATAGTTCAGCAGCAGCATGTTGGGAAAATTACTAATAACTCTTCTTTTATATCAAATTGTTGAAGCATGAT
GACAACACTTGAAAAGTATCAACAATGCAGTTACGCATCTTTGGACCCGATGTTACCGGTTAGTGATACTCAGGT
ATTGTTTATCTACTTTATCATGTCGTAAGTATATTATTTGTAAAGATATATATCAAGATAGTTCGATTGCGTACA
CTTACATTTTGATTATGTTTGGTGAATACTATTCTAATACCTTTTTTTTCCTAAAGCCTAACAAATAAAGATAA
TTAAGATGGGAACGTAATTCAAGTACAACATGGTTCCATACGTGACATATTTACACATATAGTGGAACCAAAAGA
GCAATTTTTCCTAATATCATTTTCTAAATATCACGTGTGCCCGTGATTCTTTTTTATGGACATGAATTTTTTTTT
TAATATGAGTGGAAGTAAGGTTCGATCTTTCTATCTGCTTTGATATCATATTGAATCGTGTGATTGTCTCTTTAA
AAAATTAAGCAAGAGCATATTTTATTAATTAATTGTCTTTCTCGACGTTTTTCTCTTTCAACAGATGAACTACAA
TGAGTATGTGAGGCTAAAAGCTAGAGTTGAGCTCCTTCAACGTTCTCAAAGGTAAGATATTAGTGATGTAATTAA
ATGATTTTAGTTAGATTTACATAAGTTTTTAATAAGTGAAAATTAATAGACATATTCTTGGAGAGGATTTGGGCA
CACTAAACTCGAAAGAACTTGAGCAGCTTGAGCACCAATTGGATGCATCTTTGAAGAAAGTTAGATCAAAAAAGG
TATATCCAAATACTATAACTTAAATATATTGTAACGATTTAATTAATAGCATGTGTCACGTTCATCTATTCTTTA
GTCACAATATATAGGGGCATGTCCTTAACAACGTGCCATGCCTCGATAGTCATTTTTGTCTTTTTGTGCGTATGA
ATTTAACTTTGACACAAATTTTTGTAGTAATAATAACTCATGCTTTAGCATCTTAGGAAGCAGTCATATGAAAAA
CAGAAGCATATATATATATTACATGAGTTAATTTAATTTAATATAAAATTTAATAAAATTGTGTCTCGCTATAAA
TAATTTTATTAAAAAATTATATAAATATATTATTTTTTTAACTGGCCGCAAAGTTATATAAATTGATAGAGAAAG
AGGTTTTGGTGTAAGGTTCATTTTCCAACAATTAGTTTTATAATTTGTAAGTGCACACTTTATCAGACTCAATCT
ATGCTGGATCAGCTGGCAGACCTTCAAGAAAAGGTACACTGCCTTAACATTACAAAATTAATTTATTTCATCAAA
AGCATATCATAAAATTCTGACAAATAAATATATTAGGAGCAAATGCTGGAAGAAGCAAATAAACAACTAAAAAAC
AAGGTACATATCTATATATGTGTGTTAATTAATTAAGTTGATTTTGTATTTTTGTTTAATGAATAATTGTTTGTG
ATCATCAGCTGGAAGAAAGTGCAGCTAGAATTCCACTTGGATTGTCATGGGGAAATAATGGAGGACAAACAATGG
AATACAATCGACTCCCTCCACAAACTACTGCACAACCTTTCTTTCAACCTCTCCGTTTGAATTCTTCATCGCCTC
AATTCGGGTAAGTATCTTATTTTATATGACTTAGTTTGACTTGACATAAAGTTTAATAAAGAAAGAAAGACTTTT
AAAACTTATAGTGTAAAATAAGTGAATAGATATATATGTGGTTGTACTAACACTACAACAAAAATAATTTTCAGC
GGCATTAAATATTGACATTAATAATGAGTGCTAAAGACTTTATCGGTATTAGTTAAGTGTCATTAGGATCAATGT
CGTTAAAGGCTTCACGGACATATACAAAGAGTGACAATTGCCGCTAATGATTATTTTTGTTGTAGTGAAAATGAG
TATTTTAAAGTTAAATTGTTACATAATATAGAAATATGTCAGAAACAGGACAAATATACCACCGAACTATCATAT
ATGTTATGGAGATATTCTCAGTCATACTTCTGCGACATTGGTACTCATGTCGTCCAAAAACTAGAACATATATAT
ACCCTTTATATATTAACGAAGATACAAGTGTCATAATCTTATGCACCGATTCGATATTTATTAAATATCGAATCG
ACGGATAAAATTATGTCACGTGTCCCTATTAAGTCTTCTATTAGAGTAAAAAGCATATATTCTCTAGTTTTTGAA
CGAAAAAAGGTATTAATGTCTCAAAAGTATAACGAAAAGCATTTGCATACAATTTATGATAATTTGGGGCATATT
AATTTATCATTCCCCCTTTTTTTGGCACTGATTAAAAAGAAAAAGAAAGTTATAAAAATTGGGATAGAGGGAATA
ATTGTTTCATAGGGAAAACTTAGAAGCTTCTCAGTATGTCAGTGAGAATGTGTTTCCTAATTAGTGAACTATGGT
TTGGTGAAAAATAAAGAGAAAAAAATCAGTACAAATTTTCCACTGATTAGCAATGAGAAAAATATTTGTTTCTAG
TAGTATGAGGAGAGGATAGTCCGCATAAATAATCCTTAAATTTGTGGATAAATAAACTATTTTCAATAGATTATC
GTCTCAAAATAAAATAAAATGATTGCAAGAAAAGAATAATAGGTATGCTGGTAATATGTATAATACACTCAAATT
```

-continued

TATTTGCTGTCCATGCAGATACAATCCAAATATGGGTGCAAATGATCATGAGGTTAATGCAGCAACAACTGCTCA
TAATATTAATGGATTTATTCCAGGGTGGATGCTCTAA (SEQ ID NO: 6)

Wild-type Solyc12g038510 coding sequence
ATGGGAAGAGGAAGAGTAGAACTAAAGAGAATAGAGAACAAAATAAACAGGCAAGTTACTTTTGCTAAGAGAAGA
AATGGACTTCTTAAGAAAGCTTATGAGTTATCTATACTTTGTGATGCTGAAGTTGCTCTCATCATCTTCTCTAGC
CGCGGAAAACTCTATGAGTTTTCAAGTGCTTCCAGCATGATGACAACACTTGAAAAGTATCAACAATGCAGTTAC
GCATCTTTGGACCCGATGTTACCGGTTAGTGATACTCAGATGAACTACAATGAGTATGTGAGGCTAAAAGCTAGA
GTTGAGCTCCTTCAACGTTCTCAAAGACATATTCTTGGAGAGGATTTGGGCACACTAAACTCGAAAGAACTTGAG
CAGCTTGAGCACCAATTGGATGCATCTTTGAAGAAAGTTAGATCAAAAAAGACTCAATCTATGCTGGATCAGCTG
GCAGACCTTCAAGAAAAGGAGCAAATGCTGGAAGAAGCAAATAAACAACTAAAAAACAAGCTGGAAGAAAGTGCA
GCTAGAATTCCACTTGGATTGTCATGGGGAAATAATGGAGGACAAACAATGGAATACAATCGACTCCCTCCACAA
ACTACTGCACAACCTTTCTTTCAACCTCTCCGTTTGAATTCTTCATCGCCTCAATTCGGATACAATCCAAATATG
GGTGCAAATGATCATGAGGTTAATGCAGCAACAACTGCTCATAATATTAATGGATTTATTCCAGGGTGGATGCTC
TAA (SEQ ID NO: 7)

Mutant Solyc12g038510 gene allele $j2^{TE}$
ATGGGAAGAGGAAGAGTAGAACTAAAGAGAATAGAGAACAAAATAAACAGGCAAGTTACTTTTGCTAAGAGAAGA
AATGGACTTCTTAAGAAAGCTTATGAGTTATCTATACTTTGTGATGCTGAAGTTGCTCTCATCATCTTCTCTAGC
CGCGGAAAACTCTATGAGTTTTCAAGTGCTTCCAGGTATATATATATATACATATG*CTGTTGAATGCCTTGAATC*
*GGACCCGCTACAAACAGAAAGGACGGGGTCTCGCTGCCCGGTCAGCGAGTCGGGGGGTCCAGGGGGGCGACGCG*
*CCCCCTGGCCTGGGGGTCCGGGGGGGCGGAGACGCCCCCGGGCCGACGGTATACAATGTTGTTGTATTGGGCCCT*
*TAATTTTCTGTTGATTCTGTATGTTGGGCCCAAGCCTGTTAGGGCGTAGCTTAGCACTATATATAGACGCTATGG*
*GAAACCCTATTCTGTAATTCTGTTTTTGCCTCTCCATAATAAAACTGCTCCCTCTCTTCCCGTGGACGTAGCCAA*
*TTTGTTGGTGAACCACGTAAATCTGTTGTCTTATTTTTCGCGTTTATATTTCTCGTATTATCTCAAATTCCGCA*
***CAACAANNNNNN (N*X) NNNNNNCCCCGGGCCGACGGTATACAATGTTGTTGTATTGGGCCCTTAATTTTCTGTT***
*GATTCTGTATGTTGGGCCCAAGCCTGTTAGGGCGTAGCTTAGCACTATATAGGACGTAGCCAATTTGTTGGTGAA*
*TGTAATTCTGTTTTTGCCTCTCCATAATAAAACTGCTCCCTCTCTTCCCGTGGACGTAGCCAATTTGTTGGTGAA*
*CCACGTAAATCTGTTGTCTTATTTTTGCGTTTATATTTTCTCGTATTATCTCAAATTCCGCACAACAATAT*ATA
TGTTTTTCTTCTTTTTGTGTGTGCGTATGTGTTTACTTACTTTCATTAATTAACTCAACCATATATATACATCTC
TCACCTCAATTATATATATGTTTGAGATCTGAATGTCTACGGACTCCATTTAGGTACATATCTTTGTTTAGATCA
TAAATCATCTATCTTCATTCCTAAGATCTACTAATATATATGTATAAGAAGATCCATCCATCTATTAGGTTTTTC
AACAACATATACAGTGAAATCTTATATGTGGGCCCACGTATAGCCATATGAGAAAATAGTGTGCACGTAAACATT
ATCATTACTTAATTATAGGAATATACATCCATTAGGTTTATCAACAACAATAAAATCCTCTAAATGGAGTCTAGT
CATAGGTCTAGCCGTTTGAAAATGTAAAATATATGCCGATCTTATCACTATGTCATAATAATAGATATGTTGTTA
TTGAAAGATTCTCAATCTTTTTTTTTCTTCAAGGTAGAGATTCTTAAGTGGATTCATGTTTTTTTTATCAAAAAA
GAAAAAAACAAAAGTGTCCATTTGTTCATCTAATGGGTTTTCCATGTTACCAATTCACTACACTGTTGAGATTTG
ATTATCAGATGTGTCAAGTTTCGTTTGGTTCCCTAGAAGGGAGAAAAGGCTGCTTATGCAGGCAGGGTATTAAAG
ATGATATTAATATCTGCAGTAATCAGTAACAGAATATATAAACTTAATAATAAACTTGAAGGTACTTAATTATCC
AGCAGATAATCTTCTGTCTCACCGTACACTTTTGTTATATCATAAGCATAAGAATTGTTTTATCAAATATTACCA
AACAAAACTTAGTTTTGTTTGGTAATATTTTATAAAATATGTTACCGAAAGTTACTTCCTATAACATATTTTATA
AAGAAAAAAATTAAAAACTCCATATACCTAAGAAATGTAACCCCCCTCCATAACAACAATTTAACAAAAATAAA
AACCTACTTTTTTTGAATTTGGTAAATTAGTTTTCTATCCTTTTTAGTAACTTCCTTTCTTATTTTCTTTTTATA
TTGGTAAAGTTTAATATTACACATTATTTTAACATGTTATAATTTTTTGTGATGCTTAATTATTTGATACATGTA
ATAAACCATATATTAGAGCTATAAATCAATGACAATGCATGTAGATACAACTCATTTATGATATATTTTGTTTAT
ATATATAACCAATTAGATAATTTGTCTGCGCTTTGTGCAGTCATAAATAATAATTGCATTGAACTTGCAAATATT
TTTTTTTAATATCCATACATTAAAAAAAAAGAAAGAGGAAAATTGGTTCCTAAAATATTAGCAATATTCAAACAT
TTATTTGATTATTAATCATTATCACATAACTTAAGAACGTCTAATGAATGAATTATTCACGAAATAATAAATCAT
TGGTTCTAAAAAGGAATTTCGTAATAAAATAAAAATTTAAGTTACCATATTCAAAAAAAGAAATTGTGCTTGAAC
ATGAAAATAATTATAATTTTTGAACTTGTATAATGAATTTCTTCAATTCATAAGTGGGAAATTTCATATTTATGT
AATAATAGATAATATGTAAGCTCTAATATAGTACTTTAGGTTATAGAATTTAATATAAAATATCAAAACATGAAT
TCTTGAAATTGAGTAGAGTAATTATTTTCTGCACAATGAATCGGAGACAATAACTTTGAAGAAATATAAACAATA
GAGTTCAAAAGATGTAGTCAAAAACAACAATTAATATCATAAGAATAAATTAATGAGTGTAAAAATGCATACCAC
GATATGTAAAAACAGAATGGAATATAATAAAAAAAATCGAGTTCACTGAATACACAATGTTCCTTTAAGAAAATT
ATTCTCCTCCAATACCAACGAGATTACATCCTCTAAGGATGGAAATGATTTCATTCCCCAACTTATCCATATAAA
AATAGTGGTGTTAGTATGTAACTCAATAGGAGTAAAATACACAAATATTTAATTTTGCGAAAGTAGAAGAAGAAG
ATCATATTTTTTTTTTAAAATGAGAGGATATATCACTATTTTTAAACAACAAAGGGTAGTGTTAACAAATTTTTA
TTGTGTCTTGTCTAAAAGGTTACAGCTATTTGAAAAAGTTACAACACTTCGAAAAGTGAACAACATTTCATAAAA
GTCGTAACTTTTCATAAAGTCGTAACTCTTCATAAATGTCGCAACTCTTCATAAAAATTACAACTATTGATAAAA
GTCACCACTCTTGATAAAGATCACCACTCTTCATTGAAGTTGCAACTTTTCATAAAAATCACATCTTTTAATAAA
AAAGAAAGACTAGTTTTTGGAATAAATTAATTTAAAAGAAAATTTTTGTTTGTGGTGGGGCGCCAAGTAGGCAGG
CGTAGGGTTCTTTTTATATAAATATATATGATATATGATTCAATATTTGATATATATATATATAGAGAGAGAGAT
GACAATATAAGACAATTGCAAAAAATAAAATAAAAAACTAATCGAGTAAGTAGGCAAAAAATTATTTATAAAATA
TATGTAGAATTTCTTTATCAGATATGACTGCCCAAATCTTATATTCAAACTAAAATGCAAGATCAATGGTGCTAT
ATATAGGGTTTTACACAAAAATCAAGATCTAGTCTTGCAAATTTAAATAAAAAACAGTGGTTTACGATGAGATAA
TGTAGCTTTTGTAAACAATAAAACTAGAAAAATAAATGCAAAGGCATTTTAAAGGATATAATAATGAAGATCAAA
GGCAGAGAAGGGAAGAGGCAGCAATATAATGAAGGTAACATCATGGTTCCATTCTAATATATATGCTATTTTTCT
TTAGTAAATTTCAAAAATAATGATACATTTTCATATTTGATAAATATTTAATGATACTATCAACATTTTATCTAT
ATTGAGTTCCATTTATTTGACCAAAACCTCACAAAGATGTGCTCTTCGATCTATTCAAAATTTATTCAATTTAAG
GATAGCTTTAAAACATGACAAAGTTTTCTCATATATTTCTTAAATTTTATATCCAGTCTAAATACGTATATAAAC
TAAAATGAAGAGAATAATATGAAGCTTTATTTGATGACATTGTTGAAATAACCAAAAGCTATAAGTGATACAATA
GTAAATTTACCATTGGTCAATTCAGAATTATTTAAAAGCTAAAAAAGTCATATAAGTTGGGGTTGCTCAATGTAT
AGTTTTTGGCTTGTTTTAAGCATTTTAAAACTTTTTTTAAGCGCTTTTTAACATTGCTAAACACTCAAAAAATGA
TAAATAGTATTTAAATTTGATATGATTAGCTTAAAAGTGAACTCATATACCTTCAAAGTAAAAATCCCCAATTCG
AGCTTTCAAACCACTTGATTTTGTGGATGAAATTATACTGAAGTTGAATATATCACTATTTATAGGGGTTAGTGA
ACTAATACCTTTGATTATTTGGTAGAAATATGTATCTTAGATCACCCTAATGAGCTCCCACTTTTAAAATAGGAA
AAACCTCATATGAAGTTCATCACTGTTCATTATATATCACTTTTATTCAAAAACGTTTACAAATGTTCATTGTGA
CTAAATACCCTTGAGTGTCGAGTTTTCACACCAATAAGGCCTAATTAATAGGTAAACAAAACTATGTCAATCTTC -continued AAAACGCAAATCTAATTATATTTTTAACAAGATTAGAGGTATATATACATATTCTCTTATGTTAACTCTTATTCA
TTATTGAACAAACTAAGTAAGTGTACCCAAGGTCTCAAACAACAGTTGGTACATTCTTTGTATGTCTTCCTTTGT
CTCTTAATAGTCGTCTCCTCCTGTCGATGATTCCTCCAAATACATTAATCAAAGGAAAATCTTTCGCCCTCAACT
TGCAAACTTGTCTATCTAAAATTGTTAACAAAGTTTCTTCATTAGAGAAACTATGATTTCTTGAATGTAGCAATT
TGATGTGCCATGACTATCATCTTGATCAACATGCTTCTTAACCATCAAAAGATCCTAAACTAGATGCATGTCATG
TTAGGAGACATATTAAGCTTGTATATAACTACACCAACATGCTTTAGGATCTCATAAGATCCAAAATTTCTTATT
TGGGAGATTTTCAATCCAACAACCATCATAATGAGCAACGTGATGTTATAACATCTCTCTCACACTGCCAGAACA
GTCTTATACCTTGTCGGAGTGAAGGACATCCTTAACTAAGTAGATTCACTAAGCTATACTTAAAAAGCAATAAGG
AATCATCTAAAATGTGTGACTCTTAACCCATATTGGCATACATGGTTTATGGGGGTTATTAATTGTCTGAACACT
CCCCCATATAAATCAGTGATCAATATTAATCCCAATAATATACACTATTATGATTTGAGACTACACCCTGGAAGT
GGCCGGCTCTCAAGAACCATTGCTGATCTCCAAGCCAAACCCTCATTCTGGTTGACTACAAGCTGAAGGCAAACT
CAAGTATACAAAGCTTAAAACATAATAAAAATAATATACTCAACTCGCCACAAAATAGGCATTTAAGTCTTTAAA
ACATTTTTAAAAATAAATGAAACAAACTTCTCAAACTGTAATGTATATCTATGAAGCCTCTAAATGAAAAAAATG
AAGGCAGATGAGACATACGGCATCCTAACAACTGATATAACTAAGAGTACAAGTGGAGCCCTTCGGATGTAAGGA
GGCTCATCAAAGCTAATGTGAACTCCATGTGGTATCAATGAAGCACCTATTGATGACCGTGAATACATGTATCTG
CATCATGAAACGATGCAGGCCAAAGGGCTTAGTACGTGAAATGTACGAGCATGTAAAGGGAATTCAAATACATAA
ACATAGGCTTGAACTTTGATATAAAGGAAACATACTTACCTATTTTTAACTCAAGAATAAAAAACATAGTTCAAC
TCAATGAAAAGACACTCAAGTCAGTGAAATAGGCCGCAACTCAATAATAAGATATTCGACTATGGGTAATCAACT
CTGGGTACTCTATTCAATATAAAGTAAGAATACAAATGCATTATATGGAAAGACTTTAAAACGGTAGAAAACAAC
TCAATGTATTGAAAATTCAATAGTAAATTAGTTTGTATGTAAGGAACAATATAAACTTTGTTTGTATATGAAAAT
ACAAAATAAACTTTGTGTATATAAAAGTACAAAATATCTCTGTGAAAGTTTCTCTAACCAACAACCATCACTATG
AGCTTTCTGATAATACCACGTTTCGCCCATGATGTCAGAACTGTCCTATGATTTTCCAGTTCATAAGACCTACTC
ACTAAGTGGATCCACAAGTCTATGCTAAAAAATATTTAAGGAATCGTCTAAAAAGTATGACTCATTCTACCCACG
TTGGCTACATGATTTATGGGGGTCGTAAGTTATCTAAACTCTCCTCCATATCGATGCGTAATGCTACTCACAAAT
ATACTAGCTCACATGTTTAAAAATATAACTCGTTTTGTTTGAGATCATTACTCAAAATCCTTCTCTTAAAAGAGA
TGATACTCAAACTGCTCAAAACTCTTTTGGAAATCTCAAATTCGTCTCATCTTAAATGTAAAAATATTTACTCTT
GGGAATACATAGTTATCATATATCATTTTAAAGAAAATGAACTCAACTCTGTTCTTTCTCAACTCAAGTGCTCAG
TCTTAAACCAAATTAAAAAAAAGACTTCTCAAAATAAAGTTTATGTCGAATTATGGACGTGAACAATTCAATTCA
AAGTTTTCGATAACCATAACTAAAACTAAATACTCGAGACTCAACATCTTAGAACTCAAGAACTTAAATGGTAAT
ACTTCTTTCAAGAATGCTCGACTCAGAAGGTTAATGCAGAATAATGTGCATGAATTACTCAACTAAAGGACTCAC
TGATACTACTCAATCTCAAGATTGCTCGACTCGTAGGGTTAATGCAGAATTATGTGCATGAACTACTCAACTCAA
AGACCTTCATAGGTAACATGTAGTAGCCCCATGATTTGGAATATAATCCCAAAATGATTAGGAACTCAATACTCA
GGACTTAGAACTTGAAGATAATACTACTTCTCTCAAAGATACCCAACTGACGGAGTTCATGCAGAATTTATGGGC
ATGAACTACTCGACTCAAGAGTCTAAAACACAATATGACACTCATGTATATAACTCTTCTCATTCTAATACTTGT
TTTCTCAAAACTCGGTTTAACTAAATAGTTGATCTCAAAGGATTCACAATTGAACTCAAAGACTTTCTTTGACTC
CACTCTTAATTCTCTCTTAAATTTGTATTTGAATTATGAATTTAAGAGTTATGATTCATGATATGGGGAATCTCA
ATAACAATATAGAAATTTGATAATTAGGAATAGTACTTTTAAAAGAAAACATGAATTCAACTTAAAATCAACTTA
TCTAAAAAATATTCAAATATAGGGAAAGTATCCTAGACTACTGTGCTACTGATCTGAAAGTAGATGTAGGATGTG
AGGATGAACTAGTCCAACACTATGATAGCCTTACATACCTGGAATAACGAGGTTCTTGGAAAATCTTCACTTGAA
GAAGAACTTGATTAGAAGCCTTGAAACCTAGCTTGAAGGTAAACAATCAAGAAAACCTTTCTTAAGATTCTTGAA
TTAGTTTATGAAAATCTCTATGACCAAGCATTTTGATTTTCACTAGTGATTCATAATTGTATGGAGGAATTTGAA
TTGAAAAAGATGAAATGCTTGGAGAAAAGCTATCTTTGAAGAAGCTTGAAAAAGATTGGAAAGTCCTGTACTTTG
ATTTTCCCTTAGGATTTTGTCTTAGGGTTTGAGATAGAAAAGAATGATGGACTAAAAGATGAAAATCTAATTGTT
TGGATCCTTTTTCAGCCAAGAAATCCGTTTAGGGTTTTCTTGGAGACAAACAAAATAAAAAAGACCATTTTTAAT
ATTTTTCCGTCGGCTAATTCGTAATAACATTGTATCATGTTATTGAAAGAGTCATAACTTTTTACTCAAAAATTG
GATTGATGCGAAATTAGTGGTGTTGGAAAGTAGATTCAAGTACCTCTAATTGGATAGGTTATTCCCTACATAAGT
CTTTATATTCTAAAAGATATGGTTGTTTGCACTTGACCTAAGTAGAATTTTACATGAAAACTTAATAGAGAAGGA
AACTTCAAGAACTCATCAAGAAATTTCAATTGCTCAATATTTATGGATAAATTTGTAGAAGAAACTCATGATTGA
CATGCGGGTGAATAAACCCAACACTATGGAAGCTTACATACCTCAAAGAACTAGGTTCTTGGCGAAATCTTGAAT
TTCTTCAACGAACGCTTGAAACTTTGAACTTTTTCTCTTCTTGAACTCTCAACTAAAACCCTAGGCGTATATTAG
GATTATAAAAGTTAACATGATAGGATTAGACCTTTAAAAACTTTCTAAAATGAATTAAATCTGATTTAGCATGAA
AAAGACCAAAATACCCCTTACTATTTTCGGATAACTTTTCTTAATTGGACTGCCTGACTTCAAAAAGGTATATCT
CACTCATCCGACCTCAAAATTTAGCAAATTCAGTGGCGTTAGAAAGCTAATTTAAACACCTTTCATTTTCCATCT
CATGGCACACATAACTCATTCTTTAAAGAGAGCTATGATCGTTCAAATTAACTCAAATCTTAGAAGAATTTAGGA
ATGTCTTGAACGAGCTACATCTAGTGACCTTAACACTTTGGAAAATTTTAAATTTCTTAGTAAAAACTTACTCAC
TATGAAGGATGGTTCAAGTCTTAGCTCAAAATTTTCCTAAGTTGCTATATATACTCATGCTCATATGTTTAAAAC
CAAAACCCTTCCTCGATTTGAATTAATTACCAAAAAGATTCTCTTAAAAAGATAATGCTCAAAACTCCCCCTAAA
CTCATTTGGAAATCTAGGTTTCCCTTGTTTTAAATATAAAAACATTTACTCTTGGAAATATTTAGTTCTCAGATA
TTCACTTGAAAAAAATTAAACTCGACTCTCATCATCTTCATACTCAAGTGCTCAAGTCCTAAAACAATTTATAAC
TAATTGTATAAGACTTCTCAAAATAGGGTTCATTCCGAATTATGGACGTGAACGACTCAATTCAAGGATTTCAAT
AACCATATATATAACTCAATAATAGGAACTCAACAACTCCAGAACTCAATGATACTACTCATCTCAAGAATGCTC
GACTCACAGGGTCTTTGCGAAATTATTGGGCATGAACAACTCAACTCAAAGACCTTCATTTATACCATATGGTAG
TCCCATAATAGGAATATAATCCCAAAAAAATTAGGAACTCAATACTCAAAAACTTAGAACTCGAAGATATTACTC
ATCTCAAAGATATTCAATTTATGGAATTCATGCTGAATTATGAGCATGAACGACTTGACTCAAGGATCTCAATAA
TAATGTAGACTCATGAATACACTCTTCTCATTCTCATACTCACATACTCGAGTATTAAAATAAATTATAAGTAAT
TGCAGAAGACTCCTTGAACAGACTCAAAAGGACTCCTTCGAATTTTACTCTTAATGCTACCTGAATTTTGTATTA
TAAATTTAAGGATCATGATTATGATATAAAGAATTTCTCAGCATATATGAAATGAACGAATTTGAGCATTGAACG
TCTAACCTCATTTTTTAATTATTGTGATATGTAGAGTGGTGCAAAATCACAGATACCTCTCTTGATGCATTTCTA
TAGTTACGTTGATGTGAGATTATATATAGTTCAGCAGCAGCATGTTGGGAAAATTACTAATAACTCTTCTTTTAT
ATCAAATTGTTGAAGCATGATGACAACACTTGAAAAGTATCAACAATGCAGTTACGCATCTTTGGACCCGATGTT
ACCGGTTAGTGATACTCAGGTATTGTTTATCTACTTTATCATGTCGTAAGTATATTATTTGTAAAGATATATATC
AAGATAGTTCGATTGCGTACACTTACATTTTGATTATGTTTGGTGAATACTATTCTAATACCTTTTTTTTTCCTA
AAGCCTAACAAATAAAGATAATTAAGATGGGAACGTAATTCAAGTACAACATGGTTCCATACGTGACATATTTAC
ACATATAGTGGAACCAAAAGAGCAATTTTTCCTAATATCATTTTCTAAATATCACGTGTGCCCGTGATTCTTTTT
TATGGACATGAATTTTTTTTTTAATATGAGTGGAAGTAAGGTTCGATCTTTCTATCTGCTTTGATATCATATTGA
ATCGTGTGATTGTCTCTTTAAAAAATTAAGCAAGAGCATATTTTATTAATTAATTGTCTTTCTCGACGTTTTTCT
CTTTCAACAGATGAACTACAATGAGTATGTGAGGCTAAAAGCTAGAGTTGAGCTCCTTCAACGTTCTCAAAGGTA
AGATATTAGTGATGTAATTAAATGATTTTAGTTAGATTTACATAAGTTTTTAATAAGTGAAAATTAATAGACATA
TTCTTGGAGAGGATTTGGGCACACTAAACTCGAAAGAACTTGAGCAGCTTGAGCACCAATTGGATGCATCTTTGA -continued AGAAAGTTAGATCAAAAAAGGTATATCCAAATACTATAACTTAAATATATTGTAACGATTTAATTAATAGCATGT
GTCACGTTCATCTATTCTTTAGTCACAATATATAGGGGCATGTCCTTAACAACGTGCCATGCCTCGATAGTCATT
TTTGTCTTTTTGTGCGTATGAATTTAACTTTGACACAAATTTTTGTAGTAATAATAACTCATGCTTTAGCATCTT
AGGAAGCAGTCATATGAAAAACAGAAGCATATATATATATTACATGAGTTAATTTAATTTAATATAAAATTTAAT
AAAATTGTGTCTCGCTATAAATAATTTTATTAAAAAATTATATAAATATATTATTTTTTTAACTGGCCGCAAAGT
TATATAAATTGATAGAGAAAGAGGTTTTGGTGTAAGGTTCATTTTCCAACAATTAGTTTTATAATTTGTAAGTGC
ACACTTTATCAGACTCAATCTATGCTGGATCAGCTGGCAGACCTTCAAGAAAAGGTACACTGCCTTAACATTACA
AAATTAATTTATTTCATCAAAAGCATATCATAAAATTCTGACAAATAAATATATTAGGAGCAAATGCTGGAAGAA
GCAAATAAACAACTAAAAAACAAGGTACATATCTATATATGTGTGTTAATTAATTAAGTTGATTTTGTATTTTTG
TTTAATGAATAATTGTTTGTGATCATCAGCTGGAAGAAAGTGCAGCTAGAATTCCACTTGGATTGTCATGGGGAA
ATAATGGAGGACAAACAATGGAATACAATCGACTCCCTCCACAAACTACTGCACAACCTTTCTTTCAACCTCTCC
GTTTGAATTCTTCATCGCCTCAATTCGGGTAAGTATCTTATTTTATATGACTTAGTTTGACTTGACATAAAGTTT
AATAAAGAAAGAAAGACTTTTAAAACTTATAGTGTAAAATAAGTGAATAGATATATATGTGGTTGTACTAACACT
ACAACAAAAATAATTTTCAGCGGCATTAAATATTGACATTAATAATGAGTGCTAAAGACTTTATCGGTATTAGTT
AAGTGTCATTAGGATCAATGTCGTTAAAGGCTTCACGGACATATACAAAGAGTGACAATTGCCGCTAATGATTAT
TTTTGTTGTAGTGAAAATGAGTATTTTAAAGTTAAATTGTTACATAATATAGAAATATGTCAGAAACAGGACAAA
TATACCACCGAACTATCATATATGTTATGGAGATATTCTCAGTCATACTTCTGCGACATTGGTACTCATGTCGTC
CAAAAACTAGAACATATATATACCCTTTATATATTAACGAAGATACAAGTGTCATAATCTTATGCACCGATTCGA
TATTTATTAAATATCGAATCGACGGATAAAATTATGTCACGTGTCCCTATTAAGTCTTCTATTAGAGTAAAAAGC
ATATATTCTCTAGTTTTTGAACGAAAAAAGGTATTAATGTCTCAAAAGTATAACGAAAAGCATTTGCATACAATT
TATGATAATTTGGGGCATATTAATTTATCATTCCCCCTTTTTTTGGCACTGATTAAAAAGAAAAAGAAAGTTATA
AAAATTGGGATAGAGGGAATAATTGTTTCATAGGGAAAACTTAGAAGCTTCTCAGTATGTCAGTGAGAATGTGTT
TCCTAATTAGTGAACTATGGTTTGGTGAAAAATAAAGAGAAAAAAATCAGTACAAATTTTCCACTGATTAGCAAT
GAGAAAAATATTTGTTTCTAGTAGTATGAGGAGAGGATAGTCCGCATAAATAATCCTTAAATTTGTGGATAAATA
AACTATTTTCAATAGATTATCGTCTCAAAATAAAATAAAATGATTGCAAGAAAAGAATAATAGGTATGCTGGTAA
TATGTATAATACACTCAAATTTATTTGCTGTCCATGCAGATACAATCCAAATATGGGTGCAAATGATCATGAGGT
TAATGCAGCAACAACTGCTCATAATATTAATGGATTTATTCCAGGGTGGATGCTCTAA (SEQ ID NO: 8)

Mutant Solyc12g038510 gene allele j2$^{stop}$

ATGGGAAGAGGAAGAGTAGAACTAAAGAGAATAGAGAACAAAATAAACAGGCAAGTTACTTTTGCTAAGAGAAGA
AATGGACTTCTTAAGAAAGCTTATGAGTTATCTATACTTTGTGATGCTGAAGTTGCTCTCATCATCTTCTCTAGC
CGCGGAAAACTCTATGAGTTTTCAAGTGCTTCCAGGTATATATATATATATACATATGTTTTTCTTCTTTTTGTGTG
TGCGTATGTGTTTACTTACTTTCATTAATTAACTCAACCATATATATACATCTCTCACCTCAATTATATATATGT
TTGAGATCTGAATGTCTACGGACTCCATTTAGGTACATATCTTTGTTTAGATCATAAATCATCTATCTTCATTCC
TAAGATCTACTAATATATATGTATAAGAAGATCCATCCATCTATTAGGTTTTTCAACAACATATACAGTGAAATC
TTATATGTGGGCCCACGTATAGCCATATGAGAAAATAGTGTGCACGTAAACATTATCATTACTTAATTATAGGAA
TATACATCCATTAGGTTTATCAACAACAATAAAATCCTCTAAATGGAGTCTAGTCATAGGTCTAGCCGTTTGAAA
ATGTAAAATATATGCCGATCTTATCACTATGTCATAATAATAGATATGTTGTTATTGAAAGATTCTCAATCTTTT
TTTTTCTTCAAGGTAGAGATTCTTAAGTGGATTCATGTTTTTTTTATCAAAAAAGAAAAAAACAAAAGTGTCCAT
TTGTTCATCTAATGGGTTTTCCATGTTACCAATTCACTACACTGTTGAGATTTGATTATCAGATGTGTCAAGTTT
CGTTTGGTTCCCTAGAAGGGAGAAAAGGCTGCTTATGCAGGCAGGGTATTAAAGATGATATTAATATCTGCAGTA
ATCAGTAACAGAATATATAAACTTAATAATAAACTTGAAGGTACTTAATTATCCAGCAGATAATCTTCTGTCTCA
CCGTACACTTTTGTTATATCATAAGCATAAGAATTGTTTTATCAAATATTACCAAACAAAACTTAGTTTTGTTTG
GTAATATTTTATAAAATATGTTACCGAAAGTTACTTCCTATAACATATTTTATAAAGAAAAAAATTAAAAACTCC
ATATACCTAAGAAATGTAACCCCCCCTCCATAACAACAATTTAACAAAAATAAAAACCTACTTTTTTTGAATTTG
GTAAATTAGTTTTCTATCCTTTTTAGTAACTTCCTTTCTTATTTTCTTTTTATATTGGTAAAGTTTAATATTACA
CATTATTTTAACATGTTATAATTTTTTGTGATGCTTAATTATTTGATACATGTAATAAACCATATATTAGAGCTA
TAAATCAATGACAATGCATGTAGATACAACTCATTTATGATATATTTTGTTTATATATATAACCAATTAGATAAT
TTGTCTGCGCTTTGTGCAGTCATAAATAATAATTGCATTGAACTTGCAAATATTTTTTTTTAATATCCATACATT
AAAAAAAAAGAAAGAGGAAAATTGGTTCCTAAAATATTAGCAATATTCAAACATTTATTTGATTATTAATCATTA
TCACATAACTTAAGAACGTCTAATGAATGAATTATTCACGAAATAATAAATCATTGGTTCTAAAAAGGAATTTCG
TAATAAAATAAAAATTTAAGTTACCATATTCAAAAAAAGAAATTGTGCTTGAACATGAAAATAATTATAATTTTT
GAACTTGTATAATGAATTTCTTCAATTCATAAGTGGGAAATTTCATATTTATGTAATAATAGATAATATGTAAGC
TCTAATATAGTACTTTAGGTTATAGAATTTAATATAAAATATCAAAACATGAATTCTTGAAATTGAGTAGAGTAA
TTATTTTCTGCACAATGAATCGGAGACAATAACTTTGAAGAAATATAAACAATAGAGTTCAAAAGATGTAGTCAA
AAACAACAATTAATATCATAAGAATAAATTAATGAGTGTAAAAATGCATACCACGATATGTAAAAACAGAATGGA
ATATAATAAAAAAAATCGAGTTCACTGAATACACAATGTTCCTTTAAGAAAATTATTCTCCTCCAATACCAACGA
GATTACATCCTCTAAGGATGGAAATGATTTCATTCCCCAACTTATCCATATAAAAATAGTGGTGTTAGTATGTAA
CTCAATAGGAGTAAAATACACAAATATTTAATTTTGCGAAAGTAGAAGAAGAAGATCATATTTTTTTTTTAAAAT
GAGAGGATATATCACTATTTTTAAACAACAAAGGGTAGTGTTAACAAATTTTTATTGTGTCTTGTCTAAAAGGTT
ACAGCTATTTGAAAAAGTTACAACACTTCGAAAAGTGAACAACATTTCATAAAAGTCGTAACTTTTCATAAAGTC
GTAACTCTTCATAAATGTCGCAACTCTTCATAAAAATTACAACTATTGATAAAAGTCACCACTCTTGATAAAGAT
CACCACTCTTCATTGAAGTTGCAACTTTTCATAAAAATCACATCTTTTAATAAAAAAGAAAGACTAGTTTTTGGA
ATAAATTAATTTAAAAGAAAATTTTTGTTTGTGGTGGGGCGCCAAGTAGGCAGGCGTAGGGTTCTTTTTATATAA
ATATATATGATATATGATTCAATATTTGATATATATATATATAGAGAGAGAGATGACAATATAAGACAATTGCAA
AAAATAAAATAAAAAACTAATCGAGTAAGTAGGCAAAAAATTATTTATAAAATATATGTAGAATTTCTTTATCAG
ATATGACTGCCCAAATCTTATATTCAAACTAAAATGCAAGATCAATGGTGCTATATATAGGGTTTTACACAAAAA
TCAAGATCTAGTCTTGCAAATTTAAATAAAAAACAGTGGTTTACGATGAGATAATGTAGCTTTTGTAAACAATAA
AACTAGAAAAATAAATGCAAAGGCATTTTAAAGGATATAATAATGAAGATCAAAGGCAGAGAAGGGAAGAGGCAG
CAATATAATGAAGGTAACATCATGGTTCCATTCTAATATATATGCTATTTTTCTTTAGTAAATTTCAAAAATAAT
GATACATTTTCATATTTGATAAATATTTAATGATACTATCAACATTTTATCTATATTGAGTTCCATTTATTTGAC
CAAAACCTCACAAAGATGTGCTCTTCGATCTATTCAAAATTTATTCAATTTAAGGATAGCTTTAAAACATGACAA
AGTTTTCTCATATATTTCTTAAATTTTATATCCAGTCTAAATACGTATATAAACTAAAATGAAGAGAATAATATG
AAGCTTTATTTGATGACATTGTTGAAATAACCAAAAGCTATAAGTGATACAATAGTAAATTTACCATTGGTCAAT
TCAGAATTATTTAAAAGCTAAAAAAGTCATATAAGTTGGGGTTGCTCAATGTATAGTTTTTGGCTTGTTTTAAGC
ATTTTAAAACTTTTTTTAAGCGCTTTTTAACATTGCTAAACACTCAAAAAAATGATAAATAGTATTTAAATTTGAT
ATGATTAGCTTAAAAGTGAACTCATATACCTTCAAAGTAAAAATCCCCAATTCGAGCTTTCAAACCACTTGATTT
TGTGGATGAAATTATACTGAAGTTGAATATATCACTATTTATAGGGGTTAGTGAACTAATACCTTTGATTATTTG
GTAGAAATATGTATCTTAGATCACCCTAATGAGCTCCCACTTTTAAAATAGGAAAAACCTCATATGAAGTTCATC

-continued

ACTGTTCATTATATATCACTTTTATTCAAAAACGTTTACAAATGTTCATTGTGACTAAATACCCTTGAGTGTCGA
GTTTTCACACCAATAAGGCCTAATTAATAGGTAAACAAAACTATGTCAATCTTCAAAACGCAAATCTAATTATAT
TTTTAACAAGATTAGAGGTATATATACATATTCTCTTATGTTAACTCTTATTCATTATTGAACAAACTAAGTAAG
TGTACCCAAGGTCTCAAACAACAGTTGGTACATTCTTTGTATGTCTTCCTTTGTCTCTTAATAGTCGTCTCCTCC
TGTCGATGATTCCTCCAAATACATTAATCAAAGGAAAATCTTTCGCCCTCAACTTGCAAACTTGTCTATCTAAAA
TTGTTAACAAAGTTTCTTCATTAGAGAAACTATGATTTCTTGAATGTAGCAATTTGATGTGCCATGACTATCATC
TTGATCAACATGCTTCTTAACCATCAAAAGATCCTAAACTAGATGCATGTCATGTTAGGAGACATATTAAGCTTG
TATATAACTACACCAACATGCTTTAGGATCTCATAAGATCCAAAATTTCTTATTTGGGAGATTTTCAATCCAACA
ACCATCATAATGAGCAACGTGATGTTATAACATCTCTCTCACACTGCCAGAACAGTCTTATACCTTGTCGGAGTG
AAGGACATCCTTAACTAAGTAGATTCACTAAGCTATACTTAAAAAGCAATAAGGAATCATCTAAAATGTGTGACT
CTTAACCCATATTGGCATACATGGTTTATGGGGGTTATTAATTGTCTGAACACTCCCCCATATAAATCAGTGATC
AATATTAATCCCAATAATATACACTATTATGATTTGAGACTACACCCTGGAAGTGGCCGGCTCTCAAGAACCATT
GCTGATCTCCAAGCCAAACCCTCATTCTGGTTGACTACAAGCTGAAGGCAAACTCAAGTATACAAAGCTTAAAAC
ATAATAAAAATAATATACTCAACTCGCCACAAAATAGGCATTTAAGTCTTTAAAACATTTTTAAAAATAAATGAA
ACAAACTTCTCAAACTGTAATGTATATCTATGAAGCCTCTAAATGAAAAAAATGAAGGCAGATGAGACATACGGC
ATCCTAACAACTGATATAACTAAGAGTACAAGTGGAGCCCTTCGGATGTAAGGAGGCTCATCAAAGCTAATGTGA
ACTCCATGTGGTATCAATGAAGCACCTATTGATGACCGTGAATACATGTATCTGCATCATGAAACGATGCAGGCC
AAAGGGCTTAGTACGTGAAATGTACGAGCATGTAAAGGGAATTCAAATACATAAACATAGGCTTGAACTTTGATA
TAAAGGAAACATACTTACCTATTTTTAACTCAAGAATAAAAAACATAGTTCAACTCAATGAAAAGACACTCAAGT
CAGTGAAATAGGCCGCAACTCAATAATAAGATATTCGACTATGGGTAATCAACTCTGGGTACTCTATTCAATATA
AAGTAAGAATACAAATGCATTATATGGAAAGACTTTAAAACGGTAGAAAACAACTCAATGTATTGAAAATTCAAT
AGTAAATTAGTTTGTATGTAAGGAACAATATAAACTTTGTTTGTATATGAAAATACAAAATAAACTTTGTGTATA
TAAAAGTACAAAATATCTCTGTGAAAGTTTCTCTAACCAACAACCATCACTATGAGCTTTCTGATAATACCACGT
TTCGCCCATGATGTCAGAACTGTCCTATGATTTTCCAGTTCATAAGACCTACTCACTAAGTGGATCCACAAGTCT
ATGCTAAAAAATATTTAAGGAATCGTCTAAAAAGTATGACTCATTCTACCCACGTTGGCTACATGATTTATGGGG
GTCGTAAGTTATCTAAACTCTCCTCCATATCGATGCGTAATGCTACTCACAAATATACTAGCTCACATGTTTAAA
AATATAACTCGTTTTGTTTGAGATCATTACTCAAAATCCTTCTCTTAAAAGAGATGATACTCAAACTGCTCAAAA
CTCTTTTGGAAATCTCAAATTCGTCTCATCTTAAATGTAAAAATATTTACTCTTGGGAATACATAGTTATCATAT
ATCATTTTAAAGAAAATGAACTCAACTCTGTTCTTTCTCAACTCAAGTGCTCAGTCTTAAACCAAATTAAAAAAA
AGACTTCTCAAAATAAAGTTTATGTCGAATTATGGACGTGAACAATTCAATTCAAAGTTTTCGATAACCATAACT
AAAACTAAATACTCGAGACTCAACATCTTAGAACTCAAGAACTTAAATGGTAATACTTCTTTCAAGAATGCTCGA
CTCAGAAGGTTAATGCAGAATAATGTGCATGAATTACTCAACTAAAGGACTCACTGATACTACTCAATCTCAAGA
TTGCTCGACTCGTAGGGTTAATGCAGAATTATGTGCATGAACTACTCAACTCAAAGACCTTCATAGGTAACATGT
AGTAGCCCCATGATTTGGAATATAATCCCAAAATGATTAGGAACTCAATACTCAGGACTTAGAACTTGAAGATAA
TACTACTTCTCTCAAAGATACCCAACTGACGGAGTTCATGCAGAATTTATGGGCATGAACTACTCGACTCAAGAG
TCTAAAACACAATATGACACTCATGTATATAACTCTTCTCATTCTAATACTTGTTTTCTCAAAACTCGGTTTAAC
TAAATAGTTGATCTCAAAGGATTCACAATTGAACTCAAAGACTTTCTTTGACTCCACTCTTAATTCTCTCTTAAA
TTTGTATTTGAATTATGAATTTAAGAGTTATGATTCATGATATGGGGAATCTCAATAACAATATAGAAATTTGAT
AATTAGGAATAGTACTTTTAAAAGAAAACATGAATTCAACTTAAAATCAACTTATCTAAAAAATATTCAAATATA
GGGAAAGTATCCTAGACTACTGTGCTACTGATCTGAAAGTAGATGTAGGATGTGAGGATGAACTAGTCCAACACT
ATGATAGCCTTACATACCTGGAATAACGAGGTTCTTGGAAAATCTTCACTTGAAGAAGAACTTGATTAGAAGCCT
TGAAACCTAGCTTGAAGGTAAACAATCAAGAAAACCTTTCTTAAGATTCTTGAATTAGTTTATGAAAATCTCTAT
GACCAAGCATTTTGATTTTCACTAGTGATTCATAATTGTATGGAGGAATTTGAATTGAAAAAGATGAAATGCTTG
GAGAAAAGCTATCTTTGAAGAAGCTTGAAAAAGATTGGAAAGTCCTGTACTTTGATTTTCCCTTAGGATTTTGTC
TTAGGGTTTGAGATAGAAAAGAATGATGGACTAAAAGATGAAAATCTAATTGTTTGGATCCTTTTTCAGCCAAGA
AATCCGTTTAGGGTTTTCTTGGAGACAAACAAAATAAAAAAGACCATTTTTAATATTTTTCCGTCGGCTAATTCG
TAATAACATTGTATCATGTTATTGAAAGAGTCATAACTTTTTACTCAAAAATTGGATTGATGCGAAATTAGTGGT
GTTGGAAAGTAGATTCAAGTACCTCTAATTGGATAGGTTATTCCCTACATAAGTCTTTATATTCTAAAAGATATG
GTTGTTTGCACTTGACCTAAGTAGAATTTTACATGAAAACTTAATAGAGAAGGAAACTTCAAGAACTCATCAAGA
AATTTCAATTGCTCAATATTTATGGATAAATTTGTAGAAGAAACTCATGATTGACATGCGGGTGAATAAACCCAA
CACTATGGAAGCTTACATACCTCAAAGAACTAGGTTCTTGGCGAAATCTTGAATTTCTTCAACGAACGCTTGAAA
CTTTGAACTTTTTCTCTTCTTGAACTCTCAACTAAAACCCTAGGCGTATATTAGGATTATAAAAGTTAACATGAT
AGGATTAGACCTTTAAAAACTTTCTAAAATGAATTAAATCTGATTTAGCATGAAAAAGACCAAAATACCCCTTAC
TATTTTCGGATAACTTTTCTTAATTGGACTGCCTGACTTCAAAAAGGTATATCTCACTCATCCGACCTCAAAATT
TAGCAAATTCAGTGGCGTTAGAAAGCTAATTTAAACACCTTTCATTTTCCATCTCATGGCACACATAACTCATTC
TTTAAAGAGAGCTATGATCGTTCAAATTAACTCAAATCTTAGAAGAATTTAGGAATGTCTTGAACGAGCTACATC
TAGTGACCTTAACACTTTGGAAAATTTTAAATTTCTTAGTAAAAACTTACTCACTATGAAGGATGGTTCAAGTCT
TAGCTCAAAATTTTCCTAAGTTGCTATATATACTCATGCTCATATGTTTAAAACCAAAACCCTTCCTCGATTTGA
ATTAATTACCAAAAAGATTCTCTTAAAAAGATAATGCTCAAAACTCCCCCTAAACTCATTTGGAAATCTAGGTTT
CCCTTGTTTTAAATATAAAAACATTTACTCTTGGAAATATTTAGTTCTCAGATATTCACTTGAAAAAAATTAAAC
TCGACTCTCATCATCTTCATACTCAAGTGCTCAAGTCCTAAAACAATTTATAACTAATTGTATAAGACTTCTCAA
AATAGGGTTCATTCCGAATTATGGACGTGAACGACTCAATTCAAGGATTTCAATAACCATATATATAACTCAATA
ATAGGAACTCAACAACTCCAGAACTCAATGATACTACTCATCTCAAGAATGCTCGACTCACAGGGTCTTTGCGAA
ATTATTGGGCATGAACAACTCAACTCAAAGACCTTCATTTATACCATATGGTAGTCCCATAATAGGAATATAATC
CCAAAAAAATTAGGAACTCAATACTCAAAAACTTAGAACTCGAAGATATTACTCATCTCAAAGATATTCAATTTA
TGGAATTCATGCTGAATTATGAGCATGAACGACTTGACTCAAGGATCTCAATAATAATGTAGACTCATGAATACA
CTCTTCTCATTCTCATACTCACATACTCGAGTATTAAAATAAATTATAAGTAATTGCAGAAGACTCCTTGAACAG
ACTCAAAAGGACTCCTTCGAATTTTACTCTTAATGCTACCTGAATTTTGTATTATAAATTTAAGGATCATGATTA
TGATATAAAGAATTTCTCAGCATATATGAAATGAACGAATTTGAGCATTGAACGTCTAACCTCATTTTTTAATTA
TTGTGATATGTAGAGTGGTGCAAAATCACAGATACCTCTCTTGATGCATTTCTATAGTTACGTTGATGTGAGATT
ATATATAGTTCAGCAGCAGCATGTTGGGAAAATTACTAATAACTCTTCTTTTATATCAAATTGTTGAAGCATGAT
GACAACACTTGAAAAGTATCAACAATGCAGTTACGCATCTTTGGACCCGATGTAACCGGTTAGTGATACTCAGGT
ATTGTTTATCTACTTTATCATGTCGTAAGTATATTATTTGTAAAGATATATATCAAGATAGTTCGATTGCGTACA
CTTACATTTTGATTATGTTTGGTGAATACTATTCTAATACCTTTTTTTTTCCTAAAGCCTAACAAATAAAGATAA
TTAAGATGGGAACGTAATTCAAGTACAACATGGTTCCATACGTGACATATTTACACATATAGTGGAACCAAAAGA
GCAATTTTTCCTAATATCATTTTCTAAATATCACGTGTGCCCGTGATTCTTTTTTATGGACATGAATTTTTTTTT
TAATATGAGTGGAAGTAAGGTTCGATCTTTCTATCTGCTTTGATATCATATTGAATCGTGTGATTGTCTCTTTAA
AAAATTAAGCAAGAGCATATTTTATTAATTAATTGTCTTTCTCGACGTTTTTCTCTTTCAACAGATGAACTACAA
TGAGTATGTGAGGCTAAAAGCTAGAGTTGAGCTCCTTCAACGTTCTCAAAGGTAAGATATTAGTGATGTAATTAA

ATGATTTTAGTTAGATTTACATAAGTTTTTAATAAGTGAAAATTAATAGACATATTCTTGGAGAGGATTTGGGCA
CACTAAACTCGAAAGAACTTGAGCAGCTTGAGCACCAATTGGATGCATCTTTGAAGAAAGTTAGATCAAAAAAGG
TATATCCAAATACTATAACTTAAATATATTGTAACGATTTAATTAATAGCATGTGTCACGTTCATCTATTCTTTA
GTCACAATATATAGGGGCATGTCCTTAACAACGTGCCATGCCTCGATAGTCATTTTTGTCTTTTTGTGCGTATGA
ATTTAACTTTGACACAAATTTTTGTAGTAATAATAACTCATGCTTTAGCATCTTAGGAAGCAGTCATATGAAAAA
CAGAAGCATATATATATATTACATGAGTTAATTTAATTTAATATAAAATTTAATAAAATTGTGTCTCGCTATAAA
TAATTTTATTAAAAAATTATATAAATATATTATTTTTTTAACTGGCCGCAAAGTTATATAAATTGATAGAGAAAG
AGGTTTTGGTGTAAGGTTCATTTTCCAACAATTAGTTTTATAATTTGTAAGTGCACACTTTATCAGACTCAATCT
ATGCTGGATCAGCTGGCAGACCTTCAAGAAAAGGTACACTGCCTTAACATTACAAAATTAATTTATTTCATCAAA
AGCATATCATAAAAATTCTGACAAATAAATATATTAGGAGCAAATGCTGGAAGAAGCAAATAAACAACTAAAAAAC
AAGGTACATATCTATATATGTGTGTTAATTAATTAAGTTGATTTTGTATTTTTGTTTAATGAATAATTGTTTGTG
ATCATCAGCTGGAAGAAAGTGCAGCTAGAATTCCACTTGGATTGTCATGGGGAAATAATGGAGGACAAACAATGG
AATACAATCGACTCCCTCCACAAACTACTGCACAACCTTTCTTTCAACCTCTCCGTTTGAATTCTTCATCGCCTC
AATTCGGGTAAGTATCTTATTTTATATGACTTAGTTTGACTTGACATAAAGTTTAATAAAGAAAGAAAGACTTTT
AAAACTTATAGTGTAAAATAAGTGAATAGATATATATGTGGTTGTACTAACACTACAACAAAAATAATTTTCAGC
GGCATTAAATATTGACATTAATAATGAGTGCTAAAGACTTTATCGGTATTAGTTAAGTGTCATTAGGATCAATGT
CGTTAAAGGCTTCACGGACATATACAAAGAGTGACAATTGCCGCTAATGATTATTTTTGTTGTAGTGAAAATGAG
TATTTTAAAGTTAAATTGTTACATAATATAGAAATATGTCAGAAACAGGACAAATATACCACCGAACTATCATAT
ATGTTATGGAGATATTCTCAGTCATACTTCTGCGACATTGGTACTCATGTCGTCCAAAAACTAGAACATATATAT
ACCCTTATATATTAACGAAGATACAAGTGTCATAATCTTATGCACCGATTCGATATTTATTAAATATCGAATCG
ACGGATAAAATTATGTCACGTGTCCCTATTAAGTCTTCTATTAGAGTAAAAAGCATATATTCTCTAGTTTTTGAA
CGAAAAAAGGTATTAATGTCTCAAAAGTATAACGAAAAGCATTTGCATACAATTTATGATAATTTGGGGCATATT
AATTTATCATTCCCCCTTTTTTTGGCACTGATTAAAAAGAAAAAGAAAGTTATAAAAATTGGGATAGAGGGAATA
ATTGTTTCATAGGGAAAACTTAGAAGCTTCTCAGTATGTCAGTGAGAATGTGTTTCCTAATTAGTGAACTATGGT
TTGGTGAAAAATAAAGAGAAAAAAATCAGTACAAATTTTCCACTGATTAGCAATGAGAAAAATATTTGTTTCTAG
TAGTATGAGGAGAGGATAGTCCGCATAAATAATCCTTAAATTTGTGGATAAATAAACTATTTTCAATAGATTATC
GTCTCAAAATAAAATAAAATGATTGCAAGAAAAGAATAATAGGTATGCTGGTAATATGTATAATACACTCAAATT
TATTTGCTGTCCATGCAGATACAATCCAAATATGGGTGCAAATGATCATGAGGTTAATGCAGCAACAACTGCTCA
TAATATTAATGGATTTATTCCAGGGTGGATGCTCTAA (SEQ ID NO: 9)

Mutant Solyc12g038510 gene allele $j2^{CR}$
>allele-1
ATGGGAAGAGGAAGAGTAGAACTAAAGAGAATAGAGAACAAAATAAACAGGCAAGTTACTTTTGCTAAGAGAAGA
AATGGACTTCTTAAGAAAGCTTATGAGTTATCTATACTTTGTGATGCTGAAGTTGCTCTCATCATCTTCTCTAGC
CGCGGAAAACTCTATGAGTTTTCAAGTGCTTCCAGGTATATATATATATACATATGTTTTTCTTCTTTTTGTGTG
TGCGTATGTGTTTACTTACTTTCATTAATTAACTCAACCATATATATACATCTCTCACCTCAATTATATATATGT
TTGAGATCTGAATGTCTACGGACTCCATTTAGGTACATATCTTTGTTTAGATCATAAATCATCTATCTTCATTCC
TAAGATCTACTAATATATATGTATAAGAAGATCCATCCATCTATTAGGTTTTTCAACAACATATACAGTGAAATC
TTATATGTGGGCCCACGTATAGCCATATGAGAAAATAGTGTGCACGTAAACATTATCATTACTTAATTATAGGAA
TATACATCCATTAGGTTTATCAACAACAATAAAATCCTCTAAATGGAGTCTAGTCATAGGTCTAGCCGTTTGAAA
ATGTAAAATATATGCCGATCTTATCACTATGTCATAATAATAGATATGTTGTATTGAAAGATTCTCAATCTTTT
TTTTTCTTCAAGGTAGAGATTCTTAAGTGGATTCATGTTTTTTTTATCAAAAAAGAAAAAAACAAAAGTGTCCAT
TTGTTCATCTAATGGGTTTTCCATGTTACCAATTCACTACACTGTTGAGATTTGATTATCAGATGTGTCAAGTTT
CGTTTGGTTCCCTAGAAGGGAGAAAAGGCTGCTTATGCAGGCAGGGTATTAAAGATGATATTAATATCTGCAGTA
ATCAGTAACAGAATATATAAACTTAATAATAAACTTGAAGGTACTTAATTATCCAGCAGATAATCTTCTGTCTCA
CCGTACACTTTTGTTATATCATAAGCATAAGAATTGTTTTATCAAATATTACCAAACAAAACTTAGTTTTGTTTG
GTAATATTTTATAAAATATGTTACCGAAAGTTACTTCCTATAACATATTTTATAAAGAAAAAAATTAAAAACTCC
ATATACCTAAGAAATGTAACCCCCCCTCCATAACAACAATTTAACAAAAATAAAAACCTACTTTTTTTGAATTTG
GTAAATTAGTTTTCTATCCTTTTTAGTAACTTCCTTTCTTATTTTCTTTTTATATTGGTAAAGTTTAATATTACA
CATTATTTTAACATGTTATAATTTTTTGTGATGCTTAATTATTTGATACATGTAATAAACCATATATTAGAGCTA
TAAATCAATGACAATGCATGTAGATACAACTCATTTATGATATATTTTGTTTATATATATAACCAATTAGATAAT
TTGTCTGCGCTTTGTGCAGTCATAAATAATAATTGCATTGAACTTGCAAATATTTTTTTTTAATATCCATACATT
AAAAAAAAAGAAAGAGGAAAATTGGTTCCTAAAATATTAGCAATATTCAAACATTTATTTGATTATTAATCATTA
TCACATAACTTAAGAACGTCTAATGAATGAATTATTCACGAAATAATAAATCATTGGTTCTAAAAGGAATTTCG
TAATAAAATAAAAATTTAAGTTACCATATTCAAAAAAAGAAATTGTGCTTGAACATGAAAATAATTATAATTTTT
GAACTTGTATAATGAATTTCTTCAATTCATAAGTGGGAAATTTCATATTTATGTAATAATAGATAATATGTAAGC
TCTAATATAGTACTTTAGGTTATAGAATTTAATATAAAATATCAAACATGAATTCTTGAAATTGAGTAGAGTAA
TTATTTTCTGCACAATGAATCGGAGACAATAACTTTGAAGAAATATAAACAATAGAGTTCAAAAGATGTAGTCAA
AAACAACAATTAATATCATAAGAATAAATTAATGAGTGTAAAAATGCATACCACGATATGTAAAAACAGAATGGA
ATATAATAAAAAAAATCGAGTTCACTGAATACACAATGTTCCTTTAAGAAAATTATTCTCCTCCAATACCAACGA
GATTACATCCTCTAAGGATGGAAATGATTTCATTCCCCAACTTATCCATATAAAAATAGTGGTGTTAGTATGTAA
CTCAATAGGAGTAAAATACACAAATATTTAATTTTGCGAAAGTAGAAGAAGAAGATCATATTTTTTTTTTAAAAT
GAGAGGATATATCACTATTTTTAAACAACAAAGGGTAGTGTTAACAAATTTTTATTGTGTCTTGTCTAAAAGGTT
ACAGCTATTTGAAAAAGTTACAACACTTCGAAAAGTGAACAACATTTCATAAAAGTCGTAACTTTTCATAAAGTC
GTAACTCTTCATAAATGTCGCAACTCTTCATAAAAATTACAACTATTGATAAAAGTCACCACTCTTGATAAAGAT
CACCACTCTTCATTGAAGTTGCAACTTTTCATAAAAATCACATCTTTTAATAAAAAGAAAGACTAGTTTTTGGA
ATAAATTAATTTAAAAGAAAATTTTTGTTTGTGGTGGGGCGCCAAGTAGGCAGGCGTAGGGTTCTTTTTATATAA
ATATATATGATATATGATTCAATATTTGATATATATATATATAGAGAGAGAGATGACAATATAAGACAATTGCAA
AAAATAAAATAAAAAACTAATCGAGTAGTAGGCAAAAAATTATTTATAAAATATATGTAGAATTTCTTTATCAG
ATATGACTGCCCAAATCTTATATTCAAACTAAAATGCAAGATCAATGGTGCTATATATAGGGTTTTACACAAAAA
TCAAGATCTAGTCTTGCAAATTTAAATAAAAAACAGTGGTTTACGATGAGATAATGTAGCTTTTGTAAACAATAA
AACTAGAAAAATAAATGCAAAGGCATTTTAAAGGATATAATAATGAAGATCAAAGGCAGAGAAGGGAAGAGGCAG
CAATATAATGAAGGTAACATCATGGTTCCATTCTAATATATATGCTATTTTTCTTTAGTAAATTTCAAAAATAAT
GATACATTTTCATATTTGATAAATATTTAATGATACTATCAACATTTTATCTATATTGAGTTCCATTTATTTGAC
CAAAACCTCACAAAGATGTGCTCTTCGATCTATTCAAAATTTATTCAATTTAAGGATAGCTTTAAAACATGACAA
AGTTTTCTCATATATTTCTTAAATTTTATATCCAGTCTAAATACGTATATAAACTAAAATGAAGAGAATAATATG
AAGCTTTATTTGATGACATTGTTGAAATAACCAAAAGCTATAAGTGATACAATAGTAAATTTACCATTGGTCAAT
TCAGAATTATTTAAAAGCTAAAAAAGTCATATAAGTTGGGGTTGCTCAATGTATAGTTTTTGGCTTGTTTTAAGC
ATTTTAAAACTTTTTTTAAGCGCTTTTTAACATTGCTAAACACTCAAAAAATGATAAATAGTATTTAAATTTGAT -continued ATGATTAGCTTAAAAGTGAACTCATATACCTTCAAAGTAAAAATCCCCAATTCGAGCTTTCAAACCACTTGATTT
TGTGGATGAAATTATACTGAAGTTGAATATATCACTATTTATAGGGGTTAGTGAACTAATACCTTTGATTATTTG
GTAGAAATATGTATCTTAGATCACCCTAATGAGCTCCCACTTTTAAAATAGGAAAAACCTCATATGAAGTTCATC
ACTGTTCATTATATATCACTTTTATTCAAAAACGTTTACAAATGTTCATTGTGACTAAATACCCTTGAGTGTCGA
GTTTTCACACCAATAAGGCCTAATTAATAGGTAAACAAAACTATGTCAATCTTCAAAACGCAAATCTAATTATAT
TTTTAACAAGATTAGAGGTATATATACATATTCTCTTATGTTAACTCTTATTCATTATTGAACAAACTAAGTAAG
TGTACCCAAGGTCTCAAACAACAGTTGGTACATTCTTTGTATGTCTTCCTTTGTCTCTTAATAGTCGTCTCCTCC
TGTCGATGATTCCTCCAAATACATTAATCAAAGGAAAATCTTTCGCCCTCAACTTGCAAACTTGTCTATCTAAAA
TTGTTAACAAAGTTTCTTCATTAGAGAAACTATGATTTCTTGAATGTAGCAATTTGATGTGCCATGACTATCATC
TTGATCAACATGCTTCTTAACCATCAAAAGATCCTAAACTAGATGCATGTCATGTTAGGAGACATATTAAGCTTG
TATATAACTACACCAACATGCTTTAGGATCTCATAAGATCCAAAATTTCTTATTTGGGAGATTTTCAATCCAACA
ACCATCATAATGAGCAACGTGATGTTATAACATCTCTCTCACACTGCCAGAACAGTCTTATACCTTGTCGGAGTG
AAGGACATCCTTAACTAAGTAGATTCACTAAGCTATACTTAAAAAGCAATAAGGAATCATCTAAAATGTGTGACT
CTTAACCCATATTGGCATACATGGTTTATGGGGGTTATTAATTGTCTGAACACTCCCCCATATAAATCAGTGATC
AATATTAATCCCAATAATATACACTATTATGATTTGAGACTACACCCTGGAAGTGGCCGGCTCTCAAGAACCATT
GCTGATCTCCAAGCCAAACCCTCATTCTGGTTGACTACAAGCTGAAGGCAAACTCAAGTATACAAAGCTTAAAAC
ATAATAAAAATAATATACTCAACTCGCCACAAAATAGGCATTTAAGTCTTTAAAACATTTTTAAAAATAAATGAA
ACAAACTTCTCAAACTGTAATGTATATCTATGAAGCCTCTAAATGAAAAAAATGAAGGCAGATGAGACATACGGC
ATCCTAACAACTGATATAACTAAGAGTACAAGTGGAGCCCTTCGGATGTAAGGAGGCTCATCAAAGCTAATGTGA
ACTCCATGTGGTATCAATGAAGCACCTATTGATGACCGTGAATACATGTATCTGCATCATGAAACGATGCAGGCC
AAAGGGCTTAGTACGTGAAATGTACGAGCATGTAAAGGGAATTCAAATACATAAACATAGGCTTGAACTTTGATA
TAAAGGAAACATACTTACCTATTTTTAACTCAAGAATAAAAAACATAGTTCAACTCAATGAAAAGACACTCAAGT
CAGTGAAATAGGCCGCAACTCAATAATAAGATATTCGACTATGGGTAATCAACTCTGGGTACTCTATTCAATATA
AAGTAAGAATACAAATGCATTATATGGAAAGACTTTAAAACGGTAGAAAACAACTCAATGTATTGAAAATTCAAT
AGTAAATTAGTTTGTATGTAAGGAACAATATAAACTTTGTTTGTATATGAAAATACAAAATAAACTTTGTGTATA
TAAAAGTACAAAATATCTCTGTGAAAGTTTCTCTAACCAACAACCATCACTATGAGCTTTCTGATAATACCACGT
TTCGCCCATGATGTCAGAACTGTCCTATGATTTTCCAGTTCATAAGACCTACTCACTAAGTGGATCCACAAGTCT
ATGCTAAAAAATATTTAAGGAATCGTCTAAAAAGTATGACTCATTCTACCCACGTTGGCTACATGATTTATGGGG
GTCGTAAGTTATCTAAACTCTCCTCCATATCGATGCGTAATGCTACTCACAAATATACTAGCTCACATGTTTAAA
AATATAACTCGTTTTGTTTGAGATCATTACTCAAAATCCTTCTCTTAAAAGAGATGATACTCAAACTGCTCAAAA
CTCTTTTGGAAATCTCAAATTCGTCTCATCTTAAATGTAAAAATATTTACTCTTGGGAATACATAGTTATCATAT
ATCATTTTAAAGAAAATGAACTCAACTCTGTTCTTTCTCAACTCAAGTGCTCAGTCTTAAACCAAATTAAAAAAA
AGACTTCTCAAAATAAAGTTTATGTCGAATTATGGACGTGAACAATTCAATTCAAAGTTTTCGATAACCATAACT
AAAACTAAATACTCGAGACTCAACATCTTAGAACTCAAGAACTTAAATGGTAATACTTCTTTCAAGAATGCTCGA
CTCAGAAGGTTAATGCAGAATAATGTGCATGAATTACTCAACTAAAGGACTCACTGATACTACTCAATCTCAAGA
TTGCTCGACTCGTAGGGTTAATGCAGAATTATGTGCATGAACTACTCAACTCAAAGACCTTCATAGGTAACATGT
AGTAGCCCCATGATTTGGAATATAATCCCAAAATGATTAGGAACTCAATACTCAGGACTTAGAACTTGAAGATAA
TACTACTTCTCTCAAAGATACCCAACTGACGGAGTTCATGCAGAATTTATGGGCATGAACTACTCGACTCAAGAG
TCTAAAACACAATATGACACTCATGTATATAACTCTTCTCATTCTAATACTTGTTTTCTCAAAACTCGGTTTAAC
TAAATAGTTGATCTCAAAGGATTCACAATTGAACTCAAAGACTTTCTTTGACTCCACTCTTAATTCTCTCTTAAA
TTTGTATTTGAATTATGAATTTAAGAGTTATGATTCATGATATGGGGAATCTCAATAACAATATAGAAATTTGAT
AATTAGGAATAGTACTTTTAAAAGAAAACATGAATTCAACTTAAAATCAACTTATCTAAAAAATATTCAAATATA
GGGAAAGTATCCTAGACTACTGTGCTACTGATCTGAAAGTAGATGTAGGATGTGAGGATGAACTAGTCCAACACT
ATGATAGCCTTACATACCTGGAATAACGAGGTTCTTGGAAAATCTTCACTTGAAGAAGAACTTGATTAGAAGCCT
TGAAACCTAGCTTGAAGGTAAACAATCAAGAAAACCTTTCTTAAGATTCTTGAATTAGTTTATGAAAATCTCTAT
GACCAAGCATTTTGATTTTCACTAGTGATTCATAATTGTATGGAGGAATTTGAATTGAAAAAGATGAAATGCTTG
GAGAAAAGCTATCTTTGAAGAAGCTTGAAAAAGATTGGAAAGTCCTGTACTTTGATTTTCCCTTAGGATTTTGTC
TTAGGGTTTGAGATAGAAAAGAATGATGGACTAAAAGATGAAAATCTAATTGTTTGGATCCTTTTTCAGCCAAGA
AATCCGTTTAGGGTTTTCTTGGAGACAAACAAAATAAAAAAGACCATTTTTAATATTTTTCCGTCGGCTAATTCG
TAATAACATTGTATCATGTTATTGAAAGAGTCATAACTTTTTACTCAAAAATTGGATTGATGCGAAATTAGTGGT
GTTGGAAAGTAGATTCAAGTACCTCTAATTGGATAGGTTATTCCCTACATAAGTCTTTATATTCTAAAAGATATG
GTTGTTTGCACTTGACCTAAGTAGAATTTTACATGAAAACTTAATAGAGAAGGAAACTTCAAGAACTCATCAAGA
AATTTCAATTGCTCAATATTTATGGATAAATTTGTAGAAGAAACTCATGATTGACATGCGGGTGAATAAACCCAA
CACTATGGAAGCTTACATACCTCAAAGAACTAGGTTCTTGGCGAAATCTTGAATTTCTTCAACGAACGCTTGAAA
CTTTGAACTTTTTCTCTTCTTGAACTCTCAACTAAAACCCTAGGCGTATATTAGGATTATAAAAGTTAACATGAT
AGGATTAGACCTTTAAAAACTTTCTAAAATGAATTAAATCTGATTTAGCATGAAAAAGACCAAAATACCCCTTAC
TATTTTCGGATAACTTTTCTTAATTGGACTGCCTGACTTCAAAAAGGTATATCTCACTCATCCGACCTCAAAATT
TAGCAAATTCAGTGGCGTTAGAAAGCTAATTTAAACACCTTTCATTTTCCATCTCATGGCACACATAACTCATTC
TTTAAAGAGAGCTATGATCGTTCAAATTAACTCAAATCTTAGAAGAATTTAGGAATGTCTTGAACGAGCTACATC
TAGTGACCTTAACACTTTGGAAAATTTTAAATTTCTTAGTAAAAACTTACTCACTATGAAGGATGGTTCAAGTCT
TAGCTCAAAATTTTCCTAAGTTGCTATATATACTCATGCTCATATGTTTAAAACCAAAACCCTTCCTCGATTTGA
ATTAATTACCAAAAAGATTCTCTTAAAAAGATAATGCTCAAAACTCCCCCTAAACTCATTTGGAAATCTAGGTTT
CCCTTGTTTTAAATATAAAAACATTTACTCTTGGAAATATTTAGTTCTCAGATATTCACTTGAAAAAAATTAAAC
TCGACTCTCATCATCTTCATACTCAAGTGCTCAAGTCCTAAAACAATTTATAACTAATTGTATAAGACTTCTCAA
AATAGGGTTCATTCCGAATTATGGACGTGAACGACTCAATTCAAGGATTTCAATAACCATATATATAACTCAATA
ATAGGAACTCAACAACTCCAGAACTCAATGATACTACTCATCTCAAGAATGCTCGACTCACAGGGTCTTTGCGAA
ATTATTGGGCATGAACAACTCAACTCAAAGACCTTCATTTATACCATATGGTAGTCCCATAATAGGAATATAATC
CCAAAAAAATTAGGAACTCAATACTCAAAAACTTAGAACTCGAAGATATTACTCATCTCAAAGATATTCAATTTA
TGGAATTCATGCTGAATTATGAGCATGAACGACTTGACTCAAGGATCTCAATAATAATGTAGACTCATGAATACA
CTCTTCTCATTCTCATACTCACATACTCGAGTATTAAAATAAATTATAAGTAATTGCAGAAGACTCCTTGAACAG
ACTCAAAAGGACTCCTTCGAATTTTACTCTTAATGCTACCTGAATTTTGTATTATAAATTTAAGGATCATGATTA
TGATATAAAGAATTTCTCAGCATATATGAAATGAACGAATTTGAGCATTGAACGTCTAACCTCATTTTTTAATTA
TTGTGATATGTAGAGTGGTGCAAAATCACAGATACCTCTCTTGATGCATTTCTATAGTTACGTTGATGTGAGATT
ATATATAGTTCAGCAGCAGCATGTTGGGAAAATTACTAATAACTCTTCTTTTATATCAAATTGTTGAAGCATGAT
GACAACACTTGAAAAGTATCAACAATGCAGTTACGCATCTTTGGACCCGATGTTACCGGTTAGTGATACTCAGGT
ATTGTTTATCTACTTTATCATGTCGTAAGTATATTATTTGTAAAGATATATATCAAGATAGTTCGATTGCGTACA
CTTACATTTTGATTATGTTTGGTGAATACTATTCTAATACCTTTTTTTTTCCTAAAGCCTAACAAATAAAGATAA
TTAAGATGGGAACGTAATTCAAGTACAACATGGTTCCATACGTGACATATTTACACATATAGTGGAACCAAAAGA
GCAATTTTTCCTAATATCATTTTCTAAATATCACGTGTGCCCGTGATTCTTTTTTATGGACATGAATTTTTTTTT -continued

```
TAATATGAGTGGAAGTAAGGTTCGATCTTTCTATCTGCTTTGATATCATATTGAATCGTGTGATTGTCTCTTTAA
AAAATTAAGCAAGAGCATATTTTATTAATTAATTGTCTTTCTCGACGTTTTTCTCTTTCAACAGATGAACTACAA
TGAGTATGTGAGGCTAAAAGCTAGAGTTGAGCTCCTTCAACGTTCTTCAAAGGTAAGATATTAGTGATGTAATTA
AATGATTTTAGTTAGATTTACATAAGTTTTTAATAAGTGAAAATTAATAGACATATTCTTGGAGATTTGGGCACA
CTAAACTCGAAAGAACTTGAGCAGCTTGAGCACCAArTGGATGCATCTTTGAAGAAAGTTAGATCAAAAAAGGTA
TATCCAAATACTATAACTTAAATATATTGTAACGATTTAATTAATAGCATGTGTCACGTTCATCTATTCTTTAGT
CACAATATATAGGGGCATGTCCTTAACAACGTGCCATGCCTCGATAGTCATTTTTGTCTTTTTGTGCGTATGAAT
TTAACTTTGACACAAATTTTTGTAGTAATAATAACTCATGCTTTAGCATCTTAGGAAGCAGTCATATGAAAAACA
GAAGCATATATATATATTACATGAGTTAATTTAATTTAATATAAAATTTAATAAAATTGTGTCTCGCTATAAATA
ATTTTATTAAAAAATTATATAAATATATTATTTTTTTAACTGGCCGCAAAGTTATATAAATTGATAGAGAAAGAG
GTTTTGGTGTAAGGTTCATTTTCCAACAATTAGTTTTATAATTTGTAAGTGCACACTTTATCAGACTCAATCTAT
GCTGGATCAGCTGGCAGACCTTCAAGAAAAGGTACACTGCCTTAACATTACAAAATTAATTTATTTCATCAAAAG
CATATCATAAAATTCTGACAAATAAATATATTAGGAGCAAATGCTGGAAGAAGCAAATAAACAACTAAAAAACAA
GGTACATATCTATATATGTGTGTTAATTAATTAAGTTGATTTTGTATTTTTGTTTAATGAATAATTGTTTGTGAT
CATCAGCTGGAAGAAAGTGCAGCTAGAATTCCACTTGGATTGTCATGGGGAAATAATGGAGGACAAACAATGGAA
TACAATCGACTCCCTCCACAAACTACTGCACAACCTTTCTTTCAACCTCTCCGTTTGAATTCTTCATCGCCTCAA
TTCGGGTAAGTATCTTATTTTATATGACTTAGTTTGACTTGACATAAAGTTTAATAAAGAAAGAAAGACTTTTAA
AACTTATAGTGTAAAATAAGTGAATAGATATATATGTGGTTGTACTAACACTACAACAAAAATAATTTTCAGCGG
CATTAAATATTGACATTAATAATGAGTGCTAAAGACTTTATCGGTATTAGTTAAGTGTCATTAGGATCAATGTCG
TTAAAGGCTTCACGGACATATACAAAGAGTGACAATTGCCGCTAATGATTATTTTTGTTGTAGTGAAAATGAGTA
TTTTAAAGTTAAATTGTTACATAATATAGAAATATGTCAGAAACAGGACAAATATACCACCGAACTATCATATAT
GTTATGGAGATATTCTCAGTCATACTTCTGCGACATTGGTACTCATGTCGTCCAAAAACTAGAACATATATATAC
CCTTTATATATTAACGAAGATACAAGTGTCATAATCTTATGCACCGATTCGATATTTATTAAATATCGAATCGAC
GGATAAAATTATGTCACGTGTCCCTATTAAGTCTTCTATTAGAGTAAAAAGCATATATTCTCTAGTTTTTGAACG
AAAAAAGGTATTAATGTCTCAAAAGTATAACGAAAAGCATTTGCATACAATTTATGATAATTTGGGGCATATTAA
TTTATCATTCCCCCTTTTTTTGGCACTGATTAAAAAGAAAAAGAAAGTTATAAAAAATTGGGATAGAGGGAATAAT
TGTTTCATAGGGAAAACTTAGAAGCTTCTCAGTATGTCAGTGAGAATGTGTTTCCTAATTAGTGAACTATGGTTT
GGTGAAAAAATAAAGAGAAAAAAATCAGTACAAATTTTCCACTGATTAGCAATGAGAAAAAATATTTGTTTCTAGTA
GTATGAGGAGAGGATAGTCCGCATAAATAATCCTTAAATTTGTGGATAAATAAACTATTTTCAATAGATTATCGT
CTCAAAATAAAATAAAATGATTGCAAGAAAAGAATAATAGGTATGCTGGTAATATGTATAATACACTCAAATTTA
TTTGCTGTCCATGCAGATACAATCCAAATATGGGTGCAAATGATCATGAGGTTAATGCAGCAACAACTGCTCATA
ATATTAATGGATTTATTCCAGGGTGGATGCTCTAA (SEQ ID NO: 10)

>allele-2
ATGGGAAGAGGAAGAGTAGAACTAAAGAGAATAGAGAACAAAATAAACAGGCAAGTTACTTTTGCTAAGAGAAGA
AATGGACTTCTTAAGAAAGCTTATGAGTTATCTATACTTTGTGATGCTGAAGTTGCTCTCATCATCTTCTCTAGC
CGCGGAAAACTCTATGAGTTTTCAAGTGCTTCCAGGTATATATATATATACATATGTTTTTCTTCTTTTTGTGTG
TGCGTATGTGTTTACTTACTTTCATTAATTAACTCAACCATATATATACATCTCTCACCTCAATTATATATATGT
TTGAGATCTGAATGTCTACGGACTCCATTTAGGTACATATCTTTGTTTAGATCATAAATCATCTATCTTCATTCC
TAAGATCTACTAATATATATGTATAAGAAGATCCATCCATCTATTAGGTTTTTCAACAACATATACAGTGAAATC
TTATATGTGGGCCCACGTATAGCCATATGAGAAAATAGTGTGCACGTAAACATTATCATTACTTAATTATAGGAA
TATACATCCATTAGGTTTATCAACAACAATAAAATCCTCTAAATGGAGTCTAGTCATAGGTCTAGCCGTTTGAAA
ATGTAAAATATATGCCGATCTTATCACTATGTCATAATAATAGATATGTTGTTATTGAAAGATTCTCAATCTTTT
TTTTTCTTCAAGGTAGAGATTCTTAAGTGGATTCATGTTTTTTTTATCAAAAAAGAAAAAAACAAAAGTGTCCAT
TTGTTCATCTAATGGGTTTTCCATGTTACCAATTCACTACACTGTTGAGATTTGATTATCAGATGTGTCAAGTTT
CGTTTGGTTCCCTAGAAGGGAGAAAAGGCTGCTTATGCAGGCAGGGTATTAAAGATGATATTAATATCTGCAGTA
ATCAGTAACAGAATATATAAACTTAATAATAAACTTGAAGGTACTTAATTATCCAGCAGATAATCTTCTGTCTCA
CCGTACACTTTTGTTATATCATAAGCATAAGAATTGTTTTATCAAATATTACCAAACAAAACTTAGTTTTGTTTG
GTAATATTTTATAAAATATGTTACCGAAAGTTACTTCCTATAACATATTTTATAAAGAAAAAAATTAAAAACTCC
ATATACCTAAGAAATGTAACCCCCCCTCCATAACAACAATTTAACAAAAATAAAAACCTACTTTTTTTGAATTTG
GTAAATTAGTTTTCTATCCTTTTTAGTAACTTCCTTTCTTATTTTCTTTTTATATTGGTAAAGTTTAATATTACA
CATTATTTTAACATGTTATAATTTTTTGTGATGCTTAATTATTTGATACATGTAATAAACCATATATTAGAGCTA
TAAATCAATGACAATGCATGTAGATACAACTCATTTATGATATATTTTGTTTATATATATAACCAATTAGATAAT
TTGTCTGCGCTTTGTGCAGTCATAAATAATAATTGCATTGAACTTGCAAATATTTTTTTTTAATATCCATACATT
AAAAAAAAAGAAAGAGGAAAATTGGTTCCTAAAATATTAGCAATATTCAAACATTTATTTGATTATTAATCATTA
TCACATAACTTAAGAACGTCTAATGAATGAATTATTCACGAAATAATAAATCATTGGTTCTAAAAAGGAATTTCG
TAATAAAATAAAAATTTAAGTTACCATATTCAAAAAAAGAAATTGTGCTTGAACATGAAAATAATTATAATTTTT
GAACTTGTATAATGAATTTCTTCAATTCATAAGTGGGAAATTTCATATTTATGTAATAATAGATAATATGTAAGC
TCTAATATAGTACTTTAGGTTATAGAATTTAATATAAAATATCAAAACATGAATTCTTGAAATTGAGTAGAGTAA
TTATTTTCTGCACAATGAATCGGAGACAATAACTTTGAAGAAATATAAACAATAGAGTTCAAAAGATGTAGTCAA
AAACAACAATTAATATCATAAGAATAAATTAATGAGTGTAAAAATGCATACCACGATATGTAAAAACAGAATGGA
ATATAATAAAAAAAATCGAGTTCACTGAATACACAATGTTCCTTTAAGAAAATTATTCTCCTCCAATACCAACGA
GATTACATCCTCTAAGGATGGAAATGATTTCATTCCCCAACTTATCCATATAAAAATAGTGGTGTTAGTATGTAA
CTCAATAGGAGTAAAATACACAAATATTTAATTTTGCGAAAGTAGAAGAAGAAGATCATATTTTTTTTTTAAAAT
GAGAGGATATATCACTATTTTTAAACAACAAAGGGTAGTGTTAACAAATTTTTATTGTGTCTTGTCTAAAAGGTT
ACAGCTATTTGAAAAAGTTACAACACTTCGAAAAGTGAACAACATTTCATAAAAGTCGTAACTTTTCATAAAGTC
GTAACTCTTCATAAATGTCGCAACTCTTCATAAAAATTACAACTATTGATAAAAGTCACCACTCTTGATAAAGAT
CACCACTCTTCATTGAAGTTGCAACTTTTCATAAAAATCACATCTTTTAATAAAAAAGAAAGACTAGTTTTTGGA
ATAAATTAATTTAAAAGAAAATTTTTGTTTGTGGTGGGGCGCCAAGTAGGCAGGCGTAGGGTTCTTTTTATATAA
ATATATATGATATATGATTCAATATTTGATATATATATATATAGAGAGAGAGATGACAATATAAGACAATTGCAA
AAAATAAAATAAAAAACTAATCGAGTAAGTAGGCAAAAAATTATTTATAAAATATATGTAGAATTTCTTTATCAG
ATATGACTGCCCAAATCTTATATTCAAACTAAAATGCAAGATCAATGGTGCTATATATAGGGTTTTACACAAAAA
TCAAGATCTAGTCTTGCAAATTTAAATAAAAAACAGTGGTTTACGATGAGATAATGTAGCTTTTGTAAACAATAA
AACTAGAAAAATAAATGCAAAGGCATTTTAAAGGATATAATAATGAAGATCAAAGGCAGAGAAGGGAAGAGGCAG
CAATATAATGAAGGTAACATCATGGTTCCATTCTAATATATATGCTATTTTTCTTTAGTAAATTTCAAAAATAAT
GATACATTTTCATATTTGATAAATATTTAATGATACTATCAACATTTTATCTATATTGAGTTCCATTTATTTGAC
CAAAACCTCACAAAGATGTGCTCTTCGATCTATTCAAAATTTATTCAATTTAAGGATAGCTTTAAAACATGACAA
AGTTTTCTCATATATTTCTTAAATTTTATATCCAGTCTAAATACGTATATAAACTAAAATGAAGAGAATAATATG
AAGCTTTATTTGATGACATTGTTGAAATAACCAAAAGCTATAAGTGATACAATAGTAAATTTACCATTGGTCAAT
```

-continued

```
TCAGAATTATTTAAAAGCTAAAAAAGTCATATAAGTTGGGGTTGCTCAATGTATAGTTTTTGGCTTGTTTTAAGC
ATTTTAAAACTTTTTTTAAGCGCTTTTTAACATTGCTAAACACTCAAAAAATGATAAATAGTATTTAAATTTGAT
ATGATTAGCTTAAAAGTGAACTCATATACCTTCAAAGTAAAAATCCCCAATTCGAGCTTTCAAACCACTTGATTT
TGTGGATGAAATTATACTGAAGTTGAATATATCACTATTTATAGGGGTTAGTGAACTAATACCTTTGATTATTTG
GTAGAAATATGTATCTTAGATCACCCTAATGAGCTCCCACTTTTAAAATAGGAAAAACCTCATATGAAGTTCATC
ACTGTTCATTATATATCACTTTTATTCAAAAACGTTTACAAATGTTCATTGTGACTAAATACCCTTGAGTGTCGA
GTTTTCACACCAATAAGGCCTAATTAATAGGTAAACAAAACTATGTCAATCTTCAAAACGCAAATCTAATTATAT
TTTTAACAAGATTAGAGGTATATATACATATTCTCTTATGTTAACTCTTATTCATTATTGAACAAACTAAGTAAG
TGTACCCAAGGTCTCAAACAACAGTTGGTACATTCTTTGTATGTCTTCCTTTGTCTCTTAATAGTCGTCTCCTCC
TGTCGATGATTCCTCCAAATACATTAATCAAAGGAAAATCTTTCGCCCTCAACTTGCAAACTTGTCTATCTAAAA
TTGTTAACAAAGTTTCTTCATTAGAGAAACTATGATTTCTTGAATGTAGCAATTTGATGTGCCATGACTATCATC
TTGATCAACATGCTTCTTAACCATCAAAAGATCCTAAACTAGATGCATGTCATGTTAGGAGACATATTAAGCTTG
TATATAACTACACCAACATGCTTTAGGATCTCATAAGATCCAAAATTTCTTATTTGGGAGATTTTCAATCCAACA
ACCATCATAATGAGCAACGTGATGTTATAACATCTCTCTCACACTGCCAGAACAGTCTTATACCTTGTCGGAGTG
AAGGACATCCTTAACTAAGTAGATTCACTAAGCTATACTTAAAAAGCAATAAGGAATCATCTAAAATGTGTGACT
CTTAACCCATATTGGCATACATGGTTTATGGGGGTTATTAATTGTCTGAACACTCCCCCATATAAATCAGTGATC
AATATTAATCCCAATAATATACACTATTATGATTTGAGACTACACCCTGGAAGTGGCCGGCTCTCAAGAACCATT
GCTGATCTCCAAGCCAAACCCTCATTCTGGTTGACTACAAGCTGAAGGCAAACTCAAGTATACAAAGCTTAAAAC
ATAATAAAAATAATATACTCAACTCGCCACAAAATAGGCATTTAAGTCTTTAAAACATTTTTAAAAATAAATGAA
ACAAACTTCTCAAACTGTAATGTATATCTATGAAGCCTCTAAATGAAAAAAATGAAGGCAGATGAGACATACGGC
ATCCTAACAACTGATATAACTAAGAGTACAAGTGGAGCCCTTCGGATGTAAGGAGGCTCATCAAAGCTAATGTGA
ACTCCATGTGGTATCAATGAAGCACCTATTGATGACCGTGAATACATGTATCTGCATCATGAAACGATGCAGGCC
AAAGGGCTTAGTACGTGAAATGTACGAGCATGTAAAGGGAATTCAAATACATAAACATAGGCTTGAACTTTGATA
TAAAGGAAACATACTTACCTATTTTTAACTCAAGAATAAAAAACATAGTTCAACTCAATGAAAAGACACTCAAGT
CAGTGAAATAGGCCGCAACTCAATAATAAGATATTCGACTATGGGTAATCAACTCTGGGTACTCTATTCAATATA
AAGTAAGAATACAAATGCATTATATGGAAAGACTTTAAAACGGTAGAAAACAACTCAATGTATTGAAAATTCAAT
AGTAAATTAGTTTGTATGTAAGGAACAATATAAACTTTGTTTGTATATGAAAATACAAAATAAACTTTGTGTATA
TAAAAGTACAAAATATCTCTGTGAAAGTTTCTCTAACCAACAACCATCACTATGAGCTTTCTGATAATACCACGT
TTCGCCCATGATGTCAGAACTGTCCTATGATTTTCCAGTTCATAAGACCTACTCACTAAGTGGATCCACAAGTCT
ATGCTAAAAAATATTTAAGGAATCGTCTAAAAAGTATGACTCATTCTACCCACGTTGGCTACATGATTTATGGGG
GTCGTAAGTTATCTAAACTCTCCTCCATATCGATGCGTAATGCTACTCACAAATATACTAGCTCACATGTTTAAA
AATATAACTCGTTTTGTTTGAGATCATTACTCAAAATCCTTCTCTTAAAAGAGATGATACTCAAACTGCTCAAAA
CTCTTTTGGAAATCTCAAATTCGTCTCATCTTAAATGTAAAAATATTTACTCTTGGGAATACATAGTTATCATAT
ATCATTTTAAAGAAAATGAACTCAACTCTGTTCTTTCTCAACTCAAGTGCTCAGTCTTAAACCAAATTAAAAAAA
AGACTTCTCAAAATAAAGTTTATGTCGAATTATGGACGTGAACAATTCAATTCAAAGTTTTCGATAACCATAACT
AAAACTAAATACTCGAGACTCAACATCTTAGAACTCAAGAACTTAAATGGTAATACTTCTTTCAAGAATGCTCGA
CTCAGAAGGTTAATGCAGAATAATGTGCATGAATTACTCAACTAAAGGACTCACTGATACTACTCAATCTCAAGA
TTGCTCGACTCGTAGGGTTAATGCAGAATTATGTGCATGAACTACTCAACTCAAAGACCTTCATAGGTAACATGT
AGTAGCCCCATGATTTGGAATATAATCCCAAAATGATTAGGAACTCAATACTCAGGACTTAGAACTTGAAGATAA
TACTACTTCTCTCAAAGATACCCAACTGACGGAGTTCATGCAGAATTTATGGGCATGAACTACTCGACTCAAGAG
TCTAAAACACAATATGACACTCATGTATATAACTCTTCTCATTCTAATACTTGTTTTCTCAAAACTCGGTTTAAC
TAAATAGTTGATCTCAAAGGATTCACAATTGAACTCAAAGACTTTCTTTGACTCCACTCTTAATTCTCTCTTAAA
TTTGTATTTGAATTATGAATTTAAGAGTTATGATTCATGATATGGGGAATCTCAATAACAATATAGAAATTTGAT
AATTAGGAATAGTACTTTTAAAAGAAAACATGAATTCAACTTAAAATCAACTTATCTAAAAAATATTCAAATATA
GGGAAAGTATCCTAGACTACTGTGCTACTGATCTGAAAGTAGATGTAGGATGTGAGGATGAACTAGTCCAACACT
ATGATAGCCTTACATACCTGGAATAACGAGGTTCTTGGAAAATCTTCACTTGAAGAAGAACTTGATTAGAAGCCT
TGAAACCTAGCTTGAAGGTAAACAATCAAGAAAACCTTTCTTAAGATTCTTGAATTAGTTTATGAAAATCTCTAT
GACCAAGCATTTTGATTTTCACTAGTGATTCATAATTGTATGGAGGAATTTGAATTGAAAAAGATGAAATGCTTG
GAGAAAAGCTATCTTTGAAGAAGCTTGAAAAAGATTGGAAAGTCCTGTACTTTGATTTTCCCTTAGGATTTTGTC
TTAGGGTTTGAGATAGAAAAGAATGATGGACTAAAAGATGAAAATCTAATTGTTTGGATCCTTTTTCAGCCAAGA
AATCCGTTTAGGGTTTTCTTGGAGACAAACAAAATAAAAAAGACCATTTTTAATATTTTTCCGTCGGCTAATTCG
TAATAACATTGTATCATGTTATTGAAAGAGTCATAACTTTTTACTCAAAAATTGGATTGATGCGAAATTAGTGGT
GTTGGAAAGTAGATTCAAGTACCTCTAATTGGATAGGTTATTCCCTACATAAGTCTTTATATTCTAAAAGATATG
GTTGTTTGCACTTGACCTAAGTAGAATTTTACATGAAAACTTAATAGAGAAGGAAACTTCAAGAACTCATCAAGA
AATTTCAATTGCTCAATATTTATGGATAAATTTGTAGAAGAAACTCATGATTGACATGCGGGTGAATAAACCCAA
CACTATGGAAGCTTACATACCTCAAAGAACTAGGTTCTTGGCGAAATCTTGAATTTCTTCAACGAACGCTTGAAA
CTTTGAACTTTTTCTCTTCTTGAACTCTCAACTAAAACCCTAGGCGTATATTAGGATTATAAAAGTTAACATGAT
AGGATTAGACCTTTAAAAACTTTCTAAAATGAATTAAATCTGATTTAGCATGAAAAAGACCAAAATACCCCTTAC
TATTTTCGGATAACTTTTCTTAATTGGACTGCCTGACTTCAAAAAGGTATATCTCACTCATCCGACCTCAAAATT
TAGCAAATTCAGTGGCGTTAGAAAGCTAATTTAAACACCTTTCATTTTCCATCTCATGGCACACATAACTCATTC
TTTAAAGAGAGCTATGATCGTTCAAATTAACTCAAATCTTAGAAGAATTTAGGAATGTCTTGAACGAGCTACATC
TAGTGACCTTAACACTTTGGAAAATTTTAAATTTCTTAGTAAAAACTTACTCACTATGAAGGATGGTTCAAGTCT
TAGCTCAAAATTTTCCTAAGTTGCTATATATACTCATGCTCATATGTTTAAAACCAAAACCCTTCCTCGATTTGA
ATTAATTACCAAAAAGATTCTCTTAAAAAGATAATGCTCAAAACTCCCCCTAAACTCATTTGGAAATCTAGGTTT
CCCTTGTTTTAAATATAAAAACATTTACTCTTGGAAATATTTAGTTCTCAGATATTCACTTGAAAAAAATTAAAC
TCGACTCTCATCATCTTCATACTCAAGTGCTCAAGTCCTAAAACAATTTATAACTAATTGTATAAGACTTCTCAA
AATAGGGTTCATTCCGAATTATGGACGTGAACGACTCAATTCAAGGATTTCAATAACCATATATATAACTCAATA
ATAGGAACTCAACAACTCCAGAACTCAATGATACTACTCATCTCAAGAATGCTCGACTCACAGGGTCTTTGCGAA
ATTATTGGGCATGAACAACTCAACTCAAAGACCTTCATTTATACCATATGGTAGTCCCATAATAGGAATATAATC
CCAAAAAAATTAGGAACTCAATACTCAAAAACTTAGAACTCGAAGATATTACTCATCTCAAAGATATTCAATTTA
TGGAATTCATGCTGAATTATGAGCATGAACGACTTGACTCAAGGATCTCAATAATAATGTAGACTCATGAATACA
CTCTTCTCATTCTCATACTCACATACTCGAGTATTAAAATAAATTATAAGTAATTGCAGAAGACTCCTTGAACAG
ACTCAAAAGGACTCCTTCGAATTTTACTCTTAATGCTACCTGAATTTTGTATTATAAATTTAAGGATCATGATTA
TGATATAAAGAATTTCTCAGCATATATGAAATGAACGAATTTGAGCATTGAACGTCTAACCTCATTTTTTAATTA
TTGTGATATGTAGAGTGGTGCAAAATCACAGATACCTCTCTTGATGCATTTCTATAGTTACGTTGATGTGAGATT
ATATATAGTTCAGCAGCAGCATGTTGGGAAAATTACTAATAACTCTTCTTTTATATCAAATTGTTGAAGCATGAT
GACAACACTTGAAAAGTATCAACAATGCAGTTACGCATCTTTGGACCCGATGTTACCGGTTAGTGATACTCAGGT
ATTGTTTATCTACTTTATCATGTCGTAAGTATATTATTTGTAAAGATATATATCAAGATAGTTCGATTGCGTACA
CTTACATTTTGATTATGTTTGGTGAATACTATTCTAATACCTTTTTTTTTCCTAAAGCCTAACAAATAAAGATAA
```

-continued

TTAAGATGGGAACGTAATTCAAGTACAACATGGTTCCATACGTGACATATTTACACATATAGTGGAACCAAAAGA
GCAATTTTTCCTAATATCATTTTCTAAATATCACGTGTGCCCGTGATTCTTTTTTATGGACATGAATTTTTTTTT
TAATATGAGTGGAAGTAAGGTTCGATCTTTCTATCTGCTTTGATATCATATTGAATCGTGTGATTGTCTCTTTAA
AAAATTAAGCAAGAGCATATTTTATTAATTAATTGTCTTTCTCGACGTTTTTCTCTTTCAACAGATGAACTACAA
TGAGTATGTGAGGCTAAAAGCTAGAGTTGAGCTCCTTCAACGTTC*ATGCAAAAAAATGATTATAAAAAAAGTACTG*
*CATAAAAAAAATTAGTTAATTTTTTAGGGAATCACTATGTAGGCCATAGCTAGGGGTGTTGGTGGT*TCAAAGGTAA
GATATTAGTGATGTAATTAAATGATTTTAGTTAGATTTACATAAGTTTTTAATAAGTGAAAATTAATAGACATAT
TCTTGGAGAGATTTGGGCACACTAAACTCGAAAGAACTTGAGCAGCTTGAGCACCAATTGGATGCATCTTTGAAG
AAAGTTAGATCAAAAAAGGTATATCCAAATACTATAACTTAAATATATTGTAACGATTTAATTAATAGCATGTGT
CACGTTCATCTATTCTTTAGTCACAATATATAGGGGCATGTCCTTAACAACGTGCCATGCCTCGATAGTCATTTT
TGTCTTTTTGTGCGTATGAATTTAACTTTGACACAAATTTTTGTAGTAATAATAACTCATGCTTTAGCATCTTAG
GAAGCAGTCATATGAAAAACAGAAGCATATATATATATTACATGAGTTAATTTAATTTAATATAAAATTTAATAA
AATTGTGTCTCGCTATAAATAATTTTATTAAAAAATTATATAAATATATTATTTTTTTAACTGGCCGCAAAGTTA
TATAAATTGATAGAGAAAGAGGTTTTGGTGTAAGGTTCATTTTCCAACAATTAGTTTTATAATTTGTAAGTGCAC
ACTTTATCAGACTCAATCTATGCTGGATCAGCTGGCAGACCTTCAAGAAAAGGTACACTGCCTTAACATTACAAA
ATTAATTTATTTCATCAAAAGCATATCATAAAATTCTGACAAATAAATATATTAGGAGCAAATGCTGGAAGAAGC
AAATAAACAACTAAAAAACAAGGTACATATCTATATATGTGTGTTAATTAATTAAGTTGATTTTGTATTTTTGTT
TAATGAATAATTGTTTGTGATCATCAGCTGGAAGAAAGTGCAGCTAGAATTCCACTTGGATTGTCATGGGGAAAT
AATGGAGGACAAACAATGGAATACAATCGACTCCCTCCACAAACTACTGCACAACCTTTCTTTCAACCTCTCCGT
TTGAATTCTTCATCGCCTCAATTCGGGTAAGTATCTTATTTTATATGACTTAGTTTGACTTGACATAAAGTTTAA
TAAAGAAAGAAAGACTTTTAAAACTTATAGTGTAAAATAAGTGAATAGATATATATGTGGTTGTACTAACACTAC
AACAAAAATAATTTTCAGCGGCATTAAATATTGACATTAATAATGAGTGCTAAAGACTTTATCGGTATTAGTTAA
GTGTCATTAGGATCAATGTCGTTAAAGGCTTCACGGACATATACAAAGAGTGACAATTGCCGCTAATGATTATTT
TTGTTGTAGTGAAAATGAGTATTTTAAAGTTAAATTGTTACATAATATAGAAATATGTCAGAAACAGGACAAATA
TACCACCGAACTATCATATATGTTATGGAGATATTCTCAGTCATACTTCTGCGACATTGGTACTCATGTCGTCCA
AAAACTAGAACATATATATACCCTTTATATATTAACGAAGATACAAGTGTCATAATCTTATGCACCGATTCGATA
TTTATTAAATATCGAATCGACGGATAAAATTATGTCACGTGTCCCTATTAAGTCTTCTATTAGAGTAAAAAGCAT
ATATTCTCTAGTTTTTGAACGAAAAAAGGTATTAATGTCTCAAAAGTATAACGAAAAGCATTTGCATACAATTTA
TGATAATTTGGGGCATATTAATTTATCATTCCCCCTTTTTTTGGCACTGATTAAAAAGAAAAAGAAAGTTATAAA
AATTGGGATAGAGGGAATAATTGTTTCATAGGGAAAACTTAGAAGCTTCTCAGTATGTCAGTGAGAATGTGTTTC
CTAATTAGTGAACTATGGTTTGGTGAAAAATAAAGAGAAAAAAATCAGTACAAATTTTCCACTGATTAGCAATGA
GAAAAATATTTGTTTCTAGTAGTATGAGGAGAGGATAGTCCGCATAAATAATCCTTAAATTTGTGGATAAATAAA
CTATTTTCAATAGATTATCGTCTCAAAATAAAATAAAATGATTGCAAGAAAAGAATAATAGGTATGCTGGTAATA
TGTATAATACACTCAAATTTATTTGCTGTCCATGCAGATACAATCCAAATATGGGTGCAAATGATCATGAGGTTA
ATGCAGCAACAACTGCTCATAATATTAATGGATTTATTCCAGGGTGGATGCTCTAA (SEQ ID NO: 11)

Wild-type Solyc03g114840 gene
ATGGGAAGAGGAAGAGTTGAGCTTAAGAGAATAGAAAATAAAATAAATAGGCAAGTCACTTTTGCTAAGAGAAGA
AATGGACTTCTTAAAAAAGCTTATGAACTTTCTGTTCTTTGTGATGCTGAAGTTGCCCTTATAATCTTCTCTAAT
AGGGGTAAACTCTATGAATTTTGCAGCACTTCAAGGTATTTTTTATTTTATTATATTAACATCAAAGATTTTATT
TTTTTAAAAAAAACCTTAAGTCCTTCATTACCAAAACCCTTAATTGATTTACAAAGTACTTTCATTAAATTTAGT
AATTCTTTTTTTTTTTATCTCTGACTTCAATTATAATGCAAGATCTATGTTGTCTTTATATATATTGAATTATAT
ATGTACTGTATTTTTACTATATACATATAAGATCCTTTTTTCTTTTTTTTTCTGTCTCTTTATATAAATATATTTT
AAATAGTTGATTTTGAAAGATCTACTAATGTATATTTATTTTTGGAACTTTTGTGTATATGGAATTTTTTTCTTT
TTTATGTTTTTTTTTTTGTTCTAATTGTTTTAAAAGCGTTTAAGATCAGAATGTTCTTGATTATTCTTTTAGGAAA
AAGATTTCCCATACATTGAGTTATTTTTTGATCTGTAGATTGAATTTTTTTAATGAGTTCCGATAGATTTTCGTT
CAATTTTTCAATGAAACTATTGAGGGTTGATGATTAGATAATTACTCGATTGAAAGTTTTTATTTCAAAAAAATT
ATAATTCTTCTTAATTTTATATTTATGAGATAGAGTTAGTTTAGTGATTATATGAAAAATCGTATCAGATTATTG
GGAATCGAAACTTAAAAATTCTGAAAATATTATTATAAATTTTACATGTTACAATATTTTTACTGTTAAGATTTG
ATTTGCAGACTAGGTGTCATGTTTGACAGTTGATAAAAAATCTGTTATTTTTGTTCTTTAATTCCCAAGACGGAT
AAACAAAGGCTGCTTATGTTGGTTTCCAATAAGCAGCCATAATTTTAAATATTTTTGTTAAGATTAATTAATAAC
AATTATTTCCACCAGATAATTTTCAAAATTTGTGACCCCGAGTTCATATAAATTGTTAATTTTACTGCTAGAAAT
TACATCGATAATAATTTATTTAGTGTAATCTTATAAATACGAGGGCAGTAGTGTATAGACTGTTTTTTATTAATC
CTGACTCAAAGTGAGGTAAGTTAAGTATATTTTGATTAAAAGGACTACATTTCATTTATGTATGTTTAATTAATA
TTATTTTGTAAGTCAATAAATCTAAACAACATGAGTTTATCTAGACCCTTAATTATGCACCTTCATTATCAATTT
TTTCAATACTCTCCTCAGAACATATGCTTCTCTATAATTTTGTGCACGAGTTAATCAATTCTTCCTTTTCAATAA
TTAAATATGTGATTTATGTTTAGCACTTATTTTTCGGTTAGTTAATTGATAATAGGAAAAAGCCTCTTTTTTTTT
GTGTGTGTGGTAATTAGGATCTTTATTGAATTTAAAATGACCTACTATAGAACTTGGGAGTTTTTCTTCATAATA
ATGCACTGCAACGTGTTAAAAAAAAAGAATCAAATGAAATTAATAGATGTTTACTGGATTGCCATGGTAAAGTGA
TAAGTATTAATTTCGCTTTAACTAAGAGATCATTATATTCAAGTCCCCTTGATACAAACTTGCCTTTGTAAATAA
GTGTTTTATTTTTCAATGTGAAACTTTCGCTGTTAATTTAAATTTAATTATACTTCTATATAAATACCAAACAAT
AATGTAATAAAACAAAAAATAAAAGAGTAGATGTTTCATATTGTTAATGCAGCATGGTGAAAACAATTGAAAAGT
ACCAACGTTGCAGCTATGCTACTTTGGAAGCCAACCAATCAGTTACTGATACTCAGGTACTGCTTTATATTTTAA
TTTATTTGGCTTTTTTTTAAAAAAATAATTAGTTTTGATTAATATGCATCATTTTATTTATTTTTGGCAACTCTT
TATTTATCAGTAATAAGTAATAACTTTTTAACTAGTATATTTAAAAATCACAAAATTTAAGAATATTTTAATAGA
TTCGACATATTTTAGTTTAAAAATAACAAATTAAATTATGTTTTTAATTTTTTAAATATTCTTACTATAATTATC
ATGTACTCTTTGATCTGTTCATCTTTTCCATGATAATATTATTTGGTCAGTTAGTGACATAAGAGTTTGAAATTT
AGAAAAAAGGAATATTTGGAGAAAACTGAAATGGATATTTAGAAATGAAAGTTATTTAATATAAATATAAGTATG
GGCTGCTGAGTTGGGAATCCACGCTGGAGATCTCAAGTTTGAAGCGTCTCACAAACAATAGTAATGTCTTTTTGG
TCGAGTTTGTCGGATTGGACTTGTCCGTGGCCTGTGGGTTACTTTTCCTATATGGTTTGCAAGCTATCGGGAATT
TTATCCTGGCGCACCCAAATTTGAGTTATTTTTGAGTTTTTATATGAAATAGCTTTGTGAATTCATCGAACTCCC
GAAAACATTGAACTTTACTCCAAGTTGAATTGCAGTAAAATAATAGTAGCGATTCTTTAATTTATCCTAACAGTT
TTTCGAAATAATAATCCCAAAAAAGTTTAAAATAACCATACCATAAACTTACTGGGTAAGATATTATCTGTCTAA
TAATATATAGTAGTTTCTTTTGTTTTATTAGTTTATCTAATCCATATTTCATTTCTTGATAAGTTATTCTTAATA
GGAAAATAAACTTATTTCGAAAAACTGTTTTTAAAATTTTCTTGAGTTGAGTCTTGGATGAAAAATAGTTAATTT
TGCATTAATTAATTTTGTTCTAACAAAAACTAATTAAATTTTTTTGAAGCGCATATTCACTCAAAAAATAAATAA
AAACCATCATGCATACAGGAAATGTTCTTTTTTTAATTTATTTTTTCATTGGAGCCCTGACTAATTTTATATCGG
TTCATACTTTCATAAATTACAAAAAGTTCAAAATTTAAACTAACCATATAAGTGAATAAAATAAATCAACAAAAT
ATTCACCACATAATACTTTTTAAATAGAATTTTTCATACCAAAGACCTTACTTTAATTAATTAGGGTGAGAGAAT CCTATAAGTCAATGCAAAACAATTCTATCTATCGGATTATAATCGTTGATTCATAAAATTTTAAAATCGACGATT
TTCATTTAAATGACCCTTTTTTTTCTTTCATTTTTTATTGTTATTCATCTATTTAACTTGTGAGCATCTTTCATA
TTGATATTTCAGACCCTTAAATTAATTGTTTTCTTACAGAATAACTACCACGAATATCTGAGGCTAAAAGCTAGA
GTTGAGCTCCTCCAACGATCTCAGAGGTAATTTCTGTTCACTATCTTTATCTCAAATGAATTCTCATGTTTTTAT
TTTTCGAGATTCAGATTAAATATAATTTGATGTATTATTAATTTAAATACGTTATTTAATATGGTCCTTATGTCC
AACCATTGATTTAATTTGATATTTTTTTAATGAAAATTACACAGAAACTTTCTTGGTGAAGATTTGGGCACGTTA
AGCTCGAAGGACCTTGAGCAGCTTGAGAATCAATTAGAGTCTTCCTTAAAGCAAATCAGGTCAAGGAAGGTAAAT
TATTTAATCTAATTATACAGAAAAATCATCTAAAAGTTACCTTAATTGCTAGCCCAATAAGTTTGCTATCTGTTG
ATCCTCACATTATTTTACTCACAGAAATTCACAATACCTTTATTTTTGTTTGAGTTTGAAGTATACAATTTCTTT
AAAATGTAAAATTTGAAATCTCAACAATAAGATATGTTATTGATCCTTGCAATTATGGGTAGATTGCGAATTAAA
CTATCTTGTCTTTGCTTACAACAGTCATTTTGTTTATAAACTAATTATACATAAATCCTAACTGATAGATAGTTT
ATAAAGATGAATAATGAACATAGGTCATATATTAAAAAAACAAAAAACAAAAAAAAACTAAACAAGATGAGCGAG
TCAAAAATAGTCTTAACAAAAGAATATATATATATGTATATATCATATTTGATTTGTCTATTTTTAATTTTGAAA
AAACTAAGTTAATCGATATATAATATGAAGGCATAATGCATAAATATGTCCTTTAACTTGGTTTTAAATCACATT
TATACCTCTTCGACTTTGGGTGTATACAAACAAACACTTAAACTTATATAATGTTGAACAAATAGATATATATGT
CCTACATGTCATTTTTCGTCCTAAATGGTGTCCTAAGTGTATTGTGTCACGCAGGACTCATGTGTCTATTTGTTC
AAATTTATACAAGTTTAAGTGCTTACTTATGTATAAACAAAGTTGAATGACATAAATGTGAAATAAAATCAAATT
AAAGGGCATATTTATGCATTATACCTAATACGAAAATCCATATTATTCACTAAAAAATGAGTCGGATTATATGAT
TACTTTTTTATTCATTTTGCCAATCGTATCCTACGACATTGTTTTTAATTTGCAGACACAATTCATGCTGGATCA
GCTTGCAGATCTTCAACAAAAGGTAATTATAAAATTCTACAAATTTCCAATAATTAATAAATGGAATAATTATGC
GCGAGAAATTTATCTATTTAAAATTTACGATGAATTTTAATTTTACAGGAGCAAATGCTTGCAGAATCTAATAGA
TTACTCCGTAGAAAGGTAAACTAACTTGATAGCCGTGCGTAATGAATAACTTATTTTATTTTCAAAATTATAAAT
CTAAATACTTAGGTAACTCGATAACATAAGAAGTATTTATACTGATGATATTGGTGTTGTGTTTTTTTTTATTAG
TTAGAAGAAAGTGTAGCTGGATTTCCACTTCGATTGTGTTGGGAAGATGGAGGTGATCATCAACTTATGCATCAA
CAAAATCGTCTCCCTAACACAGAGGGTTTCTTTCAGCCTCTTGGATTGCATTCTTCTTCTCCACATTTTGGGTAA
TTACTTTTATTATTATTAAAAATAATTTCAATTTTTTTACTTTTATTTCGATTAATAAATCAATGTGCACCAAG
GTACGGTCTAACATAAACAAAAATGTGGGGAATGCTCTTAAAGCCCTAACAAAAGTTATTTGGTACGTGTACTAA
TGTAATCGTACTATATATCTTACTTGATTAGTGGATGGACAGTACTGGGCACACACAATTGACATAAGTTATTAT
AAGGAAAAAAAAAAGGCCAATAATCAATATAGTCCAACATTACATTATTTATTATATAACAGGTCACTCTAGATTAAA
TGTTAATGAATAACAAAAAGTCTCATATTGATGATTAATGTGATGGGTGGGCTTCTTATAAGGCTTTGACAATCC
TACTCTCTTTGAGCTAGTTTTGGGGGTGTGACCTAATTCAACAGAACGTAGTTAAGATTGTGAAGTAAAGTTGAT
CATTGTTATAACAGGTTTAAATACTTCTAGTAAAAATAGTTCCTAGATAATCCATCGCAAAATAGCTCCTATATA
GTTAGTTGGATTTTCATATAATCTATAGCTTATACATAGCTAAATGGGAATAGATGAGAGTTTCTGTTGTTTAGA
TATGATATTTGATCGGTTTCTAAATCGTTACTATCATGTAGTGAATAATTTTCATGTTATTACTATTACATTTGA
TTGTTTCTGTGGTTATTTTTTTTTCTAGGTACAATCCTGTTAATACAGATGAGGTGAATGCAGCGGCAACTGCAC
ACAATATGAATGGATTTATTCATGGATGGATGCTTTAA (SEQ ID NO: 12)

Wild-type Solyc03g114840 coding sequence
ATGGGAAGAGGAAGAGTTGAGCTTAAGAGAATAGAAAATAAAATAAATAGGCAAGTCACTTTTGCTAAGAGAAGA
AATGGACTTCTTAAAAAAGCTTATGAACTTTCTGTTCTTTGTGATGCTGAAGTTGCCCTTATAATCTTCTCTAAT
AGGGGTAAACTCTATGAATTTTGCAGCACTTCAAGCATGGTGAAAACAATTGAAAAGTACCAACGTTGCAGCTAT
GCTACTTTGGAAGCCAACCAATCAGTTACTGATACTCAGAATAACTACCACGAATATCTGAGGCTAAAAGCTAGA
GTTGAGCTCCTCCAACGATCTCAGAGAAACTTTCTTGGTGAAGATTTGGGCACGTTAAGCTCGAAGGACCTTGAG
CAGCTTGAGAATCAATTAGAGTCTTCCTTAAAGCAAATCAGGTCAAGGAAGACACAATTCATGCTGGATCAGCTT
GCAGATCTTCAACAAAAGGAGCAAATGCTTGCAGAATCTAATAGATTACTCCGTAGAAAGTTAGAAGAAAGTGTA
GCTGGATTTCCACTTCGATTGTGTTGGGAAGATGGAGGTGATCATCAACTTATGCATCAACAAAATCGTCTCCCT
AACACAGAGGGTTTCTTTCAGCCTCTTGGATTGCATTCTTCTTCTCCACATTTTGGGTACAATCCTGTTAATACA
GATGAGGTGAATGCAGCGGCAACTGCACACAATATGAATGGATTTATTCATGGATGGATGCTTTAA (SEQ ID NO: 13)

Mutant Solyc03g114840 gene allele ej2[W]
ATGGGAAGAGGAAGAGTTGAGCTTAAGAGAATAGAAAATAAAATAAATAGGCAAGTCACTTTTGCTAAGAGAAGA
AATGGACTTCTTAAAAAAGCTTATGAACTTTCTGTTCTTTGTGATGCTGAAGTTGCCCTTATAATCTTCTCTAAT
AGGGGTAAACTCTATGAATTTTGCAGCACTTCAAGGTATTTTTTATTTTATTATATTAACATCAAAGATTTTATT
TTTTTAAAAAAAAACCTTAAGTCCTTCATTACCAAAACCCTTAATTGATTTACAAAGTACTTTCATTAAATTTAGT
AATTCTTTTTTTTTTTATCTCTGACTTCAATTATAATGCAAGATCTATGTTGTCTTTATATATATTGAATTATAT
ATGTACTGTATTTTTACTATATACATATAAGATCCTTTTTTCTTTTTTTTCTGTCTCTTTATATAAATATATTTT
AAATAGTTGATTTTGAAAGATCTACTAATGTATATTTATTTTTGGAACTTTTGTGTATATGGAATTTTTTTCTTT
TTTATGTTTTTTTTTTGTTCTAATTGTTTTAAAAGCGTTTAAGATCAGAATGTTCTTGATTATTCTTTTAGGAAA
AAGATTTCCCATACATTGAGTTATTTTTTGATCTGTAGATTGAATTTTTTTAATGAGTTCCGATAGATTTTCGTT
CAATTTTTCAATGAAACTATTGAGGGTTGATGATTAGATAATTACTCGATTGAAAGTTTTTATTTCAAAAAAATT
ATAATTCTTCTTAATTTTATATTTATGAGATAGAGTTAGTTTAGTGATTATATGAAAAATCGTATCAGATTATTG
GGAATCGAAACTTAAAAATTCTGAAAATATTATTATAAATTTTACATGTTACAATATTTTTACTGTTAAGATTTG
ATTTGCAGACTAGGTGTCATGTTTGACAGTTGATAAAAAAATCTGTTATTTTTGTTCTTTAATTCCCAAGACGGAT
AAACAAAGGCTGCTTATGTTGGTTTCCAATAAGCAGCCATAATTTTAAATATTTTTGTTAAGATTAATTAATAAC
AATTATTTCCACCAGATAATTTTCAAAATTTGTGACCCCGAGTTCATATAAATTGTTAATTTTACTGCTAGAAAT
TACATCGATAATAATTTATTTAGTGTAATCTTATAAATACGAGGGCAGTAGTGTATAGACTGTTTTTTATTAATC
CTGACTCAAAGTGAGGTAAGTTAAGTATATTTTGATTAAAAGGACTACATTTCATTTATGTATGTTTAATTAATA
TTATTTTGTAAGTCAATAAATCTAAACAACATGAGTTTATCTAGACCCTTAATTATGCACCTTCATTATCAATTT
TTTCAATACTCTCCTCAGAACATATGCTTCTCTATAATTTTGTGCACGAGTTAATCAATTCTTCCTTTTCAATAA
TTAAATATGTGATTTATGTTTAGCACTTATTTTTCGGTTAGTTAATTGATAATAGGAAAAAGCCTCTTTTTTTTT
GTGTGTGTGGTAATTAGGATCTTTATTGAATTTAAAATGACCTACTATAGAACTTGGGAGTTTTTCTTCATAATA
ATGCACTGCAACGTGTTAAAAAAAAAGAATCAAATGAAATTAATAGATGTTTACTGGATTGCCATGGTAAAGTGA
TAAGTATTAATTTCGCTTTAACTAAGAGATCATTATATTCAAGTCCCCTTGATACAAACTTGCCTTTGTAAATAA
GTGTTTTATTTTTCAATGTGAAACTTTCGCTGTTAATTTAAATTTAATTATACTTCTATATAAATACCAAACAAT
AATGTAATAAAACAAAAAATAAAAGAGTAGATGTTTCATATTGTTAATGCAGCATGGTGAAAACAATTGAAAAGT
ACCAACGTTGCAGCTATGCTACTTTGGAAGCCAACCAATCAGTTACTGATACTCAGGTACTGCTTTATATTTTAA
TTTATTTGGCTTTTTTTTAAAAAAATAATTAGTTTGATTAATATGCATCATTTTATTTATTTTTGGCAACTCTT
TATTTATCAGTAATAAGTAATAACTTTTTAACTAGTATATTTAAAAATCACAAAATTTAAGAATATTTTAATAGA -continued TTCGACATATTTTAGTTTAAAAATAACAAATTAAATTATGTTTTTAATTTTTTAAATATTCTTACTATAATTATC
ATGTACTCTTTGATCTGTTCATCTTTTCCATGATAATATTATTTGGTCAGTTAGTGACATAAGAGTTTGAAATTT
AGAAAAAAGGAATATTTGGAGAAAACTGAAATGGATATTTAGAAATGAAAGTTATTTAATATAAATATAAGTATG
GGCTGCTGAGTTGGGAATCCACGCTGGAGATCTCAAGTTTGAAGCGTCTCACAAACAATAGTAATGTCTTTTTGG
TCGAGTTTGTCGGATTGGACTTGTCCGTGGCCTGTGGGTTACTTTTCCTATATGGTTTGCAAGCTATCGGGAATT
TTATCCTGGCGCACCCAAATTTGAGTTATTTTTGAGTTTTTATATGAAATAGCTTTGTGAATTCATCGAACTCCC
GAAAACATTGAACTTTACTCCAAGTTGAATTGCAGTAAAATAATAGTAGCGATTCTTTAATTTATCCTAACAGTT
TTTCGAAATAATAATCCCAAAAAAGTTTAAAATAACCATACCATAAACTTACTGGGTAAGATATTATCTGTCTAA
TAATATATAGTAGTTTCTTTTGTTTTATTAGTTTATCTAATCCATATTTCATTTCTTGATAAGTTATTCTTAATA
GGAAAATAAACTTATTTCGAAAAACTGTTTTTAAAATTTTCTTGAGTTGAGTCTTGGATGAAAAATAGTTAATTT
TGCATTAATTAATTTTGTTCTAACAAAAACTAATTAAATTTTTTTGAAGCGCATATTCACTCAAAAAATAAATAA
AAACCATCATGCATACAGGAAATGTTCTTTTTTTAATTTATTTTTTCATTGGAGCCCTGACTAATTTTATATCGG
TTCATACTTTCATAAATTACAAAAAGTTCAAAATTTAAACTAACCATATAAGTGAATAAAATAAATCAACAAAAT
ATTCACCACATAATACTTTTTAAATAGAATTTTTCATACCAAAGACCTTACTTTAATTAATTAGGGTGAGAGAAT
CCTATAAGTCAATGCAAAACAATTCTATCTATCGGATTATAATCGTTGATTCATAAAATTTTAAAATCGACGATT
TTCATTTAAATGACCCTTTTTTTTCTTTCATTTTTTATTGTTATTCATCTATTTAACTTGTGAGCATCTTTCATA
TTGATATTTCAGACCCTTAAATTAATTGTTTTCTTACAGAATAACTACCACGAATATCTGAGGCTAAAAGCTAGA
GTTGAGCTCCTCCAACGATCTCAGAGGTAATTTCTGTTCACTATCTTTATCTCAAATGAATTCTCATGTTTTTAT
TTTTCGAGATTCAGATTAAATATAATTTGATGTATTATTAATTTAAATACGTTATTTAATATGGTCCTTATGTCC
AACCATTGATTTAATTTGATATTTTTTTAATGAAAATTACACAGAAACTTTCTTGGTGAAGATTTGGGCACGTTA
AGCTCGAAGGACCTTGAGCAGCTTGAGAATCAATTAGAGTCTTCCTTAAAGCAAATCAGGTCAAGGAAGGTAAAT
TATTTAATCTAATTATACAGAAAAATCATCTAAAAGTTACCTTAATTGCTAGCCCAATAAGTTTGCTATCTGTTG
ATCCTCACATTATTTTACTCACAGAAATTCACAATACCTTTATTTTTGTTTGAGTTTGAAGTATACAATTTCTTT
AAAATGTAAAATTTGAAATCTCAACAATAAGATATGTTATTGATCCTTGCAATTATGGGTAGATTGCGAATTAAA
CTATCTTGTCTTTGCTTACAACAGTCATTTTGTTTATAAACTAATTATACATAAATCCTAACTGATAGATAGTTT
ATAAAGATGAATAATGAACATAGGTCATATATTAAAAAAACAAAAAACAAAAAAAAACTAAACAAGATGAGCGAG
TCAAAAATAGTCTTAACAAAAGAATATATATATATGTATATATCATATTTGATTTGTCTATTTTTAATTTTGAAA
AAACTAAGTTAATCGATATATAATATGAAGGCATAATGCATAAATATGTCCTTTAACTTGGTTTTAAATCACATT
TATACCTCTTCGACTTTGGGTGTATACAAACAAACACTTAAACTTATATAATGTTGAACAAATAGATATATATGT
CCTACATGTCATTTTTCGTCCTAAATGGTGTCCTAAGTGTATTGTGTCACGCAGGACTCATGTGTCTATTTGTTC
AAATTTATACAAGTTTAAGTGCTTACTTATGTATAAACAAAGTTGAATGACATAAATGTGAAATAAAATCAAATT
AAAGGGCATATTTATGCATTATACCTAATACGAAAATCCATATTATTCACTAAAAAATGAGTCGGATTATATGAT
TACTTTTTTATTCATTTTGCCAATCGTATCCTACGACATTGTTTTTAATTTGCAGACACAATTCATGCTGGATCA
GCTTGCAGATCTTCAACAAAAGGTAATTATAAAATTCTACAAATTTCCAATAATTAATAAATGGAATAATTATGC
GCGAGAAAT*GGATGGGCTTGTCTATAATGGTAGACAAATGAAAGACTTTCTCAAGATTTTGCGGGCGGTCCGGGG*
*GGGACCACCACGGCTCCTCTCTTCTCGAGAATCCGCCGGAGTCAGATCAGTAGGGGAGTTCACACCGGGACTTGT*
*GCAGGCCCCCGTCAATTCCTTTGAGTTTCGGTCTTGCGACCGTACTCCCCAGGCGGAGTGTTTCACGGCCAACTC*
*GAAGGGGCTGAAGTTCGACGCAGAGCAAAGCATTCTTTT*CTACCCTATGTAGGCGGAATCCTCTTTTCGACTCTG
ACTCTCCCACTCCAGTCGTGAAAAAACAACAAACTAGTCAAAGGACAGCCTGCCTTATTCTTCTCCCGTTCGGGA
CCCCTATTTTCTCGGAGATAGCCTGGTCTGAGCTAGAACAGCAGATTCGTGAGCAAGAGCGTATTTCACAGCTGA
TTCAACAACAGCCATTTTTTCTGGGACCCGCAATTCCGTAGAAAGACATCACGATTCCTTGTGGACGGGGAATCG
GCAGAAAGAGATGGGTCGGATACTGGAATCTGCCCAAAAGTCCTGACTTCTATTTAAAATTTACGATGAATTTTA
ATTTTACAGGAGCAAATGCTTGCAGAATCTAATAGATTACTCCGTAGAAAGGTAAACTAACTTGATAGCCGTGCG
TAATGAATAACTTATTTTATTTTCAAAATTATAAATCTAAATACTTAGGTAACTCGATAACATAAGAAGTATTTA
TACTGATGATATTGGTGTTGTGTTTTTTTTTATTAGTTAGAAGAAAGTGTAGCTGGATTTCCACTTCGATTGTGT
TGGGAAGATGGAGGTGATCATCAACTTATGCATCAACAAAATCGTCTCCCTAACACAGAGGGTTTCTTTCAGCCT
CTTGGATTGCATTCTTCTTCTCCACATTTTGGGTAATTACTTTTATTATTATTAAAAATAATTTCAATTTTTTTT
ACTTTTATTTCGATTAATAAATCAATGTGCACCAAGGTACGGTCTAACATAAACAAAAATGTGGGGAATGCTCTT
AAAGCCCTAACAAAAGTTATTTGGTACGTGTACTAATGTAATCGTACTATATATCTTACTTGATTAGTGGATGGA
CAGTACTGGGCACACACAATTGACATAAGTTATTATAAGGAAAAAAAAAAGGCCAATAATCAATATAGTCCAACAT
TACATTATTTATTATAACAGGTCACTCTAGATTAAATGTTAATGAATAACAAAAAGTCTCATATTGATGATTAAT
GTGATGGGTGGGCTTCTTATAAGGCTTTGACAATCCTACTCTCTTTGAGCTAGTTTTGGGGGTGTGACCTAATTC
AACAGAACGTAGTTAAGATTGTGAAGTAAAGTTGATCATTGTTATAACAGGTTTAAATACTTCTAGTAAAAATAG
TTCCTAGATAATCCATCGCAAAATAGCTCCTATATAGTTAGTTGGATTTTCATATAATCTATAGCTTATACATAG
CTAAATGGGAATAGATGAGAGTTTCTGTTGTTTAGATATGATATTTGATCGGTTTCTAAATCGTTACTATCATGT
AGTGAATAATTTTCATGTTATTACTATTACATTTGATTGTTTCTGTGGTTATTTTTTTTTCTAGGTACAATCCTG
TTAATACAGATGAGGTGAATGCAGCGGCAACTGCACACAATATGAATGGATTTATTCATGGATGGATGCTTTAA
(SEQ ID NO: 14)

Mutant Solyc03g114840 gene allele ej2$^{CR}$
>allele-1
ATGGGAAGAGGAAGAGTTGAGCTTAAGAGAATAGAAAATAAAATAAATAGGCAAGTCACTTTTGCTAAGAGAAGA
AATGGACTTCTTAAAAAAGCTTATGAACTTTCTGTTCTTTGTGATGCTGAAGTTGCCCTTATAATCTTCTCTAAT
AGGGGTAAACTCTATGAATTTTGCAGCACTTCAAGGTATTTTTTATTTTATTATATTAACATCAAAGATTTTATT
TTTTTAAAAAAAACCTTAAGTCCTTCATTACCAAAACCCTTAATTGATTTACAAAGTACTTTCATTAAATTTAGT
AATTCTTTTTTTTTTTATCTCTGACTTCAATTATAATGCAAGATCTATGTTGTCTTTATATATATTGAATTATAT
ATGTACTGTATTTTTACTATATACATATAAGATCCTTTTTTCTTTTTTTTCTGTCTCTTTATATAAATATATTTT
AAATAGTTGATTTTGAAAGATCTACTAATGTATATTTATTTTTGGAACTTTTGTGTATATGGAATTTTTTTCTTT
TTTATGTTTTTTTTTTGTTCTAATTGTTTTAAAAGCGTTTAAGATCAGAATGTTCTTGATTATTCTTTTAGGAAA
AAGATTTCCCATACATTGAGTTATTTTTTGATCTGTAGATTGAATTTTTTTAATGAGTTCCGATAGATTTTCGTT
CAATTTTTCAATGAAACTATTGAGGGTTGATGATTAGATAATTACTCGATTGAAAGTTTTTATTTCAAAAAAATT
ATAATTCTTCTTAATTTTATATTTATGAGATAGAGTTAGTTTAGTGATTATATGAAAAATCGTATCAGATTATTG
GGAATCGAAACTTAAAAATTCTGAAAATATTATTATAAATTTTACATGTTACAATATTTTTACTGTTAAGATTTG
ATTTGCAGACTAGGTGTCATGTTTGACAGTTGATAAAAAATCTGTTATTTTTGTTCTTTAATTCCCAAGACGGAT
AAACAAAGGCTGCTTATGTTGGTTTCCAATAAGCAGCCATAATTTTAAATATTTTTGTTAAGATTAATTAATAAC
AATTATTTCCACCAGATAATTTTCAAAATTTGTGACCCCGAGTTCATATAAATTGTTAATTTTACTGCTAGAAAT
TACATCGATAATAATTTATTTAGTGTAATCTTATAAATACGAGGGCAGTAGTGTATAGACTGTTTTTTATTAATC
CTGACTCAAAGTGAGGTAAGTTAAGTATATTTTGATTAAAAGGACTACATTTCATTTATGTATGTTTAATTAATA
TTATTTTGTAAGTCAATAAATCTAAACAACATGAGTTTATCTAGACCCTTAATTATGCACCTTCATTATCAATTT -continued TTTCAATACTCTCCTCAGAACATATGCTTCTCTATAATTTTGTGCACGAGTTAATCAATTCTTCCTTTTCAATAA
TTAAATATGTGATTTATGTTTAGCACTTATTTTTCGGTTAGTTAATTGATAATAGGAAAAAGCCTCTTTTTTTTT
GTGTGTGTGGTAATTAGGATCTTTATTGAATTTAAAATGACCTACTATAGAACTTGGGAGTTTTTCTTCATAATA
ATGCACTGCAACGTGTTAAAAAAAAAAGAATCAAATGAAATTAATAGATGTTTACTGGATTGCCATGGTAAAGTGA
TAAGTATTAATTTCGCTTTAACTAAGAGATCATTATATTCAAGTCCCCTTGATACAAACTTGCCTTTGTAAATAA
GTGTTTTATTTTTCAATGTGAAACTTTCGCTGTTAATTTAAATTTAATTATACTTCTATATAAATACCAAACAAT
AATGTAATAAAACAAAAAATAAAAGAGTAGATGTTTCATATTGTTAATGCAGCATGGTGAAAACAATTGAAAAGT
ACCAACGTTGCAGCTATGCTACTTTGGAAGCCAACCAATCAGTTACTGATACTCAGGTACTGCTTTATATTTTAA
TTTATTTGGCTTTTTTTTAAAAAAATAATTAGTTTTGATTAATATGCATCATTTTATTTATTTTTGGCAACTCTT
TATTTATCAGTAATAAGTAATAACTTTTTAACTAGTATATTTAAAAATCACAAAATTTAAGAATATTTTAATAGA
TTCGACATATTTTAGTTTAAAAATAACAAATTAAATTATGTTTTTAATTTTTTAAATATTCTTACTATAATTATC
ATGTACTCTTTGATCTGTTCATCTTTTCCATGATAATATTATTTGGTCAGTTAGTGACATAAGAGTTTGAAATTT
AGAAAAAAGGAATATTTGGAGAAAACTGAAATGGATATTTAGAAATGAAAGTTATTTAATATAAATATAAGTATG
GGCTGCTGAGTTGGGAATCCACGCTGGAGATCTCAAGTTTGAAGCGTCTCACAAACAATAGTAATGTCTTTTTGG
TCGAGTTTGTCGGATTGGACTTGTCCGTGGCCTGTGGGTTACTTTTCCTATATGGTTTGCAAGCTATCGGGAATT
TTATCCTGGCGCACCCAAATTTGAGTTATTTTTGAGTTTTTATATGAAATAGCTTTGTGAATTCATCGAACTCCC
GAAAACATTGAACTTTACTCCAAGTTGAATTGCAGTAAAATAATAGTAGCGATTCTTTAATTTATCCTAACAGTT
TTTCGAAATAATAATCCCAAAAAAGTTTAAAATAACCATACCATAAACTTACTGGGTAAGATATTATCTGTCTAA
TAATATATAGTAGTTTCTTTTGTTTTATTAGTTTATCTAATCCATATTTCATTTCTTGATAAGTTATTCTTAATA
GGAAAATAAACTTATTTCGAAAAACTGTTTTTAAAATTTTCTTGAGTTGAGTCTTGGATGAAAAATAGTTAATTT
TGCATTAATTAATTTTGTTCTAACAAAAACTAATTAAATTTTTTTGAAGCGCATATTCACTCAAAAAATAAATAA
AAACCATCATGCATACAGGAAATGTTCTTTTTTTAATTTATTTTTTCATTGGAGCCCTGACTAATTTTATATCGG
TTCATACTTTCATAAATTACAAAAAGTTCAAAATTTAAACTAACCATATAAGTGAATAAAATAAATCAACAAAAT
ATTCACCACATAATACTTTTTAAATAGAATTTTTCATACCAAAGACCTTACTTTAATTAATTAGGGTGAGAGAAT
CCTATAAGTCAATGCAAAACAATTCTATCTATCGGATTATAATCGTTGATTCATAAAATTTTAAAATCGACGATT
TTCATTTAAATGACCCTTTTTTTTCTTTCATTTTTTATTGTTATTCATCTATTTAACTTGTGAGCATCTTTCATA
TTGATATTTCAGACCCTTAAATTAATTGTTTTCTTACAGAATAACTACCACGAATATCTGAGGCTAAAAGCTAGA
GTTGAGCTCCTCCAACGATCTCAGAGGTAATTTCTGTTCACTATCTTTATCTCAAATGAATTCTCATGTTTTTAT
TTTTCGAGATTCAGATTAAATATAATTTGATGTATTATTAATTTAAATACGTTATTTAATATGGTCCTTATGTCC
AACCATTGATTTAATTTGATATTTTTTTAATGAAAATTACACAGAAACTTTCTTGGTGAAGATTTGGGCACCTTG
AGCAGCTTGAGAATCAATTAGAGTCTTCCTTAAAGTCAAGGAAGGTAAATTATTTAATCTAATTATACAGAAAAA
TCATCTAAAAGTTACCTTAATTGCTAGCCCAATAAGTTTGCTATCTGTTGATCCTCACATTATTTTACTCACAGA
AATTCACAATACCTTTATTTTTGTTTGAGTTTGAAGTATACAATTTCTTTAAAATGTAAAATTTGAAATCTCAAC
AATAAGATATGTTATTGATCCTTGCAATTATGGGTAGATTGCGAATTAAACTATCTTGTCTTTGCTTACAACAGT
CATTTTGTTTATAAACTAATTATACATAAATCCTAACTGATAGATAGTTTATAAAGATGAATAATGAACATAGGT
CATATATTAAAAAAACAAAAAACAAAAAAAAACTAAACAAGATGAGCGAGTCAAAAATAGTCTTAACAAAAGAAT
ATATATATATGTATATATCATATTTGATTTGTCTATTTTTAATTTTGAAAAAACTAAGTTAATCGATATATAATA
TGAAGGCATAATGCATAAATATGTCCTTTAACTTGGTTTTAAATCACATTTATACCTCTTCGACTTTGGGTGTAT
ACAAACAAACACTTAAACTTATATAATGTTGAACAAATAGATATATATGTCCTACATGTCATTTTTCGTCCTAAA
TGGTGTCCTAAGTGTATTGTGTCACGCAGGACTCATGTGTCTATTTGTTCAAATTTATACAAGTTTAAGTGCTTA
CTTATGTATAAACAAAGTTGAATGACATAAATGTGAAATAAAATCAAATTAAAGGGCATATTTATGCATTATACC
TAATACGAAAATCCATATTATTCACTAAAAAATGAGTCGGATTATATGATTACTTTTTTATTCATTTTGCCAATC
GTATCCTACGACATTGTTTTTAATTTGCAGACACAATTCATGCTGGATCAGCTTGCAGATCTTCAACAAAAGGTA
ATTATAAAATTCTACAAATTTCCAATAATTAATAAATGGAATAATTATGCGCGAGAAATTTATCTATTTAAAATT
TACGATGAATTTTAATTTTACAGGAGCAAATGCTTGCAGAATCTAATAGATTACTCCGTAGAAAGGTAAACTAAC
TTGATAGCCGTGCGTAATGAATAACTTATTTTATTTTCAAAATTATAAATCTAAATACTTAGGTAACTCGATAAC
ATAAGAAGTATTTATACTGATGATATTGGTGTTGTGTTTTTTTTTATTAGTTAGAAGAAAGTGTAGCTGGATTTC
CACTTCGATTGTGTTGGGAAGATGGAGGTGATCATCAACTTATGCATCAACAAAATCGTCTCCCTAACACAGAGG
GTTTCTTTCAGCCTCTTGGATTGCATTCTTCTTCTCCACATTTTGGGTAATTACTTTTATTATTATTAAAAATAA
TTTCAATTTTTTTTACTTTTATTTCGATTAATAAATCAATGTGCACCAAGGTACGGTCTAACATAAACAAAAATG
TGGGGAATGCTCTTAAAGCCCTAACAAAAGTTATTTGGTACGTGTACTAATGTAATCGTACTATATATCTTACTT
GATTAGTGGATGGACAGTACTGGGCACACACAATTGACATAAGTTATTATAAGGAAAAAAAAAGGCCAATAATCA
ATATAGTCCAACATTACATTATTTATTATAACAGGTCACTCTAGATTAAATGTTAATGAATAACAAAAAGTCTCA
TATTGATGATTAATGTGATGGGTGGGCTTCTTATAAGGCTTTGACAATCCTACTCTCTTTGAGCTAGTTTTGGGG
GTGTGACCTAATTCAACAGAACGTAGTTAAGATTGTGAAGTAAAGTTGATCATTGTTATAACAGGTTTAAATACT
TCTAGTAAAAATAGTTCCTAGATAATCCATCGCAAAATAGCTCCTATATAGTTAGTTGGATTTTCATATAATCTA
TAGCTTATACATAGCTAAATGGGAATAGATGAGAGTTTCTGTTGTTTAGATATGATATTTGATCGGTTTCTAAAT
CGTTACTATCATGTAGTGAATAATTTTCATGTTATTACTATTACATTTGATTGTTTCTGTGGTTATTTTTTTTTC
TAGGTACAATCCTGTTAATACAGATGAGGTGAATGCAGCGGCAACTGCACACAATATGAATGGATTTATTCATGG
ATGGATGCTTTAA (SEQ ID NO: 15)

>allele-3
ATGGGAAGAGGAAGAGTTGAGCTTAAGAGAATAGAAAATAAAATAAATAGGCAAGTCACTTTTGCTAAGAGAAGA
AATGGACTTCTTAAAAAAGCTTATGAACTTTCTGTTCTTTGTGATGCTGAAGTTGCCCTTATAATCTTCTCTAAT
AGGGGTAAACTCTATGAATTTTGCAGCACTTCAAGGTATTTTTTATTTTATTATATTAACATCAAAGATTTTATT
TTTTTAAAAAAAACCTTAAGTCCTTCATTACCAAAACCCTTAATTGATTTACAAAGTACTTTCATTAAATTTAGT
AATTCTTTTTTTTTTTATCTCTGACTTCAATTATAATGCAAGATCTATGTTGTCTTTATATATATTGAATTATAT
ATGTACTGTATTTTTACTATATACATATAAGATCCTTTTTTCTTTTTTTTCTGTCTCTTTATATAAATATATTTT
AAATAGTTGATTTTGAAAGATCTACTAATGTATATTTATTTTTGGAACTTTTGTGTATATGGAATTTTTTTCTTT
TTTATGTTTTTTTTTTGTTCTAATTGTTTTAAAAGCGTTTAAGATCAGAATGTTCTTGATTATTCTTTTAGGAAA
AAGATTTCCCATACATTGAGTTATTTTTTGATCTGTAGATTGAATTTTTTTAATGAGTTCCGATAGATTTTCGTT
CAATTTTTCAATGAAACTATTGAGGGTTGATGATTAGATAATTACTCGATTGAAAGTTTTTATTTCAAAAAAATT
ATAATTCTTCTTAATTTTATATTTATGAGATAGAGTTAGTTTAGTGATTATATGAAAAATCGTATCAGATTATTG
GGAATCGAAACTTAAAAATTCTGAAAATATTATTATAAATTTTACATGTTACAATATTTTTACTGTTAAGATTTG
ATTTGCAGACTAGGTGTCATGTTTGACAGTTGATAAAAAATCTGTTATTTTTGTTCTTTAATTCCCAAGACGGAT
AAACAAAGGCTGCTTATGTTGGTTTCCAATAAGCAGCCATAATTTTAAATATTTTTGTTAAGATTAATTAATAAC
AATTATTTCCACCAGATAATTTTCAAAATTTGTGACCCCGAGTTCATATAAATTGTTAATTTTACTGCTAGAAAT
TACATCGATAATAATTTATTTAGTGTAATCTTATAAATACGAGGGCAGTAGTGTATAGACTGTTTTTTATTAATC
CTGACTCAAAGTGAGGTAAGTTAAGTATATTTTGATTAAAAGGACTACATTTCATTTATGTATGTTTAATTAATA -continued

```
TTATTTTGTAAGTCAATAAATCTAAACAACATGAGTTTATCTAGACCCTTAATTATGCACCTTCATTATCAATTT
TTTCAATACTCTCCTCAGAACATATGCTTCTCTATAATTTTGTGCACGAGTTAATCAATTCTTCCTTTTCAATAA
TTAAATATGTGATTTATGTTTAGCACTTATTTTTCGGTTAGTTAATTGATAATAGGAAAAAGCCTCTTTTTTTTT
GTGTGTGTGGTAATTAGGATCTTTATTGAATTTAAAATGACCTACTATAGAACTTGGGAGTTTTTCTTCATAATA
ATGCACTGCAACGTGTTAAAAAAAAAGAATCAAATGAAATTAATAGATGTTTACTGGATTGCCATGGTAAAGTGA
TAAGTATTAATTTCGCTTTAACTAAGAGATCATTATATTCAAGTCCCCTTGATACAAACTTGCCTTTGTAAATAA
GTGTTTTATTTTTCAATGTGAAACTTTCGCTGTTAATTTAAATTTAATTATACTTCTATATAAATACCAAACAAT
AATGTAATAAAACAAAAAATAAAAGAGTAGATGTTTCATATTGTTAATGCAGCATGGTGAAAACAATTGAAAAGT
ACCAACGTTGCAGCTATGCTACTTTGGAAGCCAACCAATCAGTTACTGATACTCAGGTACTGCTTTATATTTTAA
TTTATTTGGCTTTTTTTTAAAAAAATAATTAGTTTTGATTAATATGCATCATTTTATTTATTTTTGGCAACTCTT
TATTTATCAGTAATAAGTAATAACTTTTTAACTAGTATATTTAAAAATCACAAAATTTAAGAATATTTTAATAGA
TTCGACATATTTTAGTTTAAAAATAACAAATTAAATTATGTTTTTAATTTTTTAAATATTCTTACTATAATTATC
ATGTACTCTTTGATCTGTTCATCTTTTCCATGATAATATTATTTGGTCAGTTAGTGACATAAGAGTTTGAAATTT
AGAAAAAAGGAATATTTGGAGAAAACTGAAATGGATATTTAGAAATGAAAGTTATTTAATATAAATATAAGTATG
GGCTGCTGAGTTGGGAATCCACGCTGGAGATCTCAAGTTTGAAGCGTCTCACAAACAATAGTAATGTCTTTTTGG
TCGAGTTTGTCGGATTGGACTTGTCCGTGGCCTGTGGGTTACTTTTCCTATATGGTTTGCAAGCTATCGGGAATT
TTATCCTGGCGCACCCAAATTTGAGTTATTTTTGAGTTTTTATATGAAATAGCTTTGTGAATTCATCGAACTCCC
GAAAACATTGAACTTTACTCCAAGTTGAATTGCAGTAAAATAATAGTAGCGATTCTTTAATTTATCCTAACAGTT
TTTCGAAATAATAATCCCAAAAAAGTTTAAAATAACCATACCATAAACTTACTGGGTAAGATATTATCTGTCTAA
TAATATATAGTAGTTTCTTTTGTTTTATTAGTTTATCTAATCCATATTTCATTTCTTGATAAGTTATTCTTAATA
GGAAAATAAACTTATTTCGAAAAACTGTTTTTAAAATTTTCTTGAGTTGAGTCTTGGATGAAAAATAGTTAATTT
TGCATTAATTAATTTTGTTCTAACAAAAACTAATTAAATTTTTTTGAAGCGCATATTCACTCAAAAAATAAATAA
AAACCATCATGCATACAGGAAATGTTCTTTTTTTAATTTATTTTTTCATTGGAGCCCTGACTAATTTTATATCGG
TTCATACTTTCATAAATTACAAAAAGTTCAAAATTTAAACTAACCATATAAGTGAATAAAATAAATCAACAAAAT
ATTCACCACATAATACTTTTTAAATAGAATTTTTCATACCAAAGACCTTACTTTAATTAATTAGGGTGAGAGAAT
CCTATAAGTCAATGCAAAACAATTCTATCTATCGGATTATAATCGTTGATTCATAAAATTTTAAAATCGACGATT
TTCATTTAAATGACCCTTTTTTTTCTTTCATTTTTTATTGTTATTCATCTATTTAACTTGTGAGCATCTTTCATA
TTGATATTTCAGACCCTTAAATTAATTGTTTTCTTACAGAATAACTACCACGAATATCTGAGGCTAAAAGCTAGA
GTTGAGCTCCTCCAACGATCTCAGAGGTAATTTCTGTTCACTATCTTTATCTCAAATGAATTCTCATGTTTTTAT
TTTTCGAGATTCAGATTAAATATAATTTGATGTATTATTAATTTAAATACGTTATTTAATATGGTCCTTATGTCC
AACCATTGATTTAATTTGATATTTTTTTAATGAAAATTACACAGAAACTTTCTTGGTGAAGATTTGGGCACGTTA
AGCTTCGAAGGACCTTGAGCAGCTTGAGAATCAATTAGAGTCTTCCTTAAAGCAAATCAGGTCAAGGAAGGTAAA
TTATTTAATCTAATTATACAGAAAAATCATCTAAAAGTTACCTTAATTGCTAGCCCAATAAGTTTGCTATCTGTT
GATCCTCACATTATTTTACTCACAGAAATTCACAATACCTTTATTTTTGTTTGAGTTTGAAGTATACAATTTCTT
TAAAATGTAAAATTTGAAATCTCAACAATAAGATATGTTATTGATCCTTGCAATTATGGGTAGATTGCGAATTAA
ACTATCTTGTCTTTGCTTACAACAGTCATTTTGTTTATAAACTAATTATACATAAATCCTAACTGATAGATAGTT
TATAAAGATGAATAATGAACATAGGTCATATATTAAAAAAACAAAAAACAAAAAAAAACTAAACAAGATGAGCGA
GTCAAAAATAGTCTTAACAAAAGAATATATATATATGTATATATCATATTTGATTTGTCTATTTTTAATTTTGAA
AAAACTAAGTTAATCGATATATAATATGAAGGCATAATGCATAAATATGTCCTTTAACTTGGTTTTAAATCACAT
TTATACCTCTTCGACTTTGGGTGTATACAAACAAACACTTAAACTTATATAATGTTGAACAAATAGATATATATG
TCCTACATGTCATTTTTCGTCCTAAATGGTGTCCTAAGTGTATTGTGTCACGCAGGACTCATGTGTCTATTTGTT
CAAATTTATACAAGTTTAAGTGCTTACTTATGTATAAACAAAGTTGAATGACATAAATGTGAAATAAAATCAAAT
TAAAGGGCATATTTATGCATTATACCTAATACGAAAATCCATATTATTCACTAAAAAATGAGTCGGATTATATGA
TTACTTTTTTATTCATTTTGCCAATCGTATCCTACGACATTGTTTTTAATTTGCAGACACAATTCATGCTGGATC
AGCTTGCAGATCTTCAACAAAAGGTAATTATAAAATTCTACAAATTTCCAATAATTAATAAATGGAATAATTATG
CGCGAGAAATTTATCTATTTAAAATTTACGATGAATTTTAATTTTACAGGAGCAAATGCTTGCAGAATCTAATAG
ATTACTCCGTAGAAAGGTAAACTAACTTGATAGCCGTGCGTAATGAATAACTTATTTTATTTTCAAAATTATAAA
TCTAAATACTTAGGTAACTCGATAACATAAGAAGTATTTATACTGATGATATTGGTGTTGTGTTTTTTTTTATTA
GTTAGAAGAAAGTGTAGCTGGATTTCCACTTCGATTGTGTTGGGAAGATGGAGGTGATCATCAACTTATGCATCA
ACAAAATCGTCTCCCTAACACAGAGGGTTTCTTTCAGCCTCTTGGATTGCATTCTTCTTCTCCACATTTTGGGTA
ATTACTTTTATTATTATTAAAAATAATTTCAATTTTTTTTACTTTTATTTCGATTAATAAATCAATGTGCACCAA
GGTACGGTCTAACATAAACAAAAATGTGGGGAATGCTCTTAAAGCCCTAACAAAAGTTATTTGGTACGTGTACTA
ATGTAATCGTACTATATATCTTACTTGATTAGTGGATGGACAGTACTGGGCACACACAATTGACATAAGTTATTA
TAAGGAAAAAAAAAAGGCCAATAATCAATATAGTCCAACATTACATTATTTATTATAACAGGTCACTCTAGATTAA
ATGTTAATGAATAACAAAAAGTCTCATATTGATGATTAATGTGATGGGTGGGCTTCTTATAAGGCTTTGACAATC
CTACTCTCTTTGAGCTAGTTTTGGGGGTGTGACCTAATTCAACAGAACGTAGTTAAGATTGTGAAGTAAAGTTGA
TCATTGTTATAACAGGTTTAAATACTTCTAGTAAAAATAGTTCCTAGATAATCCATCGCAAAATAGCTCCTATAT
AGTTAGTTGGATTTTCATATAATCTATAGCTTATACATAGCTAAATGGGAATAGATGAGAGTTTCTGTTGTTTAG
ATATGATATTTGATCGGTTTCTAAATCGTTACTATCATGTAGTGAATAATTTTCATGTTATTACTATTACATTTG
ATTGTTTCTGTGGTTATTTTTTTTTCTAGGTACAATCCTGTTAATACAGATGAGGTGAATGCAGCGGCAACTGCA
CACAATATGAATGGATTTATTCATGGATGGATGCTTTAA (SEQ ID NO: 16)
```

EXAMPLES

Example 1. Bypassing Negative Epistasis on Yield in Tomato Imposed by a Domestication Gene Selection for inflorescence architecture with improved flower production and yield is common to many domesticated crops. However, tomato inflorescences resemble wild ancestors, and breeders avoided excessive branching because of low fertility. The present disclosure relates to the finding of branched variants that carry mutations in two related transcription factors that had been selected independently. As described herein, one founder mutation enlarged the leaf-like organs on fruits and was selected as fruit size increased during domestication. The other mutation eliminated the flower abscission zone, providing "jointless" fruit stems that reduced fruit dropping and facilitated mechanical harvesting. Stacking both beneficial traits caused undesirable branching and sterility due to epistasis, which breeders overcame with suppressors. However, this restricted the opportunity for productivity gains from weak branching. Exploiting natural and engineered alleles for multiple family members, we achieved a continuum of inflorescence complexity that allowed breeding of higher yielding hybrids. Characterizing and neutralizing similar cases of negative epistasis could improve productivity in many agricultural organisms.

Methods

Experimental Model and Subject Details

Plant Material and Growth Conditions

Seeds of the standard *S. lycopersicum* cultivar M82 (LA3475) were from the present stocks. Core collection germplasm (eu-sol.wur.nl) was from the seed stocks of Z. Lippman, D. Zamir, and S. Huang (Lin et al., 2014). Seeds of the jointless *S. cheesmaniae* accession LA0166 were obtained from the Charles M. Rick Tomato Genetics Resource Center (TGRC) at the University of California, Davis. The frondea mutant was obtained from the gene bank of the Leibniz Institute of Plant Genetics and Crop Plant Research (IPK) in Gatersleben, Germany. Seed of the long inflorescence (lin) mutant in the Micro-tom background (TOM-JPG5091) was provided by the University of Tsukuba, Gene Research Center, through the National Bio-Resource Project (NBRP) of the AMED, Japan (tomatoma.nbrp.jp/). The lin mutant was backcrossed four times to the standard M82 cultivar. The landrace collection (*S. lycopersicum* var. *cerasiforme*) was from the seed stocks of E. van der Knaap. Tissue samples, DNA, or seed of elite breeding lines were obtained from Syngenta, Nunhems, Monsanto, Lipman Seeds, Johnny's Seeds, and Tomato-Growers.

Seeds were either pre-germinated on moistened Whatman paper at 28° C. in complete darkness or directly sown and germinated in soil in 96-cell plastic flats. Plants were grown under long-day conditions (16-h light/8-h dark) in a greenhouse under natural light supplemented with artificial light from high-pressure sodium bulbs (~250 μmol $m^{-2}$ $s^{-1}$). Daytime and nighttime temperatures were 26-28° C. and 18-20° C., respectively, with a relative humidity of 40-60%.

Analyses of inflorescence architecture, sepal length, fruit type, and productivity traits were conducted on plants grown in the fields at Cold Spring Harbor Laboratory, Cold Spring Harbor, New York, the Cornell Long Island Horticultural Experiment Station in Riverhead, New York, and net houses in Hatzav, Israel. Analyses of sepal length in the landraces were conducted on plants grown in the fields of the Durham horticulture farm at the University of Georgia, Athens, Georgia Seeds were germinated in 96-cell flats and grown for 32 d in the greenhouse before being transplanted to the field. Plants were grown under drip irrigation and standard fertilizer regimes. Damaged or diseased plants were marked throughout the season and were excluded from the analyses.

Method Details

Plant Phenotyping For analyses of sepal length, the length of sepals and petals of 10 closed flower buds per accession were manually measured and the sepal/petal ratio was calculated. Mature floral buds of similar developmental stage were collected (1-2 days before anthesis, i.e. before flower opening). For analyses of inflorescence complexity, the number of branching events was counted on at least 5 inflorescences on each replicate plant.

Yeast Two-Hybrid Analysis

Protein interaction assays in yeast were performed using the Matchmaker Gold Yeast Two-Hybrid System (Clontech) as described before (Park et al., 2014b). The coding sequences for bait proteins were cloned into the pGBKT7 vector, and the resulting vectors were transformed into the Y2HGold yeast strain. The coding sequences for prey proteins were cloned into the pGADT7 AD vector, and the resulting vectors were transformed into the Y187 yeast strain. After mating the two yeast strains expressing bait and prey proteins, diploid yeast cells were selected and grown on dropout medium without leucine and tryptophan. To assay protein-protein interactions, clones were grown on triple-dropout medium without leucine, tryptophan, and histidine for 3 d at 30° C. To block auto-activation, 3 mM 3-amino-1,2,4-triazole (3-AT) were added or adenine was removed from the triple-dropout medium. All primer sequences used for cloning can be found in Table 2.

Meristem Imaging

Live meristems were imaged using a Nikon SMZ1500 stereomicroscope (Nikon). Shoot apices were dissected from seedlings and older leaf primordia were removed to expose meristems. Immediately after dissection, sequences of optical layers were imaged using a Nikon DS-Ri1 digital camera (Nikon) mounted on the stereomicroscope. Z-stacks of optical sections were aligned and merged to produce final focused images using the NIS Elements BR3.2 software (Nikon).

Meristem Transcriptome Profiling

Meristem collection, RNA extraction, and library preparation for s2 mutant plants was performed as previously described (Park et al., 2012). Briefly, seedling shoots were collected at the vegetative meristem (VM), transition meristem (TM), sympodial inflorescence meristem (SIM), and floral meristem (FM) stage of meristem maturation, and immediately fixed them in ice-cold acetone. Meristems were manually dissected under a stereoscope and two biological replicates consisting of 30-50 meristems from independent plants were generated. Total RNA was extracted with the PicoPure RNA Extraction kit (Arcturus) and mRNA was purified with Dynabeads mRNA Purification kits (Thermo Fisher). Barcoded libraries were prepared using the NEB-Next Ultra RNA library prep kit for Illumina according to the manufacturer's instructions, and assessed for size distribution and concentration with a Bioanalyzer 2100 (Agilent) and the Kapa Library quantification kit (Kapa Biosystems), respectively. Libraries were sequenced on a single Illumina Hiseq 2500 lane (222,279,510 million paired-end reads) at the Genome Center of Cold Spring Harbor Laboratories, Cold Spring Harbor.

Previously collected reads for wild-type tomato cultivar M82, compound inflorescence (s) mutant (Lemmon et al., 2016; Park et al., 2012), and reads for the s2 mutant were trimmed by quality using Trimmomatic (Bolger et al., 2014b) and aligned to the reference genome sequence of tomato (SL2.50) (Consortium, 2012) using Tophat2 (Kim et al., 2013). Alignments were sorted with samtools (Li et al., 2009) and gene expression quantified as unique read pairs aligned to reference annotated gene features (ITAG2.4) using HTSeq-count (Anders et al., 2015).

All statistical analyses of gene expression were conducted in R (RTeam, 2015). Expression of individual genes is shown as transcripts per million (TPM). Significant differential expression between meristem stages in wild-type tomato cultivar M82 was identified for 2,582 genes with edgeR (Robinson et al., 2009) using 2-foldchange, average 1 CPM, and FDR≤0.10 cutoffs (Lemmon et al., 2016). To compare expression dynamics by principal component analysis (PCA), z-score normalization of raw counts was used within genotype to minimize the impact of the different sequencing lengths (50 bp vs. 100 bp) and platforms (GAIIx and HiSeq2500). PCA was conducted on normalized expression values for the 2,582 dynamic genes in wild-type tomato cultivar M82, s, and s2 using the prcomp function in R (RTeam, 2015). The first two principal components were then plotted to assess acceleration or delay of the meristem maturation process in mutant samples. The proportion of TM and FM marker genes with moderate and severely delayed expression was assessed by a two-step k-means clustering. First, normalized WT expression was grouped into twelve clusters and the two clusters with the most specific TM and FM expression were designated as markers. Mutant expression from TM and FM marker genes was normalized with WT, producing WT:s and WT:s2 normalized expression datasets. Finally, k-means clustering (12 clusters) was performed on s and s2 normalized expression alone and clusters with delays in activation compared to WT were identified by hand.

Mapping-by-Sequencing

To map the causal mutations in the s2 mutant, two second-generation (F2) populations were generated by crossing s2 with the *S. lycopersicum* cultivar M82, and s2 with *S. pimpinellifolium*. From a total of 464 s2×M82 $F_2$ plants, 25 s2 mutants, 20 j2 mutants, and 13 WT siblings were selected for tissue collection, nuclei isolation, and DNA extraction. An equal amount of tissue from each plant (~0.2 g) was pooled for DNA extraction using standard protocols. Libraries were prepared with the Illumina TruSeq DNA PCR-free prep kit from 2 μg genomic DNA sheared to 550 bp insert size. From a total of 576 s2×*S. pimpinellifolium* $F_2$ plants, 16 s2 mutants, 9 j2 mutants, and 13 wild-type siblings were selected for DNA extraction. DNA was also extracted from the s2 parent (LA4371). Libraries were prepared with the Illumina TruSeq Nano DNA prep kit from 200 ng genomic DNA sheared to 550 bp insert size and 8 cycles of final amplification. All DNA libraries were sequenced on an Illumina NextSeq platform at the Cold Spring Harbor Laboratory Genome Center (Woodbury, NY). For the s2×M82 $F_2$ population, 62,317,992, 73,496,741, and 79,699,274 paired-end 151-bp reads were obtained for the s2 mutant, j2 mutant, and the WT sibling samples, respectively. For the s2×*S. pimpinellifolium* $F_2$ population, 32,979,728, 82,439,796, and 50,763,441 paired-end 151-bp reads were obtained for pools of s2,j2, and the WT siblings, respectively. For the s2 parent 48,281,689 paired-end 151-bp reads were obtained.

To map the causal mutation in the lin mutant, a $F_2$ population was generated by crossing the lin mutant with *S. pimpinellifolium*. From a total of 216 $F_2$ plants, 8 lin mutant plants were selected with the most strongly branched inflorescences and 17 WT siblings for tissue collection. An equal amount of tissue from each plant (~0.2 g) was pooled for nuclei isolation and DNA extraction using standard protocols. Barcoded libraries were prepared with the Illumina TruSeq DNA PCR-free prep kit from 2 μg genomic DNA sheared to 550 bp insert size and sequenced as above. 4,624,816 and 5,063,861 paired-end 101-bp reads were obtained for the lin mutant and the WT sibling pools, respectively. To find the lin mutation, a pool of 7 lin×*S. pimpinellifolium* $F_2$ mutant plants was resequenced on the Illumina HiSeq2500 platform, and an additional 161,827,433 paired-end 101-bp reads were obtained.

To map s2 suppressor loci in *S. pimpinellifolium,* 1,536 *S. pimpinellifolium*×s2 $F_2$ plants were regrown and 92 homozygousj$2^{TE}$ ej$2^{w}$ double mutants were selected by PCR genotyping. Primers are listed in Table 2. 18 s2 mutants, 6 moderately suppressed s2 mutants, and 2 strongly suppressed s2 mutants were selected for tissue collection, nuclei isolation, and DNA extraction. Libraries were prepared with the Illumina TruSeq DNA PCR-free prep kit from 2 μg genomic DNA sheared to 550 bp insert size, and sequenced as above. 38,060,212, 38,044,727 and 52,426,078 paired-end 151-bp reads were obtained for the pools of s2, moderately suppressed s2, and the strongly suppressed s2 plants, respectively.

Genomic DNA reads were trimmed by quality using Trimmomatic and paired reads mapped to the reference tomato genome (SL2.50) using BWA-MEM (Li, 2013; Li and Durbin, 2009). Alignments were then sorted with samtools and duplicates marked with PicardTools (Li et al., 2009, broadinstitute.github.io/picard). SNPs were called with samtools/bcftools (Li, 2011; Li et al., 2009) using read alignments for the various genomic DNA sequencing pools from this project in addition to reference M82 (Bolger et al., 2014a) and *S. pimpinellifolium* (Consortium, 2012) reads. Called SNPs were then filtered for bi-allelic high quality SNPs at least 100 bp from a called indel using bcftools (Li, 2011). Following read alignment and SNP calling, all statistics and calculations were done in R (RTeam, 2015). Read depth for each allele at segregating bi-allelic SNPs in 1 Mb sliding windows (by 100 kb) was summed for the various mutant (s2,j$2^{TE}$, or suppression of s2) and wild-type sequencing pools and mutant:non-mutant SNP ratios were calculated. Finally, mutant SNP ratio was divided by wild-type SNP ratio (+0.5) and plotted across the 12 tomato chromosomes.

Tissue Collection and RNA Extraction

For semi-quantitative RT-PCR, seeds were germinated on moistened Whatman paper at 28° C. in complete darkness. Seedlings at similar germination stages were transferred to soil in 72-cell plastic flats and grown in the greenhouse. Shoot apices were collected at the floral meristem (FM) stage of meristem maturation (Park et al., 2012), and immediately flash-frozen in liquid nitrogen. Total RNA was extracted using the RNeasy Plant Mini Kit (Qiagen) and treated with the RNase Free DNase Set (Qiagen), or the Arcturus PicoPure RNA Extraction kit (Thermo Fisher) according to the manufacturer's instructions. 100 ng to 1 μg of total RNA was used for cDNA synthesis using the SuperScript III First-Strand Synthesis System (Invitrogen). All primer sequences can be found in Table 2.

Phylogenetic Analyses and Sequence Analyses

Sequences of tomato and *Arabidopsis* SEP family members were obtained from the Phytozome v11 database (phytozome.net) and aligned using the ClustalW function in MEGA. Phylogenetic trees for proteins with 1,000 bootstrap replicates were constructed using the maximum likelihood method in MEGA6 (Tamura et al., 2013). Homologous proteins in the clades containing *Arabidopsis* SEP1/2, SEP3, and SEP4 were assigned as SEP1/2-, SEP3-, and SEP4-homologs, respectively.

For analysing linkage between EJ2 and FW3.2, the M9 SNP was genotyped at position SL2.50ch03:64799226 (Chakrabarti et al., 2013) (G in *S. pimpinellifolium* (FW3.2) and A in *S. lycopersicum* cv. M82 (fw3.2)) in accessions of the tomato core collection using published genome sequencing data (Lin et al., 2014; Tieman et al., 2017).

CRISPR/Cas9 Mutagenesis, Plant Transformation, and Selection of Mutant Alleles

CRISPR/Cas9 mutagenesis and generation of transgenic plants was performed following the standard protocol (Belhaj et al., 2013; Brooks et al., 2014). Briefly, two single-guide (sg)RNAs binding in the coding sequence of the target gene were designed using the CRISPR-P tool (cbi.hzau.edu.cn/cgi-bin/CRISPR) (Lei et al., 2014). Vectors were assembled using the Golden Gate cloning system (Werner et al., 2012). The sgRNA-1 and sgRNA-2 were cloned downstream of the *Arabidopsis* U6 promoter in the Level 1 acceptors pICH47751 and pICH47761, respectively. The Level1 constructs pICH47731-NOSpro::NPTII, pICH47742-35 S:Cas9, pICH47751-AtU6pro:sgRNA-1, and pICH47761-AtU6::sgRNA-2 were assembled in the binary Level 2 vector pAGM4723. Fifteen-μl restriction-ligation reactions were performed in a thermocycler (3 min at 37° C. and 4 min at 16° for 20 cycles, 5 min at 50° C., 5 min at 80° C., and final storage at 4° C.). All sgRNA sequences are listed in Table 2.

Final binary vectors were transformed into the tomato cultivar M82 and the tomato wild species *S. pimpinellifolium* by *Agrobacterium tumefaciens*-mediated transformation (Gupta, S. and Van Eck, 2016). After in-vitro regeneration, culture medium was washed from the root system and plants transplanted into soil. For acclimation, plants were covered with transparent plastic domes and maintained in a shaded area for 5 days. A total of 8 first-generation ($T_0$) transgenics were genotyped for induced lesions using forward and reverse primer flanking the sgRNA target sites. PCR products were separated on agarose gels and selected products were cloned into pSC-A-amp/kan vector (StrataClone Blunt PCR Cloning Kit, Stratagene). At least 6 clones per PCR product were sequenced using M13-F and M13-R primer. To plants with lesions were backcrossed to wild type and the $F_1$ generation was genotyped for desirable large deletion alleles and presence/absence of the CRISPR/Cas9 transgene using primer binding the 3' of the 35S promoter and the 5' of the Cas9 transgene, respectively. All primers are listed in Table 2. Plants heterozygous for the engineered deletion alleles and lacking the transgene were self-pollinated to isolate homozygous, non-transgenic null mutants from the $F_2$ generation.

Generation of Parental and Hybrid Lines for Cherry Tomato Breeding and Yield Trials Under Agricultural Greenhouse Conditions To test the potential of j2 ej2 and s genotypes for fresh-market tomato breeding, hybrids were generated by crossing near-isogenic lines isolated from a breeding population that was developed for breeding high-yielding, indeterminate cherry tomato cultivars with a range of fruit shapes (Dani Zamir). Depending on genotype, near-isogenic lines were generated by backcrossing once to the respective cherry parents ($BC_1$) followed by inbreeding for 3 generations ($F_3$) or by inbreeding for 3-6 generations ($F_3$—$F_6$). Fruit shapes, inflorescence types, and yield characteristics were evaluated and selected each generation. Ten replicate plants per parental and hybrid line were grown in a randomized plot design in net houses in Hatzav, Israel in the year 2017. Damaged or diseased plants were marked throughout the season and were excluded from the analyses.

j2 ej2 Hybrid Experiment

A jointless ($j2^{TE}$) processing inbred ($F_6$) wild type for EJ2 (j2 EJ2) served as parent (P-6022) for generating test and control hybrids. Test parents were isolated from a jointless ($j2^{TE}$) cherry inbred population ($BC_1F_3$), which segregated for $ej2^w$. Two $j2^{TE}$ parents (P-6086-2 and P-6086-9) and two $j2^{TE}$ $ej2^w$ parents (P-6086-4 and P-6086-8) were selected by $ej2^w$ genotyping, and were crossed to P-6022. Control hybrids were generated by crossing the $j2^{TE}$ test parents (P-6086-2 for trail-1 and P-6086-9 for trial-2) to the $j2^{TE}$ parent (P-6022). Test hybrids were generated by bulk crossing the $j2^{TE}$ $ej2^w$ test parents (P-6086-4 for trail-1 and P-6086-8 for trial-2) to the $j2^{TE}$ parent (P-6022).

s Hybrid Experiment

An indeterminate cocktail inbred ($F_3$) and a determinate cherry inbred ($F_3$) served as parents (P-6097 and P-6105, respectively) for generating test and control hybrids. Test parents were isolated from an indeterminate cherry-type $F_5$ inbred line that segregated the s mutation. One parent wild type for S (P-6089) and one s mutant parent (P-6090) were selected by phenotyping and self-fertilized. The $F_6$ generation was stable for unbranched (P-6089) and compound inflorescences (P-6090). Control and test hybrids were generated by bulk crossing the S parents (P-6097 for trail-1 and P-6105 for trial-2) to the S (P-6089) and the s (P-6090) test parents, respectively.

For analyses of yield component traits, mature green (MG) and red fruits (MR) were collected from 6 subsequent individual inflorescences and MG fruit number (MGFN), MR fruit number (MRFN), MG fruit weight (MGFW), and MR fruit weight (MRFW) was determined per inflorescence. Total fruit number (TFN) was the sum of MGFN and MRFN from each plant. Total yield (TY) was the sum of MGFW and MRFW from each plant. The average fruit weight (FW) was calculated by dividing MRFW by MRFN. From each plant, 7-10 fruits from at least one inflorescence were randomly selected to determine total soluble sugar content (Brix) in fruit juice. Brix value (percent) was quantified with a digital Brix refractometer (ATAGO Palette). For each measured yield parameter, mean values and percentage difference to the control hybrid were statistically compared using two tailed, two-sample t-tests.

Quantification and Statistical Analyses

Sampling

For quantitative analyses of flower number per inflorescence and inflorescence internode length, at least 10 inflorescences were analyzed per genotype. For quantitative analyses of inflorescence complexity at least 5 inflorescences each from 6 individual replicate plants were analyzed per genotype. For quantitative analyses of relative sepal length, at least 10 flowers were analyzed per genotype or ecotype. Hybrid inflorescence traits (number of branching events per inflorescence, total number of branches and flowers per plant) were determined for 6 subsequent inflorescences per individual plant and 9-10 individual plants per hybrid line. Total number of mature green and red fruits per individual plant was determined from 6 subsequent inflorescences per plant and 9-10 individual plants per hybrid line. Exact numbers of individuals (N) are presented in all FIGs. Statistical calculations were performed using R and Microsoft Excel. Mean values for each measured parameter were compared using two-tailed, two-samples Student's t-test.

Transcriptome Quantification

Reads for the wild-type M82, compound inflorescence (s) mutant (Lemmon et al., 2016; Park et al., 2012), and the s2 mutant were trimmed by quality using Trimmomatic v0.32 (HiSeq2500 parameters:ILLUMINACLIP:TruSeq3-PE-2.fa:2:40:15:1:FALSE LEADING:3 TRAILING:3 SLIDINGWINDOW:4:15 MINLEN:36; GAIIx parameters:ILLUMINACLIP:TruSeq2-PE.fa:2:30:10:1:FALSE LEADING:3 TRAILING:3 SLIDINGWINDOW:4:15 MINLEN:36 TOPHRED33) (Bolger et al., 2014b) and aligned to the reference genome sequence of tomato (SL2.50) (Consortium, 2012) using Tophat2 v2.0.127 (parameters: —b2-very-sensitive —read-mismatches 2—read-edit-dist 2 —min-anchor 8 —splice-mismatches 0 —min-intron-length 50 —max-intron-length 50000 —max-multihits 20) (Kim et al., 2013). Alignments were sorted with samtools (Li et al., 2009) and gene expression quantified as unique read pairs aligned to reference annotated gene features (ITAG2.4) using HTSeq-count v0.6.08 (parameters: —format=bam —order=name —stranded=no —type=exon —idattr=Parent) (Anders et al., 2015).

Figure 8A:
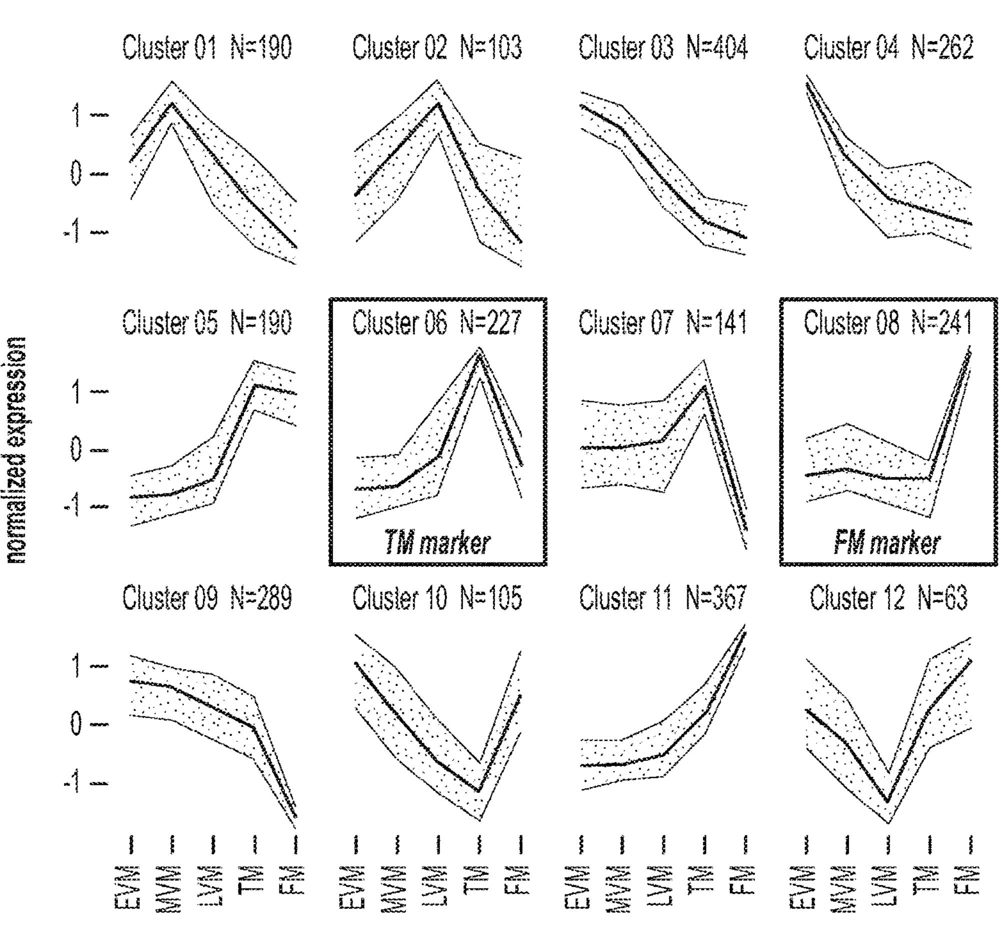
FIGS. 8A-8C show the rate of meristem maturation in s2 mutants is less delayed than in s.
Figure 8B:
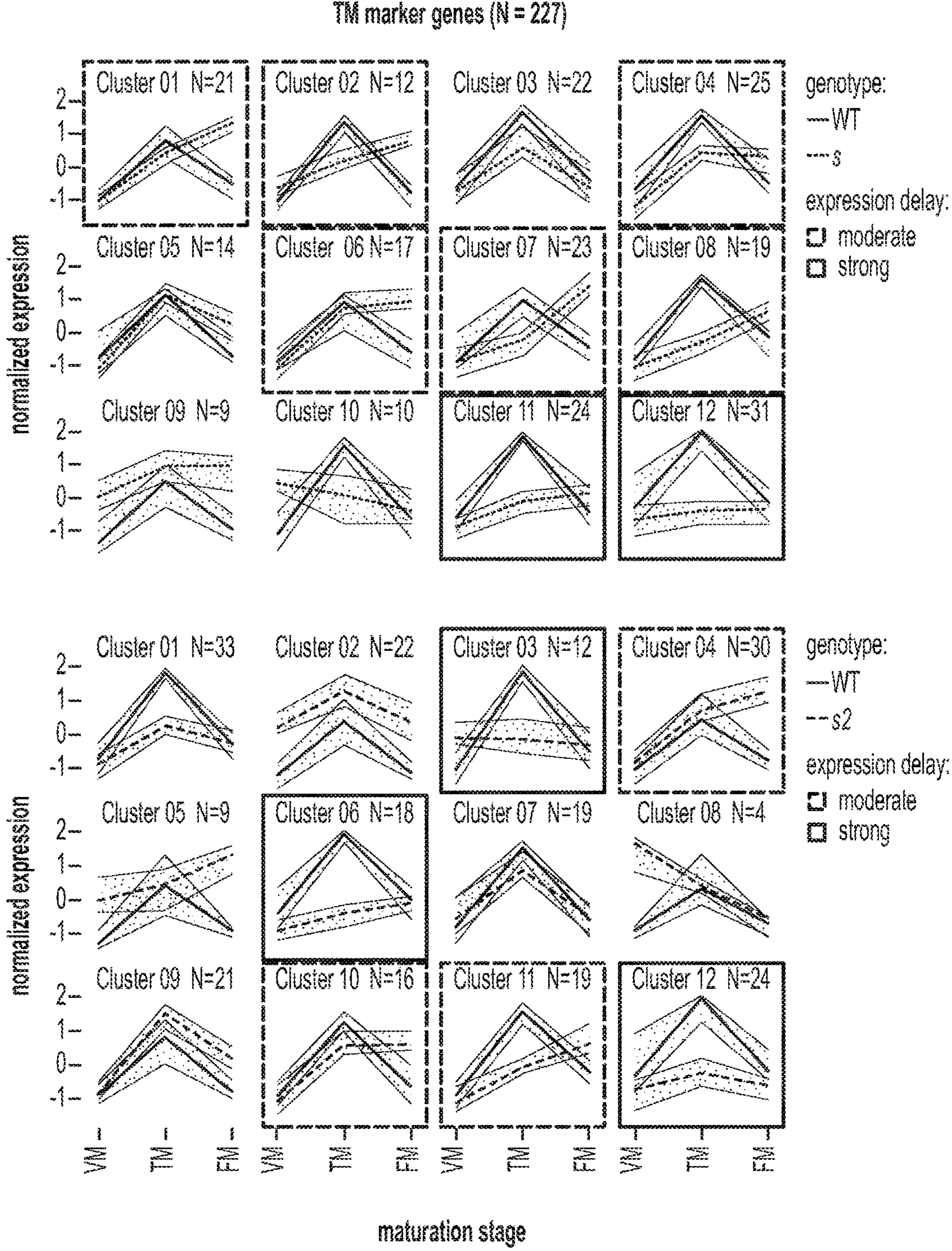
Figure 8C:
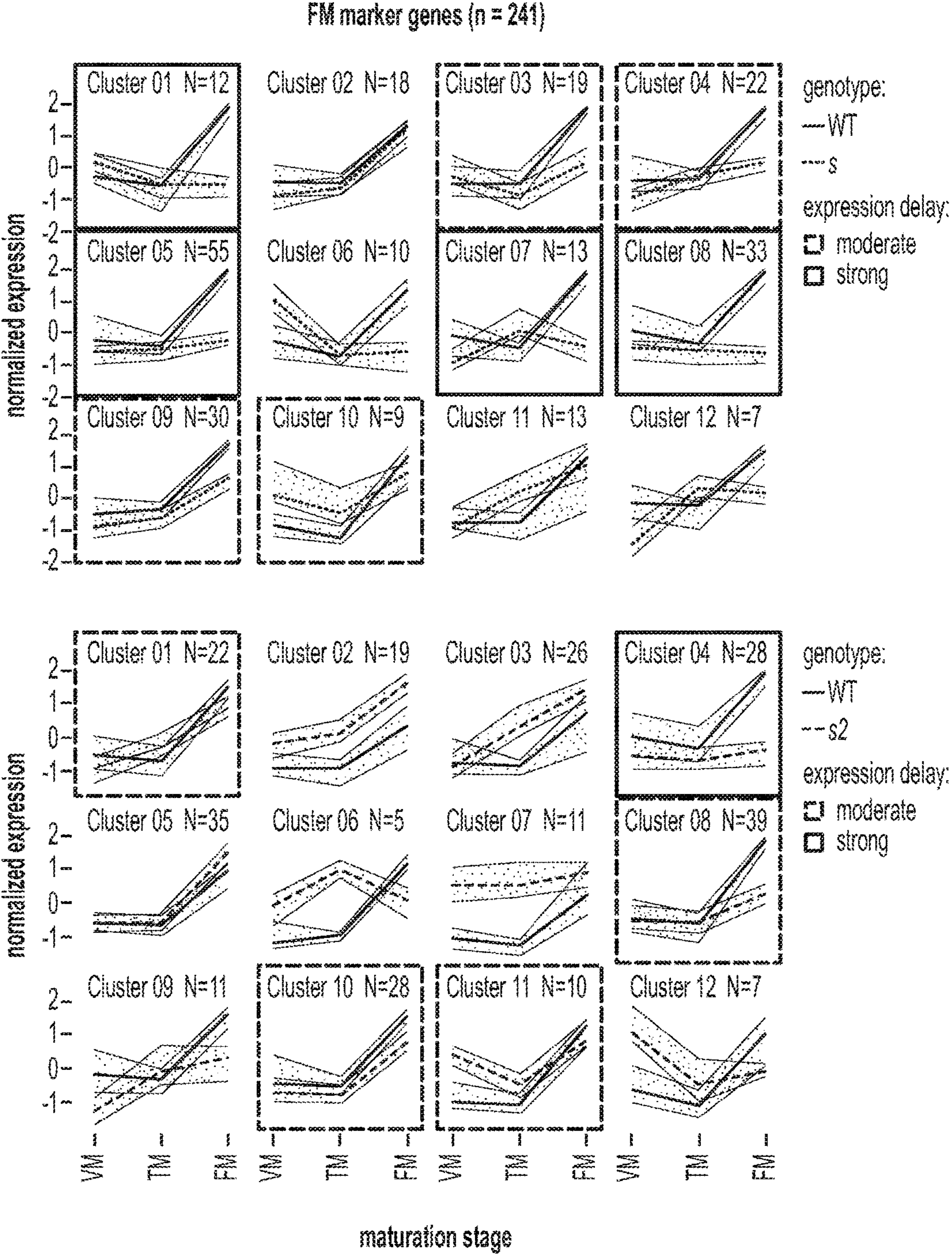

All statistical analyses of gene expression were conducted in R (RTeam, 2015). Significant differential expression between meristem stages in wild-type M82 was identified for 2,582 genes with edgeR (Robinson et al., 2009) using 2-foldchange, average 1 CPM, and FDR≤0.10 cutoffs (Lemmon et al., 2016). To compare expression dynamics between genotypes, z-score normalization was used within genotype to minimize the impact of the different sequencing lengths (50 bp vs. 100 bp) and platforms (GAIIx and HiSeq2500). A principal component analysis (PCA) was conducted on these normalized expression values for the 2,582 dynamic genes including wild-type M82, s, and s2 using the prcomp function in R (RTeam, 2015). The first two principal components were then plotted to assess modified maturation schedules in the mutant samples. The proportion of TM and FM marker genes with moderate and strongly delayed expression was assessed by a two-step k-means clustering. First, WT expression (TPM) was z-score normalized and clustered into twelve groups using the kmeans2 function from the Mfuzz package (Futschik, 2015) in R. The two clusters with the most specific TM and FM expression (clusters 06 and 08, respectively; FIG. 8A) were designated as marker clusters. Mutant s and s2 expression (TPM) from the 277 TM and 241 FM marker genes was z-score normalized with WT expression, producing a WT:s normalized expression and WT:s2 normalized expression dataset. Finally, k-means clustering (12 clusters) was performed on s (FIG. 8B) and s2 (FIG. 8C) expression alone (normalized by WT expression levels) and clusters with moderate and severe delays in activation compared to WT were manually identified.

Mapping

For mapping-by-sequencing of the various mutants, reads were trimmed by quality using Trimmomatic v0.32 (HiSeq 2500 read parameters: ILLUMINACLIP:TruSeq3-PE-2.fa: 2:40:15:1:FALSE LEADING:3 TRAILING:3 SLIDING-WINDOW:4:15 MINLEN:36; GAIIx read parameters: ILLUMINACLIP:TruSeq2-PE.fa:2:30:10:1:FALSE LEADING:3 TRAILING:3 SLIDINGWINDOW:4:15 MINLEN: 36 TOPHRED33) and paired reads mapped to the reference tomato genome (SL2.50) using BWA-MEM v0.7.10-r789 (parameters: -M) (Li, 2013). Alignments were then sorted with samtools and duplicates marked with PicardTools v1.126 (parameters: VALIDATION_STRINGENCY= LENIENT) (Li et al., 2009, broadinstitute.github.io/picard). SNPs were called with samtools/bcftools v1.3.1 (samtools mpileup parameters: —ignore-RG —max-depth 1000000 —output-tags DP,AN —min-BQ 0 —no-BAQ —uncompressed —BCF; bcftools call parameters: —multiallelic-caller —variants-only —output-type z) (Li, 2011; Li et al., 2009) using read alignments for the various sequencing pools from this project in addition to reference M82 (Bolger et al., 2014a) and *S. pimpinellifolium* (Consortium, 2012) reads. Called SNPs were then filtered for bi-allelic high quality (MQ>=50) SNPs at least 100 bp from a called indel using bcftools (Li, 2011). Following read alignment and SNP calling and filtering, all mapping statistics and calculations were done using R (RTeam, 2015). Read depth for each allele at segregating bi-allelic SNPs in 1 Mb sliding windows (by 100 kb) was summed for the various mutant (lin, s2,j2, suppression of s2) and wild-type sequencing pools and mutant:non-mutant SNP ratios were calculated. Finally, mutant SNP ratio was divided by wild-type SNP ratio (+0.5) and plotted across the tomato genome.

Data and Software Availability

Raw sequencing reads generated in this study have been deposited at the Sequence Read Archive (ncbi.nlm.nih.gov/sra) under BioProject SRP 100435.

Additional resources for the tomato core collection (please see e.g., unity.phenome-networks.com), for CRISPR design (please see e.g., cbi.hzau.edu.cn/cgi-bin/CRISPR), for sequence retrieval (please see e.g., phytozome.jgi.doe.gov/) and for data deposition (please see e.g., ncbi.nlm.nih.gov/sra) are also available to one of ordinary skill in the art.

Results

Figure 1B:
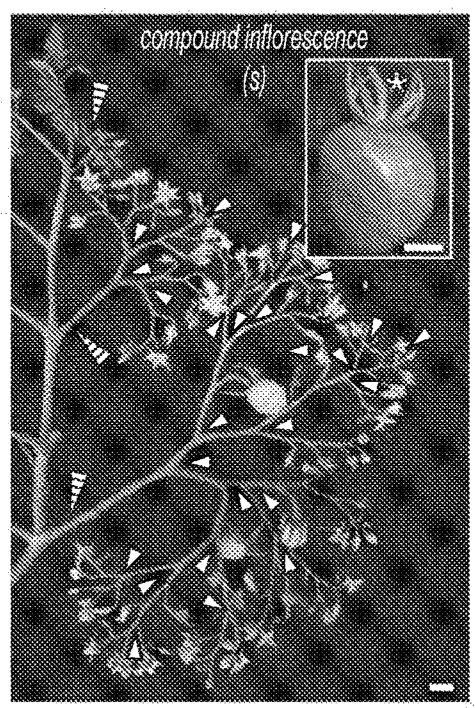
Figures 7A, 7B, 7C, 7D, 7E, 7F, 7G, 7H, 7I, 7J, 7K:
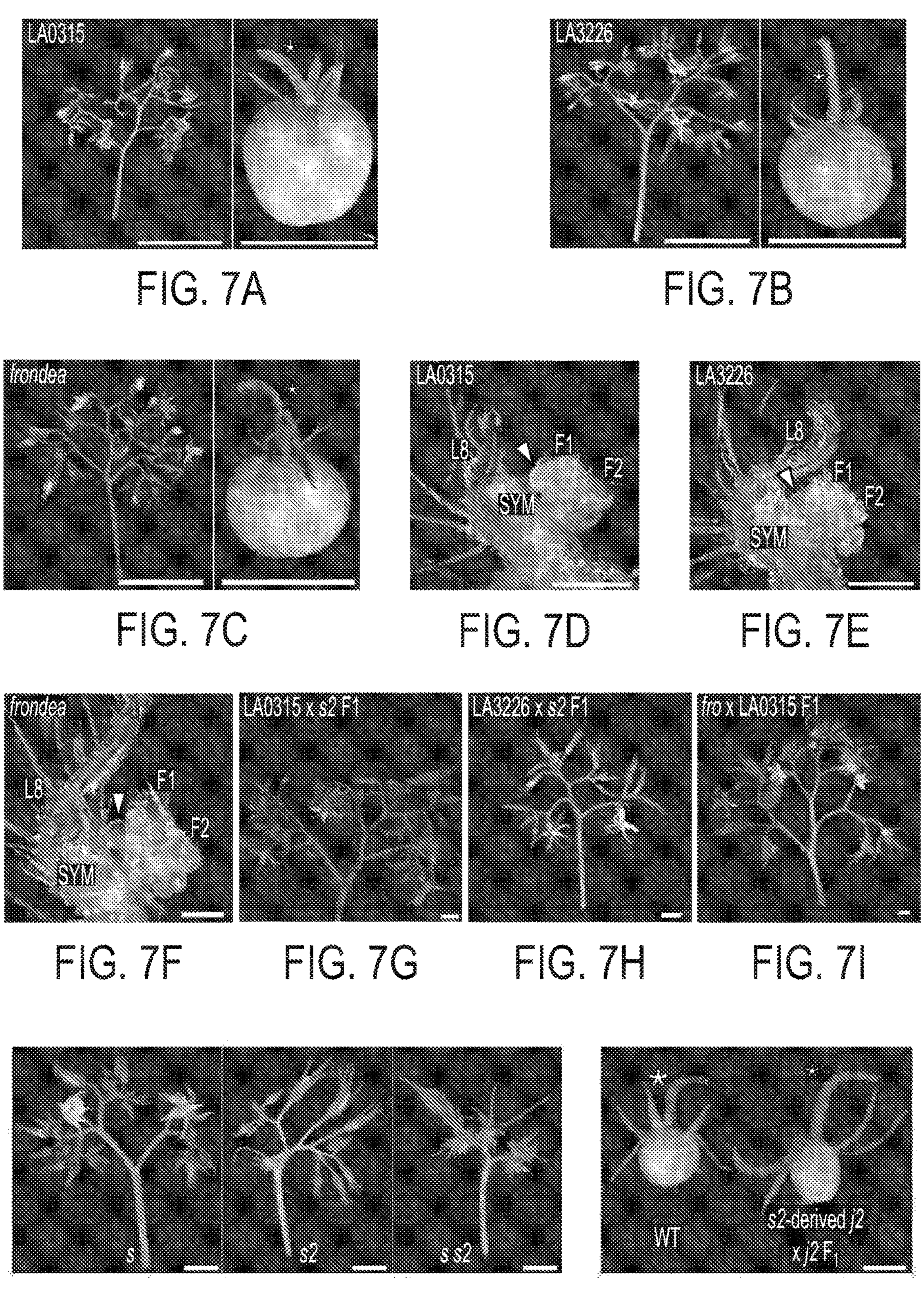
FIGS. 7A-7K show that s2 inflorescence branching variants are allelic, fail to complement the classical j2 mutant, and are genetically additive with s.

The s2 Variants Produce Branched Inflorescences and Flowers with Jointless Pedicels To explore the challenges with improving tomato inflorescences, a core collection of 4,193 wild and domesticated accessions was screened for deviation from the typical inflorescence architecture of multiple flowers arranged along a single branch (FIG. 1A) (unity.phenome-networks.com, see STAR Methods). Twenty-three extremely branched accessions were previously reported that were all defective in the gene COMPOUND INFLORESCENCE (S, homolog of *Arabidopsis* WUSCHEL-RELATED HOMEOBOX 9, WOX9) (FIG. 1B) (Lippman et al., 2008). However, three rare variants not allelic to s that branched less frequently and also lacked the abscission zone on the stems (pedicels) of flowers known as the "joint" were also found (FIGS. 1C, 1D, and 7A-7F). Searching other germplasm sources provided one additional branched jointless mutant derived from an X-ray mutagenesis (FIGS. 7C and 7F) (Stubbe, 1972). Crosses among all four accessions failed to complement (FIGS. 7G-7I). Consequently, these accessions were collectively named compound inflorescence 2 (s2).

Figure 1C:
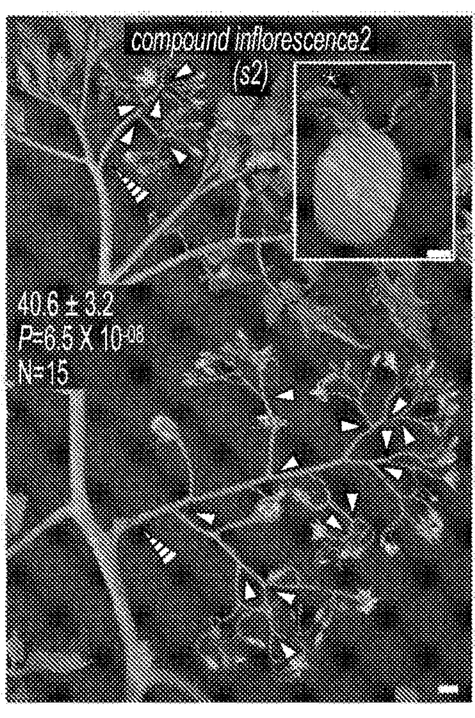
Figure 1D:
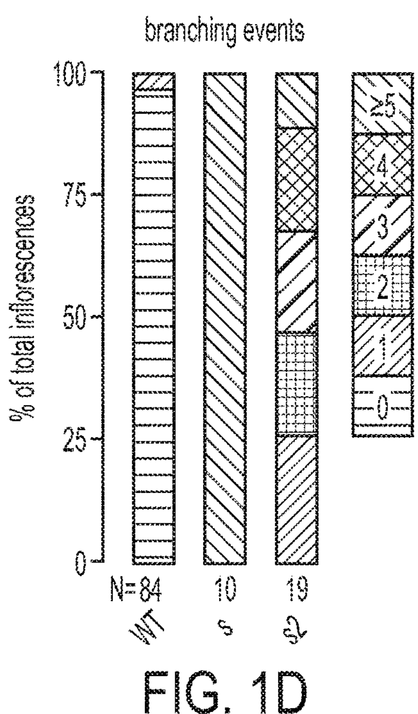
Figure 1E:
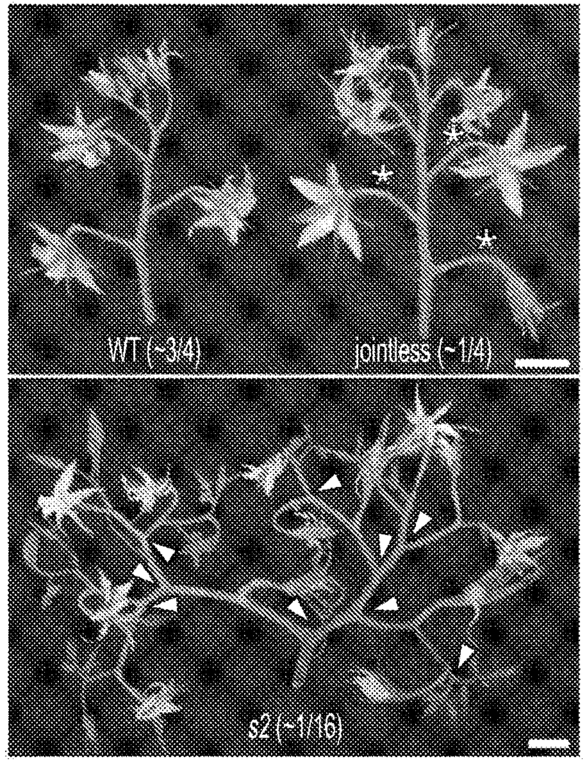

One s2 accession was designated as a reference (LA4371), and an analysis of higher-order mutants with s showed an additive genetic relationship, indicating the gene(s) underlying s2 function separately from the S gene (FIGS. 1C and 7J). It was noted during the generation of s s2 plants that s2 segregated at a ratio of ~1/16 (FIG. 1E), suggesting two unlinked recessive mutations underlie s2 phenotypes. Consistent with this, jointless plants (unbranched and branched) segregated as a single recessive mutation. This jointless trait resembled two classical jointless-2 (j2) mutants reported 50 years ago. The original j2 was discovered in the unbranched wild tomato species *S. cheesmaniae* from the Galapagos Islands (Rick, 1956a). A second allele arose spontaneously in an agricultural field, but this mutation was also associated with inflorescence branching that caused excessive flower production and poor fruit set due to epistatic interactions with the domesticated germplasm (Reynard, 1961; Rick, 1956b). Breeders selected and utilized unbranchedj2, because it reduced fruit dropping and enabled large-scale machine harvesting of processing tomatoes, while maintaining good fruit set (Robinson, 1980; Zahara and Scheuerman, 1988). Notably, the jointless phenotype of s2 was allelic to j2 (FIG. 7K), and s2 plants with normal pedicels were not found, suggesting branching required the j2 mutation. Therefore, the second locus was designated enhancer-of-jointless2 (ej2).

Figures 1F, 1G, 1H:
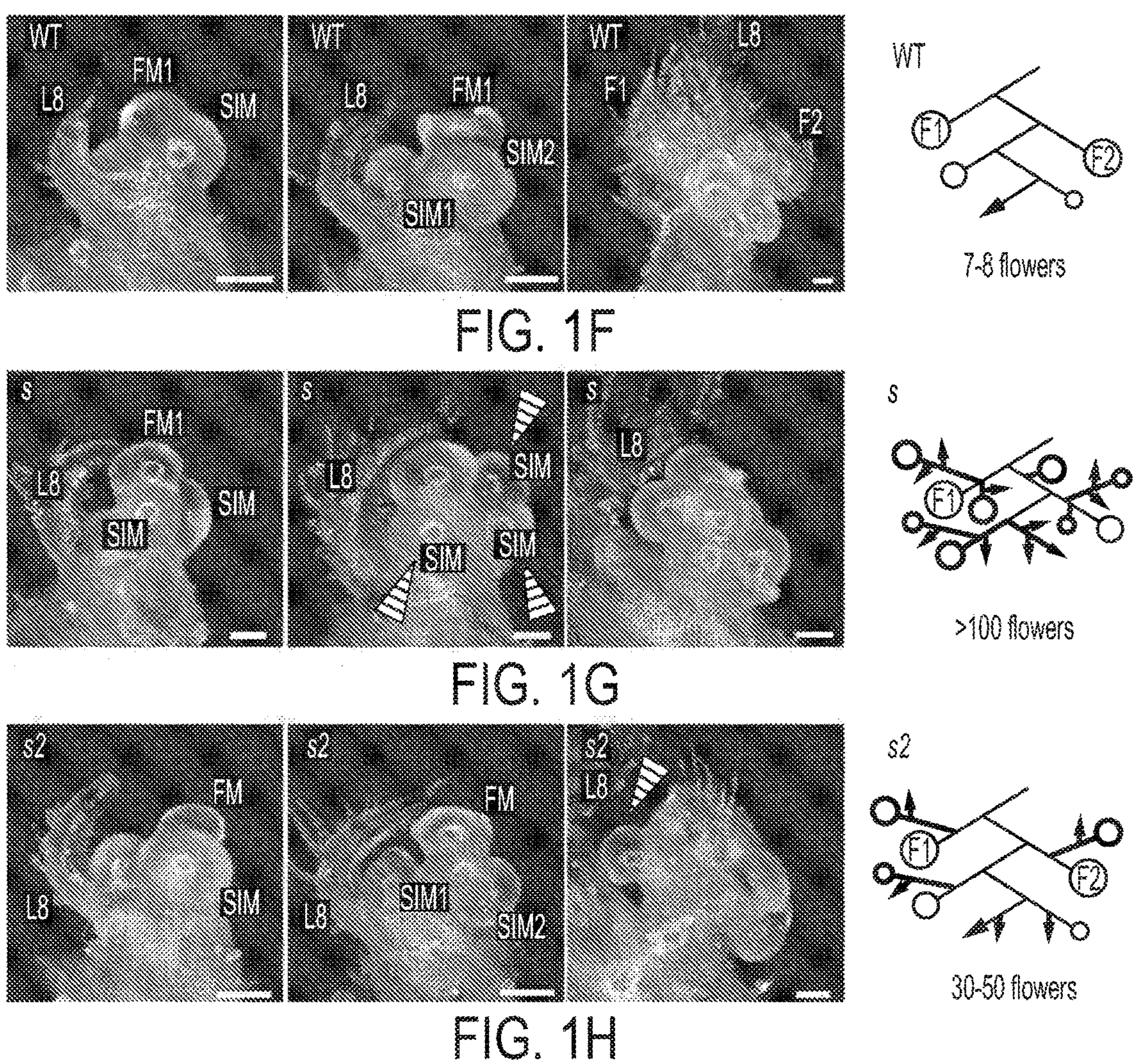

To better understand the developmental basis of s2 branching, the stages of meristem maturation during early inflorescence development were examined. Tomato inflorescences develop according to the sympodial growth program (Park et al., 2014a), in which each vegetative meristem matures into a transition meristem (TM) and terminates in a floral meristem (FM) that produces the first flower of the inflorescence. Additional flowers arise from iterative formation of specialized axillary (sympodial) inflorescence meristems (SIM), resulting in a multi-flowered inflorescence (FIG. 1F). In s mutants, both TM and SIM maturation are severely delayed, allowing multiple SIMs to form at each cycle (FIG. 1G) (Lippman et al., 2008; Park et al., 2012). Additional SIMs also formed in s2 plants, but less than in s (FIG. 1H). To determine if s2 was delayed in maturation, RNA-seq was performed on sequential s2 meristem maturation stages and compared transcriptome dynamics with existing maturation profiles for s and WT (see STAR Methods) (Park et al., 2012). A principal component analysis (PCA) using 2,582 maturation marker genes (Lemmon et al., 2016) showed fewer TM and FM marker genes were delayed during s2 meristem maturation compared to s, consistent with less branching in s2 inflorescences (FIGS. 1I-1K and 8).

Mutations in Two Related MADS-Box Genes Cause s2 Branching

Figure 2A:
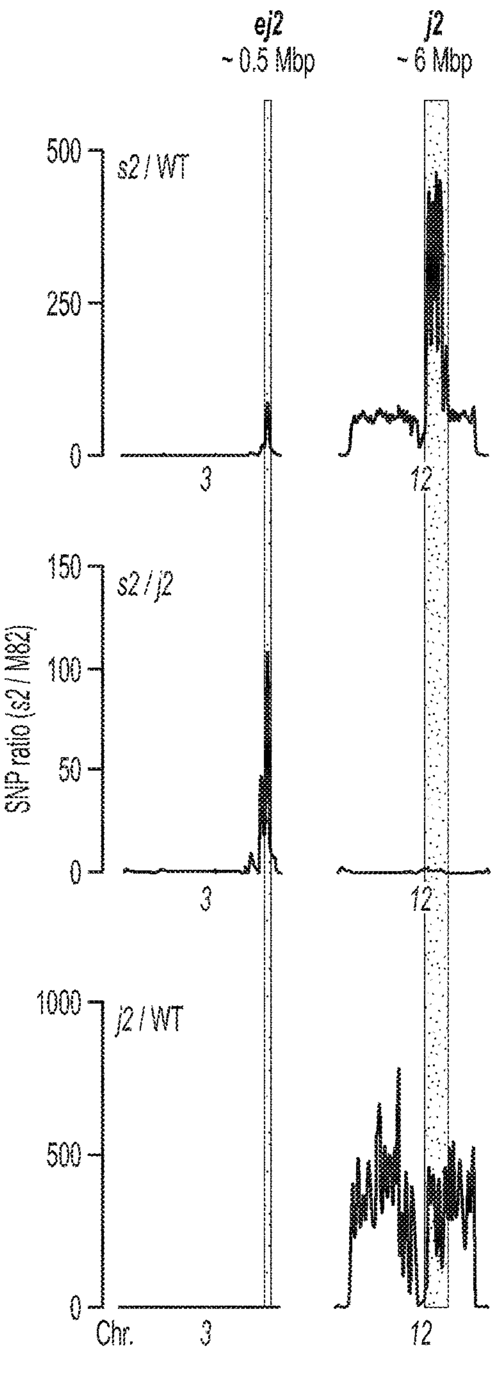
FIGS. 2A-2N show that mutations in two SEPALLATA MADS-box genes cause s2 branching.
Figure 9D:
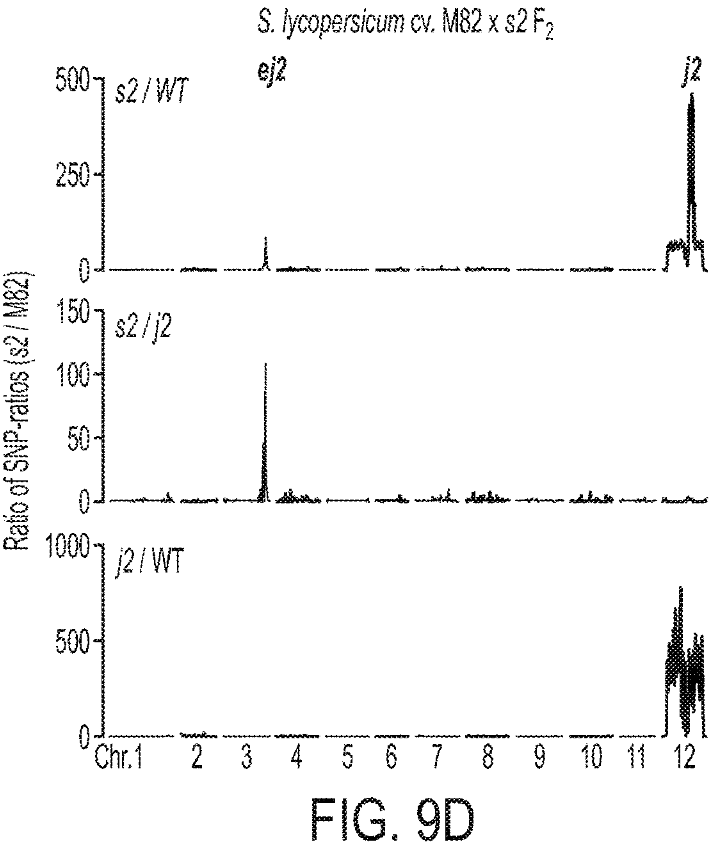
Figure 9E:
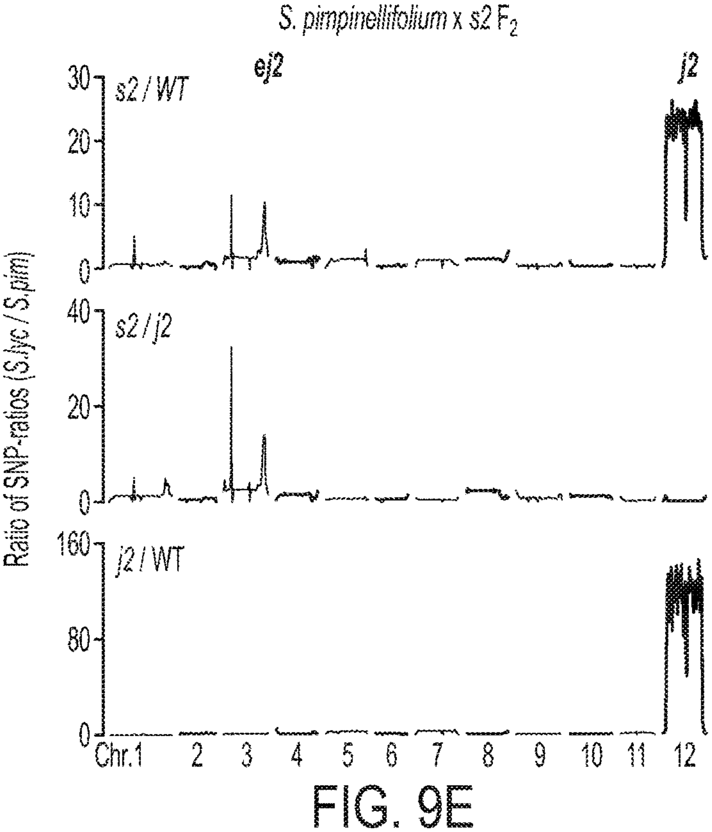

The j2 mutant was previously mapped to the centromere of chromosome 12, but poor recombination prevented identification of the responsible gene (Budiman et al., 2004; Yang et al., 2005). To clone the genes underlying j2 and ej2, two $F_2$ populations were generated from crossing s2 with the jointed (J2/J2) cultivar M82 and the wild ancestor of tomato, *S. pimpinellifolium*. In the intra-species $F_2$ population, s2 plants segregated at the expected ratio of ~1/16, but this segregation was substantially lower in the *S. pimpinellifolium* population, suggesting unknown modifier loci can suppress s2 branching (FIGS. 9A-9C). To map j2 and ej2 simultaneously, genome sequencing was performed on pools of DNA from s2,j2, and WT $F_2$ segregating plants (see STAR Methods). Comparing SNP ratios between s2 and WT pools in both populations revealed a region near the bottom of chromosome 3 and the centromere of chromosome 12 with a strong bias for SNPs from the s2 parent (FIGS. 2A, 9D, and 9E). SNP ratios between s2 and j2 revealed a bias only at the bottom of chromosome 3. These results confirmed j2 is located near the chromosome 12 centromere and revealed ej2 resides on chromosome 3.

Figure 2B:
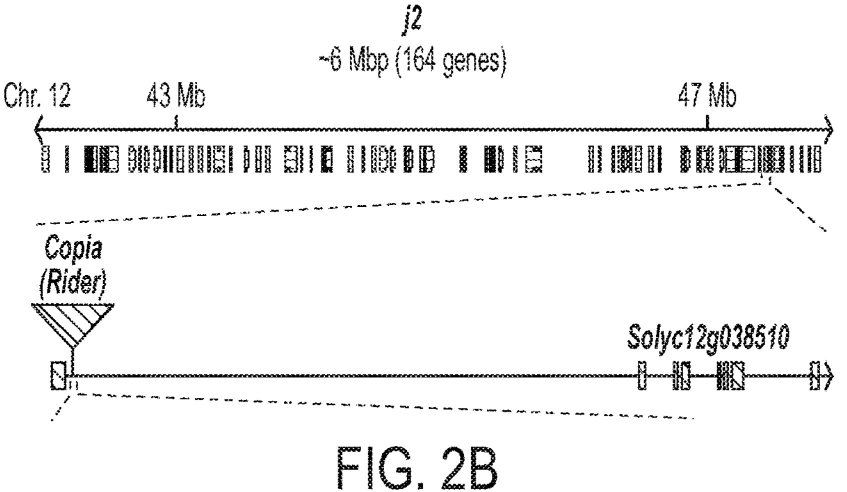
FIG. 2B shows the j2 mapping interval includes the SEP4 homolog Solyc12g038510.
Figure 2C:
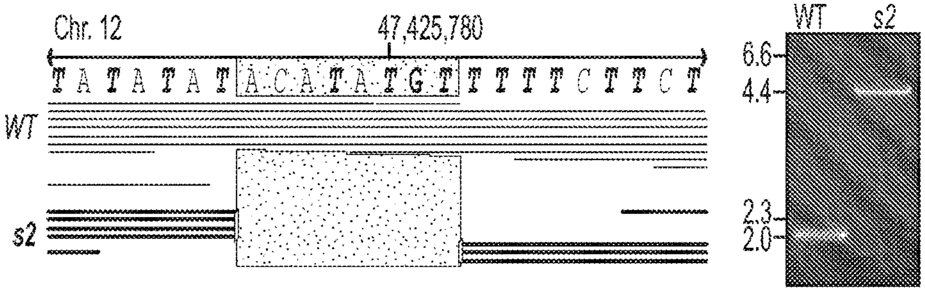
FIG. 2C shows Genomic Illumina-sequence reads showing a breakpoint in Solyc12g038510 (left), and PCR showing a Copia/Rider transposon insertion in the first intron of Solyc12g038510 in s2 mutants (right). The sequence corresponds to SEQ ID NO: 89.
Figure 2D:
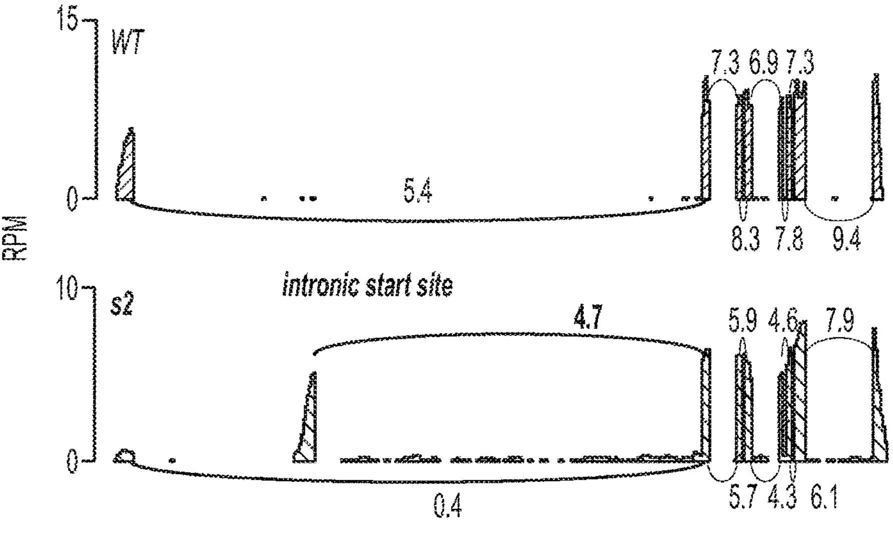
FIG. 2D shows Sashimi plots of normalized RNA-seq reads (reads per million, RPM) for Solyc12g038510 in WT (top) and s2 (bottom) floral meristems. An intronic transcriptional start site leads to out-of-frame Solyc12g038510 transcripts in s2 mutants. Numbers indicate reads supporting splice-junctions and alternative splicing in s2 is highlighted in the bottom panel by diagonal line filling.
Figures 2E, 2F, 2G:
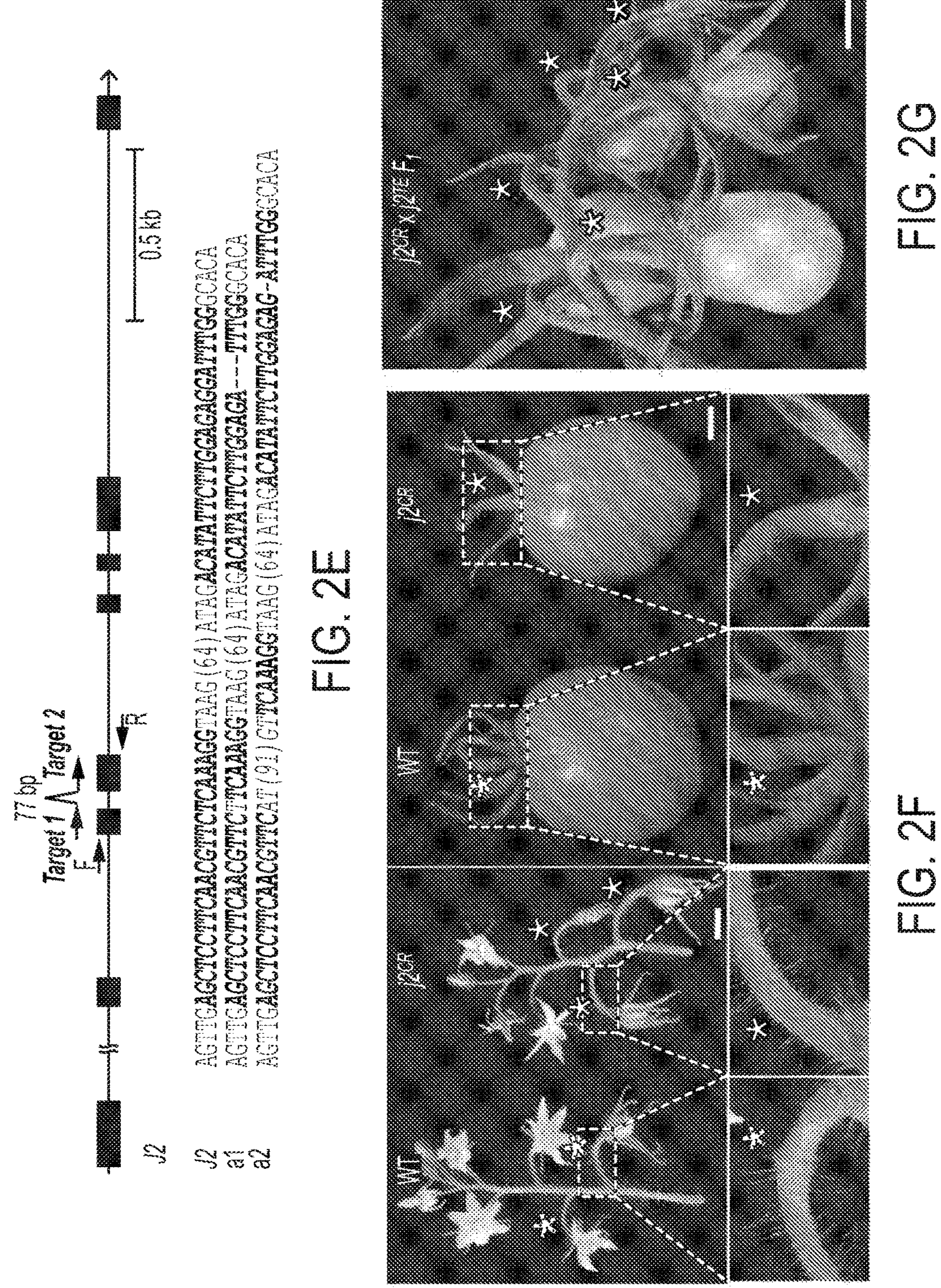
FIG. 2E shows the generation of $j2^{CR}$ null mutations by CRISPR/Cas9 using two single-guide RNAs (sgRNA, target1 and target2; arrows). Black arrows indicate forward (F) and reverse (R) primers used for genotyping and sequencing. Sequences of $j2^{CR}$ allele 1 (a1) and a2 are shown. sgRNA targets and protospacer-adjacent motif (PAM) are indicated in bold font and deletions by dashes. Insertions are indicated in italic font and sequence gap length is shown in parentheses. From top to bottom, sequences correspond to SEQ ID NOs: 90-92.
FIG. 2F shows inflorescences and fruits from WT and $j2^{CR}$ mutants showing unbranched inflorescence with jointless pedicels for $j2^{CR}$. White and dotted asterisks indicate jointed and jointless pedicels, respectively.
FIG. 2G shows a complementation test between $j2^{CR}$ and $j2^{TE}$ (jointless pedicels; asterisks).
Figure 9F:
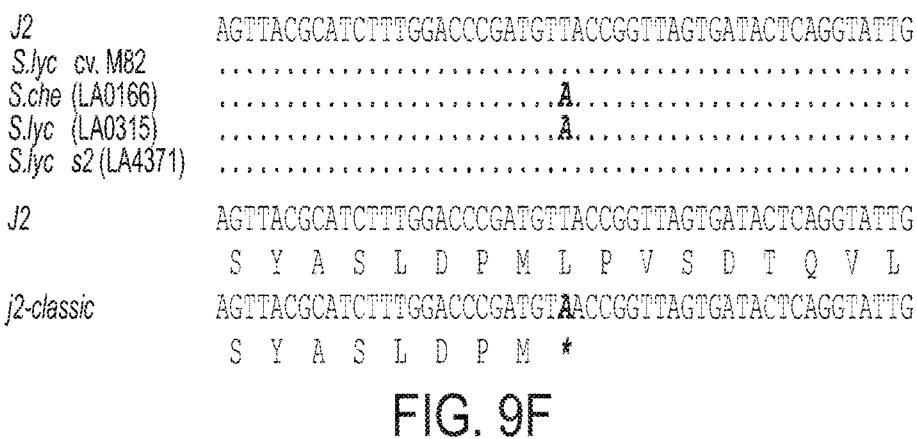
Figure 9G:
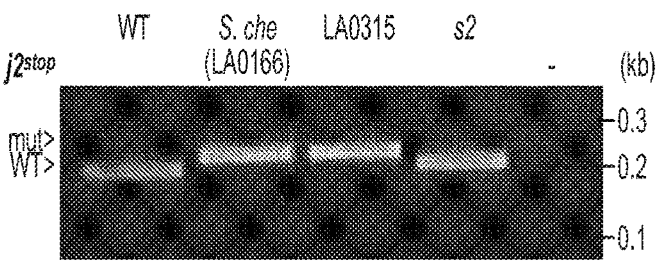
Figure 9H:
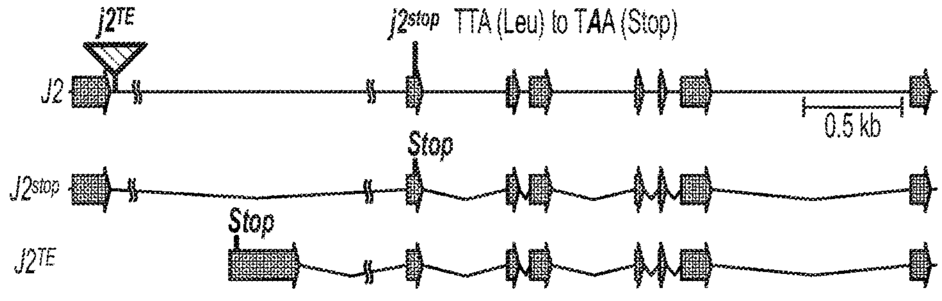

MADS-box transcription factors are known to contribute to pedicel abscission zone development in tomato (Liu et al., 2014; Mao et al., 2000; Nakano et al., 2012; Shalit et al., 2009). The jointless1 mutant (1) was mapped to chromosome 11 and found to be mutated in a homolog of the *Arabidopsis* MADS-box flowering regulator SHORT VEGETATIVE PHASE (SVP) (Hartmann et al., 2000; Mao et al., 2000). Therefore, the ~6 Mbp j2 mapping interval for MADS-box genes was searched, and among the 164 genes in this region only one candidate was found, Solyc12g038510, a homolog of the *Arabidopsis* floral organ identity MADS-box gene SEPALLATA4 (SEP4) (FIG. 2B) (Ditta et al., 2004). Previous transcriptional silencing of Solyc12g038510 resulted in jointless pedicels, but it was suggested Solyc12g038510 and J2 were different genes, because the published j2 mapping interval did not coincide with Solyc12g038510, likely from unreliable centromeric marker resolution (Budiman et al., 2004; Liu et al., 2014). However, the genomic sequencing of s2 and j2 mutants exposed a Copia/Rider-type transposable element (TE) in the first intron of Solyc12g038510 that was absent in WT (FIG. 2C). Furthermore, the s2 RNA-seq revealed that most Solyc12g038510 transcripts initiated in the first intron, resulting in an early nonsense mutation (FIGS. 2D and 9H). To validate that Solyc12g038510 is J2, CRISPR/Cas9 was used to engineer loss-of-function mutations, and the resulting $j2^{CR}$ plants developed jointless unbranched inflorescences (FIGS. 2E and 2F). Moreover, progeny from crossing $j2^{CR}$ with s2-derived j2 had jointless and unbranched inflorescences (FIG. 2G), and sequencing Solyc12g038510 in the original j2 *S. cheesmaniae* accession revealed an early stop codon (FIGS. 9F-9H). Thus, the SEP4 gene Solyc12g038510 is J2, and two natural mutations arose independently (hereafter designated $j2^{TE}$ and $j2^{stop}$) (Reynard, 1961; Rick, 1956a).

Figures 2K, 2L, 2M, 2N:
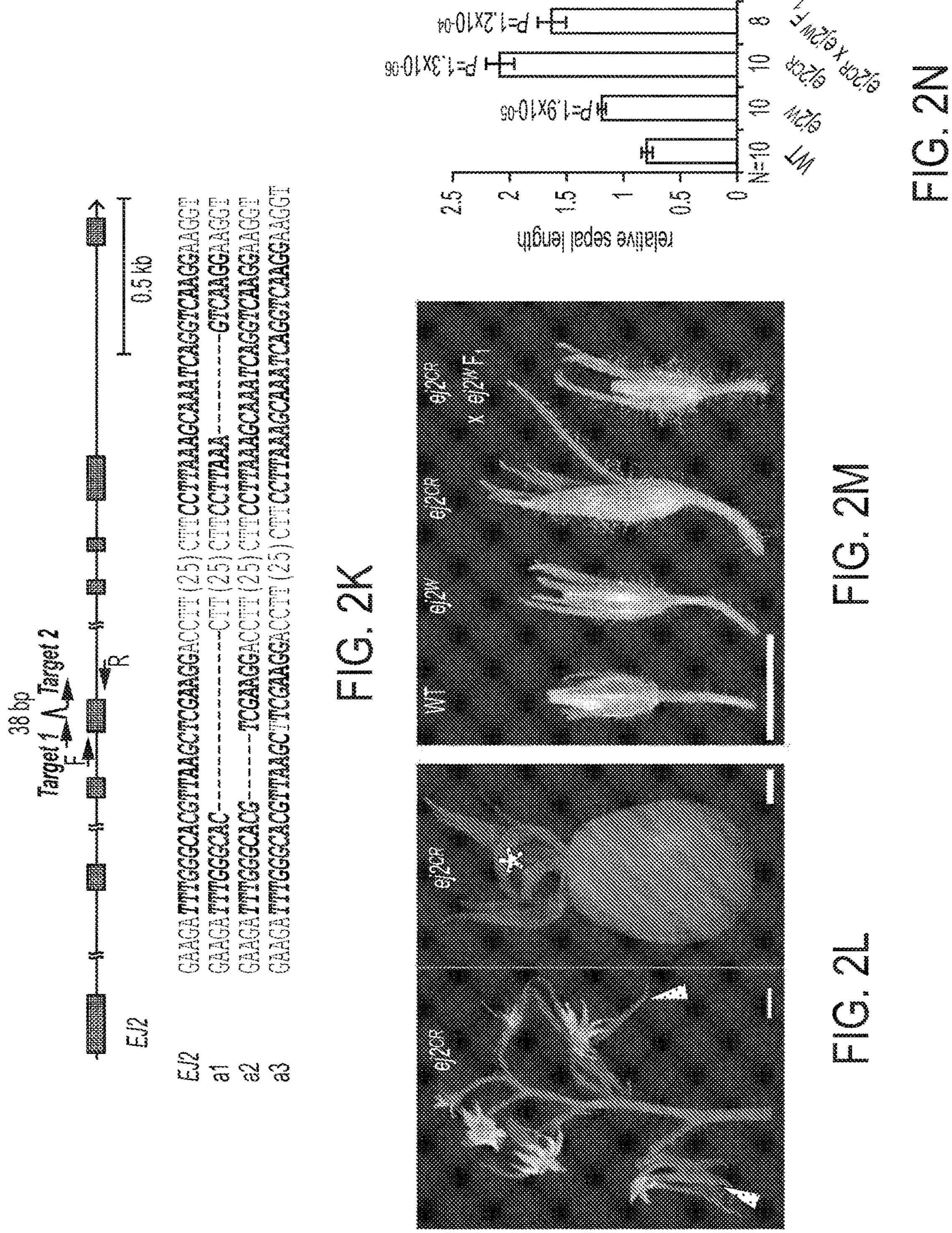
FIG. 2K shows the generation of $ej2^{CR}$ null mutations by CRISPR/Cas9. From top to bottom, sequences correspond to SEQ ID NOs: 94-97.
FIG. 2L shows unbranched $ej2^{CR}$ mutant inflorescences with extremely long sepals (arrowheads) and pear-shaped fruits. Scale bars=1 cm.
FIG. 2M shows unopened flowers showing the weak natural $ej2^{w}$ allele causes longer sepals and fails to complement $ej2^{CR}$.
Figure 9I:
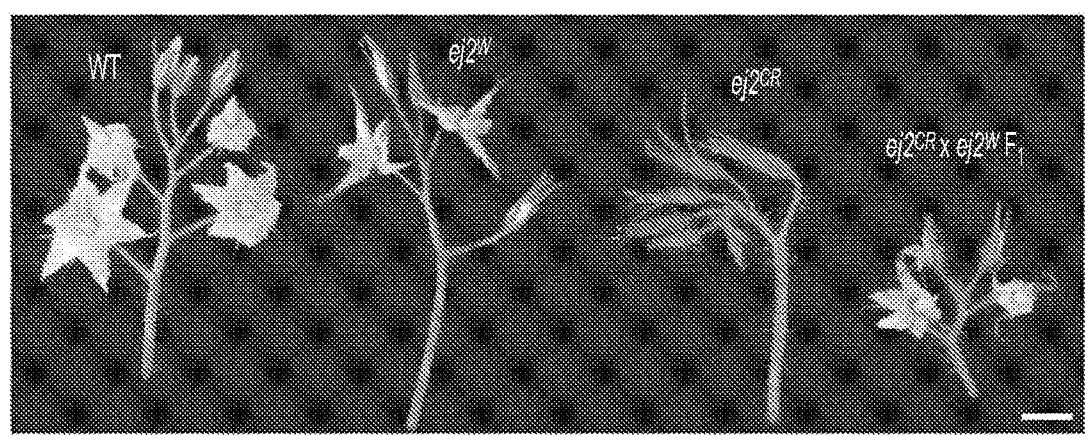

Both j2 and ej2 are required for s2 branching, suggesting the underlying genes function redundantly, similar to SEP genes in *Arabidopsis* that control floral organ identity (Ditta et al., 2004; Pelaz et al., 2000). The 66 genes were searched in the 500 kbp ej2 mapping interval for MADS-box genes and the tandemly arranged Solyc03g114830 and Solyc03g114840 were found (FIG. 2H). Solyc03g114830 is a homolog of *Arabidopsis* FRUITFULL and transcriptional knockdown of this gene causes defects in fruit ripening (Bemer et al., 2012; Wang et al., 2014). The genomic sequencing of s2 mutants did not reveal any Solyc03g114830 coding or noncoding SNPs, or large indels, and s2 fruits ripened normally. In contrast, Solyc03g114840 is another homolog of SEP4, and a 564 bp insertion was found in the 5th intron of s2 mutants, which was absent in WT (FIG. 2I). Notably, RNA-seq reads from s2 revealed a third of Solyc03g114840 transcripts were misspliced, suggesting the insertion caused a partial loss of function (FIG. 2J). To test this and uncover the phenotypic consequences of strong loss of EJ2 function, new alleles were engineered with CRISPR/Cas9 and $ej2^{CR}$ inflorescences were found to be unbranched, but the sepals (outermost leaf-like organs of the flowers) were exceptionally large and fruits were pear-shaped (FIGS. 2K and 2L). To determine if the original ej2 mutation impacted flower and/or fruit morphology, ej2 was backcrossed into M82 and relative sepal length (defined by sepal/petal length ratio) was measured. Notably, whereas there was no obvious change in fruit shape or size, ej2 sepals were 50% longer than WT but shorter than $ej2^{CR}$, consistent with a weak allele (FIGS. 2M, 2N, and 9I). Importantly, flowers of $F_1$ progeny from crossing ej2 and $ej2^{CR}$ also developed long sepals. Thus, Solyc03g114840 is EJ2, and the natural ej2 mutation is a weak loss-of-function allele (hereafter designated $ej2^{w}$).

Figure 9J:
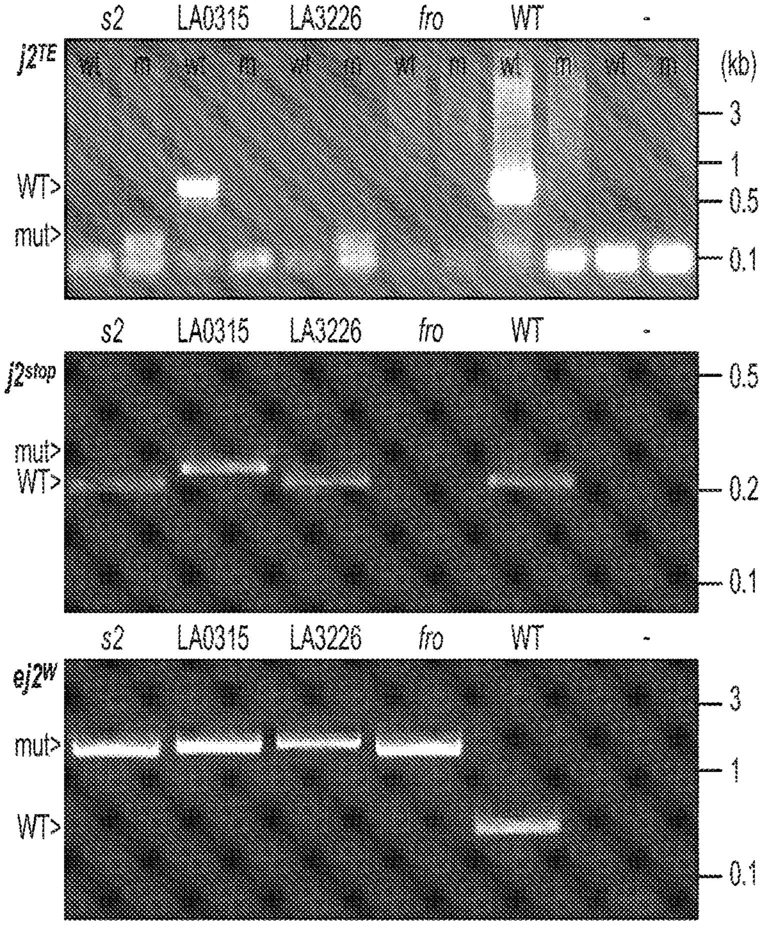

Finally, it was verified that the other s2 accessions carried mutations in both j2 and ej2. PCR genotyping showed all but one accession was double mutant for $ej2^{w}$ and either $j2^{TE}$ or $j2^{stop}$ (FIG. 9J). The last accession was homozygous for $ej2^{w}$, but J2 could not be amplified, consistent with having originated from an X-ray mutagenesis (Stubbe, 1972). Thus, the prolonged meristem maturation underlying s2 inflorescence branching is caused by mutations in two redundantly acting SEP MADS-box genes.

$Ej2^{w}$ Arose During Domestication and Hindered j2 Utilization for Breeding

Figures 3A, 3B:
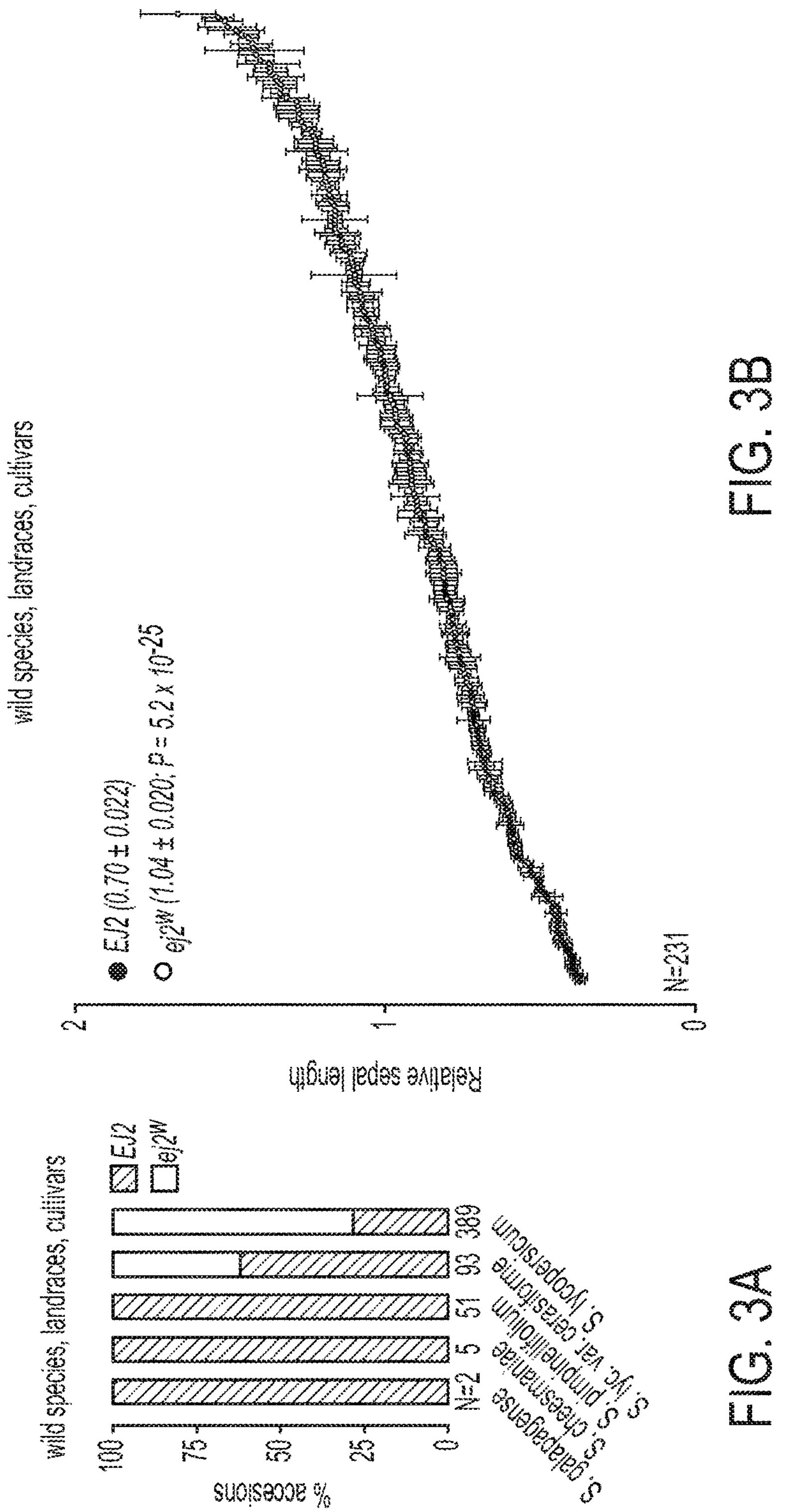
FIGS. 3A-3F show the $ej2^{w}$ variant arose during domestication and was selected during breeding of large-fruited cultivars.

In modern breeding programs, the value of jointless varieties was recognized for their potential to reduce fruit drop and post-harvest damage during mechanical harvesting for the processing tomato industry. Yet, plants carrying j1 yield poorly due to reversion of inflorescences to vegetative growth after developing a few flowers (Butler, 1936; Mao et al., 2000). Thus, j2 was widely favored over the last 50 years of breeding. However, breeders frequently experienced problems with excessive inflorescence branching and low yield upon introducing j2 into different cultivated backgrounds (Robinson, 1980), probably because of negative epistasis with $ej2^{w}$. To determine to what extent $ej2^{w}$ hindered j2 utilization in breeding, 568 wild and domesticated accessions were genotyped from the tomato core collection and more than half were found to be homozygous for the $ej2^{w}$ allele (FIG. 3A). Notably, $ej2^{w}$ was absent from *S. pimpinellifolium*, but 40% of early domesticates (landraces) were homozygous for the mutation, and the percentage doubled in cultivars. Most importantly, $ej2^{w}$ was strongly associated with long sepals, including within a subset of confirmed landraces (Blanca et al., 2015), suggesting selection during domestication (FIGS. 3B-3E). In support of this, $ej2^{w}$ is in close proximity (<46 Kbp) to a previously reported domestication and improvement selective sweep (Lin et al., 2014). Notably, a minor fruit weight QTL (fw3.2) that also arose in the landraces is in close proximity (~85 Kbp) to EJ2 (Chakrabarti et al., 2013; Zhang et al., 2012). Among 62 landraces, accessions were found that carried $ej2^w$ but not fw3.2 ($ej2^w$/FW3.2:7%) and vice versa (EJ2/fw3.2:9%,), suggesting that each mutant allele arose independently and were likely combined early in domestication. It was also found that not all cultivated lines carried both alleles ($ej2^w$/FW3.2:2%; EJ2/fw3.2:11%,), indicating that both mutations were either passed on independently during domestication and improvement, or were co-selected and then separated later by breeding.

Figures 3C, 3D, 3E, 3F:
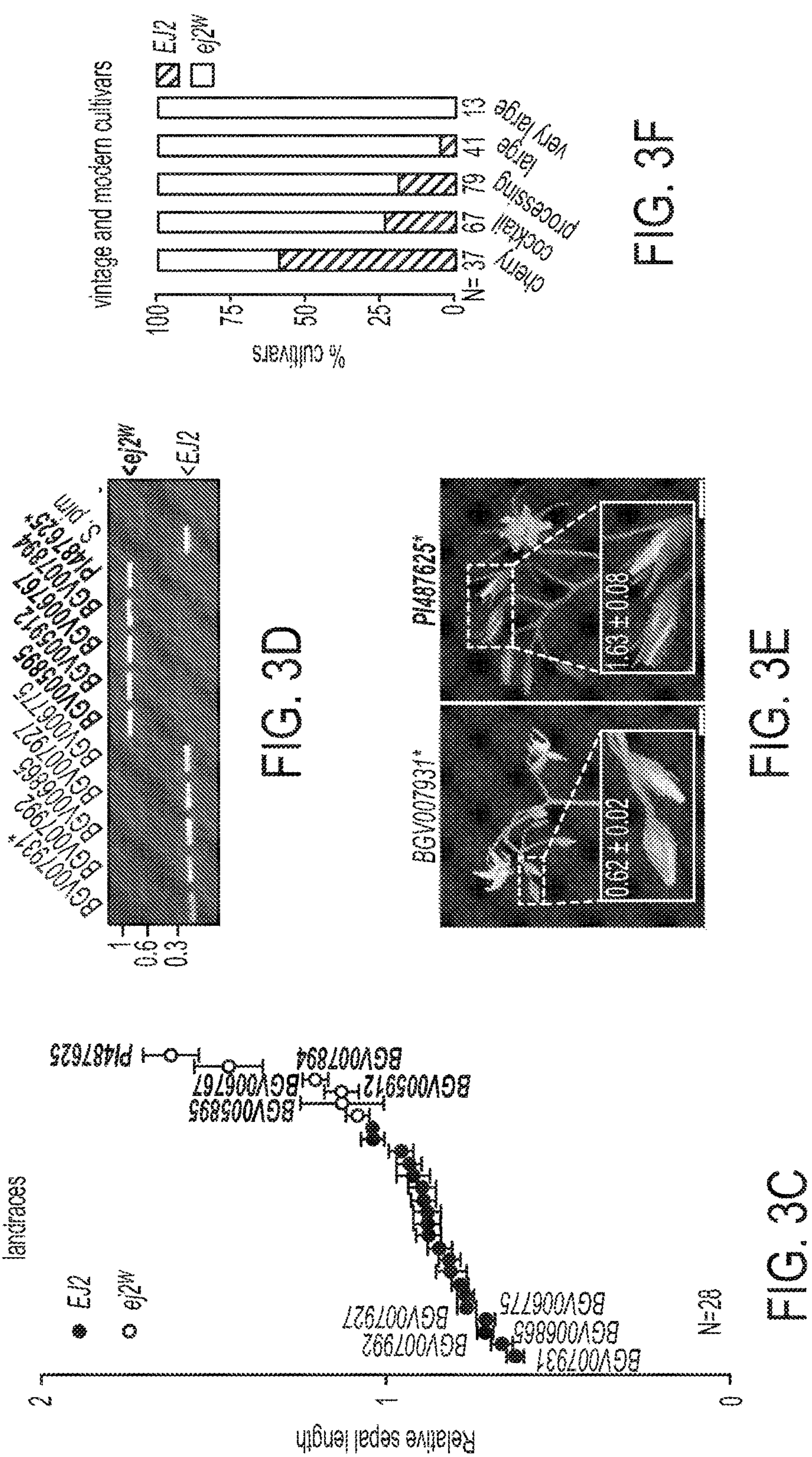
Figures 10A, 10B, 10C:
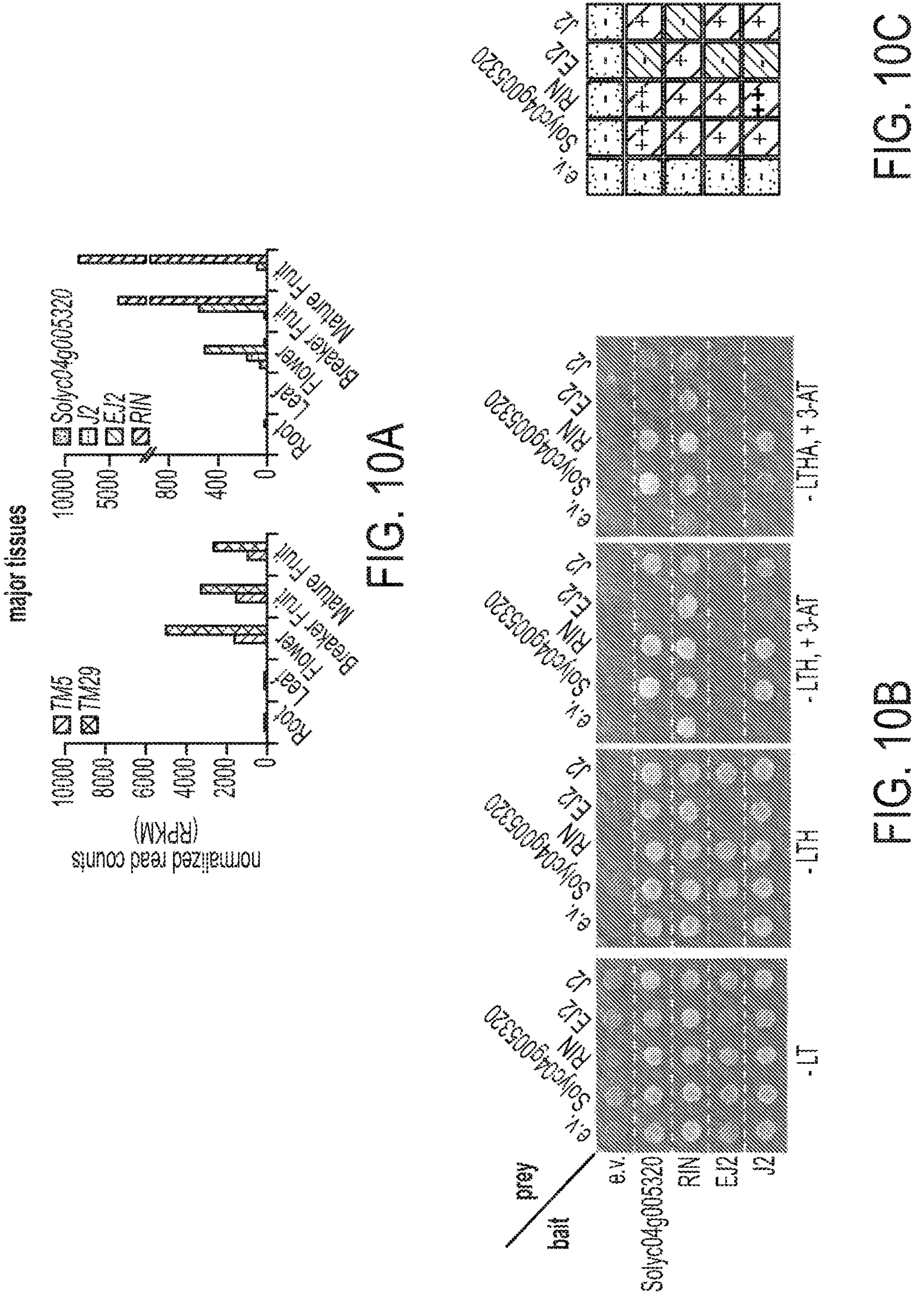
Figure 10G:
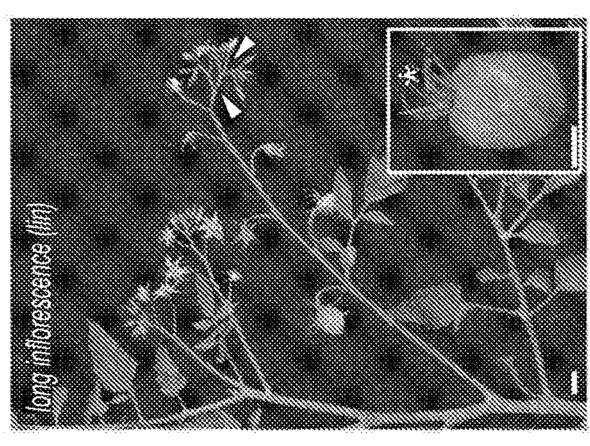
FIG. 10G shows representative lin mutant plant with elongated and weakly branched inflorescences. White arrowheads indicate branch points. Inset shows lin fruit with jointed pedicel.
Figure 10F:
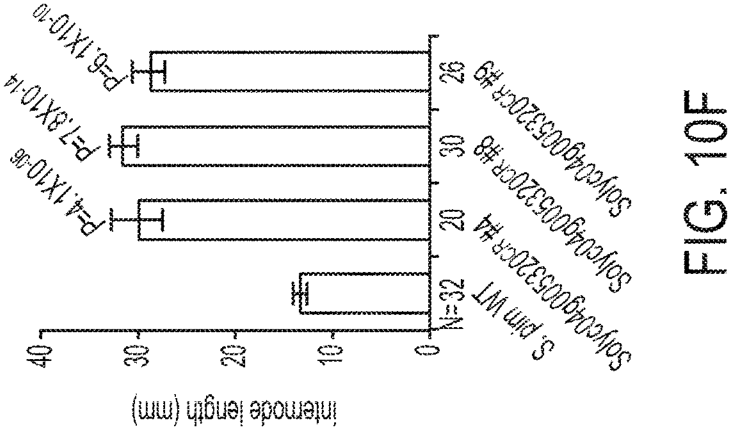
FIG. 10F shows the quantification of internode length between flowers of the same plants as in FIG. 10E. N=number of internodes.
Figure 10E:
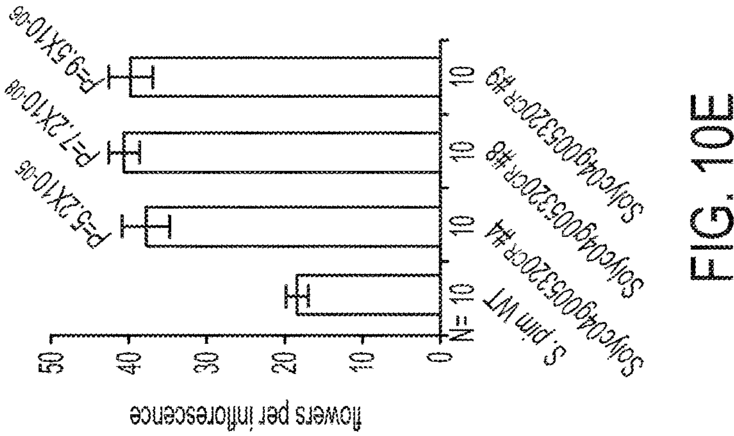
FIG. 10E shows the quantification of flowers per inflorescence for WT and 3 independent $lin^{CR}$ To transgenics. N=number of inflorescences.
Figures 10H, 10I:
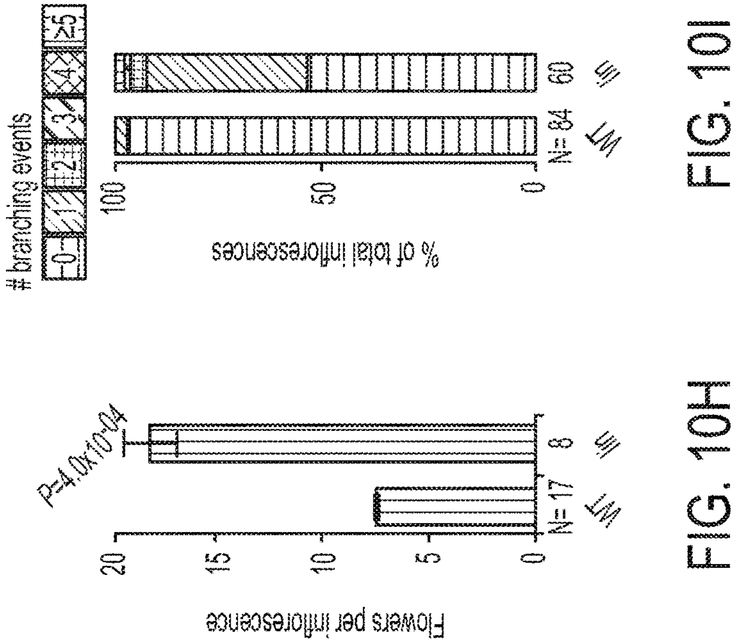
FIG. 10H shows quantification of flowers per inflorescence for WT and lin. N=number of inflorescences.
FIG. 10I shows quantification of inflorescence branching events in WT and lin.

One explanation for the early selection of $ej2^w$ and its subsequent spread in the cultivated germplasm is that larger sepals provided an enlarged calyx that was concomitantly selected as fruit size increased, perhaps with fw3.2. Such a trait would not necessarily have been selected for improved productivity by increasing fruit size or number per se, but instead could have provided improved fruit support, strong local source tissue, or simply aesthetic value for larger fruits. To determine if $ej2^w$ was selected during domestication and breeding of larger fruits, the frequency of the $ej2^w$ allele was evaluated in 258 cultivars representing five fruit sizes ranging from small "cherry" tomatoes (<5 g) to extremely large "beefsteak" varieties (>500 g). Remarkably, the frequency of the allele increased with fruit size, and nearly all (>90%) large-fruited accessions were homozygous for $ej2^w$, including 88% of vintage heirloom cultivars (Male, 1999). These results show that the $ej2^w$ allele was already widespread in larger fruit types before j2 was discovered and adopted in modern breeding (FIG. 3F). Since EJ2 is also expressed in developing fruits (FIG. 10A) and $ej2^{CR}$ fruits are elongated (FIG. 2L), it is also possible the $ej2^w$ allele impacts other fruit traits such as size/shape and/or ripening, especially in the presence of other QTL that impact these traits.

Elite Breeding Germplasm Carries Both $j2^{TE}$ and $Ej2^w$, but Branching is Suppressed Because $ej2^w$ became widespread in tomato germplasm and j2 arose much later, introducing either of the j2 alleles into most cultivars would have resulted in undesirable branching and low yield. However, it was reported these adverse effects could be overcome by breeding (Robinson, 1980). One possibility is that $ej2^w$ was segregated away through crosses. Alternatively, breeders could have identified and selected natural suppressors of branching. To test this, 153 unbranched jointed and jointless elite inbreds and hybrids were obtained from major seed companies and public breeders (see STAR Methods), and genotyped for both mutations. All jointless lines were homozygous for $j2^{TE}$, indicating the allele that arose in the domesticated germplasm was favored in breeding. Since new tomato varieties for processing and fresh-market production are developed in separate breeding programs, it was asked if $j2^{TE}$ was utilized in both. The value of the jointless trait is most recognized for mechanical harvesting of processing types, and in support of this the $j2^{TE}$ allele was present in 74% of sampled processing lines. Although less widespread, $j2^{TE}$ was also found in 34% of fresh-market lines, indicating that $j2^{TE}$ continues to be utilized in both breeding programs.

Figure 4A:
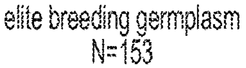
FIGS. 4A-4D show that breeders overcame negative epistasis between j2 and ej2 by selecting suppressors of s2 branching in elite germplasm.
Figure 4A:
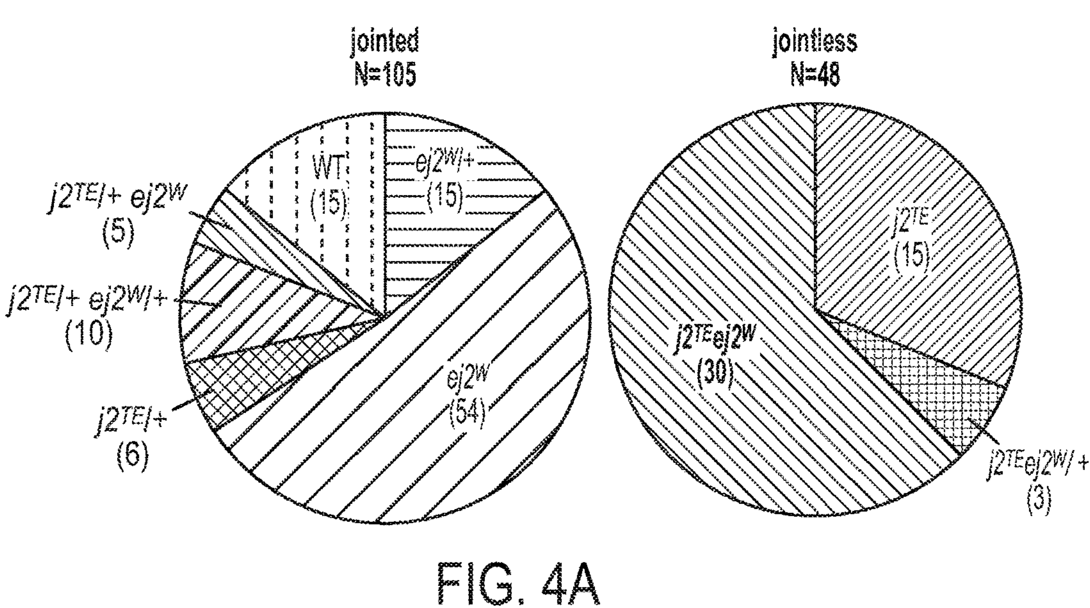
Figure 4B:
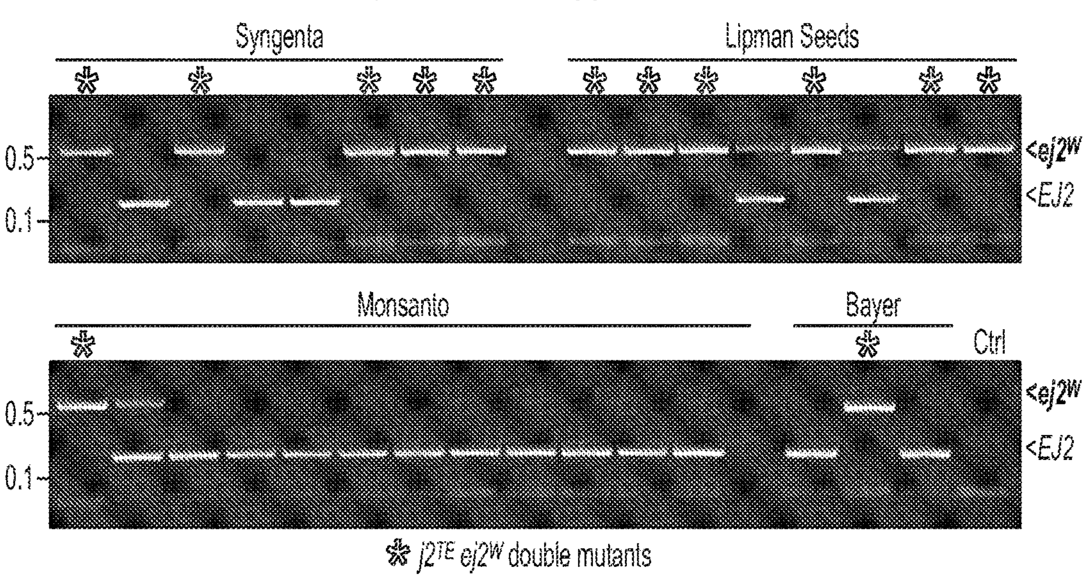
Figure 4C:
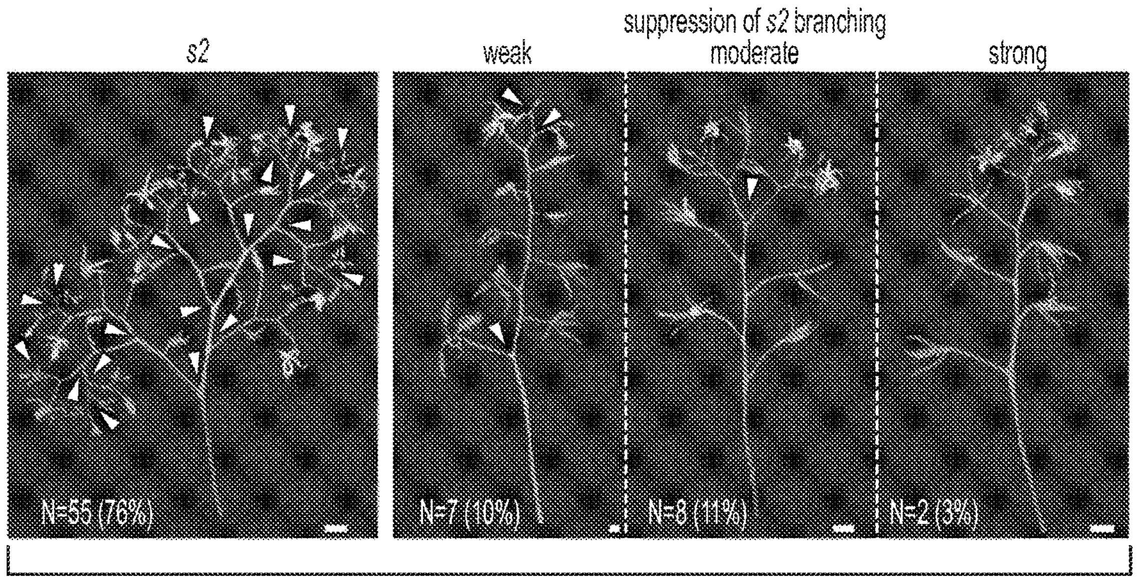
Figure 4D:
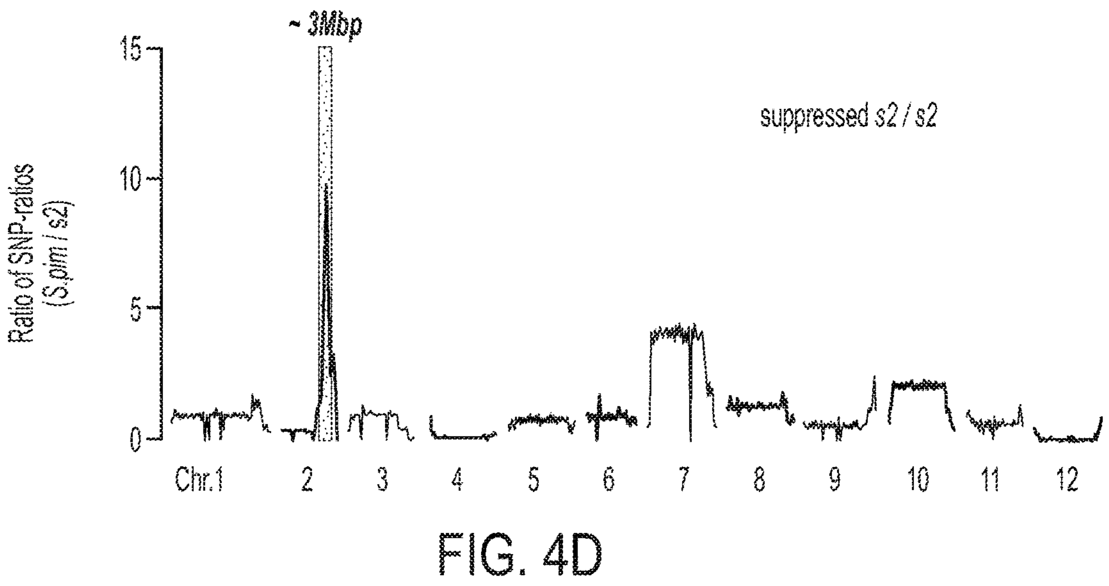

Remarkably, it was found that more than 60% of $j2^{TE}$ homozygotes in both processing and fresh-market lines were also homozygous $ej2^w$ (FIGS. 4A and 4B), supporting the hypothesis that suppressors were selected during improvement. This was reminiscent of the reduced segregation of s2 in the *S. pimpinellifolium* $F_2$ mapping population (FIGS. 9B and 9C). To map potential suppressor loci, 1,536 $F_2$ plants were regrown, and of 92 plants homozygous for both mutations, 24% showed various degrees of suppression (FIG. 4C). Using genome sequencing, one large-effect suppressor was mapped near the end of chromosome 2 in the same region as a previously reported suppressor in the domesticated germplasm (FIG. 4D) (Robinson, 1980). However, given that only a small percentage of $j2^{TE}$ $ej2^w$ $F_2$ plants displayed unbranched inflorescences, additional suppressors from breeding germplasm are likely involved, which together were needed to achieve complete suppression.

Three Meristem Expressed SEP4 Genes Modulate Inflorescence Complexity

The dissection of the negative epistasis underlying s2 branching exposed two tomato SEP4 genes that act redundantly to control meristem maturation and inflorescence development. This led to the question of to what extent these genes work with other tomato SEP family members to regulate inflorescence architecture and flower production, and could have potential for agricultural application. In *Arabidopsis*, a family of four redundant SEP genes is required to establish floral organ identity (Ditta et al., 2004; Pelaz et al., 2000). Tomato has an expanded SEP family of six members (Consortium, 2012), and a phylogenetic analysis of protein sequences showed *Arabidopsis* SEP1, 2, and 3 have two tomato homologs (Solyc05g015750/TM5 and Solyc02g089200/TM29) (FIG. 5A). In contrast, there are four homologs of SEP4, and among them is the RIPENING INHIBITOR (RIN) gene. A classical mutation in RIN blocks ripening and is widely used in hybrid breeding due to a heterozygous dosage effect that causes fruits to remain firm and ripen over a protracted period, improving shelf life (Klee and Giovannoni, 2011; Vrebalov et al., 2002).

To investigate individual and combined roles of tomato SEP genes in inflorescence development, expression patterns were first analyzed using the meristem maturation atlas and transcriptome data from other major tissues (Consortium, 2012; Park et al., 2012). Both TM5 and TM29 (SEP1/2/3 homologs) were expressed only later in reproductive development, beginning in floral meristems and extending into flowers and fruits (FIGS. 5B and 10A), supporting previously characterized roles in floral organ identity (Ampomah-Dwamena et al., 2002; Pnueli et al., 1994). RIN was only expressed in fruits, consistent with its role in ripening (FIG. 10A) (Vrebalov et al., 2002). In contrast, expression of J2, EJ2, and the fourth SEP4 homolog (Solyc04g005320) began earlier, in the TM stage of meristem maturation and in SIMs (FIG. 5B). This suggested Solyc04g005320 could function with J2 and EJ2 in meristem maturation. Moreover, given that *Arabidopsis* SEP redundancy is based on formation of multimeric protein complexes (Theissen et al., 2016), interactions were tested among all four tomato SEP4 proteins in yeast two-hybrid assays and J2, EJ2, and Solyc04g005320 were found to interact with each other and themselves, except for homomeric EJ2. These results validated previous findings (Leseberg et al., 2008), and further revealed that J2 and EJ2 interact with each other, supporting redundancy in the control of meristem maturation and inflorescence architecture (FIGS. 5C, 5D, 10B and 10C).

Figure 5E:
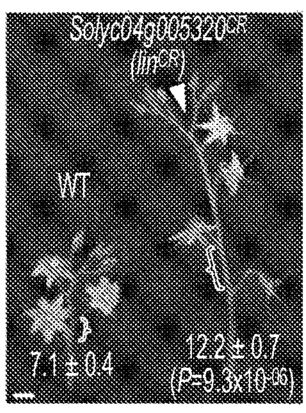

To test if Solyc04g005320 contributes to inflorescence architecture and flower production, CRISPR/Cas9 was used to engineer plants with null mutations, which resulted in exceptionally long inflorescences with nearly twice as many flowers as WT and longer internodes (FIGS. 5E and 10D). Weak branching late in inflorescence development was also frequently observed. Whether similar effects occur in genotypes that already have long inflorescences was tested by mutating Solyc04g005320 in *S. pimpinellifolium*, which produces 15-20 flowers on each inflorescence. Remarkably, internode length and flower number doubled (FIGS. 5F, 10D-10F). These phenotypes were reminiscent of a gamma-irradiation mutant designated long inflorescence (lin) that was previously mapped to an interval on chromosome 4 containing Solyc04g005320 (FIGS. 10G-10J)(see STAR Methods). Sequencing Solyc04g005320 from the lin mutant revealed a translocation in the first intron that eliminated transcription (FIGS. 10J-10L, also referred to herein as $lin^{trans}$), and crosses with a CRISPR allele failed to complement the long inflorescence phenotype.

Figure 5G:
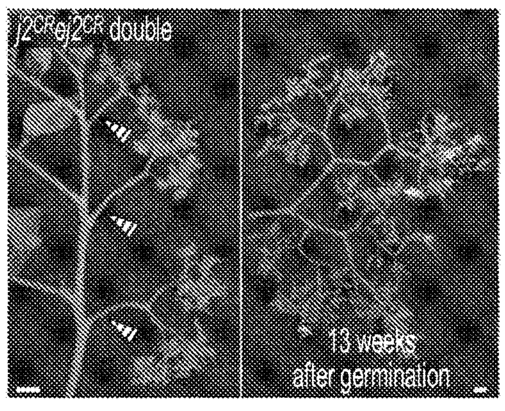
Figure 5F:
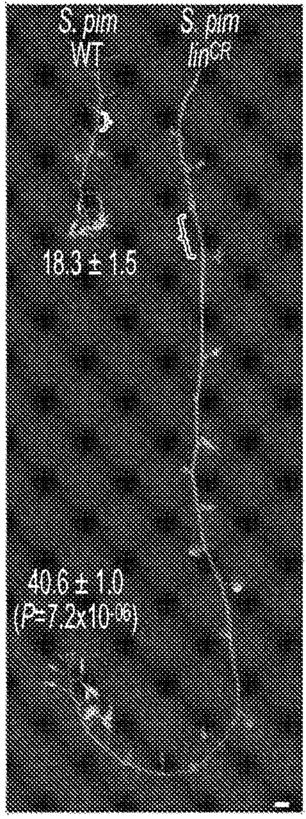
Figure 5H:
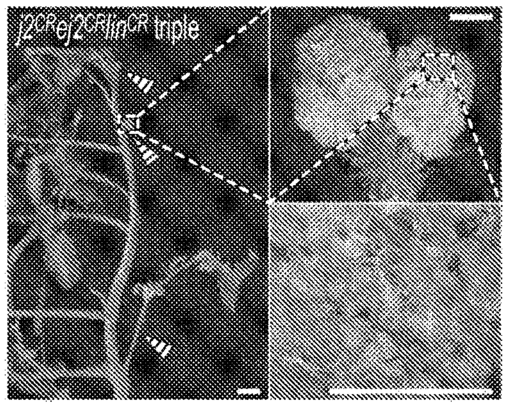
Figure 5I:
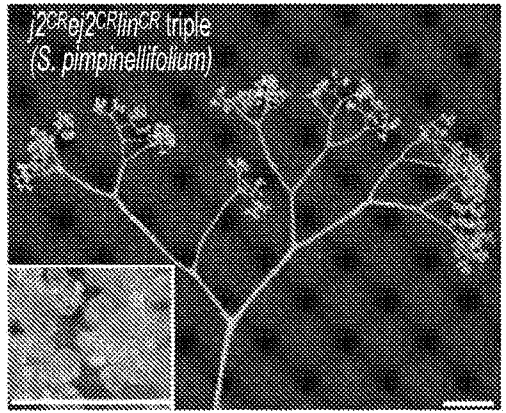
Figure 10N:
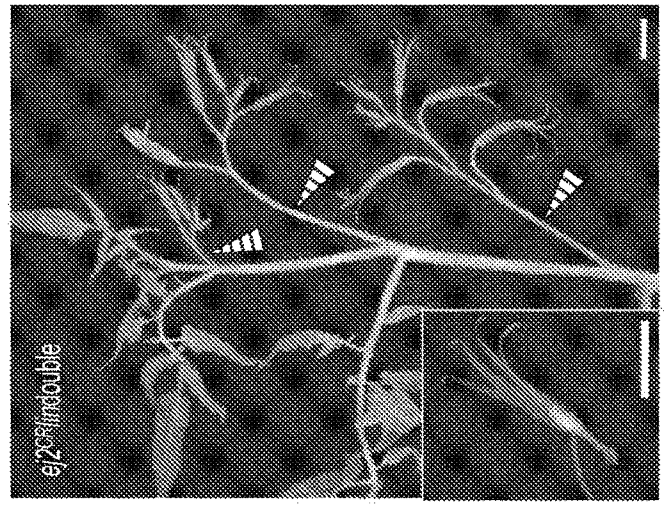
FIG. 10N shows $ej2^{CR}$ lin double mutant with long inflorescences, extremely enlarged sepals, and inner floral organ defects (inset).
Figure 10M:
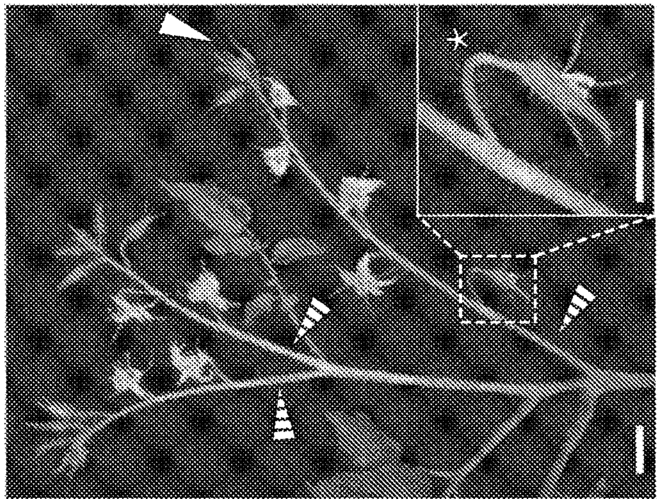
FIG. 10M shows $j2^{CR}$ lin double mutant with elongated, weakly branched inflorescences and jointless pedicel (white asterisk). White arrowheads mark branch points.
Figure 10O:
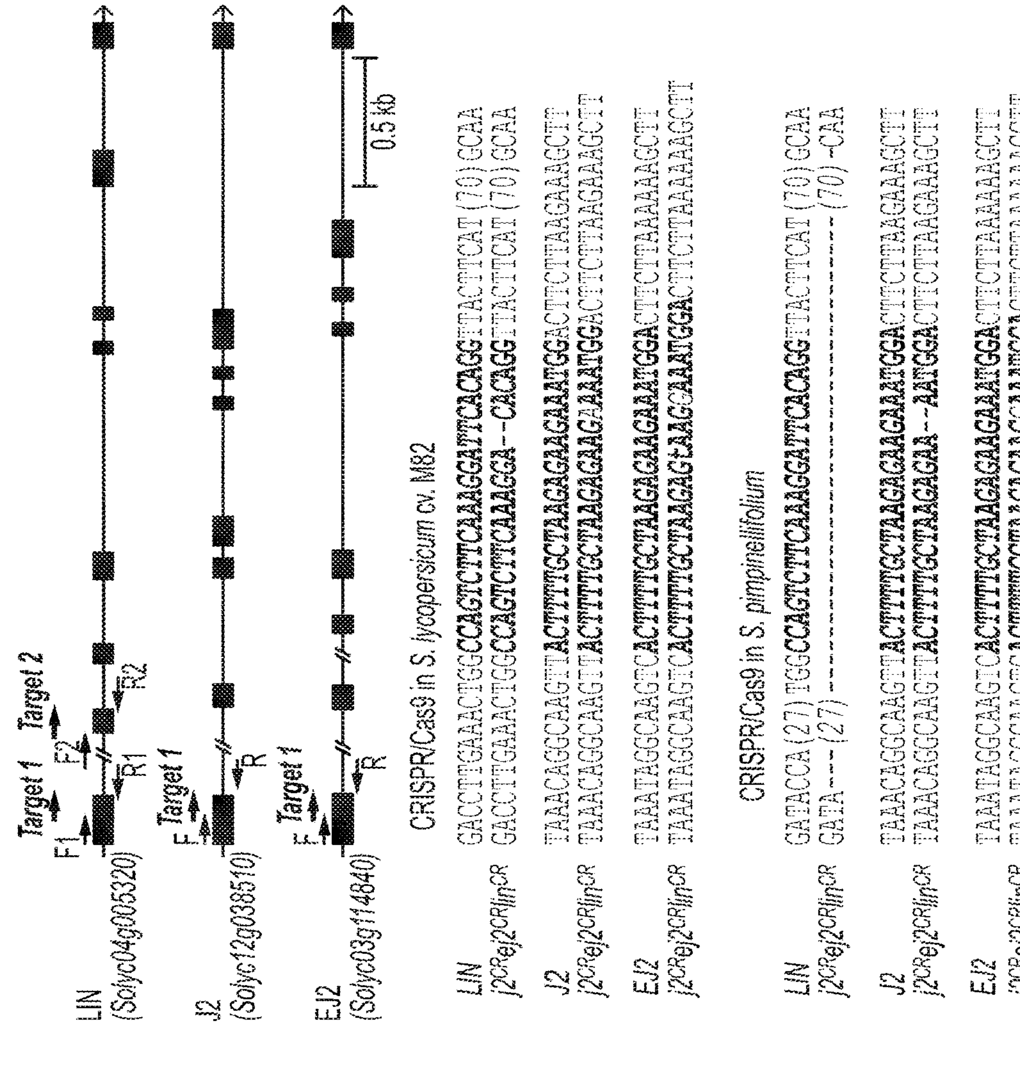
FIG. 10O shows simultaneous targeting of LIN, J2 and EJ2 by CRISPR/Cas9 with two single-guide RNAs. sgRNA, Target 1 and Target 2 on each respective gene model is shown. Note that sgRNA-1 targets all three genes. Black arrows indicate forward (F) and reverse (R) primers used for PCR genotyping and sequencing (see STAR Methods). Sequencing results of second-generation ($T_1$) transgenic j2$^{CR}$ ej2$^{CR}$ lin$^{CR}$ triple mutant plants generated in M82 (top) and *S. pimpinellifolium* (bottom). All three genes carry homozygous mutations. From top to bottom, sequences correspond to SEQ ID NOs: 113-124.
Figures 10P, 10Q, 10R, 10S:
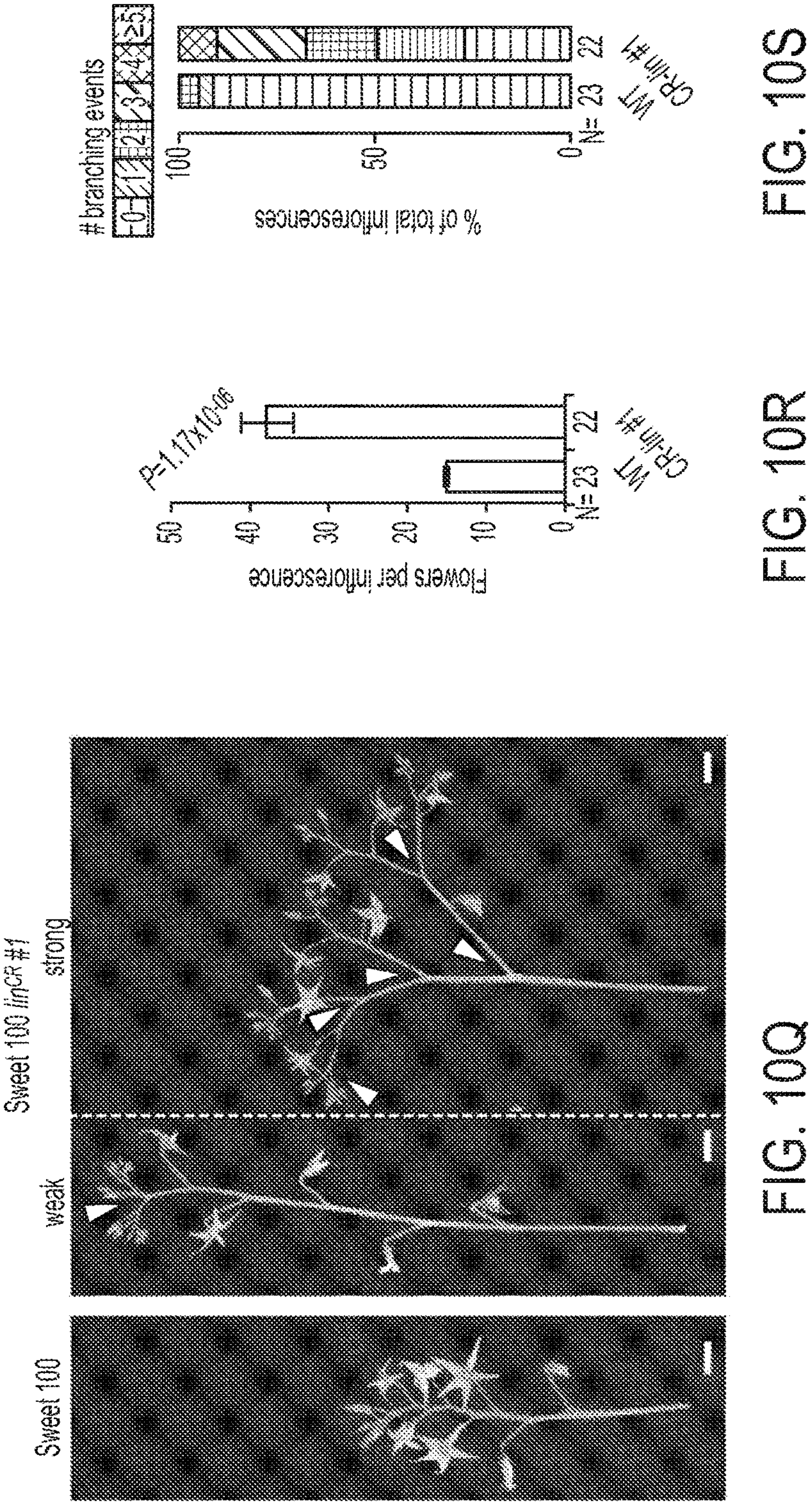

The increase in inflorescence complexity in lin mutants is modest compared to j2 $ej2^{w}$ double mutants. To study the extent of redundancy and potential dosage relationships among the three genes, strong alleles were used in the same background to create all combinations of higher-order mutants (see STAR Methods). Whereas $j2^{CR}$ was largely additive with lin (FIG. 10M), $ej2^{CR}$ and lin were synergistic for floral organ development; double-mutants had long inflorescences with more flowers that developed extremely enlarged sepals, but inner floral organs did not fully develop and fruits failed to form (FIG. 10N). As expected, $j2^{CR}$ and $ej2^{CR}$ were also synergistic, but unlike the moderately branched, highly floral inflorescences of the original $j2^{TE/stop}$ $ej2^{w}$ natural double mutants (s2), inflorescences from $j2^{CR}$ $ej2^{CR}$ plants were extraordinarily branched and rarely produced normal fertile flowers (FIG. 5G). Finally, combining all three mutants resulted in massively overproliferated SIMs without forming flowers (FIGS. 5H and 10O). The same effect was observed in *S. pimpinellifolium* $j2^{CR}$ $ej2^{CR}$ $lin^{CR}$ plants (FIGS. 5I and 10O). The sequences for *S. pimpinellifolium* $j2^{CR}$ $ej2^{CR}$ $lin^{CR}$ are shown below. Thus, J2 and EJ2 have distinct roles in floral development, but all three SEP4 genes have overlapping roles in meristem maturation and inflorescence development.

Figure 6A:
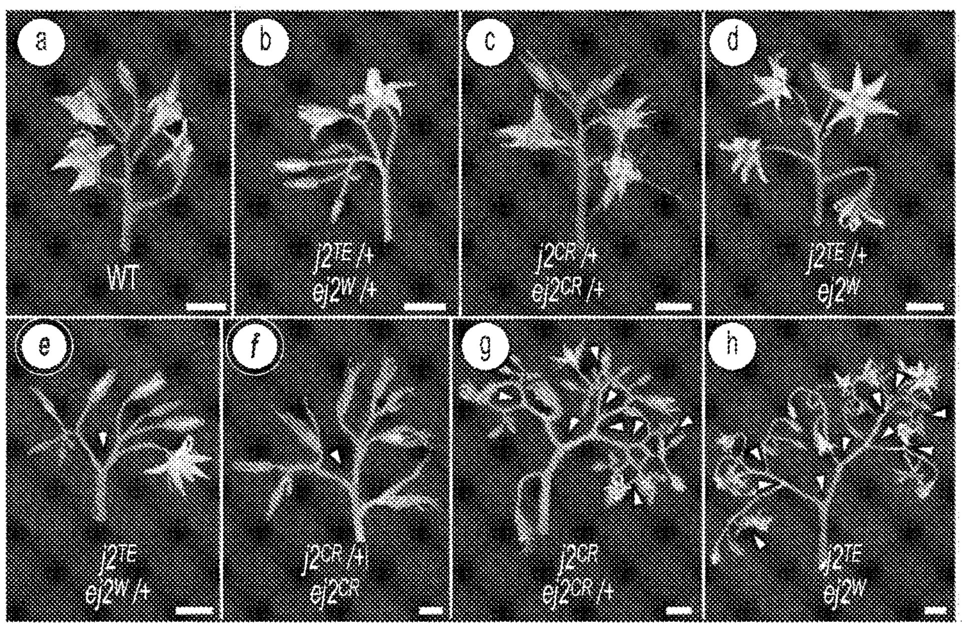
FIGS. 6A-6D show the exploiting dosage effects of key meristem maturation genes to improve flower production and fruit yield.
Figure 6B:
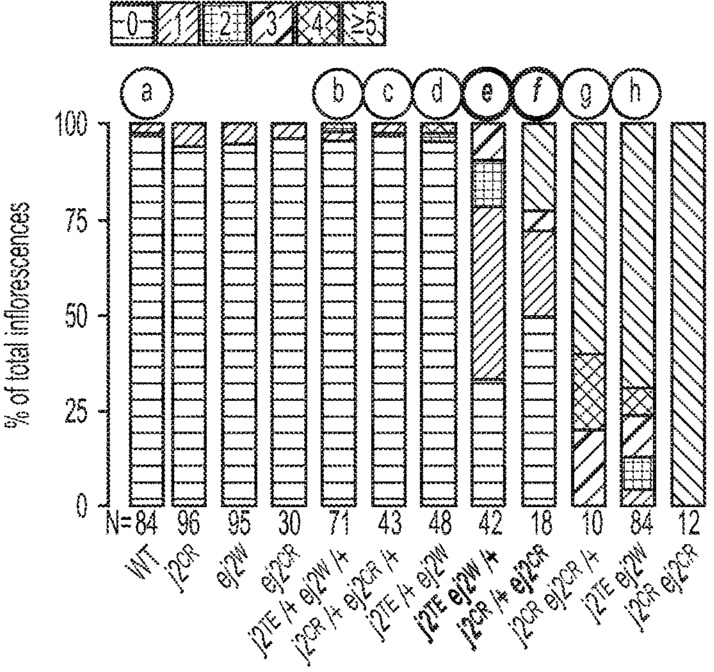
Figure 6C:
Figure 6C:
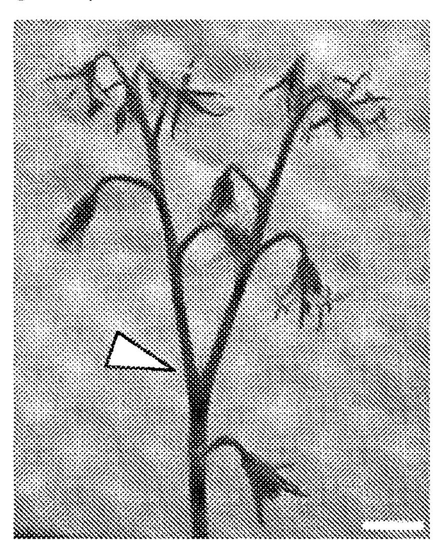
Figure 6D:
Figure 6D:
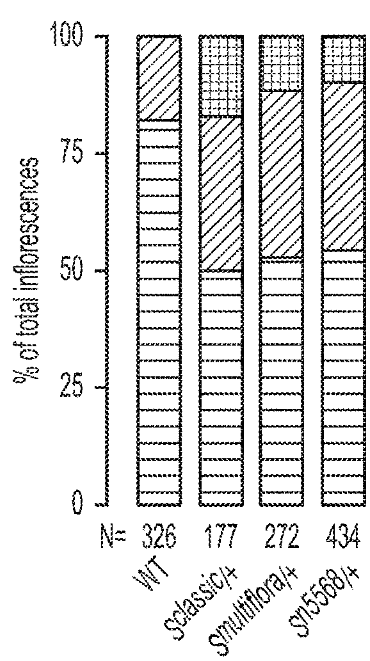

Dosage of Meristem Maturation Transcription Factors can be Exploited to Improve Inflorescence Architecture and Yield The individual and combined mutations in J2, EJ2, and LIN provided a series of three forms of increased inflorescence complexity ranging from weak (lin single mutants) to extremely severe (j2 ej2 lin triple mutants), indicating quantitative relationships among these SEP4 genes. It was previously demonstrated that dosage relationships among genes in the florigen pathway could be exploited to create a quantitative range of plant architectures that translated to improved productivity in determinate field-grown tomatoes (Park et al., 2014b; Soyk et al., 2016). It was reasoned that dosage sensitivity could be similarly used to fine-tune inflorescence architecture and flower production. To test this, a series of homozygous and heterozygous combinations of j2 strong alleles with $ej2^{w}$ or $ej2^{CR}$ in the isogenic M82 background was first created (FIGS. 6A and 6B). All double heterozygotes (e.g. j2/+$ej2^{w}$/+; j2/+$ej2^{CR}$/+) and plants heterozygous for j2 and homozygous for $ej2^{w}$ (j2/+$ej2^{w}$) produced unbranched inflorescences like the single mutants. In contrast, heterozygosity for $ej2^{w}$ in a j2 background (j2 $ej2^{w}$/+) conferred weak branching, as did j2/+$ej2^{CR}$. Notably, heterozygosity for the null $ej2^{CR}$ allele in the null j2 background (@2 $ej2^{CR}$/+) resulted in branching that matched s2 inflorescences (@2 $ej2^{w}$), further validating that $ej2^{w}$ is a weak allele and confirming a sensitive dosage relationship between these genes. Given these results, it was reasoned that other meristem maturation regulators might have similar dosage-sensitivity on inflorescence architecture and this was tested with S, a member of the WOX protein family (Graaff et al., 2009; Lippman et al., 2008). Indeed, plants heterozygous for three s mutant alleles were also mildly branched (FIGS. 6C and 6D), demonstrating dosage-sensitivity of independent meristem maturation genes allows for quantitative tuning of inflorescence architecture.

Discussion

Dose-Dependent Quantitative Variation, Weak Alleles, and Crop Improvement

This study involved exploration of the potential of genes and alleles underlying natural variation in inflorescence complexity to improve productivity. By analyzing the s2 branching variant, it was found that multiple members of the SEP4 subfamily of tomato MADS-box genes play critical redundant roles in modulating meristem maturation and inflorescence architecture. The first MADS-box family member involved in tomato domestication was further described, highlighting the growing significance of this transcription factor family in contributing to domestication and improvement of diverse crops (Singh et al., 2013; Vrebalov et al., 2002; Zhao et al., 2011). By dissecting interactions between meristem expressed SEP4 genes dosage relationships were uncovered among an allelic series of MADS-box mutations with potential for breeding. This collection of alleles, including mutations in S, comprises a toolkit to manipulate inflorescence architecture, which can now be expanded to additional regulators of meristem maturation, such as LIN. To demonstrate this, CRISPR/Cas9 was used to target LIN in the elite cherry tomato cultivar Sweet 100 and mutant lines were generated with moderately branched inflorescences and increased flower production (FIGS. 10P-10S).

The present approach for creating desirable phenotypic variation in major yield traits relies on combining specific heterozygous and homozygous mutations to obtain a quantitative range of dosage effects (Park et al., 2014b). However, exploiting gene dosage may be limited by the availability of weak alleles that confer quantitative trait modifications. For example, longer sepals and weak branching were achieved through different levels of reduced EJ2 dosage from homozygosity and heterozygosity for $ej2^{w}$, respectively. In nature, similar dosage effects often arise from mutations in transcriptional control regions (e.g., in cis-regulatory DNA). Such alleles were widely favored in crop domestication and improvement for their subtle phenotypic changes compared to null alleles that frequently display deleterious pleiotropic effects (Meyer and Purugganan, 2013; Purugganan and Fuller, 2009). For example, increased fruit size during tomato domestication depended in part on transcriptional alleles of multiple components in the classical CLAVATA-WUSCHEL stem cell circuit (Xu et al., 2015). A potentially powerful approach to engineer novel weak alleles that are being explored (Swinnen et al., 2016) is exploiting gene-editing technology to mutate cis-regulatory control regions of productivity genes. A promising target identified in this study is LIN. CRISPR/Cas9-induced weak transcriptional alleles that confer reduced LIN expression may provide subtle increases in flower production, which may be especially valuable in large-fruited cultivars where branching often negatively impacts fruit weight and yield. Notably, a rice homolog of LIN and other meristem maturation genes control panicle architecture and grain production (Kobayashi et al., 2010, 2012; Liu et al., 2013), suggesting the present findings have broad agricultural potential. New gene-editing tools should enable the engineering of diverse types and strengths of alleles that can provide customized gene dosage effects to improve a wide range of agronomic traits in many crops.

Epistasis in Evolution, Domestication, and Breeding

Progress in breeding is largely driven by loci with predictable additive effects. For example, the majority of flowering time variation in maize is determined by thousands of small additive quantitative trait loci (QTL) (Buckler et al., 2009), and the same is true for traits in other crops (Doust et al., 2014; Gao et al., 2015). Yet, epistatic interactions, both positive and negative, are also important in breeding, particularly when working with disparate germplasm. For example, interactions between interspecific quantitative trait loci (QTL) in rice can improve aluminum tolerance (Famoso et al., 2011), whereas stacking multiple wild species-derived QTL affecting the same yield traits in tomato results in less-than-additive or "diminishing returns" epistasis (Eshed and Zamir, 1996).

In recent years, several cases of negative epistasis have emerged in diverse organisms involving clashes between newly evolved and established alleles, or upon bringing together distinct genomes, either through natural or artificial means. Examples include compromised fitness gains upon combining interacting alleles in bacteria and yeast (Chou et al., 2011; Heck et al., 2006; Khan et al., 2011; Kvitek and Sherlock, 2011), hybrid necrosis between distinct accessions of *Arabidopsis* (Chae et al., 2014), and loss of protection from malaria in humans when two common resistance variants are co-inherited (Williams et al., 2005). Compared to negative epistasis in evolution and natural selection, the intense artificial selection imposed by humans during domestication and breeding could drive more frequent occurrences of epistasis. While dramatic cases like the one described in this study could be overcome through selection against interactions or suppression with modifiers, there may be many undiscovered negative interactions in agriculture with more subtle phenotypic consequences that may remain challenging to detect and dissect until high throughput quantitative phenotyping platforms (phenomics) and power in genome-wide association studies (GWAS) improves.

The present dissection of the extreme negative epistasis underlying the s2 branching syndrome has highlighted an underappreciated challenge for the next generation of crop breeding. Specifically, using rapidly advancing gene-editing technologies to introduce precise novel allelic variation for specific genes into existing germplasm may not provide desirable phenotypic outcomes, and could potentially result in negative consequences due to interactions with alleles selected and stabilized during domestication and early breeding (Mackay, 2013). That the present example of negative epistasis involved two closely related MADS-box genes suggests that engineering new alleles in gene families or related developmental pathways that already played a role in domestication and improvement may be particularly sensitive to unexpected epistatic consequences, perhaps explaining other as yet uncharacterized examples of negative epistasis in agriculture (Bomblies and Weigel, 2007; Matsubara et al., 2015; Shang et al., 2016; Zhang et al., 2011). Elucidating, neutralizing, and potentially exploiting negative epistasis, as done in the present study, could have a significant impact in helping break productivity barriers in breeding of both plants and animals.

TABLE 2

Oligos used in this study

Yeast two-hybrid assays

| Gene name | Gene ID | Forward primer | Reverse primer | Restr. enzyme |
|---|---|---|---|---|
| LIN | Solyc04 g005320 | CACCGAATTCA TGGGAAGAGGT AAGGTAGAA (SEQ ID NO: 17) | TTCGGATCCTCA AAGCATCCATCC TGGTAA (SEQ ID NO: 18) | EcoRI + BamHI |
| J2 | Solyc12 g038510 | CACCGAATTCA TGGGAAGAGGA AGAGTAGAAC (SEQ ID NO: 19) | TTCGGATCCTTA GAGCATCCACCC TGGAAT (SEQ ID NO: 20) | EcoRI + BamHI |
| EJ2 | Solyc03 g114840 | CACCGAATTCA TGGGAAGAGGA AGAGTTGAG (SEQ ID NO: 21) | TTCGGATCCTTA AAGCATCCATCC ATGAATAAATC (SEQ ID NO: 22) | EcoRI + BamHI |
| RIN | Solyc05 g012020 | CACCGAATTCA TGGGTAGAGGG AAAGTAGAA (SEQ ID NO: 23) | TTCGGATCCTCA AAGCATCCATCC AGGTACA (SEQ ID NO: 24) | EcoRI + BamHI |

Natural and induced mutant alleles analyzed in this study, and respective genotyping markers

| Gene name | Gene ID | Forward primer | Reverse primer | Allele name | Type | WT | Mutent | Restr. enzyme |
|---|---|---|---|---|---|---|---|---|
| LIN | Solyc04 g005320 | GCAAAACTTTA AATTAGTTCTA AATG (SEQ ID NO: 25) | CTTTTTGATTCA TGTGTCTGTAC (SEQ ID NO: 26) | lin | indel | 396 | — | — |

TABLE 2-continued

| Oligos used in this study | | | | | | | | |
|---|---|---|---|---|---|---|---|---|
| LIN | Solyc04 g005320 | AATATCGTGTT AGAATGTGACA C (SEQ ID NO: 27) | CTTTTTGATTCA TGTGTCTGTAC (SEQ ID NO: 28) | lin | indel | — | 358 | — |
| J2 | Solyc12 g038510 | TTACTTTTGCT AAGAGAAGAAA TGG (SEQ ID NO: 29) | CCGTCCTTTCTG TTTGTAGC (SEQ ID NO: 30) | j2-TE | Indel | — | 193 bp | — |
| J2 | Solyc12 g038510 | TTACTTTTGCT AAGAGAAGAAA TGG (SEQ ID NO: 31) | GAATCCACTTAA GAATCTCTACC (SEQ ID NO: 32) | j2-TE | Indel | 709 bp | — | — |
| J2 | Solyc12 g038510 | TATTGTGATAT GTAGAGTGGTG C (SEQ ID NO: 33) | AATACCTGAGTA TCACTAACCGTT (SEQ ID NO: 34) | j2- classic | dCAPS | 206 bp + 24 bp | 230 bp | HpaI |
| EJ2 | Solyc03 g114840 | CACAATTCATG CTGGATCAGC (SEQ ID NO: 35) | CGGAGTAATCTA TTAGATTCTGC (SEQ ID NO: 36) | ej2-w | Indel | 177 bp | 738 bp | — |
| LIN | Solyc04 g005320 | CCTTTAATAAG TTGAAAATCCC TC (SEQ ID NO: 37) | TTGAAGGTGCAT AGAACATACC (SEQ ID NO: 38) | CR-lin- a1 | Indel | 855 bp | 1390 bp | — |
| LIN | Solyc04 g005320 | CCTTTAATAAG TTGAAAATCCC TC (SEQ ID NO: 39) | TTGAAGGTGCAT AGAACATACC (SEQ ID NO: 40) | CR-lin- a2 | CAPS | 796 bp + 59 bp | 855 bp | HincII |
| J2 | Solyc12 g038510 | ATATTGAATCG TGTGATTGTCT C (SEQ ID NO: 41) | TAACTTTCTTCA AAGATGCATCC (SEQ ID NO: 42) | CR-j2- a1 | Indel | 316 bp | 411 bp | — |
| J2 | Solyc12 g038510 | ATATTGAATCG TGTGATTGTCT C (SEQ ID NO: 43) | TAACTTTCTTCA AAGATGCATCC (SEQ ID NO: 44) | CR-j2- a2 | CAPS | 316 bp | 178 bp + 139 bp | MboII |
| EJ2 | Solyc03 g114840 | AATATGGTCCT TATGTCCAACC (SEQ ID NO: 45) | TAGCAAACTTAT TGGGCTAGC (SEQ ID NO: 46) | CR-ej2- a1 | Indel | 236 bp | 211 bp | — |
| EJ2 | Solyc03 g114840 | AATATGGTCCT TATGTCCAACC (SEQ ID NO: 47) | TAGCAAACTTAT TGGGCTAGC (SEQ ID NO: 48) | CR-ej2- a2 | CAPS | 236 bp | 144 bp + 94 bp | HindIII |
| Cas9 | — | CTGACGTAAGG GATGACGCAC (SEQ ID NO: 49) | CATCTCATTACT AAAGATCTCC (SEQ ID NO: 50) | — | T- DNA | — | 446 bp | — |

RT-PCR

| Gene name | Gene ID | Forward primer | Reverse primer |
|---|---|---|---|
| LIN | Solyc04 g005320 | ATGGGAAGAGG TAAGGTAGAA (SEQ ID NO: 51) | TCAAAGCATCCA TCCTGGTAAA (SEQ ID NO: 52) |
| J2 | Solyc12 g038510 | ATGGGAAGAGG AAGAGTAGAAC (SEQ ID NO: 53) | TTAGAGCATCCA CCCTGGAAT (SEQ ID NO: 54) |

TABLE 2-continued

| Oligos used in this study | | | | |
|---|---|---|---|---|
| EJ2 | Solyc03g114840 | ATGGGAAGAGGAAGAGTTGAG (SEQ ID NO: 55) | TTAAAGCATCCATCCATGAATAAATC (SEQ ID NO: 56) | |
| UBI | Solyc01g056940 | CGTGGTGGTGCTAAGAAGAG (SEQ ID NO: 57) | ACGAAGCCTCTGAACCTTTC (SEQ ID NO: 58) | |
| CRISPR/Cas9 genome-editing | | | | |
| sgRNA name | Gene ID | Forward primer | Reverse primer | sgRNA sequence |
| LIN-sgRNA-1 | Solyc04g005320 | TGTGGTCTCAATTTTCTAGTATGTCTGATACACGTTTTAGAGCTAGAAATAGCAAG (SEQ ID NO: 59) | TGTGGTCTCAAGCGTAATGCCAACTTTGTAC (SEQ ID NO: 60) | TTCTAGTATGTCTGATACAC (SEQ ID NO: 81) |
| LIN-sgRNA-2 | Solyc04g005320 | TGTGGTCTCAATTGGAACAGCTTGAGCGTCAACGTTTTAGAGCTAGAAATAGCAAG (SEQ ID NO: 61) | TGTGGTCTCAAGCGTAATGCCAACTTTGTAC (SEQ ID NO: 62) | GGAACAGCTTGAGCGTCAAC (SEQ ID NO: 82) |
| J2-sgRNA-1 | Solyc12g038510 | TGTGGTCTCAATTAGCTCCTTCAACGTTCTCAAGTTTTAGAGCTAGAAATAGCAAG (SEQ ID NO: 63) | TGTGGTCTCAAGCGTAATGCCAACTTTGTAC (SEQ ID NO: 64) | AGCTCCTTCAACGTTCTCAA (SEQ ID NO: 83) |
| J2-sgRNA-2 | Solyc12g038510 | TGTGGTCTCAATTACATATTCTTGGAGAGGATTGTTTTAGAGCTAGAAATAGCAAG (SEQ ID NO: 65) | TGTGGTCTCAAGCGTAATGCCAACTTTGTAC (SEQ ID NO: 66) | ACATATTCTTGGAGAGGATT (SEQ ID NO: 84) |
| E32-sgRNA-1 | Solyc03g114840 | TGTGGTCTCAATTTTGGGCACGTTAAGCTCGAGTTTTAGAGCTAGAAATAGCAAG (SEQ ID NO: 67) | TGTGGTCTCAAGCGTAATGCCAACTTTGTAC (SEQ ID NO: 68) | TTTGGGCACGTTAAGCTCGA (SEQ ID NO: 85) |
| E32-sgRNA-2 | Solyc03g114840 | TGTGGTCTCAATTCCTTAAAGCAAATCAGGTCAGTTTTAGAGCTAGAAATAGCAAG (SEQ ID NO: 69) | TGTGGTCTCAAGCGTAATGCCAACTTTGTAC (SEQ ID NO: 70) | CCTTAAAGCAAATCAGGTCA (SEQ ID NO: 86) |
| LIN/J2/EJ2-sgRNA-1 | Solyc12g038510; Solyc04g005320; Solyc03g114840 | TGTGGTCTCAATTGCTTTTGCTAAGAGAAGAAAGTTTTAGAGCTAGAAATAGCAAG (SEQ ID NO: 71) | TGTGGTCTCAAGCGTAATGCCAACTTTGTAC (SEQ ID NO: 72) | GCTTTTGCTAAGAGAAGAAA (SEQ ID NO: 87) |

TABLE 2-continued

| Oligos used in this study | | | | |
|---|---|---|---|---|
| LIN/ J2/E J2- sgRNA- 2 | Solyc04 g005320 | TGTGGTCTCAA TTGCAGTCTTC AAAGGATTCAC GTTTTAGAGCT AGAAATAGCAA G (SEQ ID NO: 73) | TGTGGTCTCAAG CGTAATGCCAAC TTTGTAC (SEQ ID NO: 74) | GCAGTCT TCAAAGG ATTCAC (SEQ ID NO: 88) |

| Sequencing | | |
|---|---|---|
| Target | Forward primer | Reverse primer |
| pSC- B- amp/ kan | GTAAAACGACG GCCAG (SEQ ID NO: 75) | CAGGAAACAGCT ATGAC (SEQ ID NO: 76) |
| pICH 47761 | TCCTGTCAAAC ACTGATAG (SEQ ID NO: 77) | TAATGTACTGGG GTGGATGCAG (SEQ ID NO: 78) |
| pAGM 4723 | ATAAGCCCATC AGGGAGCAG (SEQ ID NO: 79) | CGGATAAACCTT TTCACGCC (SEQ ID NO: 80) |

REFERENCES

Ampomah-Dwamena, C., Morris, B. A., Sutherland, P., Veit, B., and Yao, J. (2002). Down-Regulation of TM29, a Tomato SEPALLATA Homolog, Causes Parthenocarpic Fruit Development and Floral Reversion. Plant Physiol 130, 605-617.

Anders, S., Pyl, P. T., and Huber, W. (2015). HTSeq-A Python framework to work with high-throughput sequencing data. Bioinformatics 31, 166-169.

Ashikari, M., Sakakibara, H., Lin, S., Yamamoto, T., Takashi, T., Nishimura, A., Angeles, E. R., Qian, Q., Kitano, H., and Matsuoka, M. (2005). Cytokinin oxidase regulates rice grain production. Science. 309, 741-745.

Belhaj, K., Chaparro-Garcia, A., Kamoun, S., and Nekrasov, V. (2013). Plant genome editing made easy: targeted mutagenesis in model and crop plants using the CRISPR/Cas system. Plant Methods 9, doi: 10.1186/1746-4811-9-39.

Bemer, M., Karlova, R., Ballester, A. R., Tikunov, Y. M., Bovy, A. G., Wolters-Arts, M., Rossetto, P. D. B., Angenent, G. C., and de Maagd, R. a (2012). The tomato FRUITFULL homologs TDR4/FUL1 and MBP7/FUL2 regulate ethylene-independent aspects of fruit ripening. Plant Cell 24, 4437-4451.

Blanca, J., Montero-Pau, J., Sauvage, C., Bauchet, G., Illa, E., Diez, M. J., Francis, D., Causse, M., van der Knaap, E., and Cañizares, J. (2015). Genomic variation in tomato, from wild ancestors to contemporary breeding accessions. BMC Genomics 16, 257.

Boden, S. A., Cavanagh, C., Cullis, B. R., Ramm, K., Greenwood, J., Jean Finnegan, E., Trevaskis, B., and Swain, S. M. (2015). Ppd-1 is a key regulator of inflorescence architecture and paired spikelet development in wheat. Nat. Plants 1, 14016.

Bolger, A., Scossa, F., Bolger, M. E., Lanz, C., Maumus, F., Tohge, T., Quesneville, H., Alseekh, S., Sorensen, I., Lichtenstein, G., et al. (2014a). The genome of the stress-tolerant wild tomato species *Solanum* pennellii. Nat. Genet 46, 1034-1038.

Bolger, A. M., Lohse, M., and Usadel, B. (2014b). Trimmomatic: A flexible trimmer for Illumina sequence data. Bioinformatics 30, 2114-2120.

Bomblies, K., and Weigel, D. (2007). Hybrid necrosis: autoimmunity as a potential gene-flow barrier in plant species. Nat. Rev. Genet. 8, 382-393.

Brooks, C., Nekrasov, V., Lippman, Z. B., and Van Eck, J. (2014). Efficient Gene Editing in Tomato in the First Generation Using the CRISPR/Cas9 System. Plant Physiol 166, 1292-1297.

Buckler, E. S., Holland, J. B., Bradbury, P. J., Acharya, C. B., Brown, P. J., Browne, C., Ersoz, E., Flint-Garcia, S., Garcia, A., Glaubitz, J. C., et al. (2009). The genetic architecture of maize flowering time. Science. 325, 714-718.

Budiman, M. A., Chang, S. B., Lee, S., Yang, T. J., Zhang, H. B., De Jong, H., and Wing, R. a. (2004). Localization of jointless-2 gene in the centromeric region of tomato chromosome 12 based on high resolution genetic and physical mapping. Theo Appl Genet 108, 190-196.

Butler, L. (1936). Inherited characters in the tomato. II. Jointless pedicels. J. Hered. 27, 25-26.

Chae, E., Bomblies, K., Kim, S. T., Karelina, D., Zaidem, M., Ossowski, S., Martin-Pizarro, C., Laitinen, R. A. E., Rowan, B. A., Tenenboim, H., et al. (2014). Species-wide genetic incompatibility analysis identifies immune genes as hot spots of deleterious epistasis. Cell 159, 1341-1351.

Chakrabarti, M., Zhang, N., Sauvage, C., Mufios, S., Blanca, J., Cañizares, J., Diez, M. J., Schneider, R., Mazourek, M., McClead, J., et al. (2013). A cytochrome P450 regulates a domestication trait in cultivated tomato. P Natl Acad Sci USA 110, 17125-17130.

Chou, H.-H., Chiu, H.-C., Delaney, N. F., Segre, D., and Marx, C. J. (2011). Diminishing Returns Epistasis Among Beneficial Mutations Decelerates Adaptation. Science. 332, 1190-1192.

Consortium, T. T. G. (2012). The tomato genome sequence provides insights into fleshy fruit evolution. Nature 485, 635-641.

Ditta, G., Pinyopich, A., Robles, P., Pelaz, S., and Yanofsky, M. F. (2004). The SEP4 Gene of *Arabidopsis thaliana* Functions in Floral Organ and Meristem Identity. Curr. Biol 14, 1935-1940.

Doebley, J., Stec, A., and Hubbard, L. (1997). The evolution of apical dominance in maize. Nature 386, 485-488.

Doebley, J. F., Gaut, B. S., and Smith, B. D. (2006). The Molecular Genetics of Crop Domestication. Cell 127, 1309-1321.

Doust, A. N., Lukens, L., Olsen, K. M., Mauro-Herrera, M., Meyer, A., and Rogers, K. (2014). Beyond the single gene: How epistasis and gene-by-environment effects influence crop domestication. Proc. Natl. Acad. Sci. 1-6.

Eshed, Y., and Zamir, D. (1996). Less-than-additive epistatic interactions of quantitative trait loci in tomato. Genetics 143, 1807-1817.

Famoso, A. N., Zhao, K., Clark, R. T., Tung, C., Wright, M. H., Kochian, L. V, and Mccouch, S. R. (2011). Genetic Architecture of Aluminum Tolerance in Rice (*Oryza sativa*) Determined through Genome-Wide Association Analysis and QTL Mapping. Plos Genet 7, e1002221. doi:10.1371/journal.pgen.1002221.

Futschik, M. (2015). Mfuzz: Soft clustering of time series gene expression data. R package version 2.30.0.

Gao, X., Zhang, X., Lan, H., Huang, J., Wang, J., and Zhang, H. (2015). The additive effects of GS3 and qGL3 on rice grain length regulation revealed by genetic and transcriptome comparisons. BMC Plant Biol. 15, 156.

Graaff, E. Van Der, Laux, T., and Rensing, S. A. (2009). Protein family review The WUS homeobox-containing (WOX) protein family. Genome Biol 10, 1-9.

Gupta, S. and Van Eck, J. (2016). Modification of plant regeneration medium decreases the time for recovery of *Solanum lycopersicum* cultivar M82 stable transgenic lines. Plant Cell Tissue Organ Cult. 127, 417-423.

Hartmann, U., Hohmann, S., Nettesheim, K., Wisman, E., Saedler, H., and Huijser, P. (2000). Molecular cloning of SVP: A negative regulator of the floral transition in *Arabidopsis*. Plant J. 21, 351-360.

Heck, J. A., Argueso, J. L., Gemici, Z., Reeves, R. G., Bernard, A., Aquadro, C. F., and Alani, E. (2006). Negative epistasis between natural variants of the *Saccharomyces cerevisiae* MLH1 and PMS1 genes results in a defect in mismatch repair. Proc. Natl. Acad. Sci. 103, 3256-3261.

Huang, X., Qian, Q., Liu, Z., Sun, H., He, S., Luo, D., Xia, G., Chu, C., Li, J., and Fu, X. (2009). Natural variation at the DEP1 locus enhances grain yield in rice. Nat. Genet 41, 494-497.

Jiao, Y., Wang, Y., Xue, D., Wang, J., Yan, M., Liu, G., Dong, G., Zeng, D., Lu, Z., Zhu, X., et al. (2010). Regulation of OsSPL14 by OsmiR156 defines ideal plant architecture in rice. Nat. Genet 42, 541-544.

Khan, A. I., Dinh, D. M., Schneider, D., Lenski, R. E., and Cooper, T. F. (2011). Negative epistasis between beneficial mutations in an evolving bacterial population. Science. 332, 1193-1196.

Kim, D., Pertea, G., Trapnell, C., Pimentel, H., Kelley, R., and Salzberg, S. L. (2013). TopHat2: accurate alignment of transcriptomes in the presence of insertions, deletions and gene fusions. Genome Biol 14, R36.

Klee, H. J., and Giovannoni, J. J. (2011). Genetics and Control of Tomato Fruit Ripening and Quality Attributes. Annu. Rev. Genet. 45, 41-59.

Kobayashi, K., Maekawa, M., Miyao, A., Hirochika, H., and Kyozuka, J. (2010). PANICLE PHYTOMER2 (PAP2), encoding a SEPALLATA subfamily MADS-box protein, positively controls spikelet meristem identity in rice. Plant Cell Physiol 51, 47-57.

Kobayashi, K., Yasuno, N., Sato, Y., Yoda, M., Yamazaki, R., Kimizu, M., Yoshida, H., Nagamura, Y., and Kyozuka, J. (2012). Inflorescence Meristem Identity in Rice Is Specified by Overlapping Functions of Three AP1/FUL-Like MADS Box Genes and PAP2, a SEPALLATA MADS Box Gene. Plant Cell 24, 1848-1859.

Komatsuda, T., Pourkheirandish, M., He, C., Azhaguvel, P., Kanamori, H., Perovic, D., Stein, N., Graner, A., Wicker, T., Tagiri, A., et al. (2007). Six-rowed barley originated from a mutation in a homeodomain-leucine zipper I-class homeobox gene. Proc. Natl. Acad. Sci. 104, 1424-1429.

Kvitek, D. J., and Sherlock, G. (2011). Reciprocal Sign Epistasis between Frequently Experimentally Evolved Adaptive Mutations Causes a Rugged Fitness Landscape. PLoS Genet. 7, e1002056.

Kyozuka, J., Tokunaga, H., and Yoshida, A. (2014). Control of grass inflorescence form by the fine-tuning of meristem phase change. Curr Opin Plant Biol 17, 110-115.

Lei, Y., Lu, L., Liu, H. Y., Li, S., Xing, F., and Chen, L. L. (2014). CRISPR-P: A web tool for synthetic single-guide RNA design of CRISPR-system in plants. Mol Plant 7, 1494-1496.

Lemmon, Z. H., Park, S. J., Jiang, K., Van Eck, J., Schatz, M. C., and Lippman, Z. B. (2016). The evolution of inflorescence diversity in the nightshades and heterochrony during meristem maturation. Genome Res. 1-11.

Leseberg, C. H., Eissler, C. L., Wang, X., Johns, M. a., Duvall, M. R., and Mao, L. (2008). Interaction study of MADS-domain proteins in tomato. J Exp Bot 59, 2253-2265.

Li, H. (2011). A statistical framework for SNP calling, mutation discovery, association mapping and population genetical parameter estimation from sequencing data. Bioinformatics 27, 2987-2993.

Li, H. (2013). Aligning sequence reads, clone sequences and assembly contigs with BWA-MEM. arXiv Prepr. arXiv 0, 3.

Li, H., and Durbin, R. (2009). Fast and accurate short read alignment with Burrows-Wheeler transform. Bioinformatics 25, 1754-1760.

Li, H., Handsaker, B., Wysoker, A., Fennell, T., Ruan, J., Homer, N., Marth, G., Abecasis, G., and Durbin, R. (2009). The Sequence Alignment/Map format and SAMtools. Bioinformatics 25, 2078-2079.

Lin, T., Zhu, G., Zhang, J., Xu, X., Yu, Q., Zheng, Z., Zhang, Z., Lun, Y., Li, S., Wang, X., et al. (2014). Genomic analyses provide insights into the history of tomato breeding. Nat. Genet 46, 1220-1226.

Lippman, Z. B., Cohen, O., Alvarez, J. P., Abu-Abied, M., Pekker, I., Paran, I., Eshed, Y., and Zamir, D. (2008). The making of a compound inflorescence in tomato and related nightshades. PLoS Biol 6, e288.

Liu, C., Teo, Z. W. N., Bi, Y., Song, S., Xi, W., Yang, X., Yin, Z., and Yu, H. (2013). A conserved genetic pathway determines inflorescence architecture in *Arabidopsis* and rice. Dev Cell 24, 612-622.

Liu, D., Wang, D., Qin, Z., Zhang, D., Yin, L., Wu, L., Colasanti, J., Li, A., and Mao, L. (2014). The SEPALLATA MADS-box protein SLMBP21 forms protein complexes with JOINTLESS and MACROCALYX as a transcription activator for development of the tomato flower abscission zone. Plant J 77, 284-296.

MacArthur, J. W., and Chiasson, L. P. (1947). Cytogenetic Notes on Tomato Species and Hybrids. Genetics 32, 165-177.

Mackay, T. F. C. (2013). Epistasis and quantitative traits: using model organisms to study gene-gene interactions. Nat Rev Genet 15, 22-33.

Male, C. J. (1999). 100 Heirloom Tomatoes for the American Garden.

Mao, L., Begum, D., Chuang, H. W., Budiman, M. a, Szymkowiak, E. J., Irish, E. E., and Wing, R. A. (2000). JOINTLESS is a MADS-box gene controlling tomato flower abscission zone development. Nature 406, 910-913.

Matsubara, K., Yamamoto, E., Mizobuchi, R., Yonemaru, J. -i., Yamamoto, T., Kato, H., and Yano, M. (2015). Hybrid Breakdown Caused by Epistasis-Based Recessive Incompatibility in a Cross of Rice (*Oryza sativa* L.). J. Hered. 106, 113-122.

Meyer, R. S., and Purugganan, M. D. (2013). Evolution of crop species: genetics of domestication and diversification. Nat Rev Genet 14, 840-852.

Mullins, M. G., Bouquet, A., and Williams, L. E. (1992). Biology of the Grapevine.

Nakano, T., Kimbara, J., Fujisawa, M., Kitagawa, M., Ihashi, N., Maeda, H., Kasumi, T., and Ito, Y. (2012). MACROCALYX and JOINTLESS interact in the transcriptional regulation of tomato fruit abscission zone development. Plant Physiol 158, 439-450.

Park, S. J., Jiang, K., Schatz, M. C., and Lippman, Z. B. (2012). Rate of meristem maturation determines inflorescence architecture in tomato. P Natl Acad Sci USA 109, 639-644.

Park, S. J., Eshed, Y., and Lippman, Z. B. (2014a). Meristem maturation and inflorescence architecture—lessons from the Solanaceae. Curr Opin Plant Biol 17, 70-77.

Park, S. J., Jiang, K., Tal, L., Yichie, Y., Gar, O., Zamir, D., Eshed, Y., and Lippman, Z. B. (2014b). Optimization of crop productivity in tomato using induced mutations in the florigen pathway. Nat Genet.

Peet, M. M., and Welles, G. (2005). Greenhouse tomato production. N Tomatoes, E. Heuvelink, Ed. (Wallingford, U. K. CABI Publ. 257-304.

Pelaz, S., Ditta, G. S., and Yanofsky, M. F. (2000). B and C foral organ identity functions require SEPALLATA MADS-box genes. Nature 405, 9-12.

Peralta, I. E., and Spooner, D. M. (2005). Morphological Characterization and Relationships of Wild Tomatoes (*Solanum* L. sect. *Lycopersicon*). Mono Syst Bot. 104, 227-257.

Pnueli, L., Hareven, D., Broday, L., Hurwitz, C., and Lifschitz, E. (1994). The TM5 MADS Box Gene Mediates Organ Differentiation in the Three Inner Whorls of Tomato Flowers. Plant Cell 6, 175-186.

Prusinkiewicz, P., Erasmus, Y., Lane, B., Harder, L. D., and Coen, E. (2007). Evolution and development of inflorescence architectures. Science. 316, 1452-1456.

Purugganan, M. D., and Fuller, D. Q. (2009). The nature of selection during plant domestication. Nature 457, 843-848.

Ramsay, L., Comadran, J., Druka, A., Marshall, D. F., Thomas, W. T. B., Macaulay, M., MacKenzie, K., Simpson, C., Fuller, J., Bonar, N., et al. (2011). INTERMEDIUM-C, a modifier of lateral spikelet fertility in barley, is an ortholog of the maize domestication gene TEOSINTE BRANCHED 1. Nat. Genet 43, 169-172.

Reynard, G. B. (1961). New Source of the j2 Gene Governing Jointless Pedicel in Tomato. Science (80-.). 134, 2102.

Rick, C. M. (1956a). Genetic and Systematic Studies on Accessions of Lycospersicon from the Galapagos Islands. Am J Bot 43, 687-696.

Rick, C. M. (1956b). A new jointless gene from the Galapagos *L. pimpinellifolium*. TGC Rep. 23.

Robinson, R. W. (1980). Pleiotropic effects of the j-2 gene. The. TGC Rep. 30, 32.

Robinson, M. D., McCarthy, D. J., and Smyth, G. K. (2009). edgeR: A Bioconductor package for differential expression analysis of digital gene expression data. Bioinformatics 26, 139-140.

RTeam, D. C. (2015). R Core Team (2015). R: A language and environment for statistical computing. R Found. Stat. Comput. Vienna, Austria. project.org/.

Shalit, A., Rozman, A., Goldshmidt, A., Alvarez, J. P., Bowman, J. L., Eshed, Y., and Lifschitz, E. (2009). The flowering hormone florigen functions as a general systemic regulator of growth and termination. P Natl Acad Sci USA 106, 8392-8297.

Shang, L., Liang, Q., Wang, Y., Zhao, Y., Wang, K., and Hua, J. (2016). Epistasis together with partial dominance, overdominance and QTL by environment interactions contribute to yield heterosis in upland cotton. Theor. Appl. Genet. 129, 1429-1446.

Singh, R., Low, E.-T. L., Ooi, L. C.-L., Ong-Abdullah, M., Ting, N.-C., Nagappan, J., Nookiah, R., Amiruddin, M. D., Rosli, R., Manaf, M. A. A., et al. (2013). The oil palm SHELL gene controls oil yield and encodes a homologue of SEEDSTICK. Nature 500, 340-344.

Soyk, S., Müller, N., Park, S. J., Schmalenbach, I., Jiang, K., Hayama, R., Zhang, L., Eck, J. Van, Schmalenbach, I., Jiménez-gómez, J. M., et al. (2016). Variation in the flowering gene SELF PRUNING 5G promotes day-neutrality in tomato and early yield. Nat Genet 1-37.

Stephenson, A. G. (1981). Flower and fruit abortion: proximate causes and ultimate functions. Ann Rev Ecol Syst 12, 253-279.

Stubbe, H. (1972). Mutanten der Kulturtomate *Lycopersicon esculentum* Miller V I. Die Kult. 16, 185-230.

Swinnen, G., Goossens, A., and Pauwels, L. (2016). Lessons from Domestication: Targeting Cis-Regulatory Elements for Crop Improvement. Trends Plant Sci 21, 506-515.

Tamura, K., Stecher, G., Peterson, D., Filipski, A., and Kumar, S. (2013). MEGA6: Molecular evolutionary genetics analysis version 6.0. Mol Biol Evol 30, 2725-2729.

Theissen, G., Melzer, R., and Rumpler, F. (2016). MADS-domain transcription factors and the floral quartet model of flower development: linking plant development and evolution. Development 143, 3259-3271.

Tieman, D., Zhu, G., Resende, M. F. R., Lin, T., Nguyen, C., Bies, D., Rambla, J. L., Beltran, K. S. O., Taylor, M., Zhang, B., et al. (2017). A chemical genetic roadmap to improved tomato flavor. Science. 355, 391-394.

Vrebalov, J., Ruezinsky, D., Padmanabhan, V., White, R., Medrano, D., Drake, R., Schuch, W., and Giovannoni, J. (2002). A MADS-Box Gene Necessary for Fruit Ripening at the Tomato Ripening-Inhibitor (Rin) Locus. Science (80-.). 296, 343-346.

Wang, S., Lu, G., Hou, Z., Luo, Z., Wang, T., Li, H., Zhang, J., and Ye, Z. (2014). Members of the tomato FRUITFULL MADS-box family regulate style abscission and fruit ripening. J. Exp. Bot. 65, 3005-3014.

Werner, S., Engler, C., Weber, E., Gruetzner, R., and Marillonnet, S. (2012). Fast track assembly of multigene constructs using Golden Gate cloning and the MoClo system. Bioeng Bugs 3, 38-43.

Williams, T. N., Mwangi, T. W., Wambua, S., Peto, T. E. A., Weatherall, D. J., Gupta, S., Recker, M., Penman, B. S., Uyoga, S., Macharia, A., et al. (2005). Negative epistasis between the malaria-protective effects of α+-thalassemia and the sickle cell trait. Nat. Genet. 37, 1253-1257.

Xu, C., Liberatore, K. L., MacAlister, C. a, Huang, Z., Chu, Y.-H., Jiang, K., Brooks, C., Ogawa-Ohnishi, M., Xiong, G., Pauly, M., et al. (2015). A cascade of arabinosyltransferases controls shoot meristem size in tomato. Nat. Genet.

Yang, T. J., Lee, S., Chang, S. Bin, Yu, Y., de Jong, H., and Wing, R. A. (2005). In-depth sequence analysis of the tomato chromosome 12 centromeric region: Identification of a large CAA block and characterization of pericentromere retrotranposons. Chromosoma 114, 103-117.

Zahara, M. B., and Scheuerman, R. W. (1988). Hand-harvesting jointless vs. jointed-stem tomatoes. Calif. Agric. 42, 14-14.

Zamir, D. (2001). Improving plant breeding with exotic genetic libraries. Nat Rev Genet 2, 3-9.

Zhang, L., Yang, G., Liu, P., Hong, D., Li, S., and He, Q. (2011). Genetic and correlation analysis of silique-traits in *Brassica napus* L. by quantitative trait locus mapping. Theor. Appl. Genet. 122, 21-31.

Zhang, N., Brewer, M. T., and van der Knaap, E. (2012). Fine mapping of fw3.2 controlling fruit weight in tomato. Theor. Appl. Genet. 125, 273-284.

Zhao, Q., Weber, A. L., McMullen, M. D., Guill, K., and Doebley, J. (2011). MADS-box genes of maize: frequent targets of selection during domestication. Genet. Res. (Camb). 93, 65-75.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A genetically-altered tomato plant comprising:

a mutant Solyc04g005320 gene comprising the sequence of SEQ ID NO: 4 or a mutant Solyc04g005320 gene comprising at least 99% sequence identity with the sequence of SEQ ID NO: 4, wherein the mutant Solyc04g005320 gene is a null allele, and wherein the genetically-altered tomato plant exhibits increased inflorescence complexity, increased flower production, and increased fruit production relative to a wild-type tomato plant.

2. The genetically-altered tomato plant of claim 1, wherein the genetically-altered tomato plant is heterozygous or homozygous for the mutant Solyc04g005320 gene.

3. The genetically-altered tomato plant of claim 1, wherein the genetically-altered tomato plant further comprises a mutant Solyc12g038510 gene comprising the sequence of SEQ ID NO: 10 or a mutant Solyc12g038510 gene comprising at least 99% sequence identity with the sequence of SEQ ID NO: 10, wherein the mutant Solyc12g038510 gene is a null allele, and wherein the genetically-altered tomato plant exhibits increased inflorescence complexity, increased flower production, increased fruit production, and a jointless pedicel relative to a wild-type tomato plant.

4. The genetically-altered tomato plant of claim 3, wherein the genetically-altered tomato plant is heterozygous or homozygous for the mutant Solyc12g038510 gene.

5. The genetically-altered tomato plant of claim 1, wherein the genetically-altered tomato plant is *Solanum lycopersicum*.

6. The genetically-altered tomato plant of claim 3, wherein the mutant Solyc04g005320 gene, the mutant Solyc12g038510 gene, or the mutant Solyc04g005320 gene and the mutant Solyc12g038510 gene is introduced using CRISPR/Cas9, chemical mutagenesis, radiation, *Agrobacterium*-mediated recombination, viral-vector mediated recombination, or transposon mutagenesis.

7. A crop harvested from the genetically-altered tomato plant as defined in claim 1.

8. A seed for producing the genetically-altered tomato plant of claim 1.

9. A method for producing a genetically-altered tomato plant comprising:

introducing a mutation into a Solyc04g005320 gene to produce a mutant Solyc04g005320 gene comprising the sequence of SEQ ID NO: 4 or a sequence comprising at least 99% sequence identity with the sequence of SEQ ID NO: 4 in a tomato plant, thereby producing the genetically-altered tomato plant containing the mutant Solyc04g005320 gene, wherein the mutant Solyc04g005320 gene is a null allele, and wherein the genetically-altered tomato plant exhibits increased inflorescence complexity, increased flower production, and increased fruit production relative to a wild-type tomato plant.

10. The method of claim 9, wherein the mutation is introduced using CRISPR/Cas9.

11. The method of claim 9, wherein the method further comprises introducing a mutation into a Solyc12g038510 gene to produce a mutant Solyc12g038510 gene comprising the sequence of SEQ ID NO: 10 or a sequence comprising at least 99% sequence identity with the sequence of SEQ ID NO: 10 in a tomato plant, thereby producing a genetically-altered tomato plant containing the mutant Solyc04g005320 gene and the mutant Solyc12g038510 gene, wherein the mutant Solyc12g038510 gene is a null allele, and wherein the genetically-altered tomato plant exhibits increased inflorescence complexity, increased flower production, increased fruit production, and a jointless pedicel relative to a wild-type tomato plant.

12. The method of claim 11, wherein the mutation(s) is/are introduced using CRISPR/Cas9.

13. The method of claim 9, wherein the genetically-altered tomato plant containing the mutant Solyc04g005320 gene is crossed to another genetically-altered tomato plant comprising a mutant Solyc12g038510 gene comprising at least 99% sequence identity with the sequence of SEQ ID NO: 10 in a tomato plant, thereby producing a genetically-altered tomato plant progeny containing the mutant Solyc04g005320 gene and the mutant Solyc12g038510 gene, wherein the mutant Solyc128038510 gene is a null allele, and wherein the genetically-altered tomato plant progeny exhibits increased inflorescence complexity, increased flower production, increased fruit production, and a jointless pedicel relative to a wild-type tomato plant.

14. A genetically-altered tomato plant produced by the method of claim 9.

15. The genetically-altered tomato plant of claim 1, wherein the mutant Solyc04g005320 gene comprises a mutation in the coding region.

16. The genetically-altered tomato plant of claim 3, wherein the mutant Solyc12g038510 gene comprises a mutation in the coding region.

* * * * *